US012214007B2

(12) United States Patent
Sonoda et al.

(10) Patent No.: US 12,214,007 B2
(45) **Date of Patent: *Feb. 4, 2025**

(54) FUSION PROTEIN INCLUDING BDNF

(71) Applicant: JCR Pharmaceuticals Co., Ltd., Hyogo (JP)

(72) Inventors: Hiroyuki Sonoda, Kobe (JP); Kenichi Takahashi, Kobe (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 368 days.

This patent is subject to a terminal disclaimer.

(21) Appl. No.: 16/473,816

(22) PCT Filed: Dec. 26, 2017

(86) PCT No.: PCT/JP2017/046735

§ 371 (c)(1),
(2) Date: Sep. 12, 2019

(87) PCT Pub. No.: WO2018/124107

PCT Pub. Date: Jul. 5, 2018

(65) Prior Publication Data

US 2020/0384061 A1 Dec. 10, 2020

(30) Foreign Application Priority Data

Dec. 26, 2016 (JP) ................................ 2016-252147

(51) Int. Cl.

*C07K 19/00* (2006.01)
*A61K 38/01* (2006.01)
*A61K 38/17* (2006.01)
*A61K 38/18* (2006.01)
*A61P 25/28* (2006.01)
*C07K 14/435* (2006.01)
*C07K 16/18* (2006.01)
*C07K 16/46* (2006.01)
*C12N 15/66* (2006.01)

(52) U.S. Cl.

CPC .......... *A61K 38/017* (2013.01); *A61K 38/185* (2013.01); *C07K 16/18* (2013.01); *C12N 15/66* (2013.01); *C07K 2317/54* (2013.01); *C07K 2317/55* (2013.01); *C07K 2317/565* (2013.01); *C07K 2317/567* (2013.01); *C07K 2317/62* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 5,154,924 | A | 10/1992 | Friden | |
| 5,442,043 | A | 8/1995 | Fukuta et al. | |
| 5,527,527 | A | 6/1996 | Friden | |
| 5,977,307 | A | 11/1999 | Friden et al. | |
| 6,472,147 | B1 | 10/2002 | Janda et al. | |
| 7,560,431 | B2 | 7/2009 | Zankel et al. | |
| 8,663,598 | B2 | 3/2014 | Yang et al. | |
| 8,785,168 | B2 | 7/2014 | LeBowitz et al. | |
| 9,994,641 | B2 * | 6/2018 | Sonoda | C12N 9/16 |
| 10,301,629 | B2 | 5/2019 | Littman et al. | |
| 10,759,864 | B2 * | 9/2020 | Sonoda | C12N 5/10 |
| 11,111,308 | B2 * | 9/2021 | Sonoda | A61P 25/00 |
| 11,130,815 | B2 | 9/2021 | Sonoda et al. | |
| 11,248,045 | B2 | 2/2022 | Sonoda et al. | |
| 2004/0101904 | A1 | 5/2004 | Pardridge et al. | |
| 2010/0077498 | A1 | 3/2010 | Pardridge et al. | |
| 2010/0266613 | A1 | 10/2010 | Harding et al. | |
| 2011/0110935 | A1 | 5/2011 | Pardridge et al. | |
| 2012/0171120 | A1 | 7/2012 | Dennis et al. | |
| 2012/0231023 | A1 | 9/2012 | Zurawski et al. | |
| 2013/0171061 | A1 | 7/2013 | Yang et al. | |
| 2013/0274446 | A1 | 10/2013 | Kumagai et al. | |
| 2014/0079691 | A1 | 3/2014 | McConnell et al. | |
| 2014/0114054 | A1 | 4/2014 | Kurosawa et al. | |
| 2015/0110791 | A1 | 4/2015 | Zhang et al. | |
| 2016/0362497 | A1 | 12/2016 | Nash et al. | |
| 2016/0369001 | A1 | 12/2016 | Sonoda et al. | |
| 2017/0044259 | A1 | 2/2017 | Tipton et al. | |
| 2017/0252458 | A1 | 9/2017 | Albone et al. | |
| 2017/0355756 | A1 | 12/2017 | Julien et al. | |
| 2018/0171012 | A1 | 6/2018 | Sonoda et al. | |
| 2018/0179291 | A1 | 6/2018 | Sonoda et al. | |

(Continued)

FOREIGN PATENT DOCUMENTS

| | | | |
|---|---|---|---|
| CA | 2607771 | A1 | 5/2009 |
| CA | 3034589 | A1 | 3/2018 |

(Continued)

OTHER PUBLICATIONS

U.S. Appl. No. 17/161,718, filed Jan. 2021, Sonoda; Hiroyuki.*
"Huntington's Disease", Cleveland Clinic, available online at https://my.clevelandclinic.org/health/diseases/14369-huntingtons-disease, 13 pages (accessed on Jan. 10, 2022) (Year: 2022).*
"Huntington's Disease", Stanford Health Care, available online at https://stanfordhealthcare.org/medical-conditions/brain-and-nerves/dementia/types/huntingtons-disease.html, (accessed on Jan. 10, 2022) (Year: 2022).*
Egan et al., Cell 112:257-269 (2003) (Year: 2003).*
Shen et al., Aging and Disease 9:523-536 (2018) (Year: 2018).*

(Continued)

*Primary Examiner* — Thea D' Ambrosio

(74) *Attorney, Agent, or Firm* — Morgan, Lewis & Bockius LLP

(57) ABSTRACT

The present invention provides a fusion protein of BDNF and an anti-human transferrin receptor antibody, in which in a heavy chain variable region of the antibody, (a) CDR1 includes an amino acid sequence of SEQ ID NO: 66 or SEQ ID NO: 67, (b) CDR2 includes an amino acid sequence of SEQ ID NO: 13 or SEQ ID NO: 14, and (c) CDR3 includes an amino acid sequence of SEQ ID NO: 15 or SEQ ID NO: 16.

41 Claims, 11 Drawing Sheets

Specification includes a Sequence Listing.

(56) References Cited

U.S. PATENT DOCUMENTS

2019/0338043 A1 11/2019 Sonoda et al.
2020/0384061 A1 12/2020 Sonoda et al.
2021/0269543 A1* 9/2021 Sonoda .................. C12N 15/62

FOREIGN PATENT DOCUMENTS

| | | | |
|---|---|---|---|
| CN | 1694895 | A | 11/2005 |
| CN | 101245107 | A | 8/2008 |
| CN | 101495141 | A | 7/2009 |
| CN | 103502273 | A | 1/2014 |
| CN | 105873947 | A | 8/2016 |
| EP | 3563863 | A1 | 11/2019 |
| EP | 3679945 | A1 | 7/2020 |
| JP | H05-500944 | A | 2/1993 |
| JP | 106-228199 | A | 8/1994 |
| JP | 2006-511516 | A | 4/2006 |
| JP | 2007-504166 | A | 3/2007 |
| JP | 2009-515819 | A | 4/2009 |
| JP | 2009-525963 | A | 7/2009 |
| JP | 2011-144178 | A | 7/2011 |
| JP | 2012-062312 | A | 3/2012 |
| JP | 2014-514313 | A | 6/2014 |
| JP | 2018-033454 | A | 3/2018 |
| WO | 91/003259 | A1 | 3/1991 |
| WO | 93/010819 | A1 | 6/1993 |
| WO | 95/02421 | A1 | 1/1995 |
| WO | 02/031510 | A1 | 4/2002 |
| WO | 02/034771 | A2 | 5/2002 |
| WO | 03/083069 | A2 | 10/2003 |
| WO | 2004/020404 | A2 | 3/2004 |
| WO | 2004/050016 | A2 | 6/2004 |
| WO | 2005/021064 | A2 | 3/2005 |
| WO | 2007/044323 | A2 | 4/2007 |
| WO | 2007/070432 | A2 | 6/2007 |
| WO | 2007/084737 | A2 | 7/2007 |
| WO | 2008/068048 | A2 | 6/2008 |
| WO | 2010/037395 | A2 | 4/2010 |
| WO | 2012/020622 | A1 | 2/2012 |
| WO | 2012/075037 | A1 | 6/2012 |
| WO | 2012/143379 | A1 | 10/2012 |
| WO | 2013/177062 | A2 | 11/2013 |
| WO | 2014/033074 | A1 | 3/2014 |
| WO | 2014/105810 | A1 | 7/2014 |
| WO | 2014/189973 | A2 | 11/2014 |
| WO | 2014/190305 | A2 | 11/2014 |
| WO | 2014/194282 | A2 | 12/2014 |
| WO | 2015/009961 | A1 | 1/2015 |
| WO | 2015/014884 | A1 | 2/2015 |
| WO | 2015/098989 | A1 | 7/2015 |
| WO | 2015/101588 | A1 | 7/2015 |
| WO | 2016/208695 | A1 | 12/2016 |
| WO | 2016/208696 | A1 | 12/2016 |
| WO | 2017/011580 | A2 | 1/2017 |
| WO | 2019/049967 | A1 | 3/2019 |

OTHER PUBLICATIONS

"Prevent", Macmillan dictionary, available online at https://www.macmillandictionary.com/us/dictionary/american/prevent, 6 pages (accessed on Jan. 12, 2022) (Year: 2022).*

Stoppe et al., Drugs & Aging 14:41-54 (1999) (Year: 1999).*

Chao, "Neurotrophins and their receptors: a convergence point for many signalling pathways," Nature Reviews Neurosicence, 4: 299-309 (2003).

Tabakman et al., "Interactions between the cells of the immune and nervous system: neurotrophins as neuroprotection mediators in CNS injury," Progress in Brain Research, 146: 387-401 (2004).

Bollen et al., "7,8-Dihydroxyflavone improves memory consolidation processes in rats and mice," Behavioural Brain Research, 257: 8-12 (2013).

Altar et al., "Efficacy of brain-derived neurotrophic factor and neurotrophin-3 on neurochemical and behavioral deficits associated with partial nigrostriatal dopamine lesions," Journal of Neurochemistry, 63: 1021-1032 (1994).

Wu, "Neuroprotection in experimental stroke with targeted neurotrophins," The Journal of the American Society for Experimental Neurotherapeutics, 2: 120-128 (2005).

Katz, Brain-derived neurotrophic factor and Rett syndrome, The Handbook of Experimental Pharmacology, 220: 481-495 (2014).

Castren, "Neurotrophins and psychiatric disorders," The Handbook of Experimental Pharmacology, 220: 461-479 (2014).

Xie et al., "Transport of nerve growth factor encapsulated into liposomes across the blood brain barrier: in vitro and in vivo studies," Journal of Controlled Release, 105: 106-119 (2005).

Ou et al., "High-dose enzyme replacement therapy in murine Hurler syndrome," Molecular Genetics and Metabolism, 111: 116-122 (2014).

Boado et al., "Genetic engineering, expression, and activity of a fusion protein of a human neurotrophin and a molecular Trojan horse for delivery across the human blood-brain barrier," Biotechnology and Bioengineering, 97: 1376-1386 (2007).

Li et al., "Genetically engineered brain drug delivery vectors: cloning, expression and in vivo application of an anti-transferrin receptor single chain antibody-streptavidin fusion gene and protein," Protein Engineering, 12: 787-796 (1999).

Bien-Ly et al., "Transferrin receptor (TfR) trafficking determines brain uptake of TfR antibody affinity variants," The Journal of Experimental Medicine, 211: 233-244 (2014).

Sade et al., "A human blood-brain barrier transcytosis assay reveals antibody transcytosis influenced by pH-dependent receptor binding," PLoS One, 9: e96340 (2014).

Zhou et al., "Monoclonal Antibody-Glial-Derived Neurotrophic Factor Fusion Protein Penetrates the Blood-Brain Barrier In the Mouse," Drug Metabolism and Disposition, 38: 566-572 (2010).

Wu et al., "Neuroprotection with noninvasive neurotrophin delivery to the brain," Proceedings of the National Academy of Sciences, 96: 254-259 (1999).

International Search Report issued in corresponding International Patent Application No. PCT/JP2017/046735 dated Apr. 3, 2018.

International Preliminary Report on Patentability and Written Opinion issued in corresponding International Patent Application No. PCT/JP2017/046735 dated Jul. 11, 2019.

"Overview of the Immune System," Immunology: A Short Course, 7th ed., Richard Coico and Geoffrey Sunshine, 61-62 (2015).

Altshuler et al., "Generation of Recombinant Antibodies and Means for Increasing Their Affinity," Biochemistry (Moscow), 75 (13): 1584-1605 (2010). (Original Russian text: Uspekhi Biologicheskoi Khimii, 50: 203-258 (2010).

Brown, et al., "Tolerance to Single, but Not Multiple, Amino Acid Replacements in Antibody VH CDR2," Journal of Immunology, 3286-3291 (1996).

Office Action issued in related Eurasian Patent Application No. 201991577 dated Feb. 26, 2021.

Kussie et al., "A Single Engineered Amino Acid Substitution Changes Antibody Fine Specificity," Journal of Immunology, 152: 146-152 (1994).

Chen et al., "Enhancement and destruction of antibody function by somatic mutation: unequal occurrence is controlled by V gene combinatorial associations," EMBO Journal, 14: 2784-2794 (1995).

Zhou et al., "Delivery of a Peptide Radiopharmaceutical to Brain with an IgG-Avidin Fusion Protein," Bioconjugate Chemistry, 22: 1611-1618 (2011).

Boado et al., "Engineering and Expression of a Chimeric Transferrin Receptor Monoclonal Antibody for Blood-Brain Barrier Delivery in the Mouse," Biotechnology and Bioengineering, 102: 1251-1258 (2009).

Walus et al., "Enhanced Uptake of rsCD4 across the Rodent and Primate Blood-Brain Barrier after Conjugation to Anti-Transferrin Receptor Antibodies," Journal of Pharmacology and Experimental Therapeutics, 277: 1067-1075 (1996).

Friden et al., "Characterization, Receptor Mapping and Blood-Brain Barrier Transcytosis of Antibodies to the Human Transferrin Receptor," Journal of Pharmacology and Experimental Therapeutics, 278: 1491-1498 (1996).

(56) References Cited

OTHER PUBLICATIONS

Pardridge et al., "Reengineering Biopharmaceuticals for Targeted Delivery Across the Blood-Brain Barrier," Methods in Enzymology, 503: 269-292 (2012).
Torres et al., "The immunoglobulin constant region contributes to affinity and specificity," Trends in Immunology 29: 91-97 (2007).
Pardridge, "Blood-brain barrier drug delivery of IgG fusion proteins with a transferrin receptor monoclonal antibody," Expert Opinion Drug Drug Delivery, 12: 207-222 (2015).
Yan et al., "Studies of the Expression and Biologic Activity of an Anti-transferrin Receptor ScFv-BDNF Fusion Protein," China Biotechnology, 26: 1-5 (2006) (see English abstract).
Bowie et al., "Deciphering the Message in Protein Sequences: Tolerance to Amino Acid Substitutions," Science, 247: 1306-1310 (1990).
Pawson et al., "Assembly of Cell Regulatory Systems Through Protein Interaction Domains," Science, 300: 445-452 (2003).
Burgess et al., "Possible Dissociation of the Heparin-binding and Mitogenic Activities of the Heparin-binding (Acidic Fibroblast) Growth Factor-1 form Its Receptor-binding Activities by Site-directed Mutagenesis of a Single Lysine Residue," Journal of Cell Biology, 111: 2129-2138 (1990).
Alaoui-Ismaili et al., "Design of second generation therapeutic recombinant bone morphogenetic proteins," Cytokine & Growth Factor Reviews, 20: 501-507 (2009).
Guo et al., "Protein tolerance to random amino acid change," PNAS, 101: 9205-9210 (2004).
Rudikoff et al., "Single amino acid substitution altering antigen-binding specificity," PNAS, 79: 1979-1983 (1982).
Holm et al., "Functional mapping and single chain construction of the anti-cytokeratin 8 monoclonal antibody TS1," Molecular Immunology, 44: 1075-1084 (2007).
MacCallum et al., "Antibody-antigen Interactions: Contact Analysis and Binding Site Topography," Journal of Molecular Biology, 262: 732-745 (1996).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology, 169: 3076-3084 (2002).
Casset et al., "A peptide mimetic of an anti-CD4 monoclonal antibody by rational design," Biochemical and Biophysical Research Communications, 307: 198-205 (2003).
Vajdos et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Chen et al., "Selection and Analysis of an Optimized Anti-VEGF Antibody: Crystal Structure of an Affinity-matured Fab In Complex with Antigen," Journal of Molecular Biology, 293: 865-881 (1999).
Gosk et al., "Targeting Anti-Transferrin Receptor Antibody (OX26) and OX26-Conjugated Liposomes to Brain Capillary Endothelial Cells Using In Situ Perfusion," Journal of Cerebral Blood Flow & Metabolism, 24: 1193-1196 (2004).
Li et al., "The role of the transferrin-transferrin-receptor system in drug delivery and targeting," Trends in Pharmacological Sciences, 23: 206-209 (2002).
Helguera et al., "An Antibody Recognizing the Apical Domain of Human Transferrin Receptor 1 Efficiently Inhibits the Entry of All New World Hemorrhagic Fever Arenaviruses," Journal of Virology, 86: 4024-4028 (2012).
Qing et al., "The in vitro antitumor effect and in vivo tumor-specificity distribution of human-mouse chimeric antibody against transferrin receptor", Cancer Immunology Immunotherapy, 55: 1111-1121 (2006).
Tucker et al., "Drug delivery to the brain via the blood-brain barrier: a review of the literature and some recent patent disclosures," Therapeutic Delivery, 2: 311-327 (2011).
Niewoehner et al., "Increased Brain Penetration and Potency of a Therapeutic Antibody Using a Monovalent Molecular Shuttle," Neuron 81: 49-60 (2014).
Formica et al., "5-Fluorouracil can cross brain-blood barrier and cause encephalopathy: should we expect the same from capecitabine? A case report on capecitabine-induced central neurotoxicity progressing to coma," Cancer Chemotherapy and Pharmacology, 58: 276-278 (2006).
International Search Report issued in corresponding International Patent Application No. PCT/JP2017/046762 dated Mar. 27, 2018.
International Preliminary Report on Patentability and Written Opinion issued in corresponding International Patent Application No. PCT/JP2017/046762 dated Jul. 11, 2019.
International Search Report issued in corresponding International Patent Application No. PCT/JP2016/068739 dated Sep. 6, 2016.
International Preliminary Report on Patentability and Written Opinion issued in corresponding International Patent Application No. PCT/JP2016/068739 dated Jan. 4, 2018.
International Search Report issued in corresponding International Patent Application No. PCT/JP2016/068738 dated Sep. 6, 2016.
International Preliminary Report on Patentability and Written Opinion issued in corresponding International Patent Application No. PCT/JP2016/068738 dated Dec. 26, 2017.
Extended European Search Report issued in counterpart European Patent Application No. 16814465.7 dated May 8, 2019.
Partial Supplemental European Search Report issued in counterpart European Patent Application No. 16814464.0 dated Dec. 17, 2018.
Extended European Search Report issued in counterpart European Patent Application No. 16814464.0 dated Mar. 25, 2019.
Office Action issued in counterpart Singapore Patent Application No. 11201710734U dated Jan. 3, 2019.
Wu et al., "Humanization of a Murine Monoclonal Antibody by Simultaneous Optimization of Framework and CDR Residues," Journal of Molecular Biology, 294: 151-162 (1999).
Holmes et al., "Structural Consequences of Humanizing an Antibody," Journal of Immunology, 2192-2201 (1997).
Zhou et al., "Brain-Penetrating IgG Iduronate 2-Sulfatase Fusion Protein for the Mouse," Drug Metabolism and Disposition, 40: 329-335 (2012).
Extended European Search Report issued in European Patent Application No. 17889016.6 dated Jul. 15, 2020.
Trowbridge et al., "Anti-transferrin receptor monoclonal antibody and toxin-antibody conjugates affect growth of human tumour cells," Nature, 294: 171-173 (1981).
Office Action issued in U.S. Appl. No. 17/161,718 dated Dec. 2, 2022.
Manich et al., "Study of the transcytosis of an anti-transferrin receptor antibody with a Fab' cargo across the blood-brain barrier in mice," European Journal of Pharmaceutical Sciences, 49: 556-564 (2013).
Chen et al., "Fusion Protein Linkers: Property, Design and Functionality," Advanced Drug Delivery Reviews, 65 (10): 1357-1369 (2013).
Office Action issued in U.S. Appl. No. 17/161,718 dated Jan. 12, 2024.
Decision to Grant issued in Japanese Patent Application No. 2017-524983 dated Apr. 18, 2018.
EBiomMedicine, "Overcoming gaps in the treatment of neurodegenerative disease," 60: 103088 (2020).
Henstridge et al., "Beyond the neuron-cellular interactions early in Alzheimer disease pathogenesis," Nature, 20: 94-108 (2019).
Notice of Reasons for Refusal issued in Japanese Patent Application No. 2017-524983 dated Jan. 23, 2018.
Office Action issued in U.S. Appl. No. 17/349,414 dated Nov. 25, 2022.
Sarter, "Animal cognition: defining the issues," Neuroscience and Biobehavioral Reviews, 28: 645-650 (2004).
Tayebati, "Animal models of cognitive dysfunction," Mechanisms of Ageing and Development, 127: 100-108 (2006).
Zuccato et al., "Role of brain-derived neurotrophic factor in Huntington's disease," Progress in Neurobiology, 81: 294-330 (2007).
Sela-Culang et al., "The structural basis of antibody-antigen recognition," Frontiers in Immunology, 4 (8): 302 (2013).

(56) References Cited

OTHER PUBLICATIONS

Office Action issued in European Patent Application No. 16814465.7 dated Apr. 18, 2024.
Notice of Allowance issued in U.S. Appl. No. 17/321,772 dated Jul. 10, 2024.
1 Hearing Notice issued in Indian Patent Application No. 201847002081 dated Jul. 8, 2024.
Bickel et al., "Delivery of peptides and proteins through the blood-brain barrier," Advanced Drug Delivery Reviews, 46: 247-279 (2001).
Office Action issued in European Patent Application No. 16814464.0 dated Sep. 24, 2024.

* cited by examiner (a) (b)

FUSION PROTEIN INCLUDING BDNF

SEQUENCE LISTING SUBMISSION VIA EFS-WEB

A computer readable text file, entitled "SequenceListing.txt," created on or about Sep. 11, 2019 with a file size of about 186 kb contains the sequence listing for this application and is hereby incorporated by reference in its entirety.

TECHNICAL FIELD

The present invention relates to BDNF capable of passing through a blood-brain barrier, and more specifically relates to a fusion protein of a new anti-human transferrin receptor antibody and BDNF, a method for producing thereof, and a method of use thereof.

BACKGROUND ART

Unlike capillary vessels present in other tissues such as muscles, the capillaries that supply blood to most tissues in the brain, excluding some areas including circumventricular organs (pineal body, pituitary gland, area postrema, and the like) form a structure in which endothelial cells of capillary vessels adhere tightly to each other by strong intercellular junction. For this reason, passive transfer of substances from blood to the brain is restricted, and although there are some exceptions, it is difficult for substances excluding a highly lipid-soluble substance or a substance having a low molecular weight (equal to or more than 200 to equal to or less than 500 daltons) and electrically neutral in the vicinity of physiological pH to migrate from the capillary vessels to the brain. Such a mechanism that restricts substance exchange between the blood and cerebral tissue fluid via capillary vessel endothelium in the brain is referred to as blood-brain barrier (BBB). In addition, the blood-brain barrier restricts substance exchange between not only the brain and blood but also tissue fluid of the central nervous system including the brain and spinal cord and blood.

The presence of the blood-brain barrier keeps the biochemical homeostasis of most of the cells of the central nervous system without being affected by fluctuations in concentration of substances such as hormones and lymphokines in the blood.

However, the presence of the blood-brain barrier poses a major challenge in drug development. For example, it has been known that brain-derived neurotrophic factor (BDNF) is one of neurotrophin families, and that the dimer thereof specifically binds to a high-affinity BDNF receptor (also referred to as TrkB; Tyrosine receptor kinase B, Tropomyosin receptor kinase B, or Tropomyosine-related Kinase B) on a target cell surface, and plays important roles in differentiation of cells, maintenance of functions, synaptogenesis, and regeneration and repair after damage in central and peripheral nervous systems (Non-Patent Literatures 1 and 2). From these effects, BDNF is expected to be developed as a therapeutic agent for various diseases, for example, neurodegenerative diseases such as Alzheimer's disease, Parkinson's disease, and Huntington's disease, spinal cord degenerative disease such as amyotrophic lateral sclerosis, diabetic neuropathy, cerebral ischemia-related disease, developmental disorder such as Rett syndrome, schizophrenia, and depression (Non-Patent Literatures 3 to 8). However, in general, it is extremely difficult for a high molecular weight protein to pass through the blood-brain barrier. Thus, there has been a great obstacle in use of the BDNF itself by peripheral administration as a therapeutic agent for diseases of the central nervous system or a therapeutic agent for diseases acting on the central nervous system.

Various methods have been developed to make a high molecular weight substance including proteins, which are expected to act on the central nervous system pass through the blood-brain barrier. For example, in a case of nerve growth factor, a method of passing through the blood-brain barrier by fusing liposome encapsulating nerve growth factor with an endothelial cell membrane of a capillary vessel in the brain has been attempted but has yet to come into practical use (Non-Patent Literature 9). In a case of α-L-iduronidase, an attempt to increase the passive transfer of enzyme in the blood-brain barrier has been performed by increasing an amount of the enzyme administered per one time and then the enzyme concentration in blood. In an animal model of Harrer's syndrome, it has been shown that abnormalities in the central nervous system (CNS) is mitigated by using that method (Non-Patent Literature 10).

In addition, an attempt to circumvent the blood-brain barrier and directly administer a high molecular weight substance into a medullary cavity or the brain has also been performed. For example, a method of administering human α-L-iduronidase into a medullary cavity of a patient of Harrer's syndrome (mucopolysaccharide type I) (Patent Literature 1), a method of administering human acid sphingomyelinase into a cerebral ventricle of a patient of Niemann-Pick's disease (Patent Literature 2), and a method of administering iduronate 2-sulfatase (I2S) into a cerebral ventricle of a model animal of Hunter's syndrome (Patent Literature 3) have been reported. According to these techniques, it is considered that it is possible to make a drug reliably act on the central nervous system, but there occurs a problem in that invasiveness becomes extremely high.

As methods of allowing a high molecular weight substance to pass through the blood-brain barrier to reach the brain, various methods of modifying a high molecular weight substance such that this has an affinity with a membrane protein present on an endothelial cell of a capillary vessel in the brain have been reported. Examples of the membrane protein present on an endothelial cell of a capillary vessel in the brain include insulin, transferrin, insulin-like growth factors (IGF-I, IGF-II), LDL, a receptor for a compound such as leptin, and the like.

For example, a technique of synthesizing a nerve growth factor (NGF) in a form of a fusion protein with insulin, and passing the fusion protein through the blood-brain barrier via a bond with an insulin receptor has been reported (Patent Literatures 4 to 6). In addition, a technique of synthesizing a nerve growth factor (NGF) in a form of a fusion protein with an anti-insulin receptor antibody, and passing the fusion protein through the blood-brain barrier via a bond with an insulin receptor has been reported (Patent Literatures 4 and 7).

A technique of synthesizing brain-derived neurotrophic factor (BDNF) in a form of a fusion protein with an anti-insulin receptor antibody, and passing the fusion protein through the blood-brain barrier via a bond with an insulin receptor has been reported (Non-Patent Literature 11). A technique of synthesizing a nerve growth factor (NGF) in a form of a fusion protein with transferrin, and passing the fusion protein through the blood-brain barrier via a bond with a transferrin receptor (TfR) has been reported (Patent Literature 8). In addition, a technique of synthesizing a nerve growth factor (NGF) in a form of a fusion protein with an anti-transferrin receptor antibody (anti-TfR antibody), and passing the fusion protein through the blood-brain barrier via a bond with TfR has been reported (Patent Literatures 4 and 9). In addition, a technique of synthesizing brain-derived neurotrophic factor (BDNF) adducted with polyethylene glycol (PEG) in a form of a conjugate chemically binding to a mouse anti-rat transferrin receptor antibody (anti-TfR antibody) via a streptavidin-biotin linker, and passing the conjugate through the blood-brain barrier via a bond with TfR in the rat has been reported (Non-Patent Literature 12).

Further focusing on the technique using an anti-TfR antibody, it has been reported that in a technique of passing a drug through the blood-brain barrier by conjugating the drug with the anti-TfR antibody, in a case of using streptavidin, a single-chain antibody can be used (Non-Patent Literature 13). In addition, it has been reported that an anti-hTfR antibody (anti-hTfR antibody having a low affinity) having a relatively great dissociation constant with a human TfR (hTfR) can be appropriately used in a technique of passing a drug through the blood-brain barrier (Patent Literatures 10 and 11 and Non-Patent Literature 14). In addition, it has been reported that the anti-TfR antibody of which affinity with hTfR changes pH-dependently can be used as a carrier for passing a drug through the blood-brain barrier (Patent Literature 12 and Non-Patent Literature 15).

CITATION LIST

Patent Literature

[Patent Literature 1] Japanese Unexamined Patent Publication No. 2007-504166
[Patent Literature 2] Japanese Unexamined Patent Publication No. 2009-525963
[Patent Literature 3] Japanese Unexamined Patent Publication No. 2012-62312
[Patent Literature 4] U.S. Pat. No. 5,154,924
[Patent Literature 5] Japanese Unexamined Patent Publication No. 2011-144178
[Patent Literature 6] US Patent No. 2004/0101904
[Patent Literature 7] Japanese Unexamined Patent Publication No. 2006-511516
[Patent Literature 8] Japanese Unexamined Patent Publication No. H06-228199
[Patent Literature 9] U.S. Pat. No. 5,977,307
[Patent Literature 10] WO2012/075037
[Patent Literature 11] WO2013/177062
[Patent Literature 12] WO2012/143379

Non Patent Literature

[Non-Patent Literature 1] Moses V. Chao. Nature Reviews Neuroscience. 4. 299-309 (2003)
[Non-Patent Literature 2] Tabakman R. Progress in Brain Research. 146. 387-401 (2004)
[Non-Patent Literature 3] Bollen E. Behavioural Brain Research. 257C. 8-12 (2013)
[Non-Patent Literature 4] Altar C. Anthony. Journal of Neurochemistry. 63. 1021-32 (1994)
[Non-Patent Literature 5] Zuccato C. Progress in Neurobiology. 81. 294-330 (2007)
[Non-Patent Literature 6] Dafang Wu. The Journal of the American Society for Experimental Neurotherapeutics. 2. 120-8 (2005)
[Non-Patent Literature 7] David M. Katz. The Handbook of Experimental Pharmacology. 220. 481-95 (2014)
[Non-Patent Literature 8] E. Castren. The Handbook of Experimental Pharmacology. 220. 461-79 (2014)
[Non-Patent Literature 9] Xie Y. J Control Release. 105. 106-19 (2005)
[Non-Patent Literature 10] Ou L. Mol Genet Metab. 111. 116-22 (2014)
[Non-Patent Literature 11] Ruben J. B. Biotechnology Bioengineering, 97. 1376-1386 (2007)
[Non-Patent Literature 12] Dafang W. Proc. Natl. Acad. Sci. USA, 96. 254-259 (1999)
[Non-Patent Literature 13] Li J Y Protein Engineering. 12. 787-96 (1999)
[Non-Patent Literature 14] Bien-Ly N. J Exp Med. 211.233-44 (2014)
[Non-Patent Literature 15] Sada H. PLoS ONE. 9. E96340 (2014)

SUMMARY OF INVENTION

Problems to be Solved by the Invention

Under the above background, an object of the present invention is to provide a fusion protein of a new anti-TfR antibody and BDNF capable of passing through a blood-brain barrier such that BDNF administered into blood can act on in the brain, a method for producing thereof, a method of use thereof, and a method of preventing and/or treating a disease within a predetermined range by administering the fusion protein.

Means for Solving the Problems

In studies to achieve the object, as a result of intensive examination, the present inventors found that specific ones included in an anti-human transferrin receptor antibody (anti-hTfR antibody) that recognizes an extracellular region of hTfR obtained by an antibody preparation method described in detail in the present specification, in particular, ones in which a heavy chain CDR1 includes an amino acid sequence of SEQ ID NO: 66 or SEQ ID NO: 67, furthermore, ones in which a heavy chain framework region 3 includes an amino acid sequence of SEQ ID NO: 68 in addition thereto remarkably efficiently pass through the blood-brain barrier when administered in the blood, and also found that those obtained by fusing the antibody with BDNF also pass through the blood-brain barrier, thereby completing the present invention. That is, the present invention provides the following.

1. A fusion protein of brain-derived neurotrophic factor (BDNF) and an anti-human transferrin receptor antibody, wherein in a heavy chain variable region of the antibody, (a) CDR1 includes an amino acid sequence of SEQ ID NO: 66 or SEQ ID NO: 67, (b) CDR2 includes an amino acid sequence of SEQ ID NO: 13 or SEQ ID NO: 14, and (c) CDR3 includes an amino acid sequence of SEQ ID NO: 15 or SEQ ID NO: 16.

2. The fusion protein of 1, wherein a heavy chain framework region 3 includes an amino acid sequence of SEQ ID NO: 68.

3. The fusion protein of 1 or 2, wherein in the heavy chain variable region, instead of the amino acid sequence of SEQ ID NO: 13 or SEQ ID NO: 14 of CDR2, an amino acid sequence having 80% or more homology to the amino acid sequence of SEQ ID NO: 13 or SEQ ID NO: 14 of CDR2 is included, and instead of the amino acid sequence of SEQ ID NO: 15 or SEQ ID NO: 16 of CDR3, an amino acid sequence having 80% or more homology to the amino acid sequence of SEQ ID NO: 15 or SEQ ID NO: 16 of CDR3 is included.

4. The fusion protein of 1 or 2, wherein in the heavy chain variable region, instead of the amino acid sequence of SEQ ID NO: 13 or SEQ ID NO: 14 of CDR2, an amino acid sequence having 90% or more homology to the amino acid sequence of SEQ ID NO: 13 or SEQ ID NO: 14 of CDR2 is included, and instead of the amino acid sequence of SEQ ID NO: 15 or SEQ ID NO: 16 of CDR3, an amino acid sequence having 90% or more homology to the amino acid sequence of SEQ ID NO: 15 or SEQ ID NO: 16 of CDR3 is included.

5. The fusion protein of 1 or 2, wherein in the heavy chain variable region, instead of at least one amino acid sequence of (a) SEQ ID NO: 66 or SEQ ID NO: 67 in CDR1, (b) SEQ ID NO: 13 or SEQ ID NO: 14 in CDR2, (c) SEQ ID NO: 15 or SEQ ID NO: 16 in CDR3, and (d) SEQ ID NO: 68 in the framework region 3, an amino acid sequence obtained by modifying them by substitution, deletion, or addition of 1 to 5 amino acids is included, wherein in CDR1, methionine, which is located at the fifth position from an N-terminal side of the amino acid sequence of SEQ ID NO: 66 or SEQ ID NO: 67, is at the same position in the modified amino acid sequence, and wherein in the framework region 3, leucine, which is located at the 17th position from an N-terminal side of SEQ ID NO: 68, is at the same position in the modified amino acid sequence.

6. The fusion protein of 1 or 2, wherein in the heavy chain variable region, instead of at least one amino acid sequence of (a) SEQ ID NO: 66 or SEQ ID NO: 67 in CDR1, (b) SEQ ID NO: 13 or SEQ ID NO: 14 in CDR2, (c) SEQ ID NO: 15 or SEQ ID NO: 16 in CDR3, and (d) SEQ ID NO: 68 in the framework region 3, an amino acid sequence obtained by modifying them by substitution, deletion, or addition of 1 to 3 amino acids is included, wherein in CDR1, methionine, which is located at the fifth position from an N-terminal side of the amino acid sequence of SEQ ID NO: 66 or SEQ ID NO: 67, is at the same position in the modified amino acid sequence, and wherein in the framework region 3, leucine, which is located at the 17th position from an N-terminal side of SEQ ID NO: 68, is at the same position in the modified amino acid sequence.

7. The fusion protein of 1 or 2, wherein the heavy chain variable region includes an amino acid sequence of SEQ ID NO: 69.

8. The fusion protein of 7, wherein in portions other than each amino acid sequence of SEQ ID NO: 66 or SEQ ID NO: 67 of CDR1 and SEQ ID NO: 68 of the framework region 3 of the heavy chain variable region, instead of the portions thereof, an amino acid sequence having 80% or more homology to the portions thereof is included.

9. The fusion protein of 7, wherein in portions other than each amino acid sequence of SEQ ID NO: 66 or SEQ ID NO: 67 of CDR1 and SEQ ID NO: 68 of the framework region 3 of the heavy chain variable region, instead of the portions thereof, an amino acid sequence having 90% or more homology to the portions thereof is included.

10. The fusion protein of 7, wherein instead of an amino acid sequence constituting the heavy chain variable region, an amino acid sequence obtained by modifying them by substitution, deletion, or addition of 1 to 5 amino acids is included, wherein in CDR1, methionine, which is located at the fifth position from an N-terminus of the amino acid sequence of SEQ ID NO: 67, is at the same position in the modified amino acid sequence, and wherein in the framework region 3, leucine, which is located at the 17th position from an N-terminus side of SEQ ID NO: 68, is at the same position in the modified amino acid sequence.

11. The fusion protein of 7, wherein instead of an amino acid sequence constituting the heavy chain variable region, an amino acid sequence obtained by modifying them by substitution, deletion, or addition of 1 to 3 amino acids is included, wherein in CDR1, methionine, which is located at the fifth position from an N-terminal side of the amino acid sequence of SEQ ID NO: 67, is at the same position in the modified amino acid sequence, and wherein in the framework region 3, leucine, which is located at the 17th position from an N-terminal side of SEQ ID NO: 68, is at the same position in the modified amino acid sequence.

12. The fusion protein of 7, wherein the heavy chain amino acid sequence includes an amino acid sequence of SEQ ID NO: 70 or SEQ ID NO: 72.

13. The fusion protein of 12, wherein instead of portions other than each amino acid sequence of SEQ ID NO: 66 or SEQ ID NO: 67 of CDR1 and SEQ ID NO: 68 of the framework region 3 of the heavy chain, an amino acid sequence having 80% or more homology to the portions thereof is included.

14. The fusion protein of 12, wherein instead of portions other than each amino acid sequence of SEQ ID NO: 66 or SEQ ID NO: 67 of CDR1 and SEQ ID NO: 68 of the framework region 3 of the heavy chain, an amino acid sequence having 90% or more homology to the portions thereof is included.

15. The fusion protein of 12, wherein instead of an amino acid sequence constituting the heavy chain, an amino acid sequence obtained by modifying them by substitution, deletion, or addition of 1 to 5 amino acids is included, wherein in CDR1, methionine, which is located at the fifth position from an N-terminal side of the amino acid sequence of SEQ ID NO: 67, is at the same position in the modified amino acid sequence, and wherein in the framework region 3, leucine, which is located at the 17th position from an N-terminal side of SEQ ID NO: 68, is at the same position in the modified amino acid sequence.

16. The fusion protein of 12, wherein instead of an amino acid sequence constituting the heavy chain, an amino acid sequence obtained by modifying them by substitution, deletion, or addition of 1 to 3 amino acids is included, wherein in CDR1, methionine, which is located at the fifth position from an N-terminal side of the amino acid sequence of SEQ ID NO: 67, is at the same position in the modified amino acid sequence, and wherein in the framework region 3, leucine, which is located at the 17th position from an N-terminal side of SEQ ID NO: 68, is at the same position in the modified amino acid sequence.

17. The fusion protein of any one of 1 to 16, wherein in a light chain variable region of the antibody, (a) CDR1 includes an amino acid sequence of SEQ ID NO: 6 or SEQ ID NO: 7, (b) CDR2 includes an amino acid sequence of SEQ ID NO: 8 or SEQ ID NO: 9, or amino acid sequence Lys-Val-Ser, and (c) CDR3 includes an amino acid sequence of SEQ ID NO: 10.
18. The fusion protein of 17, wherein in the light chain variable region, (a) instead of the amino acid sequence of SEQ ID NO: 6 or SEQ ID NO: 7 of CDR1, an amino acid sequence having 80% or more homology to the amino acid sequence of SEQ ID NO: 6 or SEQ ID NO: 7 of CDR1 is included, (b) instead of the amino acid sequence of SEQ ID NO: 8 or SEQ ID NO: 9, or amino acid sequence Lys-Val-Ser of CDR2, an amino acid sequence having 80% or more homology to the amino acid sequence of SEQ ID NO: 8 or SEQ ID NO: 9, or amino acid sequence Lys-Val-Ser of CDR2 is included, and (c) instead of the amino acid sequence of SEQ ID NO: 10 of CDR3, an amino acid sequence having 80% or more homology to the amino acid sequence of SEQ ID NO: 10 of CDR3 is included.
19. The fusion protein of 17, wherein in the light chain variable region, (a) instead of the amino acid sequence of SEQ ID NO: 6 or SEQ ID NO: 7 of CDR1, an amino acid sequence having 90% or more homology to the amino acid sequence of SEQ ID NO: 6 or SEQ ID NO: 7 of CDR1 is included, (b) instead of the amino acid sequence of SEQ ID NO: 8 or SEQ ID NO: 9, or the amino acid sequence Lys-Val-Ser of CDR2, an amino acid sequence having 90% or more homology to the amino acid sequence of SEQ ID NO: 8 or SEQ ID NO: 9, or the amino acid sequence Lys-Val-Ser of CDR2 is included, and (c) instead of the amino acid sequence of SEQ ID NO: 10 of CDR3, an amino acid sequence having 90% or more homology to the amino acid sequence of SEQ ID NO: 10 of CDR3 is included.
20. The fusion protein of 17, wherein in the light chain variable region, instead of at least one amino acid sequence of (a) SEQ ID NO: 6 or SEQ ID NO: 7 in CDR1, (b) SEQ ID NO: 8 or SEQ ID NO: 9, or the amino acid sequence Lys-Val-Ser in CDR2, and (c) SEQ ID NO: 10 in CDR3, an amino acid sequence obtained by modifying them by substitution, deletion, or addition of 1 to 5 amino acids is included.
21. The fusion protein of 17, wherein in the light chain variable region, instead of at least one amino acid sequence of (a) SEQ ID NO: 6 or SEQ ID NO: 7 in CDR1, (b) SEQ ID NO: 8 or SEQ ID NO: 9, or the amino acid sequence Lys-Val-Ser in CDR2, and (c) SEQ ID NO: 10 in CDR3, an amino acid sequence obtained by modifying them by substitution, deletion, or addition of 1 to 3 amino acids is included.
22. The fusion protein of any one of 1 to 16, wherein the light chain variable region of the antibody includes an amino acid sequence of SEQ ID NO: 17, SEQ ID NO: 18, SEQ ID NO: 19, SEQ ID NO: 20, SEQ ID NO: 21, or SEQ ID NO: 22.
23. The fusion protein of 22, wherein instead of the amino acid sequence of the light chain variable region, an amino acid sequence having 80% or more homology to the amino acid sequence of the light chain variable region is included.
24. The fusion protein of 22, wherein instead of the amino acid sequence of the light chain variable region, an amino acid sequence having 90% or more homology to the amino acid sequence of the light chain variable region is included.
25. The fusion protein of 22, wherein instead of the amino acid sequence of the light chain variable region, an amino acid sequence obtained by modifying them by substitution, deletion, or addition of 1 to 5 amino acids is included.
26. The fusion protein of 22, wherein instead of the amino acid sequence of the light chain variable region, an amino acid sequence obtained by modifying them by substitution, deletion, or addition of 1 to 3 amino acids is included.
27. The fusion protein of any one of 1 to 16, wherein the light chain of the antibody includes an amino acid sequence of SEQ ID NO: 23, SEQ ID NO: 25, SEQ ID NO: 27, or SEQ ID NO: 29.
28. The fusion protein of 27, wherein instead of the amino acid sequence of the light chain, an amino acid sequence having 80% or more homology to the amino acid sequence of the light chain is included.
29. The fusion protein of 27, wherein instead of the amino acid sequence of the light chain, an amino acid sequence having 90% or more homology to the amino acid sequence of the light chain is included.
30. The fusion protein of 27, wherein instead of the amino acid sequence of the light chain, an amino acid sequence obtained by modifying them by substitution, deletion, or addition of 1 to 5 amino acids is included.
31. The fusion protein of 27, wherein instead of the amino acid sequence of the light chain, an amino acid sequence obtained by modifying them by substitution, deletion, or addition of 1 to 3 amino acids is included.
32. The fusion protein of any one of 1 to 31, wherein the antibody is a Fab antibody, a F(ab')2 antibody, or a F(ab') antibody.
33. The fusion protein of any one of 1 to 31, wherein the antibody is a single-chain antibody selected from the group consisting of scFab, scF(ab'), scF(ab')2, and scFv.
34. The fusion protein of 33, wherein the light chain and the heavy chain of the antibody bind to each other via a linker sequence.
35. The fusion protein of 34, wherein the heavy chain binds to a C-terminal side of the light chain via a linker sequence.
36. The fusion protein of 34, wherein the light chain binds to a C-terminal side of the heavy chain via a linker sequence.
37. The fusion protein of any one of 34 to 36, wherein the linker sequence is formed of 8 to 50 amino acid residues.
38. The fusion protein of 37, wherein the linker sequence is selected from the group consisting of amino acid sequence Gly-Ser, amino acid sequence Gly-Gly-Ser, amino acid sequence Gly-Gly-Gly, each amino acid sequence of SEQ ID NO: 3, SEQ ID NO: 4, and SEQ ID NO: 5, an amino acid sequence corresponding to three consecutive amino acid sequences of SEQ ID NO: 3, and a sequence of 10 or less consecutive amino acid sequences thereof.
39. The fusion protein of any one of 1 to 38, wherein the BDNF binds to the C-terminal side or the N-terminal side of the light chain or the heavy chain of the antibody.

40. The fusion protein of 39, wherein the BDNF binds to the C-terminal side or the N-terminal side of the light chain or the heavy chain of the antibody directly or via a linker.
41. The fusion protein of 40, wherein the linker is a peptide including 1 to 50 amino acid residues.
42. The fusion protein of 41, wherein the linker is a peptide including an amino acid sequence selected from the group consisting of an amino acid sequence Gly-Ser, an amino acid sequence Gly-Gly-Ser, an amino acid sequence of SEQ ID NO: 3, an amino acid sequence of SEQ ID NO: 4, and an amino acid sequence of SEQ ID NO: 5.
43. The fusion protein of any one of 1 to 42, wherein the BDNF is human BDNF.
44. The fusion protein of 43, wherein the human BDNF includes an amino acid sequence of SEQ ID NO: 51 or an amino acid sequence substantially identical to the amino acid sequence of SEQ ID NO: 51, or the human BDNF has a function equivalent to that of the protein represented by SEQ ID NO: 51.
45. The fusion protein of any one of 1 to 44, wherein the fusion protein having affinity to both of an extracellular region of a human transferrin receptor and an extracellular region of a monkey transferrin receptor.
46. The fusion protein of 45, wherein a dissociation constant of the anti-human transferrin receptor antibody with the extracellular region of the human transferrin receptor is equal to or less than $1\times10^{-10}$ M, and a dissociation constant of the anti-human transferrin receptor antibody with the extracellular region of the monkey transferrin receptor is equal to or less than $1\times10^{-9}$ M.
47. The fusion protein of 43, wherein the light chain includes an amino acid sequence of SEQ ID NO: 23, and wherein (a) the heavy chain binds to human BDNF via a linker consisting of amino acid sequence Gly-Ser on the C-terminal side and thereby forms an amino acid sequence of SEQ ID NO: 52, or (b) the heavy chain binds to human BDNF via a linker consisting of a total of 27 amino acids formed of five consecutive amino acid sequences Gly-Gly-Gly-Gly-Ser (SEQ ID NO: 3) subsequent to the amino acid sequence Gly-Ser on the C-terminal side and thereby forms an amino acid sequence of SEQ ID NO: 54.

48. The fusion protein of any one of 1 to 31, wherein the antibody is an antigen-binding fragment.
49. The fusion protein of 48, wherein human BDNF binds to the N-terminal side of the antigen-binding fragment directly or via a linker.
50. The fusion protein of 48 or 49, wherein the antigen-binding fragment is a single-chain antibody.
51. The fusion protein of 50, wherein the light chain variable region and the heavy chain variable region of the antibody bind to each other via a linker sequence.
52. The fusion protein of 51, wherein the heavy chain variable region binds to the C-terminal side of the light chain variable region via the linker sequence.
53. The fusion protein of 51, wherein the light chain variable region binds to the C-terminal side of the heavy chain variable region via the linker sequence.
54. The fusion protein of any one of 51 to 53, wherein the linker sequence includes 8 to 50 amino acid residues.
55. The fusion protein of 54, wherein the linker sequence is selected from the group consisting of amino acid sequence Gly-Ser, amino acid sequence Gly-Gly-Ser, amino acid sequence Gly-Gly-Gly, each amino acid sequence of SEQ ID NO: 3, SEQ ID NO: 4, and SEQ ID NO: 5, an amino acid sequence corresponding to three consecutive amino acid sequences of SEQ ID NO: 3, and a sequence of 10 or less consecutive amino acid sequences thereof.
56. The fusion protein of any one of 50 to 55, wherein the antibody includes a heavy chain variable region having an amino acid sequence of SEQ ID NO: 69 and a light chain variable region having an amino acid sequence of SEQ ID NO: 18.
57. The fusion protein of 56, wherein the antibody is formed of an amino acid sequence of SEQ ID NO: 57, and human BDNF binds to the N-terminal side of the antibody directly or via a linker.
58. The fusion protein of 57, wherein the antibody is formed of an amino acid sequence of SEQ ID NO: 57, human pro-BDNF binds to the N-terminal side of the antibody via a linker, and the fusion protein includes an amino acid sequence of SEQ ID NO: 59.
59. The fusion protein of 57, wherein the antibody is formed of an amino acid sequence of SEQ ID NO: 57, human BDNF binds to the N-terminal side of the antibody via a linker, and the fusion protein includes an amino acid sequence of SEQ ID NO: 60.
60. The fusion protein of 48 or 49, wherein the antigen-binding fragment is any one of Fab, F(ab')2, or F(ab').
61. The fusion protein of 60, wherein human BDNF binds to the N-terminal side of a light chain or a heavy chain of any one of Fab, F(ab')2, or F(ab') directly or via a linker.
62. The fusion protein of 61, wherein the light chain of the antibody is formed of an amino acid sequence of SEQ ID NO: 23, the heavy chain of the antibody is a Fab heavy chain formed of an amino acid sequence of SEQ ID NO: 61, and human BDNF binds to the N-terminal side of the heavy chain directly or via a linker.
63. The fusion protein of 62, wherein the linker is a peptide including an amino acid sequence selected from the group consisting of an amino acid sequence Gly-Ser, an amino acid sequence Gly-Gly-Ser, an amino acid sequence of SEQ ID NO: 3, an amino acid sequence of SEQ ID NO: 4, and an amino acid sequence of SEQ ID NO: 5.
64. The fusion protein of 62, wherein the light chain includes an amino acid sequence of SEQ ID NO: 23, and wherein a portion including the Fab heavy chain and human pro-BDNF binding to the N-terminal side of the Fab heavy chain via a linker forms an amino acid sequence of SEQ ID NO: 63.

65. The fusion protein of 62, wherein the light chain includes an amino acid sequence of SEQ ID NO: 23, and wherein a portion including the Fab heavy chain and human BDNF binding to the N-terminal side of the Fab heavy chain via a linker forms an amino acid sequence of SEQ ID NO: 65.

66. The fusion protein of any one of 48 to 62, wherein a human IgG Fc region or a part thereof is introduced between the human BDNF and the antibody.
67. The fusion protein of 66, wherein the human IgG Fc region binds to the C-terminal side of the human BDNF directly or via a linker sequence, and the antibody binds to the C-terminal side of the human IgG Fc region directly or via a linker sequence.

68. The fusion protein of 66 or 67, wherein the human IgG Fc region includes an amino acid sequence represented by SEQ ID NO: 75.
69. The fusion protein of 68, wherein the heavy chain is obtained by binding the human IgG Fc region to the C-terminal side of the human BDNF directly or via a linker sequence, and the heavy chain binds to the C-terminal side of the human IgG Fc region directly or via a linker sequence.
70. The fusion protein of 69, wherein the light chain includes an amino acid sequence of SEQ ID NO: 23, and wherein the heavy chain is obtained by binding the human IgG Fc region to the C-terminal side of the human BDNF via a linker sequence, and the heavy chain binds to the C-terminal side of the human IgG Fc region via a linker sequence and thereby forms an amino acid sequence of SEQ ID NO: 74.
71. The fusion protein of any one of 48 to 62, wherein an albumin-affinity peptide is further introduced.
72. The fusion protein of 71, wherein the albumin-affinity peptide binds to the C-terminal side of the antibody directly or via a linker sequence.
73. The fusion protein of 71 or 72, wherein the albumin-affinity peptide includes an amino acid sequence represented by SEQ ID NO: 85.
74. The fusion protein of 73, wherein the heavy chain binds to the C-terminal side of human BDNF directly or via a linker sequence, and the albumin-affinity peptide binds to the C-terminal side of the heavy chain directly or via a linker sequence.
75. The fusion protein of 74, wherein the light chain includes an amino acid sequence of SEQ ID NO: 23, and wherein the heavy chain binds to the C-terminal side of human pro-BDNF via a linker sequence, and the albumin-affinity peptide binds to the C-terminal side of the heavy chain via a linker sequence and thereby forms an amino acid sequence of SEQ ID NO: 87.
76. The fusion protein of 74, wherein the light chain includes an amino acid sequence of SEQ ID NO: 23, and wherein the heavy chain binds to the C-terminal side of human BDNF via a linker sequence, and the albumin-affinity peptide binds to the C-terminal side of the heavy chain via a linker sequence and thereby forms an amino acid sequence of SEQ ID NO: 88.
77. A DNA fragment encoding the fusion protein of any one of 1 to 76.
78. An expression vector obtained by inserting the DNA fragment of 77.
79. A mammalian cell transformed by the expression vector of 78.
80. A pharmaceutical agent for preventing and/or treating a disease or a disorder that obtains benefits by exposure to BDNF, wherein the pharmaceutical agent comprises the fusion protein of any one of 1 to 76 as an active ingredient.
81. The pharmaceutical agent of 80, wherein the disease or the disorder is a nervous system disease or a nervous system disorder.
82. The pharmaceutical agent of 81, wherein the nervous system disease or the nervous system disorder is neurodegenerative disease, depression, schizophrenia, epilepsy, autism, Rett syndrome, West syndrome, neonatal spasm, problematic behaviors associated with dementia, anxiety, pain, Hirschsprung's disease, or REM sleep behavioral disorder.
83. The pharmaceutical agent of 82, wherein the neurodegenerative disease is cerebral neurodegenerative disease, spinal cord degenerative disease, retinal degenerative disease, or peripheral neurodegenerative disease.
84. The pharmaceutical agent of 83, wherein the cerebral neurodegenerative disease is neurodegenerative disease of a cerebral nervous system, cerebral ischemic disease, traumatic brain injury, leukoencephalopathy, or multiple sclerosis.
85. The pharmaceutical agent of 84, wherein the neurodegenerative disease of the cerebral nervous system is Alzheimer's disease, Parkinson's disease, Huntington's disease, dementia with Lewy bodies, Pick's disease, multiple system atrophy, progressive ascending paralysis, or Down syndrome.
86. Use of the fusion protein of any one of 1 to 76 for preventing and/or treating a disease or a disorder that obtains benefits by exposure to BDNF.
87. Use of the fusion protein of any one of 1 to 76 for producing a pharmaceutical agent for preventing and/or treating a disease or a disorder that can obtain benefits by exposure to BDNF.
88. A method of preventing and/or treating a disease or a disorder that obtains benefits by exposure to BDNF, the method comprising:

administering a pharmaceutical composition containing a therapeutically effective amount of the fusion protein of any one of 1 to 76 to blood of a patient having the disease or the disorder.

Effects of the Invention

The present invention enables brain-derived neurotrophic factor (BDNF) that cannot pass through the blood-brain barrier, by comprising it in a form of a fusion protein with a specific anti-hTfR antibody, to pass through the blood-brain barrier. Therefore, by administering BDNF to blood in the form of such a fusion protein with an intravenous injection and the like, it becomes possible for BDNF to act on the central nervous system.

EMBODIMENTS FOR CARRYING OUT THE INVENTION

Figure 1:
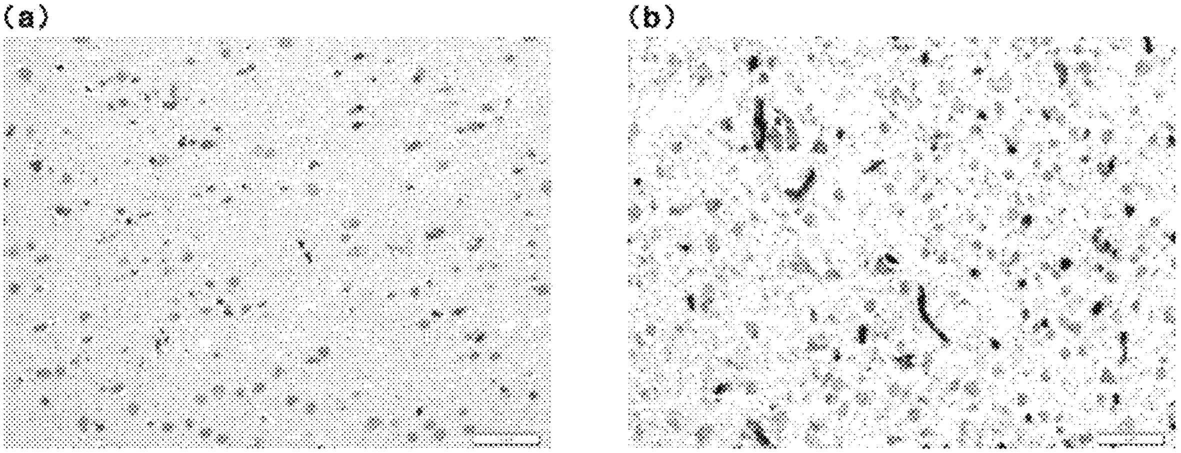
FIG. 1 A figure showing the result of immunohistochemical staining with an anti-hTfR antibody of a cerebral cortex of a cynomolgus monkey after single intravenous administration of the anti-hTfR antibody. (a) Non-administration of the anti-hTfR antibody, and (b) administration of an anti-hTfR antibody No. 3. The bar on the right bottom of each photograph is a gauge indicating 50 μm.

In the present invention, the term "antibody" is mainly any one of a human antibody, a mouse antibody, a humanized antibody, as well as a chimeric antibody between a human antibody and a non-human mammalian antibody, and a chimeric antibody between a mouse antibody and other mammalian antibody, and is not limited to them insofar as substance of interest has property to specifically bind to a certain antigen, there is no specific limitation as to the animal species of an antibody. However, the antibody is preferably a humanized antibody.

In the present invention, the term "human antibody" refers to an antibody in which the entire protein is encoded by a human-derived gene. However, for the purpose of increasing expression efficiency of a gene and the like, an antibody encoded by a gene obtained by adding mutation to an original human gene without changing an original amino acid sequence is also included in the "human antibody". In addition, an antibody produced by combining two or more genes encoding a human antibody and replacing a part of a human antibody with a part of another human antibody is also the "human antibody". The human antibody includes three complementary determining regions (CDR) of an immunoglobulin light chain and three complementary determining regions (CDR) of an immunoglobulin heavy chain. The three CDRs of the immunoglobulin light chain are on the N-terminal side, and thus are called CDR1, CDR2, and CDR3 in order. The three CDRs of the immunoglobulin heavy chain are also on the N-terminal side, and thus are called CDR1, CDR2, and CDR3 in order. An antibody obtained by modifying antigen specificity, affinity, and the like of the human antibody by replacing CDR of a human antibody with CDR of another human antibody is also included in the human antibody.

In the present invention, an antibody obtained by adding mutation such as substitution, deletion, and addition to an amino acid sequence of an original antibody by modifying a gene of an original human antibody is also included in the "human antibody". In a case of substituting an amino acid in the amino acid sequence of the original antibody with another amino acid, the number of the substituted amino acids is preferably 1 to 20, more preferably 1 to 5, and further more preferably 1 to 3. In a case of deleting an amino acid in the amino acid sequence of the original antibody, the number of the deleted amino acids is preferably 1 to 20, more preferably 1 to 5, and further more preferably 1 to 3. In addition, an antibody obtained by adding mutation by combining substitution and deletion of the amino acid is also the human antibody. In a case of adding an amino acid, preferably 1 to 20, more preferably 1 to 5, and further more preferably 1 to 3 amino acids are added to the amino acid sequence, or the N-terminus or the C-terminus of the original antibody. The antibody obtained by adding mutation by combining addition, substitution, and deletion of the amino acids is also the human antibody. An amino acid sequence of such a mutated antibody shows preferably 80% or more homology, more preferably 90% or more homology, further more preferably 95% or more homology, and even further more preferably 98% or more homology to the amino acid sequence of the original antibody. That is, in the present invention, when a "human-derived gene" is referred to, not only an original human-derived gene but also a gene obtained by adding mutation thereto is included in the human-derived gene.

In the present invention, the term "mouse antibody" refers to the mouse antibody in which the entire protein is encoded by a mouse-derived gene. However, the term "mouse antibody" also includes an antibody that is encoded by a gene produced by introducing a mutation into the original mouse gene without causing a change in its amino acid sequence but in order, for example, to improve the expression efficiency of the gene. In addition, an antibody obtained by combining two or more genes encoding a mouse antibody and replacing a part of a mouse antibody with a part of another mouse antibody is also the "mouse antibody". The mouse antibody includes three complementary determining regions (CDR) of an immunoglobulin light chain and three complementary determining regions (CDR) of an immunoglobulin heavy chain. The three CDRs of the immunoglobulin light chain are on the N-terminal side, and thus are called CDR1, CDR2, and CDR3 in order. The three CDRs of the immunoglobulin heavy chain are also on the N-terminal side, and thus are called CDR1, CDR2, and CDR3 in order. For example, an antibody obtained by modifying antigen specificity, affinity, and the like of the mouse antibody by replacing CDR of a mouse antibody with CDR of another mouse antibody is also included in the mouse antibody.

In the present invention, an antibody obtained by adding mutation such as substitution, deletion, and addition to an amino acid sequence of an original antibody by modifying a gene of an original mouse antibody is also included in the "mouse antibody". In a case substituting an amino acid in the amino acid sequence of the original antibody with another amino acid, the number of the substituted amino acids is preferably 1 to 20, more preferably 1 to 5, and further more preferably 1 to 3. In a case of deleting an amino acid in the amino acid sequence of the original antibody, the number of the deleted amino acids is preferably 1 to 20, more preferably 1 to 5, and further more preferably 1 to 3. In addition, an antibody obtained by adding mutation by combining substitution and deletion of the amino acid is also included in the "mouse antibody". In a case of adding an amino acid, preferably 1 to 20, more preferably 1 to 5, and further more preferably 1 to 3 amino acids are added to the amino acid sequence, or the N-terminus or the C-terminus of the original antibody. The antibody obtained by adding mutation by combining addition, substitution, and deletion of the amino acids is also included in the "mouse antibody". An amino acid sequence such a mutated shows preferably 80% or more homology, more preferably 90% or more homology, further more preferably 95% or more homology, and even further more preferably 98% or more homology to the amino acid sequence of the original antibody. That is, in the present invention, when a "mouse-derived gene" is referred to, not only an original mouse-derived gene but also a gene obtained by adding thereto is included in the "mouse-derived gene".

In the present invention, the term "humanized antibody" refers to an antibody in which an amino acid sequence of a part of the variable region (for example, particularly all or part of CDR) is derived from a non-human mammal while the rest originates from human. Examples of the humanized antibody include an antibody produced by substituting the three complementary determining regions (CDR) of the immunoglobulin light chain and the three complementary determining regions (CDR) of the immunoglobulin heavy chain constituting a human antibody with CDRs of another mammalian animal. The species of other mammalian animals from which CDRs transplanted at an appropriate position of the human antibody originate is not particularly limited as long as the species is a mammalian animal other than human. However, the species is preferably a mouse, a rat, a hare, a horse, or primates other than human, more preferably a mouse and a rat, and further more preferably a mouse.

In the present invention, the term "chimeric antibody" refers to an antibody obtained by linking two or more different antibody fragments, derived from two or more different species.

The chimeric antibody between a human antibody and an antibody of a non-human mammal refers to an antibody obtained by substituting a part of the human antibody with a part of the antibody of a mammal other than human. The antibody includes an Fc region, a Fab region, and a hinge region to be described later. Specific examples of such a chimeric antibody include a chimeric antibody in which an Fc region is derived from a human antibody whereas a Fab region is derived from an antibody of another mammalian animal. The hinge region is derived from any one of a human antibody or an antibody of another mammalian animal. On the contrary, the chimeric antibody includes a chimeric antibody in which an Fc region is derived from other mammalian animals whereas a Fab region is derived from a human antibody. The hinge region is derived from any one of a human antibody or an antibody of another mammalian animal.

In addition, an antibody may include a variable region and a constant region. Other examples of the chimeric antibody include a chimeric antibody in which a constant region of a heavy chain ($C_H$) and a constant region of a light chain ($C_L$) are derived from a human antibody while a variable region of a heavy chain ($V_H$) and a variable region of a light chain ($V_L$) are derived from an antibody of another mammalian antibody, and on the contrary, a chimeric antibody in which a constant region of a heavy chain ($C_H$) and a constant region of a light chain ($C_L$) are derived from an antibody of another mammalian animal, whereas a variable region of a heavy chain ($V_H$) and a variable region of a light chain ($V_L$) are derived from a human antibody. Here, species of other mammalian animals is not particularly limited as long as the species is a mammalian animal other than human. However, the species is preferably a mouse, a rat, a hare, a horse, or primates other than human, for example, a mouse.

A chimeric antibody between a mouse antibody and another mammalian animal is an antibody obtained by substituting a part of a mouse antibody with a part of an antibody of a mammalian animal other than mouse. Specific examples of such a chimeric antibody include a chimeric antibody in which an Fc region is derived from a mouse antibody, whereas a Fab region is derived from an antibody of another mammalian animal, or, on the contrary, a chimeric antibody in which an Fc region is derived from another mammalian animal, whereas a Fab region is derived from a mouse antibody. Here, species of another mammalian animal is preferably a human.

The chimeric antibody between a human antibody and a mouse antibody particularly refers to a "human/mouse chimeric antibody". Examples of the human/mouse chimeric antibody include a chimeric antibody in which an Fc region is derived from a human antibody, whereas a Fab region is derived from a mouse antibody, or, on the contrary, a chimeric antibody in which an Fc region is derived from a mouse antibody, whereas a Fab region is derived from a human antibody. The hinge region is derived from any one of a human antibody or a mouse antibody. Other specific examples of the human/mouse chimeric antibody include a chimeric antibody in which a constant region of a heavy chain ($C_H$) and a constant region of a light chain ($C_L$) are derived from a human antibody, whereas a variable region of a heavy chain ($V_H$) and a variable region of a light chain ($V_L$) are derived from a mouse antibody, and on the contrary, a chimeric antibody in which a constant region of a heavy chain ($C_H$) and a constant region of a light chain ($C_L$) are derived from a mouse antibody, whereas a variable region of a heavy chain ($V_H$) and a variable region of a light chain ($V_L$) are derived from a human antibody.

An antibody originally has a basic structure including four polypeptide chains of two immunoglobulin light chains and two immunoglobulin heavy chains. Here, in the present invention, when the term "antibody" is used, it includes, in addition to the antibody having the basic structure, (1) an antibody including two polypeptide chains of one immunoglobulin light chain and one immunoglobulin heavy chain, or, as described as follows, (2) a single-chain antibody obtained by combining a linker sequence to a C-terminal side of an immunoglobulin light chain and further combining an immunoglobulin heavy chain to the C-terminal side, (3) a single-chain antibody obtained by bonding a linker sequence to a C-terminal side of an immunoglobulin heavy chain and further bonding an immunoglobulin light chain to the C-terminal side, and (4) an antibody formed of a Fab region which is an antibody in which an Fc region is deleted from the basic structure of an antibody of the original meaning and an antibody formed of all or part of a Fab region and a hinge region (including Fab, F(ab'), and $F(ab')_2$).

Here, Fab is a molecule in which a light chain including a variable region and a $C_L$ region (constant region of light chain) and a heavy chain including a variable region and a $C_H1$ region (part 1 of constant region of heavy chain) are combined by a disulfide bond between their respective cysteine residues. In Fab, the heavy chain may further include a part of the hinge region in addition to the variable region and the $C_H1$ region (part 1 of constant region of heavy chain), but the hinge region in this case is lack of the cysteine residue that is present in the hinge region and binds the heavy chain of the antibody. In Fab, the light chain and the heavy chain bind by a disulfide bond formed between a cysteine residue present in the constant region of the light chain ($C_L$ region) and a cysteine residue present in the $C_H1$ region or the hinge region of the heavy chain. The heavy chain forming Fab is referred to as "Fab heavy chain" in the present specification. Fab is lack of a cysteine residue that is present in the hinge region and binds the heavy chain of the antibody, and is formed of one light chain and one heavy chain. In F(ab'), the heavy chain includes all or a part of the hinge region including a cysteine residue binding the heavy chain in addition to the variable region and the $C_H1$ region. $F(ab')_2$ is a molecule in which two F(ab')s bind by a disulfide bond between cysteine residues respectively present in the hinge region. The heavy chain forming F(ab') or $F(ab')_2$ is referred to as "Fab' heavy chain" in the present specification. In addition, a polymer such as dimer and trimer, in which a plurality of antibodies binds to one another directly or via a linker, is also an antibody. In addition, without being limited thereto, any one including a part of an immunoglobulin molecule and having properties of specifically binding to an antigen is included in the "antibody" in the present invention. That is, in the present invention, when an immunoglobulin light chain is referred to, the immunoglobulin light chain includes one that is derived from an immunoglobulin light chain and has an amino acid sequence of all or a part of the variable region. In addition, when an immunoglobulin heavy chain is referred to, the immunoglobulin heavy chain includes one that is derived from an immunoglobulin heavy chain and has an amino acid sequence of all or a part of the variable region. Therefore, as long as the one has an amino acid sequence of all or a part of the variable region, even if an Fc region is deleted, the one is an immunoglobulin heavy chain.

In addition, here, the Fc or Fc region is a region including a fragment formed of a $C_H2$ region (part 2 of constant region of heavy chain) and a $C_H3$ region (part 3 of constant region of heavy chain) in an antibody molecule. The Fc or Fc region may include a part of a hinge region in addition to the $C_H2$ region and the $C_H3$ region.

In addition, in the present invention, when an "antibody" is referred to, (5) scFab, scF(ab'), and $scF(ab')_2$ obtained by binding a light chain and a heavy chain constituting Fab, F(ab'), and $F(ab')_2$ shown in the above (4) via a linker sequence to make a single-chain antibody, respectively, are also included in the antibody. Here, in scFab, scF(ab'), and $scF(ab')_2$, a linker sequence may bind to a C-terminal side of the light chain, and the heavy chain may further bind to the C-terminal side thereof, or a linker sequence may bind to a C-terminal side of the heavy chain, and the light chain may further bind to the C-terminal side thereof. In addition, scFv obtained by binding a variable region of the light chain and a variable region of the heavy chain via a linker sequence to make a single-chain antibody is also included in the antibody in the present invention. In scFv, a linker sequence may bind to a C-terminal side of the variable region of the light chain and the variable region of the heavy chain may bind to the C-terminal side thereof, or a linker sequence may bind to the C-terminal side of the variable region of the heavy chain and the variable region of the light chain may further bind to the C-terminal side thereof.

In addition, the "antibody" in the present specification also includes any form of an antigen-binding fragment (antibody fragment) in which a part of a full-length antibody, which is a concept including the above (4) and (5), is deleted, in addition to a full-length antibody and the ones shown in the above (1) to (3).

The term "antigen-binding fragment" refers to a fragment of an antibody maintaining at least a part of specific binding activity with an antigen. In addition to those shown in (4) and (5), examples of the binding fragment include variable region (Fv), single-chain antibody (scFv) obtained by linking a heavy chain variable region ($V_H$) and a light chain variable region ($V_L$) via an appropriate linker, diabody which is a dimer of polypeptide including the heavy chain variable region ($V_H$) and the light chain variable region ($V_L$), minibody which is a dimer obtained by binding a part of a constant region ($C_H3$) to the heavy chain (H chain) of scFv, other low-molecular-weight antibody, and the like. However, the binding fragment is not limited to the molecules as long as the binding fragment has a binding ability to an antigen. In addition, the binding fragment includes not only that obtained by treating a full-length molecule of an antibody protein with an appropriate enzyme but also includes that produced in an appropriate host cell using a genetically engineered antibody gene.

In the present invention, when a "single-chain antibody" is referred to, the single-chain antibody refers to a protein which is obtained by binding a linker sequence to a C-terminal side of an amino acid sequence including all or a part of a variable region of an immunoglobulin light chain and further binding an amino acid sequence including all or a part of a variable region of an immunoglobulin heavy chain to the C-terminal side thereof, and is capable of specifically binding to a specific antigen. For example, those shown in the above (2), (3), and (5) are included in the single-chain antibody. In addition, a protein which is obtained by binding a linker sequence to a C-terminal side of an amino acid sequence including all or a part of a variable region of an immunoglobulin heavy chain and further binding an amino acid sequence including all or a part of a variable region of an immunoglobulin light chain to the C-terminal side thereof, and is capable of specifically binding to a specific antigen is also the "single-chain antibody" in the present invention. In a single-chain antibody obtained by binding an immunoglobulin light chain to a C-terminal side of an immunoglobulin heavy chain via a linker sequence, in general, the immunoglobulin heavy chain is lack of an Fc region. The variable region of the immunoglobulin light chain has three complementary determining regions (CDR) contributing to antigen specificity of an antibody. Similarly, the variable region of the immunoglobulin light chain also has three CDRs. These CDRs are the main regions determining antigen specificity of an antibody. Therefore, the single-chain antibody preferably contains all of three CDRs of the immunoglobulin heavy chain and all of three CDRs of the immunoglobulin light chain. Here, as long as antigen specific affinity of the antibody is maintained, a single-chain antibody in which one or a plurality of CDRs are deleted is also possible to be made.

In the single-chain antibody, a linker sequence disposed between the light chain and the heavy chain of the immunoglobulin is a peptide chain formed of preferably 2 to 50, more preferably 8 to 50, further more preferably 10 to 30, and even further more preferably 12 to 18 or 15 to 25, for example, 15 or 25 amino acid residues. There is no particular limitation as to the amino acid sequence of such a linker sequence as long as an anti-hTfR antibody in which both chains are linked by the linker sequence maintains affinity to hTfR, but the linker sequence is preferably formed of only glycine or glycine and serine. Examples of the linker sequence include amino acid sequence Gly-Ser, amino acid sequence Gly-Gly-Ser, amino acid sequence Gly-Gly-Gly, amino acid sequence Gly-Gly-Gly-Gly-Ser (SEQ ID NO: 3), amino acid sequence Gly-Gly-Gly-Gly-Gly-Ser (SEQ ID NO: 4), amino acid sequence Ser-Gly-Gly-Gly-Gly (SEQ ID NO: 5), or those including a sequence corresponding to 2 to 10 or 2 to 5 of the consecutive amino acid sequences. For example, in a case where a variable region of an immunoglobulin light chain binds to a C-terminal side of an amino acid sequence formed of the entire region of a variable region of an immunoglobulin heavy chain via a linker sequence, a linker sequence formed of a total of 15 amino acids corresponding to three consecutive amino acid sequences Gly-Gly-Gly-Gly-Ser (SEQ ID NO: 3) is preferable.

In the present invention, the term "human transferrin receptor" or "hTfR" is a membrane protein having an amino acid sequence of SEQ ID NO: 1. In an embodiment of the present invention, an anti-hTfR antibody to be fused with BDNF specifically binds to a portion from a cysteine residue at the $89^{th}$ position from an N-terminus to phenylalanine of a C-terminus (extracellular region of hTfR) in the amino acid sequence of SEQ ID NO: 1, but is not limited thereto. In addition, the word "monkey transferrin receptor" or "monkey TfR" is particularly a membrane protein having an amino acid sequence of SEQ ID NO: 2 derived from cynomolgus monkey (*Macaca fascicularis*). The anti-hTfR antibody of the present invention is an anti-hTfR antibody that also binds to a portion from a cysteine residue at the $89^{th}$ position from an N-terminus to phenylalanine of a C-terminus (extracellular region of hTfR) in an amino acid sequence of SEQ ID NO: 2, in an embodiment, but is not limited thereto.

As a production method of an antibody to hTfR, a method of producing a recombinant human transferrin receptor (rhTfR) using a cell to which an expression vector obtained by inserting an hTfR gene is introduced and immunizing an animal such as mouse using the rhTfR to obtain an antibody is general. By extracting an antibody production cell to hTfR from an immunized animal and fusing the cell with a myeloma cell, it is possible to produce a hybridoma cell having an anti-hTfR antibody producing ability.

In addition, also by immunizing an immune cell obtained from an animal such as mouse with rhTfR by in vitro immunization method, it is possible to obtain a cell producing an antibody to hTfR. In a case of using in vitro immunization method, species of the animal from which the immune cell is derived is not particularly limited, but the species of the animal is preferably mouse, rat, rabbit, guinea pig, dog, cat, horse, and primates including human, more preferably mouse, rat, and human, and further more preferably mouse and human. As an immune cell of mouse, for example, a splenic cell prepared from spleen of mouse can be used. As an immune cell of human, a cell prepared from peripheral blood, bone marrow, and spleen of human can be used. In a case of immunizing an immune cell of human by in vitro immunization method, it is possible to obtain a human antibody to hTfR.

By fused cells with a myeloma cell after immunizing an immune cell by in vitro immunization method, it is possible to produce a hybridoma cell having an antibody producing ability. In addition, by extracting mRNA from an immunized cell to synthesize cDNA, and amplifying a DNA fragment including a gene encoding a light chain and a heavy chain of immunoglobulin by PCR reaction using the cDNA templates, it is possible to artificially re-construct an antibody gene by using thereof.

In the hybridoma cell originally obtained by the above method, a cell producing an antibody recognizing a protein other than hTfR as an antigen is also included. In addition, it cannot be said that all of the hybridoma cells producing an anti-hTfR antibody produce an anti-hTfR antibody exhibiting high affinity to hTfR.

Similarly, in the artificially re-constructed antibody gene, a gene encoding an antibody recognizing a protein other than hTfR as an antigen is also included. In addition, it cannot be said that all of the genes encoding an anti-hTfR antibody has desired properties such as a property of encoding an anti-hTfR antibody exhibiting high affinity to hTfR.

Therefore, a step of selecting a hybridoma cell producing an antibody having desired properties (high affinity to hTfR) from the hybridoma cell originally obtained as above is required. In addition, in the artificially re-constructed antibody gene, a step of selecting a gene encoding an antibody having desired properties (such as high affinity to hTfR)

from the antibody gene is required. As a method of selecting a hybridoma cell producing an antibody exhibiting high affinity to hTfR (high affinity antibody) or a gene encoding high affinity antibody, a method to be described in the following is effective. A dissociation constant ($K_D$) of the antibody exhibiting high affinity to hTfR, when measured by the method described in Example 7 is preferably equal to or less than $1\times10^{-8}$ M, more preferably equal to or less than $1\times10^{-9}$ M, further more preferably equal to or less than $1\times10^{-10}$ M, and even further more preferably equal to or less than $1\times10^{-11}$ M. For example, those having a dissociation constant of $1\times10^{-13}$M to $1\times10^{-9}$M, or $1\times10^{-13}$M to $1\times10^{-10}$ M are preferable.

For example, in a case of selecting a hybridoma cell producing an antibody having high affinity to hTfR, a method of adding a recombinant hTfR to a plate and holding thereof in the plate, adding a culture supernatant of a hybridoma cell, removing an antibody not binding to the recombinant hTfR from the plate, and measuring an amount of the antibody held in the plate is used. According to the method, the higher the affinity of an antibody included in the culture supernatant of the hybridoma cell added to the plate to hTfR is, the larger the amount of the antibody held in the plate becomes. Therefore, it is possible to measure the amount of the antibody held in the plate and to select a hybridoma cell corresponding to the plate in which a larger amount of the antibody is held as a cell strain producing an anti-hTfR antibody having relatively high affinity to hTfR. By extracting mRNA from the cell strain selected in this manner, synthesizing cDNA, and amplifying a DNA fragment including a gene encoding the anti-hTfR antibody by PCR method using the cDNA as templates, it is possible to isolate a gene encoding a high affinity antibody.

In a case of selecting a gene encoding an anti-hTfR antibody having high affinity from the above artificially re-constructed antibody gene, first, the artificially re-constructed antibody gene is inserted into an expression vector, the expression vector is introduced into a host cell. At this time, as a cell used as the host cell, the cell is not particularly limited whether it is a prokaryotic cell or a eukaryotic cell as long as it is possible to express an antibody gene by introducing the expression vector obtained by inserting the artificially re-constructed antibody gene. However, a cell derived from a mammalian animal such as human, mouse, and Chinese hamster is preferable, and particularly a CHO cell derived from Chinese hamster ovary or an NS/0 cell derived from mouse myeloma is preferable. In addition, when an expression vector used for inserting and expressing a gene encoding an antibody gene is transfected into a mammalian cell, the expression vector can be used not being particularly limited as long as the expression vector can express the gene. The gene inserted into the expression vector is downstream position of a DNA sequence (the regulation site of gene expression) capable of adjusting frequency of transcription of a gene in a mammalian cell. Examples of the regulation site of gene expression capable of being used in the present invention include a promoter derived from cytomegalovirus, an SV40 initial promoter, a human elongation factor-1 alpha (EF-1α) promoter, a human ubiquitin C promoter, and the like.

The mammalian cell into which such an expression vector is introduced is to express the above-described artificially re-constructed antibody inserted into the expression vector. In a case of selecting a cell producing an antibody having high affinity to hTfR from the cell expressing an artificially re-constructed antibody obtained in this manner, a method of adding a recombinant hTfR to a plate and holding thereof in the plate, bringing a the recombinant hTfR into contact with a culture supernatant of a cell, removing an antibody not binding to the recombinant hTfR from the plate, and measuring an amount of the antibody held in the plate is used. According to the method, the higher the affinity of an antibody included in the culture supernatant of the cell to hTfR is, the larger the amount of the antibody held in the plate becomes. Therefore, it is possible to measure the amount of the antibody held in the plate and to select a cell corresponding to the plate in which a larger amount of the antibody is held as a cell strain producing an anti-hTfR antibody having relatively high affinity to hTfR, and it is possible to select a gene encoding an anti-hTfR antibody having high affinity to hTfR. By amplifying a DNA fragment including a gene encoding an anti-hTfR antibody from a cell strain selected in this manner using the PCR method, it is possible to isolate a gene encoding a high affinity antibody.

Selection of a gene encoding an anti-hTfR antibody having high affinity from the artificially re-constructed antibody gene can be performed by inserting the artificially reconstructed antibody genes into an expression vector, transforming the expression vector into *E. coli* cells, culturing the *E. coli* cells, and selecting the *E. coli* cells having the desired gene, in the same manner as in the above selection of hybridoma cells, using the culture supernatant of the *E. coli* cells or an antibody-containing solution prepared by lysing the *E. coli* cells. The selected *E. coli* line expresses a gene encoding an anti-hTfR antibody having relatively high affinity to hTfR. From this cell line, it is possible to select a gene encoding an anti-hTfR antibody having relatively high affinity to hTfR. In a case of secreting an antibody in the culture supernatant of the *E. coli*, an antibody gene may be inserted into an expression vector such that a secretion signal sequence bonds to an N-terminal side.

As another method of selecting a gene encoding an anti-hTfR antibody having high affinity, there is a method of holding an antibody encoded by the above-described artificially re-constructed antibody gene on a phage particle and expressing thereof. At this time, the antibody gene is re-constructed as a gene encoding a single-chain antibody. The method of holding an antibody on a phage particle is described in WO1997/09436, WO1995/11317, and the like, and is well known. In a case of selecting a phage holding an antibody having high affinity to hTfR from a phage holding an antibody encoded by an artificially re-constructed antibody gene, a method of adding a recombinant hTfR to a plate and holding thereof, bringing the recombinant hTfR into contact with a phage, removing a phage not binding to the recombinant hTfR from the plate, and measuring an amount of the phage held in the plate is used. According to the method, the higher the affinity of an antibody held in the phage particle to hTfR is, the larger the amount of the phage held in the plate becomes. Therefore, it is possible to measure the amount of the phage held in the plate and to select a phage particle corresponding to the plate in which a larger amount of the phage is held as a phage particle producing an anti-hTfR antibody having relatively high affinity to hTfR, and it is possible to select a gene encoding an anti-hTfR antibody having high affinity to hTfR. By amplifying a DNA fragment including a gene encoding an anti-hTfR antibody from a phage particle selected in this manner using the PCR method, it is possible to isolate a gene encoding a high affinity antibody.

Using a known binding assay such as a direct and indirect sandwich assay using enzyme immunometric assay (EIA, ELISA), a flow cytometry, a surface plasmon resonance method (hereinafter, referred to as "SPR method"), a biolayer interferometry method (hereinafter, referred to as "BLI method"), or an immunoprecipitation assay, it is possible to select a hybridoma cell producing an antibody having high affinity to hTfR. By preparing cDNA from the high affinity antibody producing cell, and using thereof as a template, amplifying a DNA fragment including a gene encoding all or a part of a light chain of an anti-hTfR antibody, a heavy chain of an anti-hTfR antibody, or a single-chain antibody which is an anti-hTfR antibody using the PCR method, it is possible to isolate the DNA fragment. Similarly, it is possible to isolate a DNA fragment including a gene encoding all or a part of a variable region of the light chain of an anti-hTfR antibody and a DNA fragment including a gene encoding all or a part of a variable region of the heavy chain of an anti-hTfR antibody by amplifying thereof using the PCR method and the like.

By inserting all or a part of a gene encoding the light chain and the heavy chain of the anti-hTfR antibody having high affinity into an expression vector, transfecting a host cell such as a mammalian cell using the expression vector, and culturing the obtained transfected cell, it is possible to produce an anti-hTfR antibody having high affinity. It is also possible to translate an amino acid sequence of an anti-hTfR antibody from a nucleic acid sequence of a gene encoding the isolated anti-hTfR antibody, and to artificially synthesize a DNA fragment encoding the amino acid sequence. In a case of artificially synthesizing a DNA fragment, by selecting an appropriate codon, it is possible to increase an expression amount of the anti-hTfR antibody in the host cell.

In order to introduce mutation such as substitution, deletion, addition, and the like into the amino acid sequence of the original anti-hTfR antibody, it is possible to add appropriate mutation to a gene encoding the anti-hTfR antibody included in the isolated DNA fragment. The gene encoding the anti-hTfR antibody after adding mutation has preferably 80% or more homology and more preferably 90% or more homology to the original gene, but homology is not particularly limited. By adding mutation to the amino acid sequence, it is possible to change the number of sugar chains binding to the anti-hTfR antibody and to increase stability of the anti-hTfR antibody in a living body.

In a case of adding mutation to a gene encoding all or the part of a variable region of a light chain of an anti-hTfR antibody, the gene after adding mutation has preferably 80% or more homology and more preferably 90% or more homology to the original gene, but homology is not particularly limited. In a case of substituting an amino acid of an amino acid sequence of the variable region of the light chain with another amino acid, the number of the amino acids to be substituted is preferably 1 to 10, more preferably 1 to 5, further more preferably 1 to 3, and even further more preferably 1 to 2. In a case of deleting an amino acid in an amino acid sequence of the variable region of the light chain, the number of the amino acids to be deleted is preferably 1 to 10, more preferably 1 to 5, further more preferably 1 to 3, and even further more preferably 1 to 2. In addition, it is also possible to add mutation to which the substitution and the deletion of the amino acids are combined. In a case of adding an amino acid to the variable region of the light chain, preferably 1 to 10, more preferably 1 to 5, further more preferably 1 to 3, and even further more preferably 1 to 2 amino acids are added inside, or on the N-terminus or C-terminus of the amino acid sequence of the variable region of the light chain. It is also possible to add mutation to which the addition, the substitution, and the deletion of the amino acids are combined. The amino acid sequence of the variable region of the light chain added with mutation has preferably 80% or more homology, more preferably 90% or more homology, and further more preferably 95% or more homology to an amino acid sequence of the variable region of the original light chain. In particular, in a case of substituting an amino acid of an amino acid sequence of CDR with another amino acid, the number of the amino acids to be substituted is preferably 1 to 5, more preferably 1 to 3, further more preferably 1 to 2, and even further more preferably 1. In a case of deleting an amino acid in the amino acid sequence of CDR, the number of amino acids to be deleted is preferably 1 to 5, more preferably 1 to 3, further more preferably 1 to 2, and even further more preferably 1. In addition, it is also possible to add mutation to which the substitution and the deletion of the amino acids are combined. In a case of adding amino acids, preferably 1 to 5, more preferably 1 to 3, further more preferably 1 to 2, and even further more preferably 1 amino acids are added inside, or on the N-terminus or C-terminus of the amino acid sequence. It is also possible to add mutation to which the addition, the substitution, and the deletion of the amino acids are combined. The amino acid sequence of each CDR added with mutation has preferably 80% or more homology, more preferably 90% or more homology, and further more preferably 95% or more homology to the amino acid sequence of each original CDR.

In a case of adding mutation to a gene encoding all or the part of a variable region of a heavy chain of an anti-hTfR antibody, the gene after adding mutation has preferably 80% or more homology and more preferably 90% or more homology to the original gene, but the homology is not particularly limited. In a case of substituting an amino acid of an amino acid sequence of the variable region of the heavy chain with another amino acid, the number of the amino acids to be substituted is preferably 1 to 10, more preferably 1 to 5, further more preferably 1 to 3, and even further more preferably 1 to 2. In a case of deleting an amino acid in an amino acid sequence of the variable region of the heavy chain, the number of the amino acids to be deleted is preferably 1 to 10, more preferably 1 to 5, further more preferably 1 to 3, and even further more preferably 1 to 2. In addition, it is also possible to add mutation to which the substitution and the deletion of the amino acids are combined. In a case of adding an amino acid to the variable region of the heavy chain, preferably 1 to 10, more preferably 1 to 5, further more preferably 1 to 3, and even further more preferably 1 to 2 amino acids are added inside, or on the N-terminus or C-terminus of the the amino acid sequence of the variable region of the heavy chain. It is also possible to add mutation to which the addition, the substitution, and the deletion of the amino acids are combined. The amino acid sequence of the variable region of the heavy chain added with mutation has preferably 80% or more homology, more preferably 90% or more homology, and further more preferably 95% or more homology to an amino acid sequence of the variable region of the original heavy chain. In particular, in a case of substituting an amino acid of an amino acid sequence of CDR with another amino acid, the number of the amino acids to be substituted is preferably 1 to 5, more preferably 1 to 3, further more preferably 1 to 2, and even further more preferably 1. In a case of deleting an amino acid in the amino acid sequence of CDR, the number of amino acids to be deleted is preferably 1 to 5, more preferably 1 to 3, further more preferably 1 to 2, and even further more preferably 1. In addition, it is also possible to add mutation to which the substitution and the deletion of the amino acids are combined. In a case of adding amino acids, preferably 1 to 5, more preferably 1 to 3, further more preferably 1 to 2, and even further more preferably 1 amino acids are added inside, or on the N-terminus or C-terminus of the amino acid sequence. It is also possible to add mutation to which the addition, the substitution, and the deletion of the amino acids are combined. The amino acid sequence of each CDR added with mutation has preferably 80% or more homology, more preferably 90% or more homology, and further more preferably 95% or more homology to the amino acid sequence of each original CDR.

It is possible to add mutation to both of the variable regions of the light chain and the heavy chain of the anti-hTfR antibody by combining mutation to the variable region of the light chain of the anti-hTfR antibody and mutation to the variable region of the heavy chain of the anti-hTfR antibody.

Examples of the substitution of the amino acid in the amino acid sequence of the light chain and the heavy chain of the anti-hTfR antibody with another amino acid include substitution between amino acids classified into the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), and amino acids having a hydroxyl group (Ser, Thr). Such substitution by similar amino acids is estimated to cause no change in a phenotype of protein (that is, conservative amino acid substitution).

In a case of adding an amino acid to the C-terminus or N-terminus by adding mutation to the anti-hTfR antibody, in a case where the added amino acid is positioned between the anti-hTfR antibody and BDNF when the anti-hTfR antibody is fused with BDNF, the added amino acid constitutes a part of a linker. In a fusion protein of the anti-hTfR antibody and BDNF, a linker sequence disposed between the anti-hTfR antibody and BDNF will be described later.

An anti-hTfR antibody obtained by culturing a cell producing an anti-hTfR antibody having relatively high affinity to hTfR selected by the above-described method and the like and an anti-hTfR antibody obtained by expressing a gene coding region of an anti-hTfR antibody having high affinity can be changed into an antibody having desired properties by introducing mutation such as substitution, deletion, and addition to the amino acid sequence. Introduction of mutation to the amino acid sequence of the anti-hTfR antibody is performed by adding mutation to a gene corresponding to the amino acid sequence.

The affinity of an anti-hTfR antibody to hTfR can be adjusted as desired by adding mutation such as substitution, deletion, and addition to an amino acid sequence of a variable region of the antibody. For example, in a case where affinity between an antibody and an antigen is high and a dissociation constant in an aqueous solution is prominently low, when administering thereof to a living body, the antibody is not dissociated from the antigen, and as a result, there is a possibility that functional inconvenience occurs. In such a case, by introducing mutation to the variable region of the antibody, the dissociation constant is adjusted in phases such as 2 to 5 times, 5 to 10 times, and 10 to 100 times that of the original antibody to acquire most preferable antibody suitable for the purpose. On the contrary, it is possible to adjust the dissociation constant in phases such as ½ to ⅕ times, ⅕ to 1/10 times, and 1/10 to 1/100 times that of the original antibody by introducing the mutation.

Introduction of mutation such as substitution, deletion, and addition to the amino acid sequence of the anti-hTfR antibody is performed by introducing mutation to a specific site of a nucleic acid sequence of a gene or randomly introducing mutation by a method such as PCR, using a gene coding region of the anti-hTfR antibody as a template.

Introduction of mutation to the amino acid sequence of the anti-hTfR antibody for the purpose of adjustment of affinity between the antibody and hTfR can be performed by transfecting a gene coding region of the anti-hTfR antibody which is a single-chain antibody into a phagemid, producing a phage obtained by expressing a single-chain antibody on a capsid surface using the phagemid, proliferating the phage while introducing mutation on the gene coding region of the single-chain antibody by action of a mutagen and the like, and selecting a phage expressing the single-chain antibody having a desired dissociation constant from the proliferated phage by the above-described method, or performing purification using an antigen column under a predetermined condition.

A dissociation constant ($K_D$) of an antibody produced by the hybridoma cell with hTfR measured by the method described in Example 7 is preferably not more than $1\times10^{-8}$ M, more preferably not more than $1\times10^{-9}$ M, further more preferably not more than $1\times10^{-10}$ M, and even further more preferably not more than $1\times10^{-11}$ M. Preferable examples of the dissociation constant of the antibody is $1\times10^{-13}$ M to $1\times10^{-9}$ M and $1\times10^{-13}$ M to $1\times10^{-10}$ M. The same also applies when the antibody is a single-chain antibody. Once an antibody is obtained, it can be modified as desired by introducing a mutation into the gene encoding the antibody to give it a desired property.

Antibody having affinity both to human and monkey TfRs can be obtained by selection of antibodies having affinity to monkey TfR from the anti-hTfR antibody. An antibody having affinity to monkey TfR can be, for example, selected by the ELISA method using a recombinant monkey TfR produced by recombinant DNA technologies. In such the ELISA method, a recombinant monkey TfR is added to a plate and held by it, brought into contact with an anti-hTfR antibody, an antibody not binding to the recombinant monkey TfR is removed from the plate, and an amount of the antibody held in the plate is measured. The higher the affinity to the recombinant monkey TfR is, the larger the amount of the antibody held in the plate becomes. Therefore, it is possible to select an antibody corresponding to the plate in which a larger amount of the antibody is held as an antibody having affinity to the monkey TfR. Here, "monkey" is preferably classified into Anthropoidea excluding human, more preferably classified into Cercopithecidae, and further more preferably classified into *Macaca*, for example, cynomolgus monkey or rhesus monkey. Particularly, cynomolgus monkey is convenient for use in evaluation.

An antibody having affinity both to human and monkey TfRs has an advantageous effect of observing kinetics in a living body when administering a fusion protein of an antibody and BDNF using a monkey. For example, in a case of developing a fusion protein of an anti-hTfR antibody and BDNF of the present invention as a pharmaceutical agent, pharmacokinetic studies of the pharmaceutical agent can be performed with a monkey. Therefore, it is possible to significantly accelerate development of the pharmaceutical agent.

In the present invention, an antibody having relatively high affinity to hTfR and also having affinity to monkey TfR, as particularly measured by the method described in Example 7, exhibits a dissociation constant with a human TfR and a monkey TfR described as follows:

(a) Dissociation constant with hTfR: Preferably not more than $1\times10^{-10}$ M, more preferably not more than $2.5\times10^{-11}$ M, further more preferably mot more than $5\times10^{-12}$ M, and even further more preferably not more than $1\times10^{-12}$ M, (b) Dissociation constant with monkey TfR: Preferably not more than $1\times10^{-9}$ M, more preferably not more than $5\times10^{-10}$ M, further more preferably not more than $1\times10^{-10}$ M, for example, not more than $7.5\times10^{-11}$ M.

Examples of the dissociation constant with hTfR and monkey TfR are, respectively, not more than $1\times10^{-10}$ M and not more than $1\times10^{-9}$ M, not more than $1\times10^{-11}$ M and not more than $5\times10^{-10}$ M, not more than $5\times10^{-12}$ M and not more than $1\times10^{-10}$ M, not more than $5\times10^{-12}$ M and not more than $7.5\times10^{-11}$ M, not more than $1\times10^{-12}$ M and not more than $1\times10^{-10}$ not more than $1\times10^{-12}$ M and not more than $7.5\times10^{-11}$ M, M. Here, although there is no particular and clear lower limit value in the dissociation constant with human TfR, examples of such the dissociation constant with human TfR can be $5\times10^{-13}$ M, $1\times10^{-13}$ M, and the like. In addition, there is also no particular and clear lower limit value in the dissociation constant with monkey TfR, and examples of such the dissociation constant with monkey TfR can be $1\times10^{-11}$ M, $1\times10^{-12}$ M, and the like. The same also applies when the antibody is a single-chain antibody.

An antibody having relatively high affinity to hTfR obtained by the method of selecting a cell producing the high affinity antibody can be a humanized antibody in a case where the antibody is an antibody of an animal other than human. The humanized antibody is an antibody obtained by substituting an appropriate region of a human antibody with the sequence (transplantation of the sequence to the human antibody) using an amino acid sequence of a part (for example, in particular all or a part of CDR) of a variable region of an antibody of an animal other than human while maintaining specificity to an antigen. For example, as the humanized antibody, an antibody obtained by substituting three complementary determining regions (CDR) of an immunoglobulin light chain and three complementary determining regions (CDR) of an immunoglobulin heavy chain constituting a human antibody with CDRs of another mammalian animal is exemplified. The species of the animal from which CDR incorporated into the human antibody is derived is not particularly limited as long as the species is a mammalian animal other than human. However, the species of the animal is preferably a mouse, a rat, a hare, a horse, or primates other than human, more preferably a mouse and a rat, and further more preferably a mouse. However, an antibody obtained by substituting a human antibody with a part of another human antibody is also possible.

A production method of a humanized antibody is known in the technical field, and a method based on a method of substituting an amino acid sequence of a complementary determining region (CDR) in a variable region of a human antibody with CDR of an antibody of a non-human mammalian animal, reported by Winter (Verhoeyen M. Science. 239. 1534-1536 (1988)) is the most general. Here, it is known that there is a case where substituting a site corresponding to a human antibody as an acceptor with not only CDR of the non-human mammalian animal but also an amino acid sequence of a region other than CDR involved in structure maintenance or binding to an antigen of CDR is required to reproduce the original activity that a donor antibody has (Queen C. Proc. Natl. Acad. Sci. USA. 86. 10029-10033 (1989)). Here, the region other than CDR refers to a framework region (FR).

Both of the variable region of the heavy chain and the variable region of the light chain of an antibody include four framework regions 1 to 4 (FR1 to FR4). FR1 is a region adjacent to CDR1 on the N-terminal side, and in each peptide constituting the heavy chain and the light chain, FR1 is formed of an amino acid sequence from the N-terminus to an amino acid adjacent to the N-terminus of CDR1. FR2 is formed of an amino acid sequence between CDR1 and CDR2 in each peptide constituting the heavy chain and the light chain. FR3 is formed of an amino acid sequence between CDR2 and CDR3 in each peptide constituting the heavy chain and the light chain. FR4 is formed of an amino acid sequence from an amino acid adjacent to the C-terminus of CDR3 to the C-terminus of the variable region. Here, without being limited to this, in the present invention, in each of the FR region, a region excluding 1 to 5 amino acids on the N-terminal side and/or 1 to 5 amino acids on the C-terminal side can be the framework region.

Production of a humanized antibody includes a process for displacing CDR (and the neighboring FR depending on the case) of an antibody of a non-human mammalian animal, instead of a variable region CDR (and the neighboring FR depending on the case) of a human antibody. In the process, a framework region of a variable region of the original human antibody can be obtained from common DNA database and the like, containing a germ cell line antibody gene sequence. For example, a germ cell line DNA sequence and an amino acid sequence of human heavy chain and light chain variable region genes can be selected from "VBase" human germ cell line database (can be acquired from www.mrc-cpe.cam.ac.uk/vbase in the Internet). In addition, the germ cell line DNA sequence and the amino acid sequence of human heavy chain and light chain variable region genes can be selected from the DNA sequence and the amino acid sequence described in published documents, for example, "Kabat EA. Sequences of Proteins of Immunological Interest, Fifth edition, the U.S. Department of Health and Human Services, NIH Publication No. 91-3242 (1991)", "Tomlinson I M. J. Mol. Biol. 227. 776-98 (1992)", "Cox J P L. Eur. J Immunol. 24:827-836 (1994)", and the like.

As described above, in the humanized antibody, a region of the antibody of a non-human mammalian animal displaced into the variable region of the original human antibody generally includes CDR itself, or CDR and its neighboring part of FR. However, FR displaced along with CDR is also involved in structure maintenance or binding to an antigen of CDR, and is considered to substantially have a function of determining complementarity of an antibody. Therefore, the term "CDR" in the present invention refers to a region displaced, or a region capable of being displaced into a humanized antibody from an antibody of a non-human mammalian animal That is, in the present invention, CDR includes a region which is generally considered as FR as long as FR is considered to be involved in structure maintenance or binding to an antigen of CDR and substantially have a function of determining complementarity of an antibody.

The anti-hTfR antibody in the present invention can efficiently bind to hTfR existing on an endothelial cell of a capillary vessel in the brain in a case where the anti-hTfR antibody is administered to the body by intravenous injection and the like. In addition, an antibody conjugating with hTfR is allowed to pass through the blood-brain barrier such mechanism as endocytosis and transcytosis into the brain. Therefore, by conjugating BDNF with an anti-hTfR antibody of the present invention, BDNF can efficiently pass through the blood-brain barrier to reach the brain. In addition, the anti-hTfR antibody of the present invention can reach cerebral parenchyma, neuron-like cells in the hippocampus, Purkinje cells of cerebellum, and the like, or at least any one thereof. And it is also expected that the antibody-hTfR antibody of the present invention reaches to the neuron-like cells of the cerebrum and neuron-like cells of substantia nigra of the mesencephalon. Therefore, by conjugating BDNF with the anti-hTfR antibody of the present invention, it is possible to make BDNF reach these tissues or cells.

The use of a fusion protein of an anti-hTfR antibody and BDNF can be an effective means to make the BDNF transfer from the blood into the brain and function there, wherein the BDNF generally cannot pass through the blood-brain barrier when intravenously administered and therefore cannot exhibit its function in the brain. In particular, the anti-hTfR antibody of the present invention can reach cerebral parenchyma, neuron-like cells in the hippocampus, Purkinje cells of cerebellum, and the like, or at least one of them. And it is also expected that the antibody-hTfR antibody of the present invention reaches to the neuron-like cells of the cerebrum and the neuron-like cells of substantia nigra of the mesencephalon. Therefore, it is possible to make BDNF function or augment their function, in these tissues or cells in the brain by administering BDNF into the blood by intravenous administration as a form of binding to an anti-hTfR antibody molecule of the present invention.

In the present specification, BDNF is a conventional protein which was discovered by Barde et al. in 1982 and was cloned by Jones et al. in 1990 (EMBO J, (1982) 1: 549-553, Proc. Natl. Acad. Sci. USA (1990) 87: 8060-8064), and, as an example, an amino acid sequence of human mature BDNF of SEQ ID NO: 51 is shown. However, a protein comprising an amino acid sequence substantially identical to the aforementioned amino acid sequence, or BDNF from other warm-blooded animals (for example, guinea pig, rat, mouse, chicken, rabbit, dog, pig, sheep, bovine, monkey, and the like) may also be the protein.

In addition, in the present specification, BDNF include not only a "protein" or a "(poly)peptide" having a specific amino acid sequence (SEQ ID NO: 51) showing human mature BDNF but also the homologues (a homologues and a splice variants), a mutant thereof, a derivatives thereof and an amino acid modified from thereof as long as those have an equivalent functions.

Here the "equivalent functions" means that the properties are qualitatively the same from a physiological or a pharmacological view, and quantitative elements such as the degree of the functions (for example, approximately 0.1 to approximately 10 times, preferably 0.5 to 2 times) or molecular weight of protein or the like, may be different. In addition, functions having of natural BDNF, for example, (1) binding affinity to a BDNF receptor (TrkB), (2) phosphorylation activity of BDNF receptor, (3) action to promote the growth of neurons and (4) action to maintain the survival of neurons, and (5) neurite outgrowth action on neurons, or (6) a protein recognized by an antibody specifically recognizing a protein consisting of an amino acid sequence of SEQ ID NO: 51 is considered to be a the "protein having equivalent functions" with BDNF.

The aforementioned functions of BDNF can be examined by using various conventional evaluation methods as described later in the section of "(2) Evaluation method of functions of BDNF" or the methods described in Example 23 and thereafter of the present specification.

Herein, examples of the homolog can include proteins of other animal species such as a mouse and a rat corresponding to human protein. These can be deductively identified from those reported by Maisonpierre et al. (Genomics (1991) 10: 558-568), the amino acid sequence of the protein described by UniProt (P21237-1, P23363-1, P25429-1, Q7YRB4-1, P14082-1, Q5IS78-1, Q95106-1), and the like. In addition, the variants include naturally existing allele variants, naturally non-existing variants, and variants having amino acid sequences modified by artificial deletion, substitution, addition or insertion. Examples of the variants include variants having at least 70%, preferably 80%, more preferably 90%, further more preferably 95%, even more preferably 97%, particularly preferably 98%, and most preferably 99% homology to a protein or a (poly)peptide with no mutation. In addition, examples of the amino acid modified form include a naturally existing amino acid modified form and naturally non-existing amino acid modified form, and specific example of the amino acid modified form is phosphorylated bodies of an amino acid.

Furthermore, in the present specification, "BDNF" may be a precursor of the above described BDNF (pre-pro-protein), which is capable of exhibiting an equivalent function to BDNF, or a pro-protein which is obtained by cleaving a signal sequence from the precursor. Thus, BDNF include not only a "protein" or a "(poly)peptide" having a specific amino acid sequence (UniProt ID No. P23560-1) showing a human BDNF precursor, but also a homologue (a homolog and a splice variants), a variant, a derivative, a pro-protein, and an amino acid modified form thereof as long as those have equivalent functions. Examples of the pro-protein of human BDNF (pro BDNF) include an amino acid sequence of SEQ ID NO: 56.

Herein, the equivalent function to the BDNF precursor means the function possessed by the BDNF precursor, for example, that a pro-protein of BDNF (pro BDNF) or mature BDNF can be generated and the equivalent function to the pro-protein of BDNF means the function possessed by the pro-protein of BDNF, for example, binding affinity to a p75 receptor.

Here, examples of the splice variant of the human BDNF precursor can include the amino acid sequence of a protein published in UniProt (P23560-2, P23560-3, P23560-4, P23560-5) and the like. In addition, a gene encoding the human BDNF precursor protein is also known. For example, examples thereof can include nucleic acid sequences of a gene published in http://www.ncbi.nlm.nih.gov (NM_001143805.1, NM_001143806.1, NM_001143807.1, NM_001143808.1, NM_001143809.1, NM_001143810.1, NM_001143811.1, NM_001143812.1, NM_001143813.1 NM_001143814.1, NM_001143816.1, NM_001709.4, NM_170731.4, NM_170732.4, NM_170733.3, NM_170734.3, NM_170735.5) and the like.

As homologues and splice variants of the BDNF precursor, proteins of other animal species such as mouse and rat corresponding to human protein and splice variants thereof can be exemplified. These can be deductively identified from nucleic acid sequences of a gene published in http://www.ncbi.nlm.nih.gov (nucleic acid sequences of a mouse BDNF gene such as NM_001048139.1, NM_001048141.1, NM_001048142.1, NM_001285416.1, NM_001285417.1, NM_001285418.1, NM_001285419.1, NM_001285420.1, NM_001285421.1, NM_001285422.1, NM_007540.4, and the like, nucleic acid sequences of a rat BDNF gene such as NM_001270630.1, NM_00127631.1, NM_001270632.1, NM_001270633.1, NM_001270634.1, NM_001270635.1, NM_001270636.1, NM_001270637.1, NM_001270638.1, NM_012513.4, and the like) and the like.

In addition, the variants of the BDNF precursor include naturally existing allele variants, naturally non-existing variants, and variants having amino acid sequences modified by artificial deletion, substitution, addition or insertion. Examples of the variants include variants having at least 70%, preferably 80%, more preferably 90%, further more preferably 95%, even more preferably 97%, particularly preferably 98%, and most preferably 99% homology to a protein or a (poly)peptide with no mutation. In addition, examples of the amino acid modifiers include naturally existing modifiers and naturally non-existing modifiers, and specifically phosphorylated bodies of an amino acid.

Examples of the amino acid sequence of SEQ ID NO: 51 or amino acid sequences substantially the same as the amino acid sequence of SEQ ID NO: 51 include the following (A) to (E):

(A) an amino acid sequence of SEQ ID NO: 51, (B) an amino acid sequence, in which one or a plurality of amino acids is deleted, added, inserted, or substituted in the amino acid sequence of SEQ ID NO: 51, and which is recognized by an antibody specifically recognizing a protein having the equivalent function with a protein having the amino acid sequence of SEQ ID NO: 51 or having the amino acid sequence of SEQ ID NO: 51, (C) an amino acid sequence, which has at least 80% or more homology to the amino acid sequence of SEQ ID NO: 51, and is recognized by an antibody specifically recognizing a protein having the equivalent function with a protein having the amino acid sequence of SEQ ID NO: 51 or having the amino acid sequence of SEQ ID NO: 51, (D) an amino acid sequence encoded by DNA having the amino acid sequence of SEQ ID NO: 50, or (E) an amino acid sequence, which is encoded by DNA having complementarity with DNA having the nucleic acid sequence of SEQ ID NO: 50 and DNA hybridized under a stringent condition, and is recognized by an antibody specifically recognizing a protein having the equivalent function with a protein having the amino acid sequence of SEQ ID NO: 51 or having the amino acid sequence of SEQ ID NO: 51.

Specifically, examples thereof include an amino acid sequence of orthologue of another mammalian animal corresponding to a human protein having the amino acid sequence of SEQ ID NO: 51, or an amino acid sequence of a splicing variant, or its orthologue, an allele variant or a polymorphic variant of a human protein having the amino acid sequence of SEQ ID NO: 51.

Here, the term "homology" means a ratio (%) of the same amino acid and similar amino acid residues with respect to all overlapping amino acid residues, in the most appropriate alignment in a case where aligning two amino acid sequences using a known mathematical algorithm in the technical field (preferably, the algorithm is obtained by considering introduction of gap of one or both of sequences for the most appropriate alignment). The term "Similar amino acid residues" means similar amino acids in terms of physicochemical characteristics, and examples thereof include amino acids classified into the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), and amino acids having a hydroxyl group (Ser, Thr). Such substitution by similar amino acids is estimated to cause no change in a phenotype of protein (that is, conservative amino acid substitution).

Homology of the amino acid sequence in the present specification can be calculated under the following condition (expected value=10; gap is allowed; matrix=BLOSUM62; filtering=OFF) using homology calculation algorithm NCBI BLAST (National Center for Biotechnology Information Basic Local Alignment SearchTool). Examples of other algorithms for determining homology of amino acid sequences include the algorithm described in Karlin et al., Proc. Natl. Acad. Sci. USA, 90: 5873-5877 (1993) [the algorithm is incorporated into NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [the algorithm is incorporated into GAP program in GCG software package], the algorithm described in Myers and Miller, CABIOS, 4: 11-17 (1988) [the algorithm is incorporated into ALIGN program which is a part of CGC sequence alignment software package (version 2.0)], the algorithm described in Pearson et al., Proc. Natl. Acad. Sci. USA, 85: 2444-2448 (1988) [the algorithm is incorporated into FASTA program in GCG software package], and the like, and these are similarly preferably used.

The stringent condition in (E) includes the condition described in Current Protocols in Molecular Biology, John Wiley & Sons, 6. 3. 1-6. 3. 6, 1999, for example, hybridization at 6×SSC (sodium chloride/sodium citrate/45° C., and washing one or more times at 0.2×SSC/0.1% SDS/50° C. to 65° C. However, those skilled in the art can appropriately select conditions of hybridization imparting stringency equivalent to the condition.

More preferably, examples of "the amino acid sequence substantially the same as the amino acid sequence of SEQ ID NO: 51" include an amino acid sequence having approximately 70% or more, preferably approximately 80% or more, more preferably approximately 90% or more, further more preferably approximately 95% or more, even further more preferably approximately 97% or more, particularly preferably approximately 98% or more, and most preferably approximately 99% or more homology to the amino acid sequence of SEQ ID NO: 51.

As the protein: BDNF in the present specification, for example, (i) an amino acid sequence in which 1 to 30, preferably 1 to 20, more preferably 1 to 10, further more preferably 1 to n (6, 5, 4, 3, or 2) amino acids are deleted from the amino acid sequence of SEQ ID NO: 51, (ii) an amino acid sequence in which 1 to 30, preferably 1 to 20, more preferably 1 to 10, further more preferably 1 to n (6, 5, 4, 3, or 2) amino acids are added to the amino acid sequence of SEQ ID NO: 51, (iii) an amino acid sequence in which 1 to 30, preferably 1 to 20, more preferably 1 to 10, further more preferably 1 to n (6, 5, 4, 3, or 2) amino acids from the amino acid sequence of SEQ ID NO: 51 are inserted into the amino acid sequence of SEQ ID NO: 51, (iv) an amino acid sequence in which 1 to 30, preferably 1 to 20, more preferably 1 to 10, further more preferably 1 to n (6, 5, 4, 3, or 2) amino acids are substituted with other amino acid sequences, or (v) so-called variants of a protein and the like containing an amino acid sequence obtained by combining these is also included.

In a case where an amino acid sequence is inserted, deleted, added, or substituted as described above, the position of the insertion, deletion, addition or substitution is not particularly limited as long as the protein to which such modification is added is recognized by an antibody specifically recognizing a protein having the equivalent function with a protein having the amino acid sequence of SEQ ID NO: 51 or having the amino acid sequence of SEQ ID NO: 51. For example, Met-BDNF added with methionine to the N-terminus and the like, in addition to mature BDNF formed of the amino acid sequence of SEQ ID NO: 51, are also used in the fusion protein of the present invention as BDNF as long as these have equivalent function with the protein formed of the amino acid sequence of SEQ ID NO: 51.

Here, as a technique for artificially performing deletion, addition, insertion, or substitution of an amino acid, for example, a technique of performing practical site-specific mutation introduction on DNA encoding the amino acid sequence of SEQ ID NO: 51 and then expressing the DNA by a common method is exemplified. Here, examples of the site-specific mutation introduction method include a method of using amber mutation (gapped-duplex method, Nucleic Acids Res., 12, 9441-9456 (1984)), a method by PCR using a primer for mutation introduction, and the like.

Preferable examples of BDNF include a human protein formed of the amino acid sequence of SEQ ID NO: 51, or the allele variant or a polymorphic variant.

The "gene encoding BDNF" is shown in (A) to (E), and represents a gene having a nucleic acid sequence encoding the amino acid sequence of SEQ ID NO: 51 or an amino acid sequence substantially the same as the amino acid sequence of SEQ ID NO: 51. Specifically, the gene encoding BDNF includes a gene having the following (F) to (J):

(F) a nucleic acid sequence encoding the amino acid sequence of SEQ ID NO: 51, (G) a nucleic acid sequence encoding an amino acid sequence in which one or a plurality of amino acids is deleted, added, inserted, or substituted in the amino acid sequence of SEQ ID NO: 51, and which is recognized by an antibody specifically recognizing a protein having the equivalent function with a protein having the amino acid sequence of SEQ ID NO: 51 or having the amino acid sequence of SEQ ID NO: 51, (H) a nucleic acid sequence encoding an amino acid sequence which has at least 80% or more homology to the amino acid sequence of SEQ ID NO: 51 and is recognized by an antibody specifically recognizing a protein having the equivalent function with a protein having the amino acid sequence of SEQ ID NO: 51 or having the amino acid sequence of SEQ ID NO: 51, (I) a nucleic acid sequence encoding an amino acid sequence encoded by DNA having a nucleic acid sequence of SEQ ID NO: 50, or (J) a nucleic acid sequence, which is encoded by DNA having complementarity with DNA having the nucleic acid sequence of SEQ ID NO: 50 and DNA hybridized under a stringent condition, and is recognized by an antibody specifically recognizing a protein having the same function with a protein having the amino acid sequence of SEQ ID NO: 51 or having the amino acid sequence of SEQ ID NO: 51.

Here, the gene may be any one of DNA such as cDNA and genome DNA, or RNA such as mRNA, and a concept including a single-chain nucleic acid sequence and a double-chain nucleic acid sequence together. In addition, in the present specification, nucleic acid sequences represented by SEQ ID NO: 2, SEQ ID NO: 24, SEQ ID NO: 26, SEQ ID NO: 28, SEQ ID NO: 30, SEQ ID NO: 38, SEQ ID NO: 40, SEQ ID NO: 50, SEQ ID NO: 53, SEQ ID NO: 55, SEQ ID NO: 58, SEQ ID NO: 64, and the like are conveniently described in the form of DNA sequences, but in a case of representing RNA sequences such as mRNA, thymine (T) is read as uracil (U).

BDNF used in the present invention may be a derivative and the like which is modified by a molecule and the like having protein stabilizing function such as polyethylene glycol (PEG) (Drug Delivery System (1998); 13:173-178).

Examples of the fusion protein of an anti-hTfR antibody and BDNF in the present invention include a type in which BDNF is fused with a C-terminal side of the "heavy chain" constituting the anti-hTfR antibody via a linker sequence. Examples of such a fusion protein include a fusion protein in which:

(1) the light chain of the humanized anti-hTfR antibody includes an amino acid sequence of SEQ ID NO: 23, and the heavy chain of the humanized anti-hTfR antibody binds on the C-terminal side to human BDNF via a linker including an amino acid sequence Gly-Ser, and thereby includes an amino acid sequence of SEQ ID NO: 52; and a fusion protein in which:

(2) the light chain of the humanized anti-hTfR antibody includes an amino acid sequence of SEQ ID NO: 23, and the heavy chain of the humanized anti-hTfR antibody binds on the C-terminal side to human BDNF via a linker including a total of 27 amino acids formed of five consecutive amino acid sequences Gly-Gly-Gly-Gly-Ser (SEQ ID NO: 3) subsequent to an amino acid sequence Gly-Ser, and thereby includes an amino acid sequence of SEQ ID NO: 54.

The fusion proteins described in (1) and (2) are (1) a fusion protein in which the light chain of the humanized anti-hTfR antibody having an amino acid sequence of SEQ ID NO: 23 is included and human BDNF having an amino acid sequence of SEQ ID NO: 51 binds to the C-terminal side of the heavy chain of the humanized anti-hTfR antibody having an amino acid sequence of SEQ ID NO: 70 via a linker including an amino acid sequence Gly-Ser; and (2) a fusion protein in which the light chain of the humanized anti-hTfR antibody having an amino acid sequence of SEQ ID NO: 23 is included and human BDNF having an amino acid sequence of SEQ ID NO: 51 binds to the C-terminal side of the heavy chain of the humanized anti-hTfR antibody having an amino acid sequence of SEQ ID NO: 70 via a linker including a total of 27 amino acid sequences formed of five consecutive amino acid sequences Gly-Gly-Gly-Gly-Ser (SEQ ID NO: 3) subsequent to an amino acid sequence Gly-Ser.

In (1) and (2), it is possible to substitute the heavy chain of the humanized anti-hTfR antibody from a heavy chain having an amino acid sequence of SEQ ID NO: 70 to a heavy chain having an amino acid sequence of SEQ ID NO: 72. Those having an amino acid sequence of SEQ ID NO: 70 and an amino acid sequence of SEQ ID NO: 72 are respectively an IgG1 type antibody and an IgG4 type antibody. As a nucleic acid sequence encoding the one having an amino acid sequence of SEQ ID NO: 70, a nucleic acid sequence represented by SEQ ID NO: 71 can be exemplified, and as a nucleic acid sequence encoding the one having an amino acid sequence of SEQ ID NO:72, a nucleic acid sequence represented by SEQ ID NO: 76 can be exemplified.

Such a fusion protein can be produced by transforming a host cell such as a mammalian cell by an expression vector obtained by inserting a DNA fragment having a nucleic acid sequence (SEQ ID NO: 53) encoding the amino acid sequence of SEQ ID NO: 52 and an expression vector obtained by inserting a DNA fragment having a nucleic acid sequence SEQ ID NO: 24) encoding an anti-hTfR antibody light chain having an amino acid sequence of SEQ ID NO: 23, and culturing the host cell, or can be produced by transforming a host cell such as a mammalian cell by an expression vector obtained by inserting a DNA fragment having a nucleic acid sequence (SEQ ID NO: 55) encoding an amino acid sequence of SEQ ID NO: 54 and an expression vector obtained by inserting a DNA fragment having a nucleic acid sequence (SEQ ID NO: 24) encoding an anti-hTfR antibody light chain having an amino acid sequence of SEQ ID NO: 23, and culturing the host cell.

Examples of preferable embodiments of the anti-hTfR antibody to which human BDNF binds include an antigen-binding fragment of the antibody, specifically, a single-chain antibody, Fab, F(ab'), $F(ab')_2$, and the like.

An example of a specific embodiment of the fusion protein of a humanized anti-hTfR antibody and BDNF in the present invention in a case where the anti-hTfR antibody is a single-chain antibody includes a fusion protein including an amino acid sequence of SEQ ID NO: 59 or 60, in which a single-chain antibody binds to the C-terminal side of human BDNF via a first linker including a total of 27 amino acids formed of five consecutive amino acid sequences Gly-Gly-Gly-Gly-Ser (SEQ ID NO: 3) subsequent to an amino acid sequence Gly-Ser. Here, the single-chain antibody is a single-chain antibody having an amino acid sequence of SEQ ID NO: 57, in which a variable region of a light chain having an amino acid sequence of SEQ ID NO: 18 binds to the C-terminus of a heavy chain having an amino acid sequence of SEQ ID NO: 69 via a second linker including a total of 15 amino acids formed of three consecutive amino acid sequences Gly-Gly-Gly-Gly-Ser (SEQ ID NO: 3). Therefore, in a case where the anti-hTfR antibody is a single-chain antibody, an example of a specific embodiment of the fusion protein of an anti-hTfR antibody and human BDNF of the present invention includes a fusion protein in which human BDNF binds to an N-terminal side of a single-chain antibody including a heavy chain variable region having an amino acid sequence of SEQ ID NO: 69 and a light chain variable region having an amino acid sequence of SEQ ID NO: 18 directly or via a linker.

Such a fusion protein in which the anti-hTfR antibody is a single-chain antibody can be produced by transforming a host cell such as a mammalian cell by an expression vector obtained by inserting a DNA fragment having a nucleic acid sequence (SEQ ID NO: 58) encoding an amino acid sequence of SEQ ID NO: 59, and culturing the host cell.

Examples of other specific embodiments of the fusion protein of a humanized anti-hTfR antibody and human BDNF in the present invention in a case where the anti-hTfR antibody is a single-chain antibody includes a fusion protein in which an anti-hTfR antibody light chain having an amino acid sequence described in SEQ ID NO:23 binds to the C-terminal side of a Fab heavy chain of a humanized anti-hTfR antibody No. 3N having an amino acid sequence described in SEQ ID NO: 61 via a linker including 32 amino acids formed of an amino acid sequence Gly-Gly subsequent to six consecutive amino acid sequences represented by SEQ ID NO: 3, and a fusion protein in which human BDNF binds to a single-chain antibody having an amino acid sequence described in SEQ ID NO: 90. The human BDNF may bind to any one of the C-terminal side or the N-terminal side of the single-chain antibody, but preferably binds to the N-terminal side. In addition, the human BDNF can bind to the single-chain antibody directly or via a linker.

In the present invention, in a case where a plurality of linker sequences is included in one peptide chain, for convenience, each linker sequence is referred to as a first linker sequence and a second linker sequence in an order from the N-terminal side.

In a case where the anti-hTfR antibody is Fab, an example of a specific embodiment of the fusion protein of a humanized anti-hTfR antibody and human BDNF of the present invention includes a fusion protein in which a region including a variable region and a $C_H1$ region of an anti-hTfR antibody heavy chain is fused with the C-terminal side of human BDNF via a linker sequence including a total of 25 amino acids formed of five consecutive amino acid sequences Gly-Gly-Gly-Gly-Ser (SEQ ID NO: 3). At this time, in addition to the $C_H1$ region, a part of a hinge region may be included, but the hinge region does not include a cysteine residue forming a disulfide bond between heavy chains. Those represented by SEQ ID NO: 63 and SEQ ID NO: 65 are preferable examples thereof. The one represented by SEQ ID NO: 63 includes an amino acid sequence of human pro BDNF represented by SEQ ID NO: 56 and the one represented by SEQ ID NO: 65 includes an amino acid sequence of human mature BDNF represented by SEQ ID NO: 51.

An amino acid sequence of an anti-hTfR antibody Fab heavy chain in SEQ ID NO: 63 and SEQ ID NO: 65 corresponds to a portion at $1^{st}$ to $226^{th}$ positions from the N-terminus of an amino acid sequence of a heavy chain of a humanized anti-hTfR antibody represented by SEQ ID NO: 70, and includes an amino acid sequence of SEQ ID NO: 61. A portion at $1^{st}$ to $118^{th}$ positions from the N-terminus of SEQ ID NO: 61 corresponds to the variable region (SEQ ID NO: 69), a portion at $119^{th}$ to $216^{th}$ positions correspond to the $C_H1$ region, and a portion at $217^{th}$ to $226^{th}$ position corresponds to the hinge region. An example of a specific embodiment of the fusion protein of a humanized anti-hTfR antibody and human BDNF in the present invention, in a case where an anti-hTfR antibody is Fab, includes a fusion protein in which BDNF binds to the N-terminal side of the heavy chain of any one of Fab, $F(ab')_2$, or F(ab') of the humanized anti-hTfR antibody, and the fusion protein is exemplified as a preferable embodiment.

An example of a specific embodiment of the fusion protein of a humanized anti-hTfR antibody and human BDNF in a case where the anti-hTfR antibody is Fab includes a fusion protein in which the light chain includes an amino acid sequence of SEQ ID NO: 23, the heavy chain includes a Fab heavy chain including an amino acid sequence of SEQ ID NO: 61, and human BDNF binds to the N-terminal side of the heavy chain directly via a linker. More specifically, the fusion protein includes:

(1) a fusion protein in which the light chain includes an amino acid sequence of SEQ ID NO: 23, and a portion including human pro BDNF binding to the Fab heavy chain and the N-terminal side via a linker includes an amino acid sequence of SEQ ID NO: 63; and (2) a fusion protein in which the light chain includes an amino acid sequence of SEQ ID NO: 23, and a portion including human BDNF binding to the Fab heavy chain and the N-terminal side via a linker includes an amino acid sequence of SEQ ID NO: 65.

Such a fusion protein in which the anti-hTfR antibody is Fab can be produced by transfecting a host cell such as a mammalian cell by an expression vector obtained by inserting a DNA fragment having a nucleic acid sequence (SEQ ID NO: 62) encoding an amino acid sequence of SEQ ID NO: 63 and an expression vector obtained by inserting a DNA fragment having a nucleic acid sequence (SEQ ID NO: 24) encoding an anti-hTfR antibody light chain having an amino acid sequence of SEQ ID NO: 23, and culturing the host cell.

Such a fusion protein in which the anti-hTfR antibody is Fab can be produced by transfecting a host cell such as a mammalian cell by an expression vector obtained by inserting a DNA fragment having a nucleic acid sequence (SEQ ID NO: 64) encoding an amino acid sequence of SEQ ID NO: 65 and an expression vector obtained by inserting a DNA fragment having a nucleic acid sequence (SEQ ID NO: 24) encoding an anti-hTfR antibody light chain having an amino acid sequence of SEQ ID NO: 23, and culturing the host cell.

In a case where the human BDNF (hBDNF) is added with mutation and an amino acid is added to the C-terminus or the N-terminus, the added amino acid is positioned between hBDNF and an anti-hTfR antibody when hBDNF is fused with the anti-hTfR antibody, the added amino acid constitutes a part of a linker.

As a method of binding an anti-hTfR antibody to BDNF, there is a method of performing binding via a non-peptide linker or a peptide linker. As the non-peptide linker, there can be used polyethylene glycol, polypropylene glycol, a copolymer between ethylene glycol and propylene glycol, polyoxyethylated polyol, polyvinyl alcohol, polysaccharides, dextran, polyvinyl ether, a biodegradable polymer, a lipid polymer, chitins, hyaluronic acid, or the derivatives, or combinations thereof. The peptide linker is a peptide chain formed of 1 to 50 amino acids bonded by a peptide bond or the derivatives, in which the N-terminus and the C-terminus respectively form a covalent bond with any one of an anti-hTfR antibody or BDNF, and thereby binds the anti-hTfR antibody and BDNF to each other.

The one obtained by conjugating the anti-hTfR antibody with BDNF of the present invention using PEG as a non-peptide linker is particularly referred to as anti-hTfR antibody-PEG-BDNF. The anti-hTfR antibody-PEG-BDNF can be produced by binding the anti-hTfR antibody and PEG to each other to produce anti-hTfR antibody-PEG, and then binding the anti-hTfR antibody-PEG and BDNF to each other. Or, the anti-hTfR antibody-PEG-BDNF can be produced by binding BDNF and PEG to each other to produce BDNF-PEG, and then binding BDNF-PEG and the anti-hTfR antibody to each other. In a case of binding PEG to the anti-hTfR antibody and BDNF, PEG obtained by modified with a functional group such as carbonate, carbonyl imidazole, active ester of carboxylic acid, azlactone, cyclic imide thione, isocyanate, isothiocyanate, imidate, and aldehyde is used. The functional group introduced into the PEG mainly reacts with an amino group in the anti-hTfR antibody and BDNF molecules, and thereby PEG binds to the anti-hTfR antibody and BDNF via a covalent bond. At this time, the molecular weight and the shape of the used PEG are not particularly limited, but the average molecular weight (MW) is preferably MW=500 to 60,000, and more preferably MW=500 to 20,000. For example, PEG of which the average molecular weight is approximately 300, approximately 500, approximately 1,000, approximately 2,000, approximately 4,000, approximately 10,000, approximately 20,000, and the like can be appropriately used as a non-peptide linker.

For example, anti-hTfR antibody-PEG is obtained by mixing an anti-hTfR antibody and aldehyde group-modified PEG (ALD-PEG-ALD) with each other such that a molar ratio of the modified PEG to the antibody is 11, 12.5, 15, 110, 120, and the like, and adding a reducing agent such as $NaCNBH_3$ thereto to perform reaction. Subsequently, by reacting the anti-hTfR antibody-PEG with BDNF under the presence of a reducing agent such as $NaCNBH_3$, anti-hTfR antibody-PEG-BDNF is obtained. On the contrary, anti-hTfR antibody-PEG-BDNF can be also obtained by binding BDNF and ALD-PEG-ALD to each other first to produce BDNF-PEG, and then binding BDNF-PEG and the anti-hTfR antibody to each other.

BDNF is considered to act on a dimer since the dimer binds to a high affinity BDNF receptor on a target cell surface, but the number of BDNF conjugating with an anti-hTfR antibody may be one, or may be two. For example, a dimer can be formed by reacting a fusion protein in which one-molecule BDNF binds to an anti-hTfR antibody with BDNF, or a fusion protein in which two-molecule BDNF binds to an anti-hTfR antibody may be formed. In addition, the bond may be obtained by inserting DNA encoding the anti-hTfR antibody and BDNF into an expression vector as shown below, or may be produced by producing the anti-hTfR antibody and BDNF respectively and chemically bonding thereof. Specifically, the N-terminus or the C-terminus of BDNF binds to the C-terminal side or the N-terminal side of the heavy chain or the light chain of the anti-hTfR antibody, respectively, via a linker sequence or directly, and thereby the anti-hTfR antibody and BDNF can be integrated. As a preferable embodiment of a fusion protein of BDNF and the anti-hTfR antibody, a fusion protein in which the C-terminus of BDNF binds to the N-terminal side of a heavy chain or a light chain of an anti-hTfR antibody via a linker or directly is exemplified.

As described above, a preferable embodiment of the anti-hTfR antibody conjugating with human BDNF includes an antigen-binding fragment of the antibody, specifically, a single-chain antibody, Fab, F(ab'), and $F(ab')_2$. Therefore, as a preferable embodiment of a fusion protein of BDNF and an anti-hTfR antibody, the following ones can be exemplified.

(1) A fusion protein of BDNF and an anti-hTfR antibody, in which the anti-hTfR antibody is an antigen-binding fragment, and human BDNF binds to the N-terminal side of the antigen-binding fragment directly or via a linker.

(2) A fusion protein of BDNF and an anti-hTfR antibody, in which the anti-hTfR antibody is a single-chain antibody, and human BDNF binds to the N-terminal side of the single-chain antibody directly or via a linker.

(3) A fusion protein of BDNF and an anti-hTfR antibody, in which the anti-hTfR antibody is any one of Fab, F(ab'), and $F(ab')_2$, and human BDNF binds to the N-terminal side of the heavy chain or the light chain of Fab, F(ab'), and $F(ab')_2$ directly or via a linker.

Here, in the case of (3), human BDNF can particularly preferably binds to the N-terminal side of any one of Fab, F(ab'), and $F(ab')_2$ of the anti-hTfR antibody. Therefore, more specifically, the following one can be exemplified.

(4) A fusion protein of BDNF and an anti-hTfR antibody, in which the anti-hTfR antibody is any one of Fab, F(ab'), and $F(ab')_2$, and human BDNF binds to the N-terminal side of the heavy chain of Fab, F(ab'), and $F(ab')_2$ directly or via a linker.

In a case where the anti-hTfR antibody in the fusion protein is a Fab type, it is further possible to produce a new fusion protein of a type obtained by incorporating an Fc region of another IgG thereinto. In this manner, it is possible to increase stability of the fusion protein in a living body such as in the blood compared to the original fusion protein. Examples of such a fusion protein including an Fc region include a fusion protein in which human IgG Fc region binds to the C-terminal side of human BDNF directly or via a linker, and then a Fab heavy chain of the anti-hTfR antibody binds to the C-terminal side thereof directly or via a linker.

A linker sequence between human BDNF and a human IgG Fc region is formed of preferably 1 to 50 amino acids. Here, the number of the amino acids is appropriately adjusted as, for example, 1 to 17, 1 to 10, 10 to 40, 20 to 34, 23 to 31, 25 to 29, 27, and the like. Such a linker sequence is not particularly limited to the amino acid sequence, but preferably formed of glycine and serine. For example, an amino acid sequence formed of one amino acid either glycine or serine, an amino acid sequence Gly-Ser, an amino acid sequence Gly-Gly-Ser, an amino acid sequence Gly-Gly-Gly-Gly-Ser (SEQ ID NO: 3), an amino acid sequence Gly-Gly-Gly-Gly-Gly-Ser (SEQ ID NO: 4), an amino acid sequence Ser-Gly-Gly-Gly-Gly-(SEQ ID NO: 5), or a sequence in which 1 to 10, or 2 to 5 of these amino acid sequences are linked together, and is formed of 50 or less amino acids, an amino acid sequence formed of 2 to 17, 2 to 10, 10 to 40, 20 to 34, 23 to 31, 25 to 29, or 25 amino acids, and the like can be exemplified. For example, an amino acid sequence including a total of 25 amino acids in which five amino acid sequences Gly-Gly-Gly-Gly-Ser (SEQ ID NO: 3) are linked together can be appropriately used. The same applies to a linker sequence between a human IgG Fc region and a Fab heavy chain.

In a case of producing a fusion protein including a human IgG Fc region, the human IgG Fc region may bind to any one of the heavy chain and the light chain of the original anti-hTfR antibody. In addition, the original antibody may be any antigen-binding fragment including Fab, $F(ab')_2$, F(ab'), and a single-chain antibody.

The type of IgG of the introduced human IgG Fc region is not particularly limited, and may be any one of IgG1 to IgG4. In addition, the introduced human IgG Fc region may be all of the Fc region or a part thereof. A preferable embodiment of such a human IgG Fc region includes a region which is all region of Fc of human IgG1 and has an amino acid sequence represented by SEQ ID NO: 75. The Fc region is preferably introduced such that BDNF and the Fc region and the Fab heavy chain are positioned in an order from the N-terminal side. For example, as a fusion protein obtained by introducing the Fc region, a fusion protein including an amino acid sequence represented by SEQ ID NO: 74 in which all of the Fc region binds to the C-terminal side of BDNF and the Fab heavy chain of the anti-hTfR antibody binds to the C-terminal side, respectively, via a linker sequence is exemplified.

The fusion protein of the anti-hTfR antibody and hBDNF (anti-hTfR antibody-hBDNF fusion protein) can be modified to have affinity to albumin. The modification, for example, can be performed by introducing properties having affinity to albumin (for example, compound, peptide, protein, and the like having affinity to albumin) to the anti-hTfR antibody-hBDNF fusion protein. The anti-hTfR antibody-hBDNF fusion protein subjected to modification (modified fusion protein) binds to albumin and circulates in the blood. Albumin has a function of stabilizing a protein binding thereto. Therefore, the modified fusion protein has a longer half-life in the blood when administered into a living body, so that the medicinal efficacy of the modified fused protein can be enhanced. Modifying the fusion protein such that the fusion protein has affinity to albumin is more effective in a case where an anti-hTfR antibody in the anti-hTfR antibody-hBDNF fusion protein is lack of an Fc region contributing to stability of the antibody, for example, in a case where the anti-hTfR antibody is Fab.

In addition, in a case where the anti-hTfR antibody-hBDNF fusion protein shows immunogenicity when administered into a living body, performing modification such that the fusion protein has affinity to albumin is also effective. As the modified fusion protein binds to albumin, a site showing immunogenicity in the anti-hTfR antibody-hBDNF fusion protein is inhibited from being presented to an immune cell, which mitigates the immunogenicity.

In a case where a substance having affinity to albumin is introduced into the anti-hTfR antibody-hBDNF fusion protein, a portion into which the substance is introduced may be any one of a light chain of the anti-hTfR antibody, a heavy chain of the anti-hTfR antibody, hBDNF, and a linker portion, and the substance may be introduced into two or more portions thereof.

As a peptide or a protein having affinity to albumin, for example, a peptide obtained by modifying an albumin-binding domain of a protein derived from *Streptococcus* strain G418 (Alm T. Biotechnol J. 5. 605-17 (2010)) having an amino acid sequence represented by SEQ ID NO: 85 to show alkali resistance can be used, but is not limited thereto. As a method of binding a peptide or a protein having affinity to albumin (albumin-affinity peptide) to the anti-hTfR antibody-hBDNF fusion protein, there is a method of performing binding via a non-peptide linker or a peptide linker. As the non-peptide linker, polyethylene glycol, polypropylene glycol, a copolymer between ethylene glycol and propylene glycol, polyoxyethylated polyol, polyvinyl alcohol, polysaccharides, dextran, polyvinyl ether, a biodegradable polymer, a lipid polymer, chitins, hyaluronic acid, or the derivatives, or combinations thereof can be used. The peptide linker is a peptide chain formed of 1 to 50 amino acids bonded by a peptide bond or the derivatives, in which the N-terminus and the C-terminus respectively form a covalent bond with any one of an anti-hTfR antibody or BDNF, and thereby binds the anti-hTfR antibody and BDNF to each other.

The protein obtained by binding an albumin-affinity peptide and an anti-hTfR antibody-hBDNF fusion protein using PEG as the non-peptide linker is particularly referred to as albumin-affinity peptide-PEG-fusion protein. The albumin-affinity peptide-PEG-fusion protein can be produced by binding an albumin-affinity peptide and PEG to each other to produce albumin-affinity peptide-PM and then binding the albumin-affinity peptide-PEG and the anti-hTfR antibody-hBDNF fusion protein to each other. Or, the albumin-affinity peptide-PEG-fusion protein can be produced by binding the anti-hTfR antibody-hBDNF fusion protein and PEG to each other to produce anti-hTfR antibody-hBDNF fusion protein-PEG, and then binding the anti-hTfR antibody-hBDNF fusion protein-PEG and the albumin-affinity peptide. In a case of binding PEG to the albumin-affinity peptide and the anti-hTfR antibody-hBDNF fusion protein, PEG obtained by modified with a functional group such as carbonate, carbonyl imidazole, active ester of carboxylic acid, azlactone, cyclic imide thione, isocyanate, isothiocyanate, imidate, and aldehyde is used. The functional group introduced into the PEG mainly reacts with an amino group in the albumin-affinity peptide and the anti-hTfR antibody-hBDNF fusion protein molecules, and thereby PEG binds to the albumin-affinity peptide and the anti-hTfR antibody-hBDNF fusion protein via a covalent bond. At this time, the molecular weight and the shape of the used PEG are not particularly limited, but the average molecular weight (MW) is preferably MW=500 to 60,000, and more preferably MW=500 to 20,000. For example, PEG of which the average molecular weight is approximately 300, approximately 500, approximately 1,000, approximately 2,000, approximately 4,000, approximately 10,000, approximately 20,000, and the like can be appropriately used as a non-peptide linker.

For example, albumin-affinity peptide-PEG is obtained by mixing an albumin-affinity peptide and aldehyde group-modified PEG (ALD-PEG-ALD) with each other such that a molar ratio of the modified PEG to the albumin-affinity peptide is 11, 12.5, 15, 110, 120, and the like, and adding a reducing agent such as $NaCNBH_3$ thereto to perform reaction. Subsequently, by reacting the albumin-affinity peptide-PEG with the anti-hTfR antibody-hBDNF fusion protein under the presence of a reducing agent such as $NaCNBH_3$, albumin-affinity peptide-PEG-fusion protein is obtained. On the contrary, albumin-affinity peptide-PEG-fusion protein can be also obtained by binding anti-hTfR antibody-hBDNF fusion protein and ALD-PEG-ALD to each other first to produce anti-hTfR antibody-hBDNF fusion protein-PEG and then binding the anti-hTfR antibody-hBDNF fusion protein-PEG and the albumin-affinity peptide to each other.

The anti-hTfR antibody-hBDNF fusion protein can be fused with the albumin-affinity peptide. The fusion protein (anti-hTfR antibody-hBDNF-albumin-affinity peptide) can be obtained by inserting a DNA fragment in which cDNA encoding the albumin-affinity peptide is disposed in-frame on a 3'-terminal side or a 5'-terminal side of cDNA encoding a heavy chain or a light chain of the anti-hTfR antibody-hBDNF fusion protein directly or via a DNA fragment encoding a linker sequence into an expression vector for mammalian cell, and culturing a mammalian cell introduced with the expression vector. In a case where the DNA fragment encoding albumin-affinity peptide binds to the heavy chain (or the heavy chain and the fusion protein of hBDNF), the expression vector for mammalian cell into which the light chain constituting the anti-hTfR antibody and the cDNA fragment encoding the fusion protein light chain of hBDNF (or light chain) are inserted is also similarly introduced into a host cell, and in a case where a DNA fragment encoding the albumin-affinity peptide to a light chain (or light chain and fusion protein of hBDNF), the expression vector for mammalian cell into which the heavy chain constituting the anti-hTfR antibody and the cDNA fragment encoding the fusion protein of hBDNF (or heavy chain) are inserted is also similarly introduced into a host cell. That is, the albumin-affinity peptide may bind to any one of the N-terminal side or the C-terminal side of the heavy chain (including heavy chain and fusion protein of hBDNF) or the light chain (including light chain and fusion protein of hBDNF) of anti-hTfR antibody-hBDNF fusion protein, but in a case where hBDNF binds to the N-terminal side of the heavy chain of the anti-hTfR antibody, the albumin-affinity peptide preferably binds to the C-terminal side of the anti-hTfR antibody, and particularly preferably binds to the C-terminal side of the heavy chain. For example, as a fusion protein into which an albumin-affinity peptide is introduced, a fusion protein in which a heavy chain of an antibody binds to the C-terminal side of human BDNF directly or via a linker sequence, and an albumin-affinity peptide binds to the C-terminal side of the heavy chain directly or via a linker sequence is exemplified.

In a case where the anti-hTfR antibody-hBDNF fusion protein is fused with an albumin-affinity peptide, it is possible to perform fusion via a linker sequence. Here, the linker sequence is preferably formed of 1 to 50 amino acids. Here, the number of the amino acids is appropriately adjusted as, for example, 1 to 17, 1 to 10, 10 to 40, 20 to 34, 23 to 31, 25 to 29, 27, and the like. Such a linker sequence is not particularly limited to the amino acid sequence, but preferably formed of glycine and serine. For example, an amino acid sequence formed of one amino acid either glycine or serine, an amino acid sequence Gly-Ser, an amino acid sequence Gly-Gly-Ser, an amino acid sequence Gly-Gly-Gly-Gly-Ser (SEQ ID NO: 3), an amino acid sequence Gly-Gly-Gly-Gly-Gly-Ser (SEQ ID NO: 4), an amino acid sequence Ser-Gly-Gly-Gly-Gly-(SEQ ID NO: 5), or a sequence in which 1 to 10, or 2 to 5 of these amino acid sequences are linked together, and is formed of 50 or less amino acids, an amino acid sequence formed of 2 to 17, 2 to 10, 10 to 40, 20 to 34, 23 to 31, 25 to 29, or 25 amino acids, and the like can be exemplified. For example, an amino acid sequence including a total of 15 amino acids in which three amino acid sequences Gly-Gly-Gly-Gly-Ser (SEQ ID NO: 3) are linked together can be appropriately used.

Examples of an anti-hTfR antibody-hBDNF fusion protein into which an albumin-affinity peptide is introduced include a fusion protein in which a human anti-hTfR antibody 3NFab heavy chain having an amino acid sequence (SEQ ID NO: 84) corresponding the $1^{st}$ to $216^{th}$ of the amino acid sequence represented by SEQ ID NO: 61 is fused with a C-terminal side of a pro-protein of hBDNF having an amino acid sequence represented by SEQ ID NO: 56 via a linker sequence formed of a total of 25 amino acids obtained by repeating the amino acid sequence Gly-Gly-Gly-Gly-Ser represented by SEQ ID NO: 3 five times, and an albumin-binding domain (ABD) represented by SEQ ID NO: 85 is further fused with the C-terminal side via a linker sequence formed of a total of 15 amino acids obtained by repeating the amino acid sequence Gly-Gly-Gly-Gly-Ser represented by SEQ ID NO: 3 three times.

Binding affinity to albumin of the anti-hTfR antibody-hBDNF fusion protein into which an albumin-affinity peptide is introduced is preferably equal to or less than $1\times10^{-7}$ M, more preferably equal to or less than $5\times10^{-7}$ M, further more preferably equal to or less than $1\times10^{-8}$ M, and even further more preferably equal to or less than $1\times10^{-9}$ M when measured by a biolayer interference method described in Example 7.

The Fab antibody can be stabilized in the blood also by methods other than introduction of an Fc region or an albumin-affinity peptide. For example, the Fab antibody can be stabilized by PEG-modifying the Fab antibody, or a fusion body between the Fab antibody and another protein. The technique is generally performed in the field of protein pharmaceutical agent, and PEGylated erythropoietin, interferon, and the like are practically used as a pharmaceutical agent product. In addition, the Fab antibody can be stabilized by introducing mutation to these. For example, the Fab antibody can be stabilized by substituting methionine at the $4^{th}$ position from the N-terminal side of the light chain with leucine. However, the method of introducing mutation is not limited thereto, and mutation may be introduced to the heavy chain. In addition, the method of stabilizing the Fab antibody is not limited thereto, and all of known techniques can be used.

In a fusion protein of a type obtained by binding BDNF to the N-terminal side of the "light chain" constituting an anti-hTfR antibody, an anti-human transferrin receptor antibody includes an amino acid sequence including all or a part of a variable region of the light chain and an amino acid sequence including all or a part of the heavy chain, and BDNF binds to the N-terminal side of the light chain. Here, the light chain of the anti-hTfR antibody and BDNF may directly bind to each other, or may bind to each other via a linker.

In a fusion protein of a type obtained by binding BDNF to the N-terminal side of the "heavy chain" constituting an anti-hTfR antibody, an anti-human transferrin receptor antibody includes an amino acid sequence including all or a part of a variable region of the light chain and an amino acid sequence including all or a part of a variable region of the heavy chain, and BDNF binds to the N-terminal side of the heavy chain. Here, the heavy chain of the anti-hTfR antibody and BDNF may directly bind to each other, or may bind to each other via a linker.

In a fusion protein of a type obtained by binding BDNF to the C-terminal side of the "light chain" constituting an anti-hTfR antibody, an anti-human transferrin receptor antibody includes an amino acid sequence including all or a part of a variable region of the light chain and an amino acid sequence including all or a part of a variable region of the heavy chain, and BDNF binds to the C-terminal side of the heavy chain. Here, the heavy chain of the anti-hTfR antibody and BDNF may directly bind to each other, or may bind to each other via a linker.

In a fusion protein of a type obtained by binding BDNF to the C-terminal side of the "heavy chain" constituting an anti-hTfR antibody, an anti-human transferrin receptor antibody includes an amino acid sequence including all or a part of a variable region of the light chain and an amino acid sequence including all or a part of a variable region of the heavy chain, and BDNF binds to the C-terminal side of the heavy chain. Here, the heavy chain of the anti-hTfR antibody and BDNF may directly bind to each other, or may bind to each other via a linker.

Such a fusion protein of the anti-hTfR antibody and BDNF can be obtained by inserting a DNA fragment, in which cDNA (SEQ ID NO: 50) encoding BDNF is arranged in-frame on a 3'-terminal side or a 5'-terminal side of cDNA encoding the heavy chain or the light chain of an anti-hTfR antibody directly or via a DNA fragment encoding a linker sequence, into an expression vector for mammalian cell, and culturing a mammalian cell transfected with the expression vector. In a case where the DNA fragment encoding BDNF binds to the heavy chain, an expression vector for mammalian cell into which a cDNA fragment encoding the light chain constituting the anti-hTfR antibody is also similarly transfected into a host cell, and in a case where a DNA fragment encoding BDNF binds to a light chain, an expression vector for mammalian cell into which cDNA fragment encoding the heavy chain of the anti-hTfR antibody is inserted is also similarly transfected into a host cell.

Here, in the mammalian cell, by inserting an expression vector for mammalian cell into which a cDNA fragment encoding a fusion protein obtained by binding BDNF to the C-terminal side of the heavy chain (or light chain) of the anti-hTfR antibody directly or via a linker sequence and an expression vector for mammalian cell into which a cDNA fragment encoding the light chain (or heavy chain) of the anti-hTfR antibody is inserted into the same host cell, it is possible to produce a fusion protein obtained by binding BDNF to the C-terminal side of the heavy chain (or light chain) of the anti-hTfR antibody and a fusion protein including the heavy chain (or light chain) of the anti-hTfR antibody.

In addition, by transfecting an expression vector for mammalian cell into which a cDNA fragment encoding a fusion protein obtained by binding BDNF to the N-terminal side of the heavy chain (or light chain) of the anti-hTfR antibody directly or via a linker sequence and an expression vector for mammalian cell into which a cDNA fragment encoding the light chain (or heavy chain) of the anti-hTfR antibody is inserted into the same host cell, it is possible to produce a fusion protein obtained by binding BDNF to the N-terminal side of the heavy chain (or light chain) of the anti-hTfR antibody and a fusion protein including the light chain (or heavy chain) of the anti-hTfR antibody.

In a case where the anti-hTfR antibody is a single-chain antibody, a fusion protein of the anti-hTfR antibody and BDNF can be obtained by inserting a DNA fragment, in which a cDNA encoding a single-chain anti-hTfR antibody is linked to a 5'-terminus or a 3'-terminus of cDNA encoding BDNF directly or via a DNA fragment encoding a linker sequence, into an expression vector for mammalian cell, eukaryote cell such as yeast, or prokaryote such as *E. coli*, and performing expression in a cell corresponding to these transfected with the expression vector.

In a case where the anti-hTfR antibody is Fab, a fusion protein of the anti-hTfR antibody and BDNF can be obtained by transfecting an expression vector (for mammalian cell, eukaryote cell such as yeast, or prokaryote such as *E. coli*) into which a DNA fragment obtained by linking a cDNA encoding any one of the heavy chain or the light chain of the Fab to the 5'-terminal side or the 3'-terminal side of cDNA encoding BDNF directly or via a DNA fragment encoding a linker sequence is inserted and an expression vector into which a cDNA fragment encoding the other one of the Fab heavy chain and the light chain is inserted into the same host cell, and performing expression in the cell.

In a case of arranging a linker sequence between the anti-hTfR antibody and BDNF, the linker sequence is preferably formed of 1 to 50 amino acids. Here, the number of the amino acids is appropriately adjusted as, for example, 1 to 17, 1 to 10, 10 to 40, 20 to 34, 23 to 31, 25 to 29, 27, and the like. Such a linker sequence is not particularly limited to the amino acid sequence as long as an anti-hTfR antibody linked thereto maintains affinity to hTfR and the linked BDNF can exhibit physiological activity under a physiological condition, but preferably formed of glycine and serine. For example, an amino acid sequence is formed of one amino acid either glycine or serine, an amino acid sequence Gly-Ser, an amino acid sequence Gly-Gly-Ser, an amino acid sequence Gly-Gly-Gly-Gly-Ser (SEQ ID NO: 3), an amino acid sequence Gly-Gly-Gly-Gly-Gly-Ser (SEQ ID NO: 4), an amino acid sequence Ser-Gly-Gly-Gly-Gly-(SEQ ID NO: 5), or a sequence in which 1 to 10, or 2 to 5 of these amino acid sequences are linked together, and is formed of 50 or less amino acids, an amino acid sequence formed of 2 to 17, 2 to 10, 10 to 40, 20 to 34, 23 to 31, 25 to 29, or 25 amino acids, and the like can be exemplified. For example, an amino acid sequence including a total of 25 amino acid sequences acids in which five amino acid sequences Gly-Gly-Gly-Gly-Ser (SEQ ID NO: 3) are linked together can be appropriately used.

In a fusion protein of the anti-hTfR antibody and BDNF, in a case where the anti-hTfR antibody is a single-chain antibody, an amino acid sequence including all or a part of a variable region of the immunoglobulin light chain and an amino acid sequence including all or a part of a variable region of the immunoglobulin heavy chain generally bind to each other via a linker sequence. At this time, as long as affinity to hTfR of the anti-hTfR antibody is maintained, the fusion protein may be a fusion protein in which a linker sequence binds to a C-terminal side of the amino acid sequence including all or a part of a variable region of the immunoglobulin light chain, and the amino acid sequence including all or a part of a variable region of the immunoglobulin heavy chain further binds to the C-terminal side thereof, and the fusion protein may be a fusion protein in which a linker sequence binds to the C-terminal side of the amino acid sequence including all or a part of a variable region of the immunoglobulin heavy chain, and the amino acid sequence including all or a part of a variable region of the immunoglobulin light chain binds to the C-terminal side thereof.

The linker sequence arranged between the light chain and the heavy chain of the immunoglobulin is formed of preferably 2 to 50, more preferably 8 to 50, further more preferably 10 to 30, even further more preferably 12 to 18 or 15 to 25, for example, 15 or 25 amino acids. Such a linker sequence is not particularly limited to the amino acid sequence as long as an anti-hTfR antibody of which both chains are linked to each other by the linker sequence maintains affinity to hTfR and BDNF binding to the antibody can exhibit physiological activity under a physiological condition, but preferably formed of only glycine or glycine and serine. For example, an amino acid sequence Gly-Ser, an amino acid sequence Gly-Gly-Ser, an amino acid sequence Gly-Gly-Gly, an amino acid sequence Gly-Gly-Gly-Gly-Ser (SEQ ID NO: 3), an amino acid sequence Gly-Gly-Gly-Gly-Gly-Ser (SEQ ID NO: 4), an amino acid sequence Ser-Gly-Gly-Gly-Gly- (SEQ ID NO: 5), or a sequence in which 2 to 10, or 2 to 5 of these amino acid sequences are linked together. For example, in a case where a variable region of the immunoglobulin light chain binds to the C-terminal side of an amino acid sequence formed of all region of a variable region of the immunoglobulin heavy chain via a linker sequence, an amino acid sequence including a total of 15 amino acid sequences in which three amino acid sequences Gly-Gly-Gly-Gly-Ser represented by SEQ ID NO: 3 (SEQ ID NO: 3) are linked together can be appropriately used.

As an example of a specific embodiment of the fusion protein of an anti-hTfR antibody and BDNF, a fusion protein in which human BDNF is fused with the C-terminal side of an anti-hTfR antibody heavy chain via the amino acid sequence Gly-Ser as a linker sequence, and which has an amino acid sequence of SEQ ID NO: 52 is exemplified. By using a host cell obtained by transforming by transfecting an expression vector into which a DNA fragment having a nucleic acid sequence of SEQ ID NO: 53 encoding the fusion protein is inserted and a DNA fragment having a nucleic acid sequence of SEQ ID NO: 24 encoding an anti-hTfR antibody light chain having an amino acid sequence of SEQ ID NO: 23 together, it is possible to produce a fusion protein of an anti-hTfR antibody and human BDNF.

In a case where the anti-hTfR antibody is that of an animal other than human, when administering thereof to human, there is a high concern that antigen-antibody reaction to the antibody is caused, and unpreferable side effects occur. By making the antibody of an animal other than human into a humanized antibody, it is possible to decrease antigenicity and to suppress occurrence of the side effects resulting from the antigen-antibody reaction when administered to human. In addition, according to an experiment using a monkey, it has been reported that the humanized antibody is stabilized in the blood compared to a mouse antibody, and it is considered that it is possible to maintain the therapeutic effect for a long period of time that much. It is also possible to suppress occurrence of the side effects resulted from antigen-antibody reaction by using a human antibody as the anti-hTfR antibody.

In a case where the anti-hTfR antibody is a humanized antibody or a human antibody, more details are described as follows. In a light chain of a human antibody, there is a λ chain or a κ chain. The light chain constituting the anti-hTfR antibody may be any one of the λ chain or the κ chain. In addition, in a heavy chain of a human antibody, there are a γ chain, a μ chain, a α chain, a σ chain, and a ε chain, and respectively correspond to IgG, IgM, IgA, IgD, and IgE. The heavy chain constituting the anti-hTfR antibody may be any one of the γ chain, the μ chain, the α chain, the σ chain, and the ε chain, but is preferably the γ chain. In addition, in the γ chain of the human heavy chain, there are a γ1 chain, a γ2 chain, a γ3 chain, and a γ4 chain, and respectively correspond to IgG1, IgG2, IgG3, and IgG4. In a case where the heavy chain constituting the anti-hTfR antibody is a y chain, the γ chain may be any one of the γ1 chain, the γ2 chain, the γ3 chain, and the γ4 chain, and is preferably the γ1 chain or the γ4 chain. The anti-hTfR antibody is a humanized antibody or a human antibody, and in a case where the anti-hTfR antibody is IgG, the light chain of the human antibody may be any one of the λ chain or the k chain and the heavy chain of the human antibody may be any one of the γ1 chain, the γ2 chain, the γ3 chain, and the γ4 chain, but is preferably the γ1 chain or the γ4 chain. For example, as an embodiment of a preferable anti-hTfR antibody, an anti-hTfR antibody in which the light chain is a λ chain and the heavy chain is a γ1 chain is exemplified.

In a case where the anti-hTfR antibody is a humanized antibody or a human antibody, by binding a C-terminus (or N-terminus) of BDNF to an N-terminus (or C-terminus) of the heavy chain or the light chain of the anti-hTfR antibody, respectively, via a linker sequence or directly by a peptide bond, it is possible to link the anti-hTfR antibody and BDNF to each other. In a case of binding BDNF to the N-terminal side (or C-terminal side) of the heavy chain of the anti-hTfR antibody, the C-terminus (or N-terminus) of BDNF binds to the N-terminus (or C-terminus) of the γ chain, the μ chain, the α chain, the σ chain, and the ε chain of the anti-hTfR antibody, respectively, via a linker sequence or directly by a peptide bond. In a case of binding BDNF to the N-terminal side (or C-terminal side) of the light chain of the anti-hTfR antibody, the C-terminus (or N-terminus) of BDNF binds to the N-terminus (or C-terminus) of the λ chain or the κ chain of the anti-hTfR antibody, respectively, via a linker sequence or directly by a peptide bond. However, in a case where the anti-hTfR antibody is (Fab, F(ab'), and $F(ab')_2$) of an antibody formed of a Fab region which is lack of an Fc region or an antibody including all or a part of the Fab region and a hinge region, it is possible to bind the C-terminus or the N-terminus of BDNF to the N-terminus (or C-terminus) of the heavy chain or the light chain constituting Fab, F(ab'), and $F(ab')_2$, respectively, via a linker sequence or directly by a peptide bond.

In a fusion protein of a type obtained by binding BDNF to the C-terminal side or the N-terminal side of the "light chain" of the anti-hTfR antibody (which is a humanized antibody or a human antibody), the anti-hTfR antibody includes an amino acid sequence including all or a part of a variable region of the light chain and an amino acid sequence including all or a part of a variable region of the heavy chain, in which BDNF binds to the C-terminal side or the N-terminal side of the light chain. Here, the light chain and BDNF of the anti-hTfR antibody may directly bind to each other, or may fuse to each other via a linker.

In a fusion protein of a type obtained by binding BDNF to the C-terminal side or the N-terminal side of the "heavy chain" of the anti-hTfR antibody (which is a humanized antibody or a human antibody), the anti-human transferrin receptor antibody includes an amino acid sequence including all or a part of a variable region of the light chain and an amino acid sequence including all or a part of a variable region of the heavy chain, in which BDNF binds to the C-terminal side or the N-terminal side of the heavy chain. Here, the heavy chain and BDNF of the anti-hTfR antibody may directly bind to each other, or may bind to each other via a linker.

In a case where a linker sequence is arranged between the anti-hTfR antibody and BDNF, the linker sequence is formed of preferably 1 to 50, more preferably 10 to 40, further more preferably 20 to 34, for example, 27 amino acids. The number of the amino acids constituting the linker sequence is appropriately adjusted as, for example, 1 to 17, 1 to 10, 10 to 40, 20 to 34, 23 to 31, 25 to 29, 27, and the like. Such a linker sequence is not particularly limited to the amino acid sequence as long as the anti-hTfR antibodies linked by the linker sequence maintain affinity to hTfR and the linked BDNF can exhibit physiological activity under a physiological condition, but preferably formed of glycine and serine. For example, an amino acid sequence formed of one amino acid either, an amino acid sequence Gly-Ser, an amino acid sequence Gly-Gly-Ser, an amino acid sequence Gly-Gly-Gly-Gly-Ser (SEQ ID NO: 3), an amino acid sequence Gly-Gly-Gly-Gly-Gly-Ser (SEQ ID NO: 4), an amino acid sequence Ser-Gly-Gly-Gly-Gly-(SEQ ID NO: 5), or a sequence in which 1 to 10, or 2 to 5 of these amino acid sequences are linked together, and is formed of 50 or less amino acids, an amino formed of 2 to 17, 2 to 10, 10 to 40, 20 to 34, 23 to 31, 25 to 29, or 25 amino acids, and the like can be exemplified. For example, an amino acid sequence including a total of 25 amino acid sequences acids in which five amino acid sequences Gly-Gly-Gly-Gly-Ser (SEQ ID NO: 3) are linked together can be appropriately used as a linker sequence.

Specific affinity of the anti-hTfR antibody to hTfR mainly depends on the amino acid sequences of CDRs of the heavy chain and the light chain of the anti-hTfR antibody. There is no particular limitation as to the amino acid sequences of CDRs insofar as the anti-hTfR antibody has a specific affinity to monkey TfR in addition to hTfR.

In the present invention, when the anti-hTfR antibody is a humanized antibody or a human antibody, an antibody having relatively high affinity to hTfR and also having affinity to monkey TfR, as particularly measured by the method described in Example 7, exhibits a dissociation constant with human TfR and monkey TfR described as follows:

(a) Dissociation constant with hTfR: Preferably not more than $1\times10^{-10}$ M, more preferably not more than $2.5\times10^{-11}$ M, further more preferably not more than $5\times10^{-12}$ M, and even further more preferably not more than $1\times10^{-12}$ M, (b) Dissociation constant with monkey TfR: Preferably not more than $1\times10^{-9}$ M, more preferably not more than $5\times10^{-10}$ M, further more preferably not more than $1\times10^{-10}$ M, for example, not more than $7.5\times10^{-11}$ M.

Examples of the dissociation constant with hTfR and monkey TfR are, respectively, not more than $1\times10^{-10}$ M and not more than $1\times10^{-9}$ M, not more than $1\times10^{-11}$ M and not more than $5\times10^{-10}$ M, not more than $5\times10^{-12}$ M and not more than $1\times10^{-10}$ M, not more than $5\times10^{-12}$ M and not more than $7.5\times10^{-11}$ M, not more than $1\times10^{-12}$ M and not more than $1\times10^{-10}$ not more than $1\times10^{-12}$ M and not more than $7.5\times10^{-11}$ M, M. Here, although there is no particular and clear lower limit value in the dissociation constant with human TfR, examples of such dissociation constant with human TfR can be $5\times10^{-13}$ M, $1\times10^{-13}$ M, and the like. In addition, there is also no particular and clear lower limit value in the dissociation constant with monkey TfR, examples of such dissociation constant with monkey TfR can be $5\times10^{-11}$ M, $1\times10^{-11}$ M, $1\times10^{-12}$ M, and the like. The same also applies when the antibody is a single-chain antibody.

As a preferable embodiment of an antibody having affinity to hTfR to be fused with BDNF, an antibody in which CDR of a heavy chain of the antibody has an amino acid sequence shown below is exemplified. That is:

An antibody in which CDR1 includes an amino acid sequence of SEQ ID NO: 66 or SEQ ID NO: 67, CDR2 includes an amino acid sequence of SEQ ID NO: 13 or SEQ ID NO: 14, and CDR3 includes an amino acid sequence of SEQ ID NO: 15 or SEQ ID NO: 16.

As a further specific embodiment of the antibody having affinity to hTfR, an antibody in which CDR has an amino acid sequence shown below can be exemplified. That is:

An antibody in which CDR1 includes an amino acid sequence of SEQ ID NO: 66, CDR2 includes an amino acid sequence of SEQ ID NO: 13, and CDR3 includes an amino acid sequence of SEQ ID NO: 15.

In the preferable embodiment, as a preferably amino acid sequence of a framework region 3 of a heavy chain of the antibody, the one having an amino acid sequence of SEQ ID NO: 68 is exemplified.

As a preferable combination of the light chain and the heavy chain of an antibody having affinity to hTfR, the one in which CDR has an amino acid sequence shown below can be exemplified. That is:

A combination between a light chain in which CDR1 includes an amino acid sequence of SEQ ID NO: 6 or SEQ ID NO: 7, CDR2 includes an amino acid sequence of SEQ ID NO: 8 or SEQ ID NO: 9, or an amino acid sequence Lys-Val-Ser, and CDR3 includes an amino acid sequence of SEQ ID NO: 10, and a heavy chain in which CDR1 includes an amino acid sequence of SEQ ID NO: 66 or SEQ ID NO: 67, CDR2 includes an amino acid sequence of SEQ ID NO: 13 or SEQ ID NO: 14, and CDR3 includes an amino acid sequence of SEQ ID NO: 15 or SEQ ID NO: 16.

As a specific embodiment of combination of the light chain and the heavy chain of the antibody having affinity to hTfR, an antibody in which CDR has an amino acid sequence shown below can be exemplified. That is:

A combination between a light chain in which in which CDR1 includes an amino acid sequence of SEQ ID NO: 6, CDR2 includes an amino acid sequence of SEQ ID NO: 8, and CDR3 includes an amino acid sequence of SEQ ID NO: 10, and a heavy chain in which CDR1 includes an amino acid sequence of SEQ ID NO: 66, CDR2 includes an amino acid sequence of SEQ ID NO: 13, and CDR3 includes an amino acid sequence of SEQ ID NO: 15.

As a preferable embodiment of a humanized antibody having affinity to hTfR antibody, an antibody having an amino acid sequence shown below can be exemplified. That is:

An anti-hTfR antibody, in which a variable region of the light chain includes an amino acid selected from the group consisting of amino acid sequences represented by SEQ ID NO: 17, SEQ ID NO: 18, SEQ ID NO: 19, SEQ ID NO: 20, SEQ ID NO: 21, and SEQ ID NO: 22, and a variable region of the heavy chain includes an amino acid represented by SEQ ID NO: 69.

Amino acid sequences of the light chain variable region represented by SEQ ID NO: 17, SEQ ID NO: 18, SEQ ID NO: 19, SEQ ID NO: 20, SEQ ID NO: 21, and SEQ ID NO: 22 are amino acid sequences in which CDR1 includes an amino acid sequence of SEQ ID NO: 6 or SEQ ID NO: 7, CDR2 includes an amino acid sequence of SEQ ID NO: 8 or SEQ ID NO: 9, and CDR3 includes an amino acid sequence of SEQ ID NO: 10, respectively. However, in the amino acid sequences of SEQ ID NO: 17 to SEQ ID NO: 22, amino acid sequences of CDRs are not limited thereto, and the region including the amino acid sequences of the CDRs, and an amino acid sequence including three or more amino acids obtained by optionally linking amino acid sequences of the CDRs can also be CDRs.

Amino acid sequences of the heavy chain variable region represented by SEQ ID NO: 69 respectively include amino acid sequences in which CDR1 includes an amino acid sequence of SEQ ID NO: 66 or SEQ ID NO: 67, CDR2 includes an amino acid sequence of SEQ ID NO: 13 or SEQ ID NO: 14, and CDR3 includes an amino acid sequence of SEQ ID NO: 15 or SEQ ID NO: 16. However, in the amino acid sequences of SEQ ID NO: 69, amino acid sequences of CDRs are not limited thereto, and the region including the amino acid sequences of the CDRs, and an amino acid sequence including three or more amino acids obtained by optionally linking amino acid sequences of the CDRs can also be CDRs.

Examples of a further specific embodiment of a humanized antibody having affinity to hTfR include:

(1a) an antibody in which a variable region of the light chain includes an amino acid sequence of SEQ ID NO: 18, and a variable region of the heavy chain includes an amino acid sequence of SEQ ID NO: 69, (1b) an antibody in which a variable region of the light chain includes an amino acid sequence of SEQ ID NO: 20 and a variable region of the heavy chain includes an amino acid sequence of SEQ ID NO: 69, (1c) an antibody in which a variable region of the light chain includes an amino acid sequence of SEQ ID NO: 21 and a variable region of the heavy chain includes an amino acid sequence of SEQ ID NO: 69, and (1d) an antibody in which a variable region of the light chain includes an amino acid sequence of SEQ ID NO: 22 and a variable region of the heavy chain includes an amino acid sequence of SEQ ID NO: 69.

Examples of a further specific embodiment of a humanized antibody having affinity to hTfR include:

(2a) an antibody in which the light chain includes an amino acid sequence of SEQ ID NO: 23 and the heavy chain includes an amino acid sequence of SEQ ID NO: 70 or SEQ ID NO: 72, (2b) an antibody in which the light chain includes an amino acid sequence of SEQ ID NO: 25 and the heavy chain includes an amino acid sequence of SEQ ID NO: 70 or SEQ ID NO: 72, (2c) an antibody in which the light chain includes an amino acid sequence of SEQ ID NO: 27 and the heavy chain includes an amino acid sequence of SEQ ID NO: 70 or SEQ ID NO: 72, (2d) an antibody in which the light chain includes an amino acid sequence of SEQ ID NO: 29 and the heavy chain includes an amino acid sequence of SEQ ID NO: 70 or SEQ ID NO: 72.

Examples of a further specific embodiment of a humanized antibody which is Fab having affinity to hTfR include:

(3a) an antibody in which the light chain includes an amino acid sequence of SEQ ID NO: 23 and the Fab heavy chain includes an amino acid sequence of SEQ ID NO: 61, (3b) an antibody in which the light chain includes an amino acid sequence of SEQ ID NO: 25 and the Fab heavy chain includes an amino acid sequence of SEQ ID NO: 61, (3c) an antibody in which the light chain includes an amino acid sequence of SEQ ID NO: 27 and the Fab heavy chain includes an amino acid sequence of SEQ ID NO: 61, and (3d) an antibody in which the light chain includes an amino acid sequence of SEQ ID NO: 29 and the Fab heavy chain includes an amino acid sequence of SEQ ID NO: 61.

In a case where the anti-hTfR antibody is Fab, examples of a specific embodiment of an antibody in which another Fc region is introduced into a fusion protein include:

(4a) an antibody in which the light chain includes an amino acid sequence of SEQ ID NO: 23 and the Fab heavy chain in which a Fc region is introduced includes an amino acid sequence of SEQ ID NO: 81, (4b) an antibody in which the light chain includes an amino acid sequence of SEQ ID NO: 25 and the Fab heavy chain in which a Fc region is introduced includes an amino acid sequence of SEQ ID NO: 81, (4c) an antibody in which the light chain includes an amino acid sequence of SEQ ID NO: 27 and the Fab heavy chain in which a Fc region is introduced includes an amino acid sequence of SEQ ID NO: 81, and (4d) an antibody in which the light chain includes an amino acid sequence of SEQ ID NO: 29 and the Fab heavy chain in which a Fc region is introduced includes an amino acid sequence of SEQ ID NO: 81.

The amino acid sequence represented by SEQ ID NO: 81 is an amino acid sequence obtained by binding a human IgG Fc region having an amino acid sequence represented by SEQ ID NO: 75 to the N-terminal side of an amino acid sequence (amino acid sequence 61) of a Fab heavy chain of a humanized anti-hTfR antibody 3N via a linker sequence including a total of 25 amino acids of five consecutive amino acid sequences Gly-Gly-Gly-Gly-Ser (SEQ ID NO: 3).

In (4a) to (4d), for example, a human IgG Fc region binds to the C-terminal side of human BDNF directly or via a linker sequence, and an anti-human transferrin receptor antibody binds to the C-terminal side of the human IgG Fc region directly or via a linker sequence.

Examples of a preferable embodiment of the human IgG Fc region include the one having an amino acid sequence of SEQ ID NO: 75. In addition, examples of a fusion protein into which a human IgG Fc region is introduced include a fusion protein having an amino acid sequence of SEQ ID NO: 74 in which a Fc region binds to the C-terminal side of BDNF and the Fab heavy chain of an anti-hTfR antibody binds to the C-terminal side thereof, respectively, via a linker sequence.

In a case where the anti-hTfR antibody is Fab, examples of a specific embodiment of the anti-hTfR antibody in which an albumin-affinity peptide is introduced into a fusion protein include an anti-hTfR antibody, in which the albumin-affinity peptide is an albumin-binding domain having an amino acid sequence represented by SEQ ID NO: 85, (5a) the light chain includes an amino acid sequence of SEQ ID NO: 23, and the Fab heavy chain into which an albumin-affinity peptide is introduced includes an amino acid sequence of SEQ ID NO: 89, (5b) the light chain includes an amino acid sequence of SEQ ID NO: 25, and the Fab heavy chain into which an albumin-affinity peptide is introduced includes an amino acid sequence of SEQ ID NO: 89, (5c) the light chain includes an amino acid sequence of SEQ ID NO: 27, and the Fab heavy chain into which an albumin-affinity peptide is introduced includes an amino acid sequence of SEQ ID NO: 89, (5d) the light chain includes an amino acid sequence of SEQ ID NO: 29, and the Fab heavy chain into which an albumin-affinity peptide is introduced includes an amino acid sequence of SEQ ID NO: 89.

The amino acid sequence represented by SEQ ID NO: 89 is an amino acid sequence obtained by binding an albumin-affinity peptide having an amino acid sequence represented by SEQ ID NO: 85 to the C-terminal side of an amino acid sequence (amino acid sequence 61) of the Fab heavy chain of a humanized anti-hTfR antibody 3N via a linker sequence including a total of 15 amino acids of three consecutive amino acid sequences Gly-Gly-Gly-Gly-Ser (SEQ ID NO: 3).

In (5a) to (5d), for example, an anti-human transferrin receptor antibody binds to the C-terminal side of human BDNF directly or via a linker sequence, and an albumin-affinity peptide binds to the C-terminal side of the anti-human transferrin receptor antibody directly or via a linker sequence.

Examples of a preferable embodiment of an albumin-affinity peptide include an albumin-affinity peptide having an amino acid sequence of SEQ ID NO: 85. In addition, examples of a fusion protein into which an albumin-affinity peptide is introduced include a fusion protein having an amino acid sequence of SEQ ID NO: 87 or SEQ ID NO: 88 in which a Fab heavy chain binds to the C-terminal side of human pro BDNF or human BDNF and an albumin-affinity peptide binds to the C-terminal side thereof via a linker sequence, respectively.

A preferable embodiment of the humanized antibody having affinity to hTfR was exemplified as described above. To the light chain and the heavy chain of the anti-hTfR antibody it is possible to appropriately add mutation such as substitution, deletion, addition, and the like to an amino acid sequence of the variable region, for the purpose of adjusting affinity of hTfR to an anti-hTfR antibody to be desirable. Or to the light chain and the heavy chain of the anti-hTfR antibody it is possible to appropriately add mutation such as substitution, deletion, addition, and the like to hBDNF, for the purpose of adjusting functions of hBDNF to be desirable.

In a case of substituting an amino acid of an amino acid sequence of a variable region of a light chain with another amino acid, the number of the substituted amino acids is preferably 1 to 10, more preferably 1 to 5, further more preferably 1 to 3, and even further more preferably 1 to 2. In a case of deleting an amino acid in the amino acid sequence of the variable region of the light chain, the number of the deleted amino acids is preferably 1 to 10, more preferably 1 to 5, further more preferably 1 to 3, and even further more preferably 1 to 2. In addition, it is possible to add mutation in which substitution and deletion of the amino acids are combined.

In a case of adding an amino acid to the variable region of the light chain, preferably 1 to 10, more preferably 1 to 5, further more preferably 1 to 3, even further more preferably 1 to 2 amino acids are added inside, or on the N-terminal side or the C-terminal side in the amino acid sequence of the variable region of the light chain. It is possible to add mutation in which addition, substitution, and deletion of the amino acids are combined. The amino acid sequence of the variable region of the light chain to which mutation is added has preferably 80% or more homology, more preferably 90% or more homology, and further more preferably 95% or more homology to the original amino acid sequence of the variable region of the light chain.

In a case where an amino acid is substituted with another amino acid in each amino acid sequence of each CDR or each framework region of the light chain, the number of the substituted amino acids is preferably 1 to 5, more preferably 1 to 3, further more preferably 1 to 2, and even further more preferably 1. In a case where an amino acid is deleted in each amino acid of sequence of each CDR or each framework region, the number of the deleted amino acids is preferably 1 to 5, more preferably 1 to 3, further more preferably 1 to 2, and even further more preferably 1. In addition, it is possible to add mutation in which substitution and deletion of the amino acids are combined.

In a case where an amino acid is added in each amino acid sequence of each CDR or each framework region of the light chain, preferably 1 to 5, more preferably 1 to 3, further more preferably 1 to 2, and even further more preferably 1 amino acids are added inside, or on the N-terminal side or the C-terminal side in the amino acid sequence. It is possible to add mutation in which addition, substitution, and deletion of the amino acids are combined. Each amino acid sequence of each CDR or each framework region to which mutation is added has preferably 80% or more homology, more preferably 90% or more homology, and further more preferably 95% or more homology to the original amino acid sequence of each CDR.

In a case where an amino acid of an amino acid sequence represented by SEQ ID NO: 69 which is a variable region of the heavy chain is substituted with another amino acid, the number of the substituted amino acids is preferably 1 to 10, more preferably 1 to 5, further more preferably 1 to 3, and even further more preferably 1 to 2. In a case where an amino acid is deleted in the amino acid sequence of a variable region of the heavy chain, the number of the deleted amino acids is preferably 1 to 10, more preferably 1 to 5, further more preferably 1 to 3, and even further more preferably 1 to 2. In addition, it is possible to add mutation in which substitution and deletion of the amino acids are combined.

In a case where an amino acid is added to the amino acid sequence represented by SEQ ID NO: 69 which is a variable of the heavy chain, preferably 1 to 10, more preferably 1 to 5, further more preferably 1 to 3, and even further more preferably 1 to 2 amino acids are added to the amino acid sequence of a variable region of the heavy chain or the N-terminal side or the C-terminal side. It is possible to add mutation in which addition, substitution, and deletion of the amino acids are combined. The amino acid sequence of a variable region of the heavy chain to which mutation is added has preferably 80% or more homology, more preferably 90% or more homology, and further more preferably 95% or more homology to the original amino acid sequence of a variable region of the heavy chain.

In particular, in a case where an amino acid in each amino acid sequence of each CDR or each framework region, of the amino acid sequences represented by SEQ ID NO: 69, is substituted with another amino acid, the number of the substituted amino acids is preferably 1 to 5, more preferably 1 to 3, further more preferably 1 to 2, and even further more preferably 1. In a case where an amino acid in each amino acid sequence of each CDR is deleted, the number of the deleted amino acids is preferably 1 to 5, more preferably 1 to 3, further more preferably 1 to 2, and even further more preferably 1. In addition, it is possible to add mutation in which substitution and deletion of the amino acids are combined.

In a case where an amino acid is added to each amino acid sequence of each CDR or each framework region in the amino acid sequence represented by SEQ ID NO: 69, preferably 1 to 5, more preferably 1 to 3, further more preferably 1 to 2, and even further more preferably 1 amino acids are added to the amino acid sequence or the N-terminal side or the C-terminal side. It is possible to add mutation in which addition, substitution, and deletion of the amino acids are combined. Each amino acid sequence of each CDR to which mutation is added has preferably 80% or more homology, more preferably 90% or more homology, and further more preferably 95% or more homology to the original amino acid sequence of each CDR.

In a case where mutation such as substitution, deletion, and addition is added to the amino acid sequence represented by SEQ ID NO: 69 which is a variable region of the heavy chain of an anti-hTfR antibody as above, methionine which is an amino acid at the $5^{th}$ position from the N-terminal side of the original CDR1 and leucine which is an amino acid at the $17^{th}$ position from the N-terminal side of the framework region 3 are conserved at the same position as that before mutation. In addition, the amino acid sequence of CDR1 and the framework region 3 of the heavy chain are preferably conserved.

By combining mutation to the variable region of the light chain of the anti-hTfR antibody and mutation to the variable region of the heavy chain of the anti-hTfR antibody with each other, it is possible to add mutation to both of the variable region of the light chain and the variable region of the heavy chain of the anti-hTfR antibody.

Substitution of an amino acid with another amino acid in the amino acid sequence of the heavy chain and the light chain of the anti-hTfR antibody includes substitution between amino acids classified into the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), and amino acids having a hydroxyl group (Ser, Thr). Such substitution by similar amino acids is estimated to cause no change in a phenotype of protein (that is, conservative amino acid substitution). However, SEQ ID NO: 83 which is an amino acid sequence of a framework region 3 of hTfR of an antibody No. 3 (non-disclosed at the time of application of the present application) on which the present inventors confirm to have the same kind of effect as that of the present invention is an amino acid in which the $17^{th}$ position is Trp, and the framework region 3 of the heavy chain of the anti-hTfR antibody No. 3N in the present invention with respect to this has an amino acid sequence of SEQ ID NO: 68, and the $17^{th}$ position is substituted with Leu from the N-terminal side. In addition, in an amino acid sequence of CDR1, Thr at the $5^{th}$ position of SEQ ID NO: 12 is substituted with Met as represented by SEQ ID NO: 66. Trp and Leu are not in the similar relationship to the above, and Thr and Met are also not in the similar relationship to the above. However, as will be described later, the antibody No. 3N including the substitution is unexpectedly the same in terms of the effect as the antibody No. 3, and exhibits a further excellent effect.

In a case where mutation is added to an anti-hTfR antibody or hBDNF, and an amino acid is added to the C-terminal side or the N-terminal side, in a case where the added amino acid is positioned between the anti-hTfR antibody and BDNF when the anti-hTfR antibody is fused with BDNF, the added amino acid constitutes a part of a linker.

(1) Method of Producing Fusion Protein

The fusion protein of the present invention can be produced by a method described in examples described below or a known method in the field.

For example, cells or transgenic animals and plants producing the fusion protein of the present invention can be obtained by respectively constructing an expression vector having DNA encoding a fusion protein formed by fusing C-terminus of BDNF with the N-terminus of the heavy chain of the anti-human transferrin receptor antibody, which is acquired as described in Examples 16 and 17 of the present specification, directly or via a linker (e.g., consisting of 25 amino acids obtained by repeating SEQ ID NO: 3 five times) and an expression vector for animals or plants having DNA encoding the light chain of the antibody, and then co-transfection of both expression vectors into appropriate host cells. Or, cells or transgenic animals and plants producing the fusion protein of the present invention can be obtained by respectively constructing an expression vector having DNA encoding a fusion protein formed by fusing the C-terminus of BDNF with the N-terminus of the light chain of the anti-human transferrin receptor antibody directly or via linker (Examples of such linker include which are composed of 25 amino acids consisting of repeating SEQ ID NO: 3 five times) and an expression vector having DNA encoding the heavy chain of the antibody, and then co-transfection of both expression vectors into appropriate host cells.

The gene of the fusion protein constructed as described above can be expressed and obtained according to publicly-known methods. In order to maximize an expression level of the fusion protein, nucleotide sequence of the fusion protein gene may be optimized depending on the frequency of codon usage of cells or animal species used in the expression of the fusion protein. In a case of mammalian cells, the fusion protein can be expressed using a commonly used useful promoter, an antibody gene to be expressed, DNA consisting of poly A signal functionally ligated to the downstream of the 3'-end thereof, or a vector consisting of it. Examples of the promoter/enhancer include human cytomegalovirus immediate early promoter/enhancer.

In addition, examples of other promoter/enhancer, which can be used for the expression of the antibody in the present invention, are a virus promoter/enhancer such as retrovirus, polyomavirus, adenovirus, and simian virus 40 (SV40) and a promoter/enhancer derived from a mammalian cell such as human elongation factor 1α (hEF1μ).

For example, in a case of using an SV40 promoter/enhancer, expression may be easily performed according to a method of Mulligan et al. (Mulligan, R. C. et al., Nature (1979) 277, 108-114), and in a case of using an hEF1α promoter/enhancer, expression may be easily performed according to a method of Mizushima et al. (Mizushima, S. AND Nagata, S. Nucleic Acids Res. (1990) 18, 5322).

In a case of *E. coli*, the commonly used useful promoter, the signal sequence for antibody secretion, and the antibody gene to be expressed may be functionally ligated, to express the antibody thereof. Examples of such promoters include lacZ promoter, araB promoter, and the like. In a case of using the lacZ promoter, expression may be performed according to a method of Ward et al. (Ward, E. S. et al., Nature (1989) 341, 544-546; Ward, E. S. et al., FASEB J. (1992) 6, 2422-2427), and in a case of using the araB promoter, expression may be performed according to a method of Better et al. (Better, M. et al., Science (1988) 240, 1041-1043).

As a signal sequence for antibody secretion, in a case of performing production in periplasm of *E. coli*, a pelB signal sequence (Lei, S. P. et al., J. Bacteriol. (1987) 169, 4379-4383) may be used (for example, refer to WO 96/30394).

As replication origin, those derived from SV40, polyomavirus, adenovirus, bovine papillomavirus (BPV), and the like can be used, and the expression vector can include an aminoglycoside phosphotransferase (APH) gene, a thymidine kinase (TK) gene, an *E. coli* xanthanum phosphoribosyltransferase (Ecogpt) gene, a dihydrofolate reductase (dhfr) gene, and the like as a selection marker for amplification of gene copy number in the host cells.

In a case of using eukaryotic cell, there are production systems using animal cells, plant cells, or fungal cells. As the animal cell, (1) mammalian cells, such as CHO, HEK293, COS, myeloma, BHK (baby hamster kidney), HeLa, Vero, and the like, (2) amphibian cells, such as *Xenopus* oocyte, or (3) insect cells, such as sf9, sf21, and Tn5 are known. As plant cells, cells derived from *Nicotiana tabacum* are known, and these may be subjected to callus-culture. As fungal cells, yeast, such as *Saccharomyces* genus, *Saccharomyces cerevisiae*, the filamentous bacteria, *Aspergillus* genus, *Aspergillus niger*, and the like are known.

In a case of using prokaryotic cells, there are a production systems using bacterial cells. As the bacterial cells, *E. coli* and *Bacillus subtilis* are known.

An antibody can be obtained by introducing the targeted antibody gene with transformation and cultivation of the transformed cells in vitro. Culturing is performed by a known method. For example, as a culturing media, DMEM, MEM, RPMI1640, and IMDM can be used, and serum replacement such as fetal calf serum (FCS) can be also used in combination. In addition, the antibody can be produced in vivo by transplanting the antibody gene transformed cells into the abdominal cavity of animals As an in vivo production system, a production system using an animal and a production system using a plant are exemplified. In a case of using an animal, there are production systems using mammalian animals, insects or the like.

As the mammalian animal, a goat, a pig, a sheep, a mouse, a bovine, and the like can be used (Vicki Glaser, SPECTRUM Biotechnology Applications, 1993). In addition, as the insect, a silkworm can be used. In a case of using the plant, for example, tobacco can be used.

A fusion protein can be produced and harvested by transforming the fusion protein gene into the animal or the plant, and then the fusion protein is expressed in the body of the animal or the plant. For example, a fusion protein can be prepared by transforming gene inserted into the gene encoding a protein specifically produced in milk such as goat β-casein. A DNA fragment including the fusion gene into which an antibody gene is inserted is injected into a goat embryo, and the embryo is transplanted into a female goat. The desired fusion protein can be obtained from milk produced by a transgenic goat which was born from the embryo-received goat, or by the offspring goat thereof. In order to increase an amount of milk containing the desired fusion protein produced from the transgenic goat, hormones may be used for the transgenic goat as appropriate (Ebert, K. M. et al., Bio/Technology (1994) 12, 699-702).

In addition, in a case of using a silkworm, the desired antibody can be obtained from body fluid of the silkworm which is infected with baculovirus into which the target fusion protein gene has been inserted (Maeda, S. et al., Nature (1985) 315, 592-594). Moreover, in a case of using a tobacco, a targeted fusion protein gene is inserted into a plant expression vector, such as pMON 530, and the vector is transfected into a bacteria such as *Agrobacterium tumefaciens*. Thereafter, the desired fusion protein can be obtained from the leaves of the tobacco plant such as *Nicotiana tabacum* infected with the bacteria (Julian, K.-C. Ma et al., Eur. J. Immunol. (1994) 24, 131-138).

The fusion protein produced and expressed as described above can be separated from the host cells, intra and extra of the cells and can be purified to a homogeneous state. The fusion protein used in the present invention can be separated and purified by affinity chromatography. Examples of columns used in the affinity chromatography include protein A column, protein G column, and protein L column. Examples of resins used in the protein A column include Hyper D, POROS, Sepharose F. F., and the like. Other than these methods, commonly used protein separation and purification may be used, and are not limited at all. As necessary, combining chromatography other than the above described affinity chromatography, filtration, ultrafiltration, salting-out, dialysis and the like may work to separate and to purify the antibody used in the present invention. Examples of the chromatography include ion exchange chromatography, hydrophobic chromatography, gel filtration, and the like. The chromatography method can be applied to HPLC (high performance liquid chromatography). In addition, reverse phase HPLC may be also used.

A homodimer of BDNF specifically binds to a BDNF receptor (TrkB) which is present on a target cell surface, and BDNF plays an important role in differentiation of cells, maintenance of functions, synaptogenesis, and regeneration and repair after damage in impairment of central and peripheral nervous systems (Non-Patent Literatures 1 and 2). Because of such actions, BDNF has been focused as a protein widely applicable to treatment of diseases associated with damage of the central and peripheral nervous systems.

In addition, it has been reported that a reduction in the expression or amount of BDNF occurs in various diseases associated with nervous systems such as Huntington's disease, Parkinson's disease, and Alzheimer's disease (Nuerosci. Lett. (1999) 270: 45-48), and it has been shown that BDNF, which is continuously injected into the brain or the intrathecal space of these disease model animals by using an osmotic pressure pump and the like, exhibits effects such as suppression of the nerve cell death in the striatum, improvement of movement disorder, and amelioration of memory deficits (J. Nuerosci. (2004) 24: 7727-7739, Proc. Natl. Acad. Sci. USA (1992) 89: 11347-11351, Nat. Med. (2009) 15: 331-337).

In addition, it is also known that BDNF has various actions such as promotion of proliferation and differentiation of tooth-related cells or vascular endothelial cells, eating regulation, and sugar metabolism (Tissue Eng. (2005) 11: 1618-629, Obesity study (2009) 15: 97-99).

From these, BDNF is expected to be developed as a therapeutic agent for various diseases, for example, neurodegenerative diseases such as Alzheimer's disease, Parkinson's disease, and Huntington's disease, spinal cord degenerative disease such as amyotrophic lateral sclerosis, diabetic neuropathy, cerebral ischemia-related disease, developmental disorder such as Rett syndrome, schizophrenia, and depression (Non-Patent Literatures 3 to 8, WO91/03568).

Although BDNF cannot pass through the blood-brain barrier (BBB), the fusion protein (hBDNF-anti-hTfR antibody fusion protein) of the present invention can pass through BBB. Therefore, the peripherally administered fusion protein of the present invention is transferred to the brain, and exhibits intrinsic effects of BDNF. Such functions of BDNF can be checked by the following methods.

(2) Method of Evaluating Functions of BDNF

Functions of BDNF can be evaluated in vitro by examining binding affinity for the BDNF receptor (TrkB) (Eur J Neurosci (1994) 6: 1389-1405), activation of the BDNF receptor using the phosphorylation of the BDNF receptor as an indicator (Biochim Biophys Acta (2015) 1852: 862-872), intracellular signal transmission enhancing activity such as intracellular calcium increase induced by activation of the BDNF receptor (Nature Reviews Neuroscience (2009) 10: 850-860), proliferation promoting action to TrKB-expressing nerve cells (Proceedings of Gifu College of Pharmacy (2006) 55: 53-54), cell survival effect (Prog Neuropsychopharmacol Biol Psychiatry (2015) 60: 11-17), an neurite outgrowth action (J Biol Chem (2007) 282: 34525-34534). The cells used in vitro may be endogenously TrkB expressing cells or exogenously forcibly TrkB expressed cells. For example, cells prepared by transfecting a TrkB gene to BAF cells, CHO cells, PC-12 cells, and the like and then allowing the gene to forcibly express therein, or primary cultured nerve cells of hippocampus or corpus striatum and the like, can be used.

In addition, functions of BDNF can be evaluated in vivo by examining therapeutic effects (Proc. Natl. Acad. Sci. USA (1994) 91: 8920-8924) on animal models of the disease such as Parkinson's disease, Huntington's disease, Alzheimer's disease, and the like. For example, using methods as described in Examples 2 to 5, in vivo bioactivity of BDNF of the fusion protein (TfR antibody-BDNF fusion protein) of the present invention can be evaluated by examining the ameliorating effect of movement impairment in Parkinson's disease model animals, the restorative effect of dopamine contents in corpus striatum, regenerative effect of dopamine neuron in corpus striatum, and the like. As Parkinson's disease models, mice or monkeys treated with MPTP, which is known to specifically destroy dopamine neurons, can be used.

(3) Use of Fusion Protein

The improvement of the disease or disorder of a certain disease model animal, for example, a Parkinson's disease model animal, by peripheral administration of the fusion protein of the present invention (hBDNF-anti-hTfR antibody fusion protein), demonstrates that the fusion protein of the present invention has reached a necessary site (e.g., in the brain) to the extent that BDNF can exhibit its intrinsic effects. This means that the fusion protein of the present invention can be widely used, not only for the aforementioned diseases, but also for treating diseases and disorders benefiting from the exposure to BDNF.

The present invention can be used for treating a disease or a disorder benefiting from the exposure to BDNF by administering of a pharmaceutical composition containing a therapeutically effective amount of the fusion protein of the present invention as an active ingredient. Therefore, the present invention also provides an agent for preventing and/or treating of a disease or a disorder benefiting from the exposure to BDNF containing the fusion protein of the present invention as an effective component. Herein, the term "treat" means not only complete cure but also improvement in symptoms.

The disease or the disorder benefiting from the exposure to the fusion protein of the present invention include not only a disease or a disorder caused by a reduction in the expression level or amount of BDNF, but also a disease or a disorder that can be treated by actions of BDNF. Examples of the disease or the disorder include a nervous system disease or a nervous system disorder (neurodegenerative disease, depression, schizophrenia, epilepsy, autism, Rett syndrome, West syndrome, neonatal spasm, problematic behaviors associated with dementia (e.g., wandering, aggressive behavior, and the like), anxiety, pain, Hirschsprung's disease, REM sleep behavioral disorder, and the like), and other diseases or disorders. Examples of the neurodegenerative disease include cerebral neurodegenerative disease, spinal cord degenerative disease, retinal degenerative disease, and peripheral neurodegenerative disease as follows.

Examples of the cerebral neurodegenerative disease include neurodegenerative disease of the cerebral nervous system (Alzheimer's disease, Parkinson's disease, Huntington's disease, dementia with Lewi bodies, Pick's disease, multiple system atrophy, progressive ascending paralysis, Down syndrome, and the like), cerebral ischemic disease (stroke, cerebral infarction, transient ischemic attack, subarachnoidal hemorrhage, ischemic encephalopathy, cerebral infarction (Lacunar stroke, atherothrombotic brain infarction, cardiogenic cerebral infarction, hemorrhagic cerebral infarction, and other infarctions), and the like), traumatic brain injury, leukoencephalopathy, multiple sclerosis, and the like.

Examples of the spinal cord degenerative disease include amyotrophic lateral sclerosis (ALS), spinal cord injury, spinal cord disorder developed by various causes, spinal progressive muscle atrophy, spinocerebellar degeneration, and the like. Examples of the retinal degenerative disease include age-related macular degeneration (AMD), diabetic retinopathy, retinal pigmentary degeneration, hypertensive retinopathy, glaucoma, and the like.

Examples of the peripheral neurodegenerative disease include diabetic neuropathy, peripheral nerve injury, traumatic peripheral neuropathy, intoxication, peripheral neuropathy caused by other toxic substances, peripheral neuropathy caused by cancer chemotherapy, Guillain-Barre syndrome, peripheral neuropathy caused by deficiency of vitamin and the like, amyloid peripheral neuropathy, ischemic peripheral neuropathy, peripheral neuropathy associated with malignant tumor, uremic peripheral neuropathy, peripheral neuropathy due to physical causes, Charcot-Marie-Tooth disease, alcoholic peripheral neuropathy, autonomic nerve abnormality (hypoglycemia unawareness, gastroparesis, neuropathic diarrhea and constipation, erection failure, orthostatic hypotension, arrhythmia, cardiac failure, Indolent myocardial infarction, paridrosis, neurogenic bladder dysfunction, and the like), bladder dysfunction (e.g., uninhibited bladder, reflex bladder, autonomic bladder, sensory paralytic bladder, motor paralytic bladder, and the like), and the like.

Examples of other diseases or disorders include periodontal disease, diabetes, diabetic cardiomyopathy, diabetic foot lesion, inflammatory bowel disease (for example, ulcerative colitis, Crohn's disease, and the like), hearing impairment, bone disease (for example, osteoporosis, and the like), articular disease (for example, Charcot's joint disease, degenerative joint disease, rheumatism, and the like), and the like.

The fusion protein of the present invention can be used as a pharmaceutical agent, which is to expect its function in the central nervous system (CNS) after administered into the blood. Such a pharmaceutical agent can be administered to a patient by intravenous injection such as intravenous infusion and the like, subcutaneous injection, and intramuscular injection, but the administration route is not particularly limited thereto.

(4) Administration Form, Administration Dose, and Administration Method

The fusion protein of the present invention can be provided to medical organizations in the form of a lyophilized product, an aqueous preparation, or the like, as a pharmaceutical agent. In a case of the aqueous preparation, it can be provided in the form of preparations in which one of the pharmaceutical agents is dissolved in a solution containing a stabilizer, buffer, and an isotonizer in advance, and sealed in a vial or a syringe. The preparation sealed in a syringe is generally referred to as a prefilled syringe-type preparation. Taking the form of a prefilled syringe preparation facilitates patient's self-administration of the pharmaceutical agent.

In a case of being provided as an aqueous preparation, the concentration of BDNF conjugate with an anti-hTfR antibody contained in the aqueous preparation should be appropriately adjusted depending on the usage and dose, and is 0.01 to 5 mg/mL, for example. In addition, the stabilizer contained in the aqueous preparation is not particularly limited insofar as they are pharmaceutical acceptable, but a non-ionic surfactant can be preferably used. As such a non-ionic surfactant, polysorbate, poloxamer, and the like can be used alone or in combination. Among polysorbates, polysorbate 20 and polysorbate 80 are used. As poloxamer, poloxamer 188 (polyoxyethylene (160) polyoxypropylene (30) glycol) are particularly preferable. In addition, the concentration of the non-ionic surfactant contained in the aqueous preparation is preferably 0.01 to 1 mg/mL, more preferably 0.01 to 0.5 mg/mL, and further more preferably 0.1 to 0.5 mg/mL. As the stabilizer, an amino acid such as histidine, arginine, methionine, and glycine can be used. A concentration of the amino acid contained in the aqueous preparation in a case of using a stabilizer is preferably 0.1 to 40 mg/mL, more preferably 0.2 to 5 mg/mL, and further more preferably 0.5 to 4 mg/mL. The buffer contained in the aqueous preparation is not particularly limited insofar as it is pharmaceutically acceptable, but a phosphate buffer is preferable, and a sodium phosphate buffer is particularly preferable. A concentration of sodium phosphate in a case of using sodium phosphate buffer as the buffer is preferably 0.01 to 0.04 M. In addition, a pH of the aqueous preparation adjusted by the buffer is preferably 5.5 to 7.2. The isotonizer contained in the aqueous preparation is not particularly limited insofar as it is pharmaceutically acceptable, and sodium chloride or mannitol can be preferably used alone or in combination as an isotonizer.

An administration dose of the above described pharmaceutical agent containing the fusion protein of the present invention is different depending on the administration subject, the subject disease, the symptoms, the administration route, and the like, but for example, in a case that a pharmaceutical agent is used for treating and/or preventing neurodegenerative diseases, the administration dose is set, as an effective amount, for example, therapeutically effective amount, such that a concentration as BDNF in the brain is at least not less than approximately 0.001 ng/g, and preferably more than 0.01, 0.1, 1, 10, or 100 ng/g brain. In addition, the increased BDNF level in the brain is preferably maintained even several days (1, 2, 3, 4, 5, 6, and 7 days), two weeks, and further 1 month had passed after an single administration, and the concentration thereof maintained in the brain, for example, is preferably maintained as being approximately 1 ng/g brain, approximately 10 ng/g brain, approximately 100 ng/g brain, or more than approximately 100 ng/g brain.

For example, the administration dose is not limited thereto, but in some embodiments, the single administration dose can be selected within a range of 0.0001 to 1,000 mg/kg body weight. Alternatively, the dose can be selected within a range of 0.01 to 100,000 mg per patient. In general, the administration dose of approximately 0.01 to 1000 mg, approximately 0.1 to 100 mg, approximately 1 to 100 mg, approximately 0.05 to 500 mg, approximately 0.5 to 50 mg, or approximately 5 mg to 50 mg, for example, is administrated by intravenous administration. In a case where a patient has particularly severe symptoms, the administration dose may be increased depending on the symptoms.

A composition of the present invention, for example, the fusion protein of the present invention may be used alone, or within a range not impairing the effect of the present invention, depending on the necessity, the composition of the present invention is administered to a patient along with another pharmaceutical product or with other treatment methods, as a composition in the same preparation or a different composition. Examples of a pharmaceutical agent used together with the pharmaceutical composition of the present invention in Alzheimer's dementia include therapeutic agents for an Alzheimer's disease, for example, an acetylcholinesterase inhibitor such as donepezil hydrochloride, rivastigmine, galanthamine hydrogen bromide hydrochloric acid, or memantine hydrochloride. In addition, an anti-Aβ antibody which is currently at the stage of clinical development, such as Solanezumab (N Engl J Med. (2014) 370: 311-21) and Gantenelmab (Arch Neurol. (2012) 69: 198-207), or the like, and a β-amyloid production inhibitor such as verubecestat (AAIC 2013, Boston: Abs 01-06-05, July 2013) AZD-3293 (AAIC 2014, Copenhargen: AbsP1-363, July 2014), and the like is also exemplified. Examples of the treatment methods used together with the pharmaceutical composition of the present invention in the Alzheimer's dementia include a brain activity rehabilitation therapy and the like. Examples of the pharmaceutical agent used for Parkinson's disease in combination with the pharmaceutical composition of the present invention include therapeutic agents for Parkinson's disease, for example, a dopamine replacement therapy drug such as Levodopa, a dopamine receptor agonist such as talipexole, pramipexole, and bromocriptine, a dopamine degrading enzyme inhibitor such as MAO-B inhibitor and COMT inhibitor, and a dopamine release promoter such as amantadine and nouriast. Examples of a therapeutic method used along with the pharmaceutical composition of the present invention in Parkinson's disease include a thalamic stimulation surgery, a globus pallidus stimulation surgery, and a subthalamic nucleus stimulation surgery. Examples of the pharmaceutical agent used for Huntington's disease in combination with the pharmaceutical composition of the present invention include a therapeutic agent for Huntington's disease, for example, a monoamine vesicle transporter 2 inhibiting drug such as tetrabenazine Examples of the pharmaceutical agent used for cerebral ischemic disease in combination with the pharmaceutical composition of the present invention include a brain-protecting drug such as Radicut. Examples of the therapeutic method used for cerebral ischemic disease in combination with the pharmaceutical composition of the present invention include a thrombolytic therapy, a rehabilitation therapy, and the like.

A timing for administration of the pharmaceutical composition of the present invention is not particularly limited, and the timing may be administered, as appropriate, before and after, or simultaneously with the administration of other pharmaceutical agents or the therapy.

EXAMPLES

Hereinafter, the present invention is described in further details referring to examples, but the present invention is not intended to be limited to examples. Examples 1 to 15-3 are for reference examples (antibody No. 3).

[Example 1] Construction of hTfR Expression Vector

Employing human spleen Quick Clone cDNA (Clontech Corporation) as a template and using primer-hTfR5' (SEQ ID NO: 41) and primer-hTfR3' (SEQ ID NO: 42), PCR was performed to amplify the gene fragment encoding a human transferrin receptor (hTfR). The amplified gene fragment encoding hTfR was digested with MluI and NotI, and was inserted between MluI and NotI sites of pCI-neo vector (Promega Corporation). The obtained vector was named pCI-neo (hTfR). Subsequently, this vector was digested with MluI and NotI to cut out the gene fragment encoding hTfR, and this fragment was inserted between MluI and NotI sites of pE-mIRES-GS-puro which is an expression vector described in an international publication WO2012/063799 to construct an hTfR expression vector, pE-mIRES-GS-puro (hTfR).

[Example 2] Preparation of Recombinant hTfR

After introducing pE-mIRES-GS-puro (hTfR) to CHO-K1 cell by an electroporation method, selective culture of the cells was conducted in a CD OPTICHO medium (Invitrogen Corporation) including methionine sulfoximine (MSX) and pureomycin to obtain recombinant hTfR expression cells. The recombinant hTfR expression cells were cultured, and a recombinant hTfR was prepared.

[Example 3] Immunization of Mouse with Recombinant hTfR

Mice were immunized with a recombinant hTfR prepared in Example 2 as an antigen. The immunization was performed by intravenously or intraperitonealy injection of the antigen into mice.

[Example 4] Production of Hybridoma Cells

After approximately one week from the last injection of the cells, the spleen of the mice was extracted and homogenized to separate splenic cells. The obtained splenic cells were fused with cells of mouse myeloma cell line (P3. X63. Ag8. 653) by the polyethylene glycol method. After cell fusion, the cells were suspended on an RPMI1640 medium including (1×) HAT supplement (Life Technologies Corporation) and 10% Ultra low IgG fetal bovine serum (Life Technologies Corporation), and the cell suspension was dispensed onto 20 of 96-well plate by 200 μL/well. After culturing the cell for 10 days in a carbon dioxide gas incubator (37° C., 5% $CO_2$), each well was observed with a microscope, and the wells that contain a single colony were selected.

When the cells in each well reached near confluence, the culture supernatant was collected as a culture supernatant of hybridoma, and subjected to the following screening process.

[Example 5] Screening of High-Affinity Antibody Producing Cell Line

The recombinant hTfR solution (Sino Biologics Inc.) was diluted with a 50 mM sodium carbonate buffer solution (pH 9.5 to 9.6) to 5 μg/mL to prepare a solid phase solution. After 50 μL of the solid phase solution was added to each well of a Nunc MAXISORP flat-bottom 96-well plate (substrate: polystyrene, manufactured by Nunc corporation), the plate was left to stand at room temperature for 1 hour to let recombinant hTfR adsorb onto the plate and fixed. The solid phase solution was discarded, each well was washed with 250 μL of washing solution (PBS-T: PBS containing 0.05% Tween20) three times, 200 μL of blocking solution (PBS containing 1% BSA) then was added to each well, and the plate was left to stand at room temperature for 1 hour.

The blocking solution was discarded, and each well was washed with 250 μL of PBS-T three times. Subsequently, 50 μL of culture supernatant of hybridoma was added to each well, and the plate was left to stand at room temperature for 1 hour, thereby binding the mouse anti-hTfR antibody contained in the culture supernatant to the recombinant hTfR. At this time, as a control, 50 μL of culture supernatant of a hybridoma that did not produce mouse anti-hTfR antibody was added to some wells. In addition, 50 μL of a culture medium of hybridoma was added to the wells, as mock wells, beside those wells to which the culture supernatant was added. Measurement was performed at n=2. Subsequently, the solution was discarded, and each well was washed with 250 μL of PBS-T three times.

100 μL of an HRP-labeled goat anti-mouse immunoglobulin antibody solution (Promega Corporation) was added to each of the above wells, and the plate was left to stand at room temperature for 1 minute. Subsequently, the solution was discarded, and each well was washed with 250 μL of PBS-T three times. Then, 50 μL of a chromophoric substrate solution, TMB Stabilized Substrate for Horseradish Peroxidase (Promega Corporation), was added to each well and the plate was left to stand at room temperature for 10 to 20 minutes. Subsequently, following addition of 100 μL of a stop solution (2N sulfuric acid), the absorbance of each well was measured at 450 nm using a plate reader. The mean values of two wells of each culture supernatant and the control was acquired, respectively, and the measurement values were obtained by subtracting the mean values of two mock-wells disposed per each culture supernatant and the control, respectively from the mean value.

14 types of hybridoma cells corresponding to culture supernatant added to the wells showing a high measurement value were selected as the cell lines (high-affinity antibody producing cell line) that produce antibodies showing high affinities to hTfR (high-affinity anti-hTfR antibody). The 14 types of cell lines were numbered as clone 1 line to clone 14 line. Clone 3 line was selected from these cell lines, and used in the following experiments. In addition, an anti-hTfR antibody produced by clone 3 line was set as anti-hTfR antibody number 3.

[Example 6] Analysis of the Variable-Region Amino Acid Sequence of the High-Affinity Anti-hTfR Antibody cDNA was prepared from clone 3 line selected in Example 5, and a gene encoding a light chain and a heavy chain of the antibody was amplified using the cDNA as a template. By translating the nucleotide sequence of the amplified genes, the respective amino acid sequences of the light chain and heavy chain variable regions were determined for the anti-hTfR antibody number 3 produce by the cell line.

The anti-hTfR antibody number 3 was found to include the amino acid sequence represented by SEQ ID NO: 48 in the variable region of the light chain and an amino acid sequence represented by SEQ ID NO: 49 in the variable region of the heavy chain. In addition, the variable region of the light chain was found to include the amino acid sequence represented by SEQ ID NO: 6 or SEQ ID NO: 7 in CDR1, SEQ ID NO: 8 or SEQ ID NO: 9 in CDR2, and SEQ ID NO: 10 in CDR3, and the variable region of the heavy chain includes the amino acid sequence represented by SEQ ID NO: 11 or SEQ ID NO: 12 in CDR1, SEQ ID NO: 13 or SEQ ID NO: 14 in CDR2, and SEQ ID NO: 15 or SEQ ID NO: 16 in CDR3. However, CDRs are not limited to those which consist of these amino acid sequences, but the region including these amino acid sequences and the amino acid sequences formed of three consecutive amino acids including a part of the above amino acid sequences are also considered to be CDRs.

Sequence numbers of amino acid sequences included in CDR1 to CDR3 of the variable region of the light chain and the CDR1 to CDR3 of the variable region of the heavy chain of the anti-hTfR antibody No. 3 are shown collectively in Table 1. However, Table 1 just exemplifies the amino acid sequences of each CDR. The amino acid sequences of each CDR are not limited to the amino acid sequences described in Table 1, and it is considered that the amino acid sequences of a region including these amino acid sequences and the amino acid sequences formed of three or more consecutive amino acids including a part of these amino acid sequences are also obtained as CDRs.

[Table 1] Sequence Numbers of amino acid sequence included in CDR1 to CDR3 of variable region of the light chain and the heavy chain of the anti-hTfR antibody No. 3 (example of amino acid sequence of each CDR)

| Antibody | Variable region of light chain | | | Variable region of heavy chain | | |
|---|---|---|---|---|---|---|
| number | CDR1 | CDR2 | CDR3 | CDR1 | CDR2 | CDR3 |
| 3 | 6, 7 | 8, 9 | 10 | 11, 12 | 13, 14 | 15, 16 |

[Example 7] Measurement of Affinity of Anti-hTfR Antibody to Human TfR and Monkey TfR The affinity of the anti-hTfR antibody to human TfR and monkey TfR were measured on OctetRED96 (ForteBio Corporation, a division of Pall Corporation), a analysis system for biomolecular interaction utilizing Biolayer Interferometry (BLI). The basic principles of the biolayer interferometry are briefly explained below. When light of a specific wavelength is projected down toward the layer of immobilized biomolecules on the surface of sensor chip, lights reflect from each two layers of biomolecule and internal reference, produce interference wave of the light. As molecules in a analyte sample bind to biomoleculer of a sensor chip surface, the thickness of a layer at a sensor tip increases, which results in a shift of interference wave. By measuring a change in the wavelength shift, quantitation of number of molecules bound to biomolecules immobilized onto the sensor chip surface and kinetics analysis of it can be performed in real time. The measurement was generally performed by operation manual attached to the OctetRED96. As human TfR, a recombinant human TfR (r human TfR: Sino Biological Inc.) was used, which had the amino acid sequence of the extracellular region of hTfR, i.e. the cysteine residue at the $89^{th}$ position from the N-terminus to the phenylalanine at the C-terminus of the amino acid sequence set forth as SEQ ID NO: 1, with a histidine tag added to the N-terminus. As monkey TfR, a recombinant monkey TfR (r monkey TfR: Sino Biological Inc.) was used, which had the amino acid sequence of the extracellular region of a cynomolgus monkey, i.e. the cysteine residue at the $89^{th}$ position from the N-terminus to the phenylalanine of the C-terminus of the amino acid sequence set forth as SEQ ID NO: 2, with a histidine tag added to the N-terminus.

Clone 3 line selected in Example 5 was diluted with an RPMI1640 medium containing (1×) HAT supplement (Life Technologies Corporation) and 10% Ultra low IgG fetal bovine serum (Life Technologies Corporation) so as to adjust the cell density to approximately $2\times10^5$ cells/mL, 200 mL of the cell suspension was added to 1 L of a conical flask, and cultured at 37° C., 5% $CO_2$ and 95% air and at approximately a stirring rate of 70 rpm in a humid environment for 6 to 7 days. The culture supernatant was subjected to centrifugation, and then filtered through a 0.22 μm filter (Millipore Corporation) to harvest the culture supernatant. The collected culture supernatant was loaded onto a Protein G column (column volume: 1 mL, GE Healthcare Corporation) that had been equilibrated in advance with three column volumes of 20 mM Tris buffer solution (pH 8.0) containing 150 mM NaCl. Subsequently, after the column was washed with 5 column volumes of the same buffer, the adsorbed antibody was eluted with 4 column volumes of 50 mM glycine buffer solution (pH 2.8) containing 150 mM NaCl, and an elution fraction was collected. The elution fractions were adjusted to pH 7.0 by adding 1 M Tris buffer solution (pH 8.0) thereto. These were used as purified products of anti-TfR antibody No. 3 in the experiments described below.

The purified product of anti-hTfR antibody No. 3 was subjected to two-fold serial dilution with HBS-P+ (10 mM HEPES containing 150 mM NaCl, 50 μm EDTA, and 0.05% Surfactant P20) to prepare antibody solutions of seven different concentrations, 0.78125 to 50 nM (0.117 to 7.5 μg/mL). These antibody solutions were used as the sample solutions. The r human TfR and r monkey TfR were respectively diluted with HBS-P+ to prepare 25 μg/mL solutions, which were used as r human TfR-ECD (Histag) solution and a r human TfR-ECD (Histag) solution, respectively.

Each sample solutions prepared above by 2-fold serial dilution were filled, 200 μL/well, to 96 well plate, black (greiner bioone Inc.). Each solutions of r human TfR-ECD (Histag) and the r human TfR-ECD (Histag) prepared above, were filled, 200 μL/well, to predetermined wells. To respective wells for baseline, dissociation, and washing, HBS-P+ were filled, 200 μL/well. To wells for regeneration, 10 mM Glycine-HCL, pH 1.7 was filled, 200 μL/well. To wells for activation, 0.5 mM $NiCl_2$ solution was filled by 200 μL/well. The plate and biosensor (Biosensor/Ni-NTA: ForteBio Inc., a division of Pall Corporation) were set to prescribed position of the OctetRED96.

After OctetRED96 was run under the condition shown in the following Table 2 to collect data, the binding interaction curve was fitted to a 1:1 binding model or to a 2:1 binding model using the analysis software attached to the OctetRED96, the association rate constant (kon) and the dissociation rate constant (koff) of anti-hTfR antibody to r human TfR and r monkey TfR were measured, and the dissociation constants ($K_D$) were calculated. The measurement was performed at 25° C. to 30° C.

TABLE 2

Operating condition of OctetRED96

| | Step | Contact time (sec) | Speed (rpm) | Threshold |
|---|---|---|---|---|
| 1 | Baseline 1 | 60 | 1000 | — |
| 2 | Load | 600 | 1000 | 1.5 to 2.0 |
| 3 | Baseline 2 | 60 | 1000 | — |
| 4 | Association | 180 | 1000 | — |
| 5 | Dissociation | 540 | 1000 | — |
| 6 | Regeneration | 5 | 1000 | — |

TABLE 2-continued

| Operating condition of OctetRED96 | | | | |
|---|---|---|---|---|
| Step | | Contact time (sec) | Speed (rpm) | Threshold |
| 7 | Washing | 5 | 1000 | — |
| Steps 6 and 7 are repeated 6 to 7 times. | | | | |
| 8 | Activation | 60 | 1000 | — |
| Steps 1-8 are repeated until all the samples are measured.. | | | | |

The table 3 shows the measurement results of the association rate constant (kon) and the dissociation rate constant (koff) of anti-hTfR antibody No. 3 to human TfR and monkey TfR, and the dissociation constants ($K_D$).

TABLE 3

| Affinity of anti-hTfR antibody No. 3 to human TfR and monkey TfR | | | |
|---|---|---|---|
| | kon ($M^{-1}s^{-1}$) | koff ($s^{-1}$) | $K_D$ (M) |
| Human TfR | $6.53 \times 10^5$ | $<1.0 \times 10^{-7}$ | $<1.0 \times 10^{-12}$ |
| Monkey TfR | $3.89 \times 10^5$ | $<1.0 \times 10^{-7}$ | $<1.0 \times 10^{-12}$ |

As a result of affinity measurement of anti-hTfR antibody to the human TfR, the dissociation constant of the anti-fTfR antibody No. 3 with to human TfR was equal to or less than $1\times10^{-12}$ M, and the dissociation constant with monkey TfR was also equal to or less than $1\times10^{-12}$ M. These results reveals that the anti-hTfR antibody No. 3 has high affinity to not only human TfR but also monkey TfR.

[Example 7-2] Evaluation of Brain Uptake of Anti-hTfR Antibody in Mice

Subsequently, in the anti-hTfR antibody No. 3, the fact that each antibody passes through BBB and migrates into the brain was evaluated in an hTfR knock-in mouse (hTfR-KI mouse) in which a gene encoding an extracellular region of a mouse transferrin receptor was substituted with a gene encoding an extracellular region of a human transferrin receptor gene. The hTfR-KI mouse was produced by the following method. In addition, as the anti-hTfR antibody No. 3, a purified product prepared in Example 7 was used.

A DNA fragment having the nucleic acid sequence represented by SEQ ID NO: 45, in which a neomycin-resistant gene sandwiched between loxP sequences was disposed on a 3' side of cDNA encoding a chimeric hTfR in which an intracellular region is an amino acid sequence of a mouse TfR, and an extracellular region is an amino acid sequence of a human TfR, was chemically synthesized. The DNA fragment was inserted into a targeting vector having the nucleic acid sequence represented by SEQ ID NO: 46 as a 5' arm sequence and the nucleic acid sequence represented by SEQ ID NO: 47 as a 3' arm sequence by a common method, and this was introduced into a mouse ES cell by an electroporation method. The mouse ES cell after gene introduction was subjected to selective culturing in the presence of neomycin to select the mouse ES cell in which the targeting vector was inserted into chromosome by homologous recombination. The obtained gene recombinant mouse ES cell was injected into an eight-cell embryo (host embryo) of ICR mouse, and transplanted into a pseudo-pregnant mouse (recipient mouse) obtained by hybridization with a mouse subjected to vasoligation. Hair color determination was performed on the obtained offspring (chimera mouse), and an entity of which ES cell contributed to the formation of a living body with high efficiency, that is, an entity with a high ratio of white color hair to total hair was selected. The chimera mouse entity was in conjunction with the ICR mouse to obtain an F1 mouse. An F1 mouse of white color was selected, DNA extracted from a tail tissue was analyzed, and a mouse in which a mouse transferrin receptor gene was substituted with a chimeric hTfR on a chromosome was set as a hTfR-KI mouse.

The purified product of the anti-hTfR antibody No. 3 was fluorescent-labeled by fluorescein isothiocyanate (FITC) according to the added operation manual using Fluorescein Labeling Kit-$NH_2$ (Dongjindo Laboratories). A PBS solution including the FITC fluorescent-labeled antibody was prepared. The antibody solution was intravenous-injected into a single hTfR-KI mouse (male, 10 to 12 weeks) such that a dosage of the administered anti-hTfR antibody was 3 mg/kg. In addition, as a control, a PBS solution including FITC fluorescent-labeled mouse IgG1 (Sigma Corporation) prepared in the same manner was intravenous-injected into a single hTfR-KI mouse (male, 10 to 12 weeks) at a dosage of 3 mg/kg. Systemic perfusion was performed with a physiological saline after approximately 8 hours from the intravenous injection, and the brain (portion including cerebrum and cerebellum) was collected. After a weight (wet weight) of the extracted brain was measured, T-PER (Thermo Fisher Scientific Corporation) including Protease Inhibitor Cocktail (Sigma Corporation) was added to homogenate the brain tissue. The homogenate was centrifuged to recover a supernatant, and an amount of an FITC fluorescent-labeled antibody included in the supernatant was measured by the following method. First, an anti-FITC antibody (Bethyl Corporation) was added to each well of High Bind Plate (Meso Scale Diagnostics Corporation) by 10 μL, left still for 1 hour, and fixed onto the plate. Subsequently, SuperBlock Blocking buffer in PBS (Thermo Fisher Scientific Corporation) was added to each well by 150 μL, and shaken for 1 hour to block the plate. Subsequently, the supernatant of the homogenate of the brain tissue was added to each well by 25 μL, and shaken for 1 hour. Subsequently, a SULFO-TAG Anti-Mouse antibody (Goat) (Meso Scale Diagnostics Corporation) was added to each well by 25 μL, and shaken for 1 hour. Subsequently, Read buffer T (Meso Scale Diagnostics Corporation) was added to each well by 150 μL, and a light emission amount from each well was measured using a SECTOR Imager 6000 reader. A calibration curve was prepared from a measurement value of a standard sample of an FITC fluorescent-labeled anti-hTfR antibody with known concentrations, and by interpolating a measurement value of each specimen thereto, an amount (concentration of anti-hTfR antibody in the brain tissue) of an antibody included per gram weight (wet weight) of the brain was calculated. The result is shown in Table 4.

In comparison with the control, a concentration in the brain tissue of the anti-hTfR antibody No. 3 was approximately 27.8 times. The result shows that the anti-hTfR antibody No. 3 has a property of actively passing through BBB and mitigating into the brain.

TABLE 4

| Concentration of anti-hTfR antibody in brain tissue | | |
|---|---|---|
| Antibody number | Brain tissue (μg/g wet weight) | Relative value to control |
| Control | 0.003 | 1 |
| 3 | 0.0833 | 27.8 |

[Example 8] Pharmacokinetic Analysis of Anti-hTfR Antibody in Monkey

The anti-hTfR antibody No. 3 was intravenously administered once to a male cynomolgus monkey at a dosage of 5.0 mg/kg, and systemic perfusion was performed with a physiological saline after 8 hours of administration. In addition, as a negative control, a single entity not administered with an anti-hTfR antibody was subjected to systemic perfusion in the same manner. After perfusion, a brain tissue including medulla oblongata was extracted. Using the brain tissue, the following concentration measurement and immunohistochemical staining of the anti-hTfR antibody were performed. As the anti-hTfR antibody No. 3, a purified product of an antibody described in Example 7 was used.

The concentration measurement of the anti-hTfR antibody in the brain tissue was generally performed in the following procedure. The brain tissue was divided into the cerebrum, the cerebellum, the hippocampus, and the medulla oblongata, and then each of the acquired tissue was homogenated with an RIPA Buffer (Waco Pure Chemical Industry) including Protease Inhibitor Cocktail (Sigma-Aldrich Corporation), and centrifuged to recover a supernatant. Affinipure Goat Anti mouse IgG Fcγ pAb (Jackson ImmunoResearch Corporation) was added to each well of High Bind Plate (Meso Scale Diagnostics Corporation) by 10 μL, left still for 1 hour, and fixed onto the plate. Subsequently, SuperBlock blocking buffer in PBS (Thermo Fisher Scientific Corporation) was added to each well by 150 μL, and shaken for 1 hour to block the plate. Subsequently, the supernatant of the homogenate of the brain tissue was added to each well by 25 μL, and shaken for 1 hour. Subsequently, Affinipure Goat Anti mouse IgG Fab-Biotin (Jackson ImmunoResearch Corporation) was added to each well by 25 μL, and shaken for 1 hour. Subsequently, SULFO-Tag-Streptavidin (Meso Scale Diagnostics Corporation) was added to each well by 25 μL, and shaken for 0.5 hour. Subsequently, Read buffer T (Meso Scale Diagnostics Corporation) was added to each well by 150 μL, and a light emission amount from each well was measured using a SECTOR Imager 6000 reader (Meso Scale Diagnostics Corporation). A calibration curve was prepared from a measurement value of a standard sample of an anti-hTfR antibody with known concentrations, and by interpolating a measurement value of each specimen thereto, an amount (concentration of anti-hTfR antibody in the brain tissue) of an antibody included per gram weight (wet weight) of each brain tissue was calculated.

A result of the concentration measurement of the anti-hTfR antibody in the brain tissue is shown in Table 5. In all of the cerebrum, the cerebellum, the hippocampus, and the medulla oblongata, accumulation of the anti-hTfR antibody No. 3 was recognized. The result shows that the anti-hTfR antibody No. 3 has a property of passing through the blood-brain barrier and being accumulated in the brain tissue, and shows that by binding a drug to function in the brain tissue to the antibody, it is possible to efficiently accumulate the drug in the brain tissue.

TABLE 5

| | Concentration of anti-hTfR antibody in brain tissue (μg/g wet weight) | | | |
|---|---|---|---|---|
| Antibody number | Cerebrum | Cerebellum | Hippocampus | Cervical spinal cord |
| 3 | 0.72 | 0.6 | 0.33 | 0.31 |

The immunohistochemical staining of the anti-hTfR antibody in the brain tissue was generally performed in the following procedure. Using a Tissue-Tek Cryo 3DM (Sakura Finetek Co., Ltd.), the acquired tissue was rapid-frozen to −80° C. to produce a frozen block of the tissue. The frozen block was sliced into 4 μm, and then attached onto a MAS-coated slide glass (Matsunami Glass Co., Ltd.). 4% paraformaldehyde (Waco Pure Chemical Industry) was reacted with the tissue slice at 4° C. for 5 minutes, and the tissue slice was fixed onto the slide glass. Subsequently, a methanol solution (Waco Pure Chemical Industry) including 0.3% hydrogen peroxide water was reacted with the tissue slice for 30 minutes, and endogenous peroxidase was deactivated. Subsequently, the slide glass was reacted with SuperBlock blocking buffer in PBS at room temperature for 30 minutes to block the slide glass. Subsequently, Mouse IgG-heavy and light chain Antibody (Bethyl Laboratories Inc.) was reacted with the tissue slice at room temperature for 1 hour. The tissue slice was subjected to color development with a DAB substrate (3,3'-diaminobenzidine, Vector Laboratories), subjected to contrast staining with Mayer hematoxylin (Merck Corporation), subjected to dehydration and penetration, and then enclosed, and observed with an optical microscope.

FIG. 1 shows a result of immunohistochemical staining of an anti-hTfR antibody of a cerebral cortex. In the cerebral cortex of the monkey to which the anti-hTfR antibody No. 3 was administered, specific staining of the blood vessel was checked (FIG. 1*b*). In addition, specific staining was widely checked also in a cerebral parenchyma region other than a cerebral blood vessel. On the other hand, it was shown that in a cerebral cortex of a monkey not administered with an anti-hTfR antibody present as a control, staining was not recognized, and there was almost no staining of the background (FIG. 1*a*).

Figure 2:
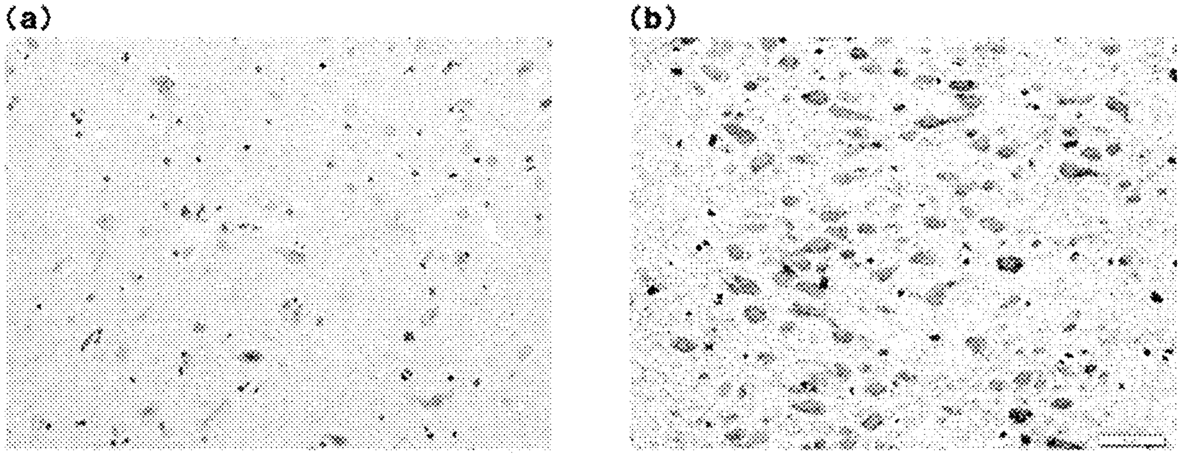
FIG. 2 A figure showing the result of immunohistochemical staining with an anti-hTfR antibody of hippocampus of a cynomolgus monkey after single intravenous administration of the anti-hTfR antibody. (a) Non-administration of the anti-hTfR antibody, and (b) administration of the anti-hTfR antibody No. 3. The bar on the right bottom of each photograph is a gauge indicating 50 μm.

FIG. 2 shows a result of immunohistochemical staining of an anti-hTfR antibody of hippocampus. In the cerebral cortex of the monkey to which the anti-hTfR antibody No. 3 was administered, specific staining of the blood vessel was checked (FIG. 2*b*). In addition, specific staining was checked also in nerve-like cells, and specific staining was checked also in a cerebral parenchyma region other than a cerebral blood vessel. On the other hand, it was shown that in a hippocampus of a monkey not administered with an anti-hTfR antibody present as a control, staining was not recognized, and there was almost no staining of the background (FIG. 2*a*).

Figure 3:
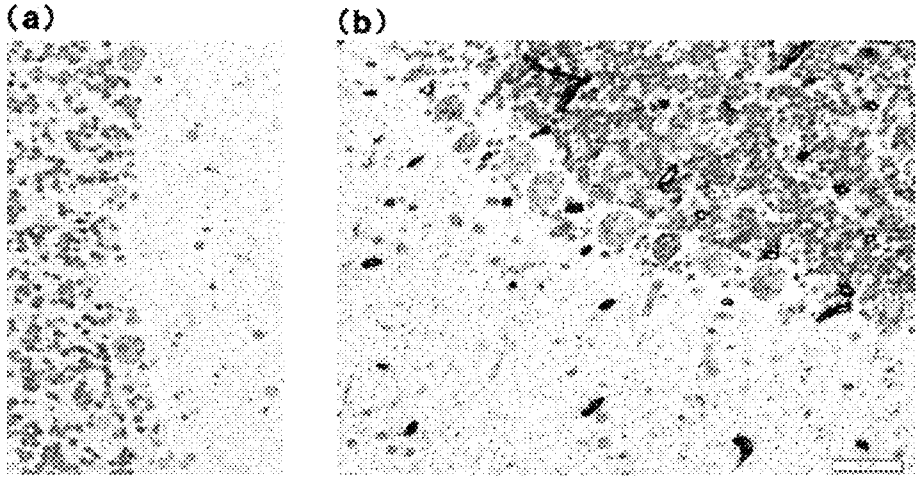
FIG. 3 A figure showing the result of immunohistochemical staining with an anti-hTfR antibody of a cerebellum of a cynomolgus monkey after single intravenous administration of the anti-hTfR antibody. (a) Non-administration of the anti-hTfR antibody, and (b) administration of the anti-hTfR antibody No. 3. The bar on the right bottom of each photograph is a gauge indicating 50 μm.

FIG. 3 shows a result of immunohistochemical staining of an anti-hTfR antibody of a cerebellum. In the cerebral cortex of the monkey to which the anti-hTfR antibody No. 3 was administered, specific staining of the blood vessel was checked (FIG. 3*b*). In addition, specific staining was checked also in Purkinje cells. On the other hand, it was shown that in a cerebellum of a monkey not administered with an anti-hTfR antibody present as a control, staining was not recognized, and there was almost no staining of the background (FIG. 3*a*).

From the above result of immunohistochemical staining of the cerebrum, the hippocampus, and the cerebellum, it was found that the anti-hTfR antibody No. 3 was able to bind to hTfR present on the cerebrovascular endothelial surface, and after binding to hTfR, passed through the blood-brain barrier and migrated into the cerebral parenchyma, and the anti-hTfR antibody No. 3 was taken into the nerve-like cells from the cerebral parenchyma in the hippocampus, and into the Purkinje cells in the cerebellum.

[Example 9] Preparation of Humanized Anti-hTfR Antibody

Humanization of an amino acid sequence included a variable region of the light chain and the heavy chain of the anti-hTfR antibody No. 3 was attempted. Then, a humanized variable region of the light chain having the amino acid sequences represented by SEQ ID NO: 17 to SEQ ID NO: 22 and a humanized variable region of the heavy chain having the amino acid sequences represented by SEQ ID NO: 31 to SEQ ID NO: 36 were obtained (amino acid sequences 1 to 6 of the variable region of the light chain of the humanized anti-hTfR antibody No. 3 and amino acid sequences 1 to 6 of the variable region of the heavy chain of the humanized anti-hTfR antibody No. 3).

[Example 10] Construction of Gene Encoding Humanized Anti-hTfR Antibody

Regarding the anti-hTfR antibody No. 3 above, DNA fragments were artificially synthesized which contained a gene encoding the full length of the light chain and the heavy chain including variable regions of the light chain and the heavy chain of the humanized anti-hTfR antibody, respectively. At this time, a MluI sequence and a sequence encoding a leader peptide were introduced into the 5' side of the gene encoding the full length of the light chain in an order from the 5' end, and a NotI sequence was introduced into the 3' end. In addition, a MluI sequence and a sequence encoding a leader peptide were introduced into the 5' side of the gene encoding the full length of the heavy chain, for example, in an order from the 5' end, and a NotI sequence was introduced into the 3' side. The leader peptide introduced above is to function as secretion signal when the light chain and the heavy chain of the humanized antibody are expressed in mammalian cells as host cells so that the light chain and the heavy chain are secreted out of the cells.

Regarding the light chain of the anti-hTfR antibody No. 3, a DNA fragment (SEQ ID NO: 24) was synthesized, which included a gene encoding the full length of the light chain (hereinafter, the light chain of humanized anti-hTfR antibody No. 3) consisting of the amino acid sequence represented by SEQ ID NO: 23 having the amino acid sequence represented by SEQ ID NO: 18 in the variable region. Regarding the heavy chain of the anti-hTfR antibody No. 3, a DNA fragment (SEQ ID NO: 38) was synthesized, which included a gene encoding the full length of the heavy chain (hereinafter, the heavy chain of humanized anti-hTfR antibody No. 3) consisting of the amino acid sequence represented by SEQ ID NO: 37 having the amino acid sequence represented by SEQ ID NO: 32 in the variable region. The heavy chain of the humanized anti-hTfR antibody encoded by the DNA fragment represented by SEQ ID NO: 38 is IgG1.

Regarding the light chain of the anti-hTfR antibody No. 3, a DNA fragment (SEQ ID NO: 26) encoding the full length of the light chain (hereinafter, the light chain of humanized anti-hTfR antibody No. 3-2) consisting of the amino acid sequence represented by SEQ ID NO: 25 having the amino acid sequence represented by SEQ ID NO: 20 in the variable region, a DNA fragment (SEQ ID NO: 28) encoding the full length of the light chain (hereinafter, the light chain of humanized anti-hTfR antibody No. 3-3) consisting of the amino acid sequence represented by SEQ ID NO: 27 having the amino acid sequence represented by SEQ ID NO: 21 in the variable region, and a DNA fragment (SEQ ID NO: 30) encoding the full length of the light chain (hereinafter, the light chain of humanized anti-hTfR antibody No. 3-4) consisting of an amino acid sequence represented by SEQ ID NO: 29 having an amino acid sequence represented by SEQ ID NO: 22 in a variable region were also synthesized.

In addition, regarding the heavy chain of the anti-hTfR antibody No. 3, a DNA fragment (SEQ ID NO: 40) was synthesized, which included a gene encoding the full length of the heavy chain (hereinafter, the heavy chain IgG4 of humanized anti-hTfR antibody No. 3) consisting of the amino acid sequence represented by SEQ ID NO: 39 having the amino acid sequence represented by SEQ ID NO: 32 in a variable region. The heavy chain of the humanized anti-hTfR antibody encoded by the DNA fragment represented by SEQ ID NO: 40 is IgG4.

[Example 11] Construction of Humanized Anti-hTfR Antibody Expression Vector pEF/myc/nuc vector (Invitrogen Corporation) was digested with KpnI and NcoI to cut out. a region including EF-1$\alpha$ promoter and its first intron, and the resultant product was blunt-ended with T4 DNA polymerase. pCI-neo (Invitrogen Corporation) was digested with BglII and EcoRI to cut out, a region including enhancer/promoter of CMV and the intron, and then the resultant product was blunt-ended with T4 DNA polymerase. The above-mentioned region including EF-1$\alpha$ promoter and its first intron was inserted thereto, and a pE-neo vector was constructed. The pE-neo vector was digested with SfiI and BstXI to remove a region of approximately 1 kbp including a neomycin-resistant gene. PCR was performed employing pcDNA3.1/Hygro (+) (Invitrogen Corporation) as a template and using primer-Hyg-Sfi5' (SEQ ID NO: 43) and primer-Hyg-BstX3' (SEQ ID NO: 44), to amplify hygromycin gene. The amplified hygromycin gene was digested with SfiI and BstXI, and inserted into the above pE-neo vector from which the neomycin-resistant gene had been removed to construct a pE-hygr vector.

The pE-hygr vector and the pE-neo vector were respectively digested with MluI and NotI. The DNA fragment (SEQ ID NO: 24) encoding the light chain and the DNA fragment (SEQ ID NO: 38) encoding the heavy chain of the humanized anti-hTfR antibody No. 3, both synthesized in Example 10, were digested with MluI and NotI, and the fragments thus obtained were inserted between MluI and NotI sites of the pE-hygr vector and the pE-neo vector, respectively. The obtained vectors were used respectively as an expression vector for the light chain of the humanized anti-hTfR antibody No. 3, pE-hygr (LC3), and an expression vector for the heavy chain of the humanized anti-hTfR antibody No. 3, pE-neo (HC3), in the experiments described below.

In addition, regarding the light chain of the anti-hTfR antibody No. 3, a DNA fragment (SEQ ID NO: 26) encoding the light chain of the humanized anti-hTfR antibody No. 3-2, a DNA fragment (SEQ ID NO: 28) encoding the light chain of the humanized anti-hTfR antibody No. 3-3, and a DNA fragment (SE ID NO: 30) encoding the light chain of the humanized anti-hTfR antibody No. 3-4, synthesized in Example 10, were digested with MluI and NotI, and each fragment thus obtained were inserted between MluI and NotI sites of the pE-hygr vector to construct pE-hygr (LC3-2) of the light chain expression vector of the humanized anti-hTfR antibody No. 3-2, pE-hygr (LC3-3) of the light chain expression vector of the humanized anti-hTfR antibody No. 3-3, and pE-hygr (LC3-4) of the light chain expression vector of the humanized anti-hTfR antibody No. 3-4, respectively.

Further, in the same manner as above, regarding the heavy chain of the anti-hTfR antibody No. 3, a DNA fragment (SEQ ID NO: 40) encoding the heavy chain IgG4 of the humanized anti-hTfR antibody No. 3, synthesized in Example 10 was digested with MluI and NotI, and the fragment thus obtained was inserted between MluI and NotI sites of the pE-neo vector to construct pE-neo (HC3-IgG4) of the heavy chain IgG4 expression vector of the humanized anti-hTfR antibody No. 3.

[Example 12] Establishment of Cells for Expression Humanized Anti-hTfR Antibody

CHO cells (CHO-K1: acquired from American Type Culture Collection) were transformed with pE-hygr (LC3), the vector for the light chain expression vector, and pE-neo (HC3), the vector for the heavy chain expression, both constructed in Example 11, as follows, using GenePulser (Bio-Rad Laboratories Inc.). Transfection of the cells was generally performed by the following method. CHO-K1 cells, $5\times10^5$ cells, were seeded in a 3.5-cm culture dish containing CD OPTICHO medium (Life Technologies Corporation) and cultured at 37° C. overnight under a condition of 5% $CO_2$. The medium was exchanged with an OPTI-MEM I medium (Life Technologies Corporation) and the cells were suspended at the density of $5\times10^6$ cell/mL. 100 μL of a cell suspension was acquired, and pE-hygr (LC3) and pE-neo (HC3) plasmid DNA solutions, both having been diluted to 100 μg/mL with the OPTI-MEM I medium, were added thereto by 5 μL, respectively. These plasmids were transfected into the cells by electroporation using GenePulser (Bio-Rad Laboratories Inc.). The cells then were cultured at 37° C. overnight under the condition of 5% $CO_2$, and subjected to selection culture in the CD OPTICHO medium supplemented with 0.5 mg/ml of hygromycin and 0.8 mg/ml of G418.

Subsequently, the cells selected by the selection culture were seeded on a 96-well plates such that one or less cell per well was seeded by kimiting dilution. The cells then were cultured for approximately 10 days so that monoclonal colonies were formed. Respective culture supernatants of the wells in which a monoclonal colony was formed was collected, the amount of the humanized antibody contained in culture supernatants was determined by the ELISA method, and humanized antibody high expression cell lines were selected.

The ELISA method at this time was generally performed by the following method. A resultant product obtained by diluting a goat anti-human IgG polyclonal antibody solution into 4 μg/mL with 0.05 M hydrogen carbonate buffer solution (pH 9.6) was added to each well of 96 well-microtiter plate (Nunc Corporation) by 100 uL, left still at room temperature for at least 1 hour, and the antibody was adsorbed onto the plate. Subsequently, after washing each well with PBS-T three times, a Starting Block (PBS) Blocking Buffer (Thermo Fisher Scientific Corporation) was added to each well by 200 μL, and the plate was left still at room temperature for 30 minutes. After washing each well with PBS-T three times, a culture supernatant or a human IgG standard product diluted with a product obtained by adding 0.5% BSA and 0.05% Tween20 (PBS-BT) to PBS into an appropriate concentration was added to each well by 100 μL, and the plate was left still at room temperature for at least 1 hour. After washing the plate with PBS-t three times, an HRP-labeled anti-human IgG polyclonal antibody solution diluted with PBS-BT was added to each well by 100 μL, and the plate was left still at room temperature for at least 1 hour. After washing each well with PBS-T three times, 0.4 mg/ml o-phenylenediamine including a phosphate-citric acid buffer solution (pH 5.0) was added to each well by 100 μL, and left still at room temperature for 8 to 20 minutes. Subsequently, 1 mol/L sulfuric acid was added to each well by 100 μL to stop reaction, and using a 96-well plate reader, absorbance at 490 nm of each well was measured. A cell corresponding to a well showing a high measurement value was set as a high expression cell line of the humanized anti-hTfR antibody No. 3. This was set as an antibody No. 3 expression line.

In addition, similarly, a CHO cell was transformed using the light chain expression vector pE-hygr (LC3-2) and the heavy chain expression vector pE-neo (HC3) constructed in Example 11 to obtain a high expression cell line of the humanized anti-hTfR antibody No. 3-2. This was set as an antibody No. 3-2 expression line.

In addition, similarly, a CHO cell was transformed using the light chain expression vector pE-hygr (LC3-3) and the heavy chain expression vector pE-neo (HC3) constructed in Example 11 to obtain a high expression cell line of the humanized anti-hTfR antibody No. 3-3. This was set as an antibody No. 3-3 expression line.

In addition, similarly, a CHO cell was transformed using the light chain expression vector pE-hygr (LC3-4) and the heavy chain expression vector pE-neo (HC3) constructed in Example 11 to obtain a high expression cell line of the humanized anti-hTfR antibody No. 3-4. This was set as an antibody No. 3-4 expression line.

In addition, similarly, a CHO cell was transformed using the light chain expression vector pE-hygr (LC3) and the heavy chain expression vector pE-neo (HC3-IgG4) constructed in Example 11 to obtain a high expression cell line of the humanized anti-hTfR antibody No. 3 (IgG4). This was set as an antibody No. 3 (IgG4) expression line.

In addition, similarly, a CHO cell was transformed using the light chain expression vector pE-hygr (LC3-2) and the heavy chain expression vector pE-neo (HC3-IgG4) constructed in Example 11 to obtain a high expression cell line of the humanized anti-hTfR antibody No. 3-2 (IgG4). This was set as an antibody No. 3-2 (IgG4) expression line.

[Example 13] Purification of Humanized Anti-hTfR Antibody

The antibody No. 3 expressing cell line, the antibody No. 3-2 expressing cell line, the antibody No. 3-3 expressing cell line, and the antibody No. 3-4 expressing cell line obtained in Example 12 were respectively diluted with a CD OPTICHO medium to the density of approximately $2\times10^5$ cells/mL, 200 ml of the cell suspension was added to 1 L-conical flask, and cultured for 6 to 7 days in a humid environment at 37° C., 5% $CO_2$ and 95% air with stirring rate of approximately 70 rpm. Each culture supernatant was harvested by centrifugation, and filtered through 0.22 μm filter (Millipore Corporation) to prepare culture supernatant. To each culture supernatant thus obtained, five fold volumes of 20 mM Tris buffer solution (pH 8.0) containing 150 mM NaCl was added, and loaded onto a Protein A column (column volume: 1 mL, Bio-Rad Laboratories Inc.) which had been equilibrated in advance with three column volumes of 20 mM Tris buffer solution (pH 8.0) containing 150 mM NaCl. Subsequently, after washing the column with five column volumes of the same buffer solution, and the adsorbed humanized antibody was eluted with four column volumes of 50 mM glycine buffer solution (pH 2.8) containing 150 mM NaCl, and an elution fractions were collected. 1 M Tris buffer solution (pH 8.0) was added to elution fraction to be neutralized. And these were used as purified antibody preparation.

Here, the antibody purified from the culture supernatant of the antibody No. 3 expressing cell line was designated as humanized anti-hTfR antibody No. 3. The antibody purified from the culture supernatant of the antibody No. 3-2 expressing cell line was designated as humanized anti-hTfR antibody No. 3-2. The antibody purified from the culture supernatant of the antibody No. 3-3 expressing cell line was designated as humanized anti-hTfR antibody No. 3-3. And, the antibody purified from the culture supernatant of the antibody No. 3-4 expressing cell line was designated as humanized anti-hTfR antibody No. 3-4.

Further, the antibody No. 3 (IgG4) expressing cell line and the antibody No. 3-2 (IgG4) expressing cell line obtained in Example 12 were also cultured in the same manner as above, and from their culture supernatants, the purified humanized anti-hTfR antibody No. 3 (IgG4) and humanized anti-hTfR antibody No. 3-2 (IgG4) were obtained, respectively. These two kinds of antibodies were used in the pharmacokinetic analysis using monkey described in Example 15.

[Example 14] Measurement of Affinity of Humanized Anti-hTfR Antibodies to Human TfR and Monkey TfR The affinity of the humanized anti-hTfR antibody obtained in Example 13 to human TfR and monkey TfR was measured by the method described in Example 7. Table 6 shows the measurement results of the association rate constant (kon) and the dissociation rate constant (koff) of the humanized anti-hTfR antibodies No. 3 to No. 3-4 (corresponding No. 3 to No. 3-4 in the table, respectively) to human TfR, and the dissociation constant ($K_D$).

TABLE 6

Affinity of humanized anti-hTfR antibody to human TfR

| Antibody No. | kon ($M^{-1}s^{-1}$) | koff ($s^{-1}$) | $K_D$ (M) |
|---|---|---|---|
| 3 | $1.19 \times 10^6$ | $<1.0 \times 10^{-7}$ | $<1.0 \times 10^{-12}$ |
| 3-2 | $6.06 \times 10^5$ | $1.45 \times 10^{-5}$ | $2.39 \times 10^{-11}$ |
| 3-3 | $6.00 \times 10^5$ | $1.25 \times 10^{-5}$ | $2.09 \times 10^{-11}$ |
| 3-4 | $1.01 \times 10^6$ | $<1.0 \times 10^{-7}$ | $<1.0 \times 10^{-12}$ |

Table 7 shows the measurement result of the association rate constant (kon) and the dissociation rate constant (koff) of the humanized anti-hTfR antibodies No. 3 to No. 3-4 (corresponding to No. 3 to No. 3-4 in the table, respectively) to monkey TfR, and the dissociation constant ($K_D$).

TABLE 7

Affinity of humanized anti-hTfR antibody to monkey TfR

| Antibody No. | kon ($M^{-1}s^{-1}$) | koff ($s^{-1}$) | $K_D$ (M) |
|---|---|---|---|
| 3 | $6.03 \times 10^5$ | $6.76 \times 10^{-4}$ | $1.12 \times 10^{-9}$ |
| 3-2 | $4.95 \times 10^5$ | $8.76 \times 10^{-4}$ | $1.77 \times 10^{-9}$ |
| 3-3 | $4.88 \times 10^5$ | $9.32 \times 10^{-4}$ | $1.91 \times 10^{-9}$ |
| 3-4 | $5.19 \times 10^5$ | $1.35 \times 10^{-4}$ | $2.60 \times 10^{-10}$ |

The result of measurement of affinity the humanized anti-hTfR antibody No. 3 to No. 3-4 to the human TfR shows that the dissociation constant of the humanized anti-hTfR antibody No. 3 to No. 3-4 with human TfR was less than $1\times10^{-12}$ M (Table 6). And, the dissociation constants of the humanized anti-hTfR antibody No. 3-2 and No. 3-3 with human TfR were $2.39\times10^{-11}$ M and $2.09\times10^{-11}$ M, respectively. On the other hand, the dissociation constant of an anti-hTfR antibodies corresponding to those antibodies prior to humanization (antibody No. 3) with human TfR was less than $1\times10^{-12}$ M (Table 3). These results show that high affinity of those anti-hTfR antibodies to human TfR was maintained before and after humanization of the antibody.

Then, based on the result of measurement of affinity of the humanized anti-hTfR antibodies to monkey TfR, it was observed that the dissociation constant of humanized anti-hTfR antibodies No. 3 to No. 3-4, with monkey TfR while the dissociation constant of anti-hTfR antibodies No. 3 prior to humanization corresponding to these antibodies, to monkey TfR was less than $1\times10^{-12}$ M, the dissociation constant after humanization was $2.60\times10^{-10}$ M to $1.91\times10^{-9}$ M, showing a lower of affinity to monkey TfR (Tables 3 and 7). Although a decrease in affinity to monkey TfR was observed in the humanized anti-hTfR antibody No. 3, the result shows that high affinity of anti-hTfR antibody to monkey TfR was not lost after humanization of an antibody but was generally maintained.

[Example 15] Pharmacokinetic Analysis of Humanized Anti-hTfR Antibody in Monkey Using four kinds of antibodies of the humanized anti-hTfR antibody No. 3, the humanized anti-hTfR antibody No. 3-2, the humanized anti-hTfR antibody No. 3 (IgG4), and the humanized anti-hTfR antibody No. 3-2 (IgG4), pharmacokinetic analysis using a monkey was performed. The humanized anti-hTfR antibody No. 3 is an antibody in which the heavy chain is IgG1, and the humanized anti-hTfR antibody No. 3 (IgG4) is an antibody in which the heavy chain of the humanized anti-hTfR antibody No. 3 is IgG4 with the variable region being as it is. In addition, the humanized anti-hTfR antibody No. 3-2 is an antibody in which the heavy chain is IgG1, and the humanized anti-hTfR antibody No. 3-2 (IgG4) is an antibody in which the heavy chain of the humanized anti-hTfR antibody No. 3-2 is IgG4 with the variable region being as it is. The four kinds of antibodies were respectively administered to male cynomolgus monkeys at a dose of 5.0 mg/kg by single intravenous administration, peripheral blood was collected before administration, two minutes, thirty minutes, two hours, four hours, and eight hours after administration, and systemic perfusion was performed after blood collection. In addition, as a negative control, trastuzumab HERCEPTIN, Chugai Pharmaceutical Co.) which is a humanized antibody to Her2 protein was administered to an entity, peripheral blood was collected before administration, 2 minutes, 30 minutes, 2 hours, four hours, and eight hours after administration, and systemic perfusion was performed after blood collection.

After perfusion, a brain tissue including medulla oblongata, a spinal cord tissue, and other tissues (including liver, heart, spleen, and bone marrow) were extracted. Using the brain tissue, the spinal cord tissue, and other tissues, the following concentration measurement and immunohistochemical staining of a humanized anti-hTfR antibody were performed.

The concentration measurement of a humanized anti-hTfR antibody in the tissues and the peripheral blood was generally performed by the following procedure. Regarding the brain, the collected tissues were divided into the cerebral cortex, the cerebellum, the hippocampus, and the medulla oblongata, and then the concentration measurement of the humanized anti-hTfR antibody was performed. Each of the collected tissues was homogenated with a RIPA Buffer (Waco Pure Chemical Industry) including Protease Inhibitor Cocktail (Sigma-Aldrich Corporation), and centrifuged to recover a supernatant. Regarding the peripheral blood, the supernatant was separated. Anti-Human Kappa Light Chain Goat IgG Biotin (Immuno-Biological Laboratories Co, Ltd.), Sulfo-tag anti-human IgG (H+L) antibody (Bethyl Corporation), and the brain tissue homogenate were added to a streptavidin plate (Meso Scale Diagnostics Corporation) blocked with SuperBlock blocking buffer in PBS (Thermo Fisher Scientific Corporation), shaken for 1 hour, and fixed onto the plate. Subsequently, Read buffer T (Meso Scale Diagnostics Corporation) was added to each well by 150 μL, and a light emission amount was measured from each well using a SECTOR Imager 6000 reader. A calibration curve was prepared from a measurement value of a standard sample of an anti-hTfR antibody with known concentrations, and by interpolating a measurement value of each specimen thereto, an amount of an antibody included in each tissue and the peripheral blood was calculated. The concentration measurement was repeatedly performed three times for each sample.

The result of the concentration measurement of the humanized anti-hTfR antibody in the brain tissue and the spinal cord tissue is shown in Table 8.

TABLE 8

Concentration of humanized anti-hTfR antibody in brain tissue (μg/g wet weight)

| Antibody number | Cerebral cortex | Cerebellum | Hippocampus | Medulla oblongata | Spinal cord |
|---|---|---|---|---|---|
| 3 | 0.67 ± 0.12 | 0.61 ± 0.02 | 0.49 ± 0.02 | 0.59 ± 0.10 | 0.46 ± 0.17 |
| 3-2 | 1.05 ± 0.07 | 0.72 ± 0.04 | 0.72 ± 0.07 | 0.69 ± 0.03 | 0.46 ± 0.02 |
| 3(IgG4) | 0.65 ± 0.05 | 0.59 ± 0.03 | 0.56 ± 0.02 | 0.59 ± 0.02 | 0.46 ± 0.07 |
| 3-2(IgG4) | 0.76 ± 0.02 | 0.57 ± 0.07 | 0.62 ± 0.05 | 0.73 ± 0.16 | 0.48 ± 0.03 |
| Negative control | 0.0082 ± 0.0032 | 0.0090 ± 0.0067 | 0.0053 ± 0.0009 | 0.011 ± 0.003 | 0.15 ± 0.04 |

For all of antibodies of the humanized anti-hTfR antibody No. 3, the humanized anti-hTfR antibody No. 3-2, the humanized anti-hTfR antibody No. 3 (IgG4), and the humanized anti-hTfR antibody No. 3-2 (IgG4), accumulation in the cerebral cortex, the cerebellum, the hippocampus, the medulla oblongata, and the spinal cord was recognized (Table 8). The amount was, for the humanized anti-hTfR antibody No. 3, approximately 82 times in the cerebral cortex, approximately 68 times in the cerebellum, approximately 92 times in the hippocampus, approximately 54 times in the medulla oblongata, and approximately 3.1 times in the spinal cord, compared to trastuzumab (HERCEPTIN) of the negative control, for the humanized anti-hTfR antibody No. 3-2, approximately 128 times in the cerebral cortex, approximately 80 times in the cerebellum, approximately 136 times in the hippocampus, approximately 63 times in the medulla oblongata, and approximately 3.1 times in the spinal cord, compared to trastuzumab of the negative control, for the humanized anti-hTfR antibody No. 3 (IgG4), approximately 79 times in the cerebral cortex, approximately 66 times in the cerebellum, approximately 106 times in the hippocampus, approximately 54 times in the medulla oblongata, and approximately 3.1 times in the spinal cord, compared to trastuzumab of the negative control, and for the humanized anti-hTfR antibody No. 3-2 (IgG4), approximately 93 times in the cerebral cortex, approximately 63 times in the cerebellum, approximately 117 times in the hippocampus, approximately 66 times in the medulla oblongata, and approximately 3.2 times in the spinal cord, compared to trastuzumab of the negative control (Table 9). The result shows that these four kinds of humanized anti-hTfR antibodies have a property of passing through the blood-brain barrier and being accumulated in the brain tissue, and shows that by binding a drug to function in the brain tissue to these antibodies, it is possible to efficiently accumulate the drug in the brain tissue.

TABLE 9

Accumulation amount of humanized anti-hTfR antibody in brain tissue (multiplication factor of accumulation amount compared to negative control)

| Antibody number | Cerebral cortex | Cerebellum | Hippocampus | Medulla oblongata | Spinal cord |
|---|---|---|---|---|---|
| 3 | 82 | 68 | 92 | 54 | 3.1 |
| 3-2 | 128 | 80 | 136 | 63 | 3.1 |
| 3(IgG4) | 79 | 66 | 106 | 54 | 3.1 |
| 3-2(IgG4) | 93 | 63 | 117 | 66 | 3.2 |
| Negative control | 1 | 1 | 1 | 1 | 1 |

Figure 4:
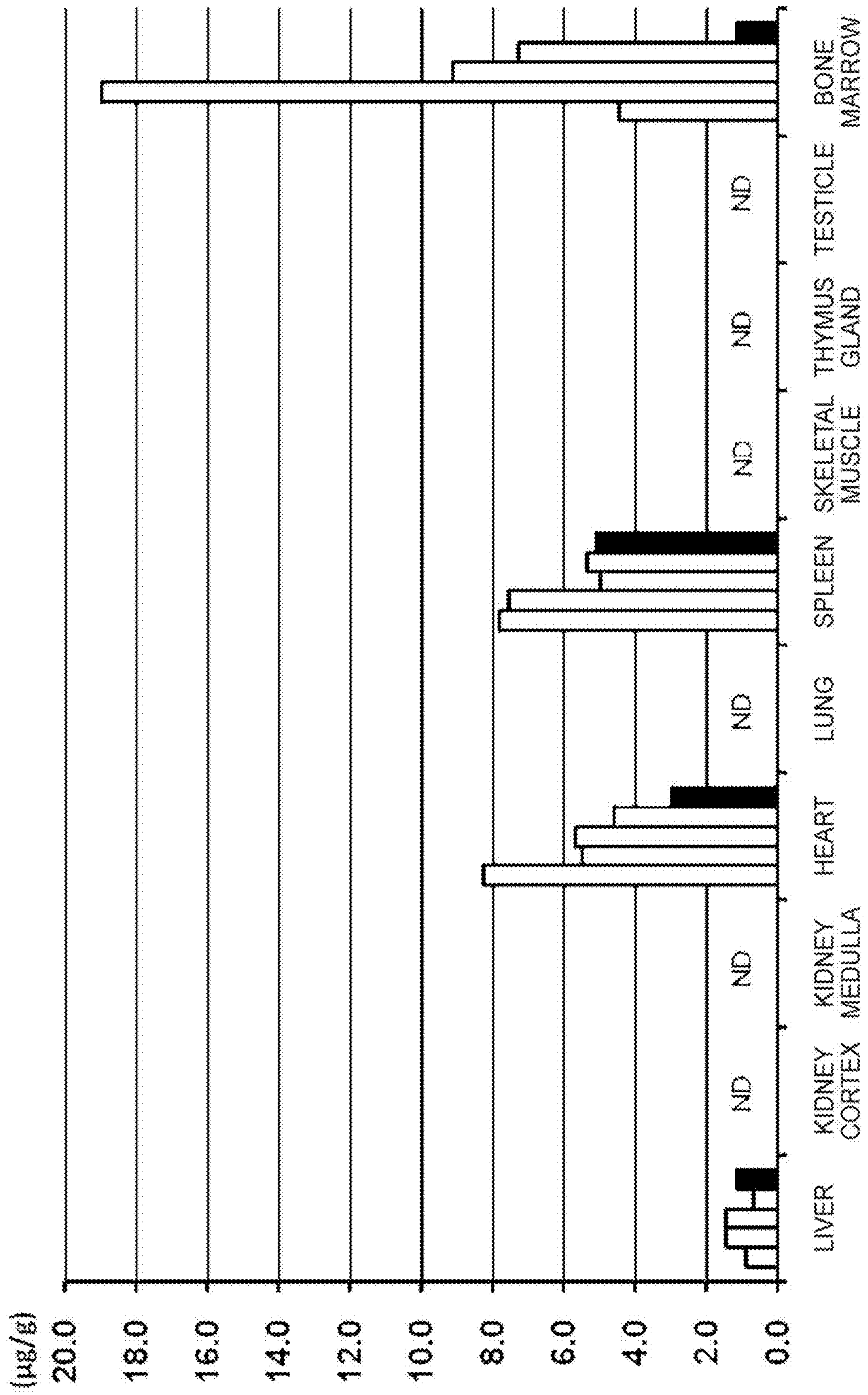
FIG. 4 A figure showing the accumulation amounts of a humanized anti-hTfR antibody to various organs other than the brain of a cynomolgus monkey after single intravenous administration. The axis of ordinate indicates an amount (μg/g wet weight) of the humanized anti-hTfR antibody per wet weight of each organ. The white bar indicates administration of a humanized anti-hTfR antibody No. 3, a humanized anti-hTfR antibody No. 3-2, a humanized anti-hTfR antibody No. 3 (IgG4), and a humanized anti-hTfR antibody No. 3-2 (IgG4), respectively, in an order from left to right, and the black bar indicates an accumulation amounts of the humanized anti-hTfR antibody in each organ of a monkey administered with Trastuzumab (HERCEPTIN). ND means not determined.

Subsequently, the result of concentration measurement of the humanized anti-hTfR antibody in each tissue of liver, heart, spleen, and bone marrow is shown in FIG. 4. In liver and heart, in all of the four kinds of the humanized anti-hTfR antibodies and trastuzumab of the negative control, accumulation was recognized, but the amount was equivalent in the humanized anti-hTfR antibodies and trastuzumab. In heart, there was a tendency that the accumulation amount of the humanized anti-hTfR antibodies was greater than that of trastuzumab of the negative control, but the amount was only 1.5 to 2.8 times that of the negative control. In spleen, there was a tendency that the accumulation amount of the humanized anti-hTfR antibodies was remarkably greater than that of trastuzumab of the negative control, and the amount was 3.5 to 16 times that of the negative control. Regarding accumulation of the humanized anti-hTfR antibodies in the spinal cord, an expression amount of TfR is great in the spinal cord which is a hematopoietic organ, and it is considered that the reason is that by binding to TfR, a large amount of the humanized anti-hTfR antibodies were accumulated compared to the negative control. This data shows that the four kinds of humanized anti-hTfR antibodies have a property of being specifically accumulated in the cerebrum, the cerebellum, the hippocampus, and the medulla oblongata which are the central nervous system, and shows that by binding a drug to function in the brain tissue to these antibodies, it is possible to efficiently accumulate the drug in the brain tissue.

Subsequently, the result of measurement of kinetics in blood of the humanized anti-hTfR antibodies is shown in Table 9-2. It was shown that the four kinds of humanized anti-hTfR antibodies exhibit a high concentration in blood of 60 μg/mL or more even after 8 hours from administration, similar to trastuzumab of the negative control, and are stabilized in the blood (Table 9-2).

TABLE 9-2

Kinetics in blood of humanized anti-hTfR antibody (μg/mL blood)

| Antibody | Time after administration | | | | |
|---|---|---|---|---|---|
| number | 2 Minutes | 30 Minutes | 2 Hours | 4 Hours | 8 Hours |
| 3 | 173 | 147 | 128 | 117 | 97.5 |
| 3-2 | 124 | 99.5 | 78.5 | 76.5 | 61 |
| 3(IgG4) | 141 | 113 | 99 | 95 | 83 |
| 3-2(IgG4) | 132 | 111 | 93.5 | 99 | 95.5 |
| Negative control | 124 | 92.5 | 96 | 75.5 | 60.5 |

Immunohistochemical staining of a humanized anti-hTfR antibody in the brain tissue was performed by the method described in Example 8. However, at this time, instead of Mouse IgG-heavy and light chain Antibody (Bethyl Laboratories Inc.), Human IgG-heavy and light chain Antibody (Bethyl Laboratories Inc.) was used.

Figure 5:
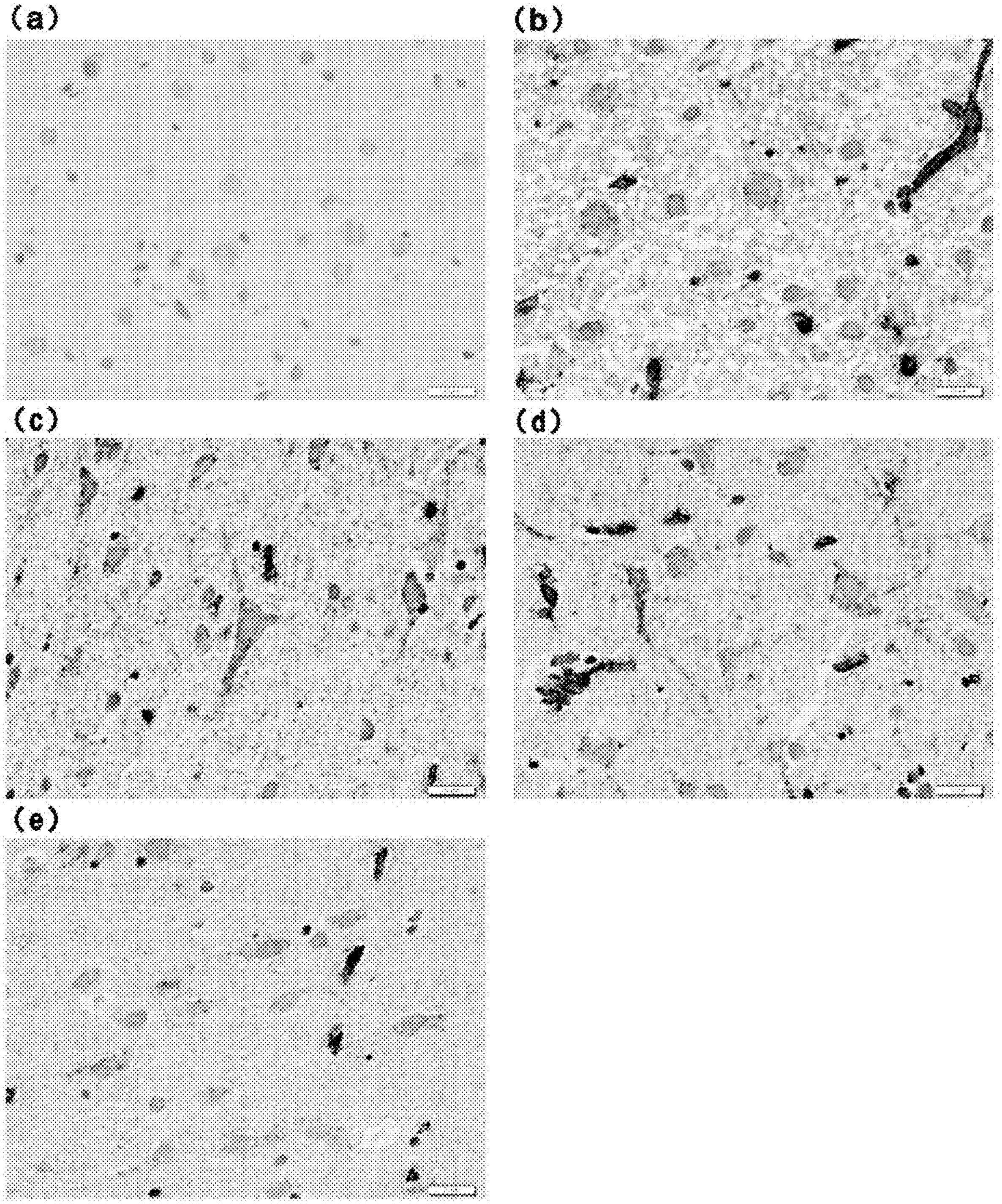
FIG. 5 A figure showing the result of immunohistochemical staining with a humanized anti-hTfR antibody of a cerebral cortex of a cynomolgus monkey after single intravenous administration. (a) Administration of HERCEPTIN, (b) administration of a humanized anti-hTfR antibody No. 3, (c) administration of a humanized anti-hTfR antibody 3-2, (d) administration of a humanized anti-hTfR antibody No. 3 (IgG4), and (e) administration of a humanized anti-hTfR antibody No. 3-2 (IgG4). The bar on the right bottom of each photograph is a gauge indicating 20 μm.

FIG. 5 shows a result of immunohistochemical staining of a humanized anti-hTfR antibody of a cerebral cortex. In the cerebral cortex of a monkey administered with the humanized anti-hTfR antibody No. 3, the humanized anti-hTfR antibody 3-2, the humanized anti-hTfR antibody No. 3 (IgG4), and the humanized anti-hTfR antibody No. 3-2 (IgG4), specific staining of the blood vessel and the nerve-like cells was checked (respectively, FIGS. 5*b* to 5*e*). In particular, in the cerebral cortex of a monkey administered with the humanized anti-hTfR antibody No. 3-2 (FIG. 5*c*), specific staining was widely checked also in the cerebral parenchyma region other than the cerebral blood vessel. In the cerebral cortex of a monkey administered with HERCEPTIN as a control, staining was not recognized, and it was shown that the tissue staining observed in FIGS. 5*b* to 5*e* was specific to the humanized anti-hTfR antibody (FIG. 5*a*).

Figure 6:
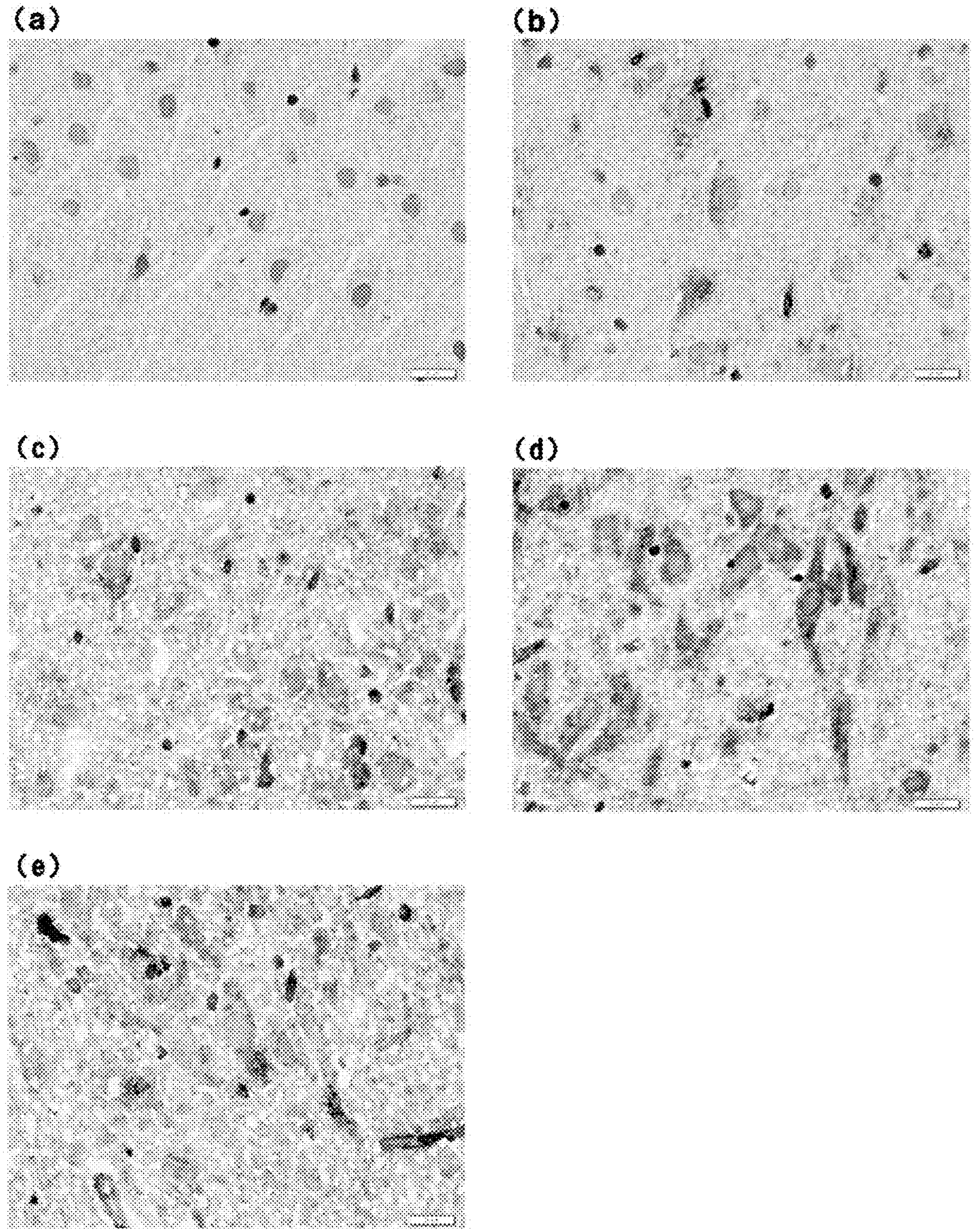
FIG. 6 A figure showing the result of immunohistochemical staining with a humanized anti-hTfR antibody of hippocampus of a cynomolgus monkey after single intravenous administration. (a) Administration of HERCEPTIN, (b) administration of a humanized anti-hTfR antibody No. 3, (c) administration of a humanized anti-hTfR antibody No. 3-2, (d) administration of a humanized anti-hTfR antibody No. 3 (IgG4), and (e) administration of a humanized anti-hTfR antibody No. 3-2 (IgG4). The bar on the right bottom of each photograph is a gauge indicating 20 μm.

FIG. 6 shows a result of immunohistochemical staining of a humanized anti-hTfR antibody of hippocampus. In the hippocampus of a monkey administered with the humanized anti-hTfR antibody No. 3, the humanized anti-hTfR antibody 3-2, the humanized anti-hTfR antibody No. 3 (IgG4), and the humanized anti-hTfR antibody No. 3-2 (IgG4), specific staining of the blood vessel and the nerve-like cells was checked (respectively, FIGS. 6*b* to 6*e*). In the hippocampus of a monkey administered with HERCEPTIN as a control, staining was not recognized, and it was shown that the tissue staining observed in FIGS. 6*b* to 6*e* was specific to the humanized anti-hTfR antibody (FIG. 6*a*).

Figure 7:
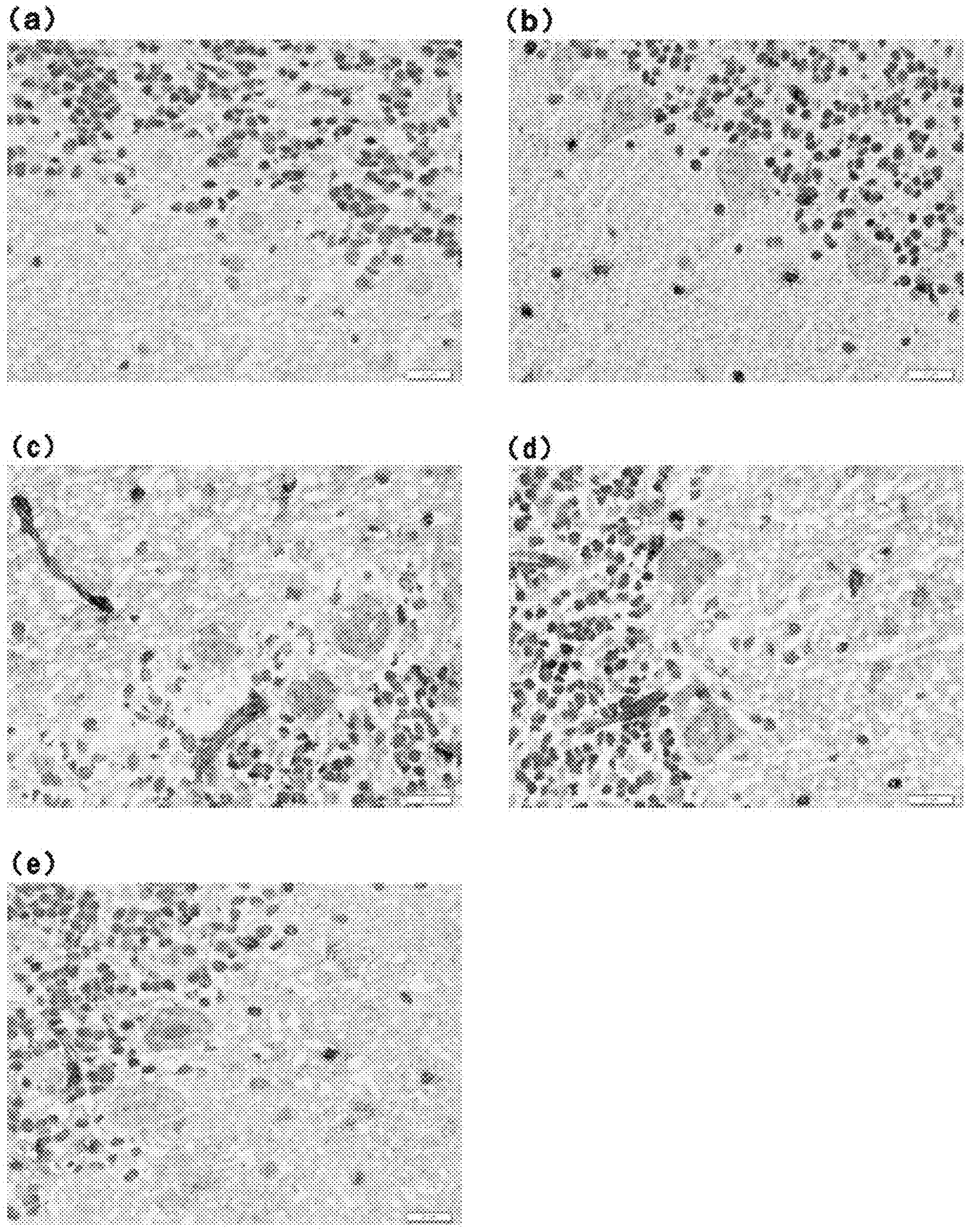
FIG. 7 A figure showing the result of immunohistochemical staining with respect to a humanized anti-hTfR antibody of cerebellum of a cynomolgus monkey after single intravenous administration. (a) Administration of HERCEPTIN, (b) administration of a humanized anti-hTfR antibody No. 3, (c) administration of a humanized anti-hTfR antibody No. 3-2, (d) administration of a humanized anti-hTfR antibody No. 3 (IgG4), and (e) administration of a humanized anti-hTfR antibody No. 3-2 (IgG4). The bar on the right bottom of each photograph is a gauge indicating 20 μm.

FIG. 7 shows a result of immunohistochemical staining of a humanized anti-hTfR antibody of a cerebellum. In the cerebellum of a monkey administered with the humanized anti-hTfR antibody No. 3, the humanized anti-hTfR antibody 3-2, the humanized anti-hTfR antibody No. 3 (IgG4), and the humanized anti-hTfR antibody No. 3-2 (IgG4), specific staining of the blood vessel and the Purkinje cells was checked (respectively, FIGS. 7*b* to 7*e*). In the cerebellum of a monkey administered with HERCEPTIN as a control, staining was not recognized, and it was shown that the tissue staining observed in FIGS. 7*b* to 7*e* was specific to the humanized anti-hTfR antibody (FIG. 7*a*).

Figure 8:
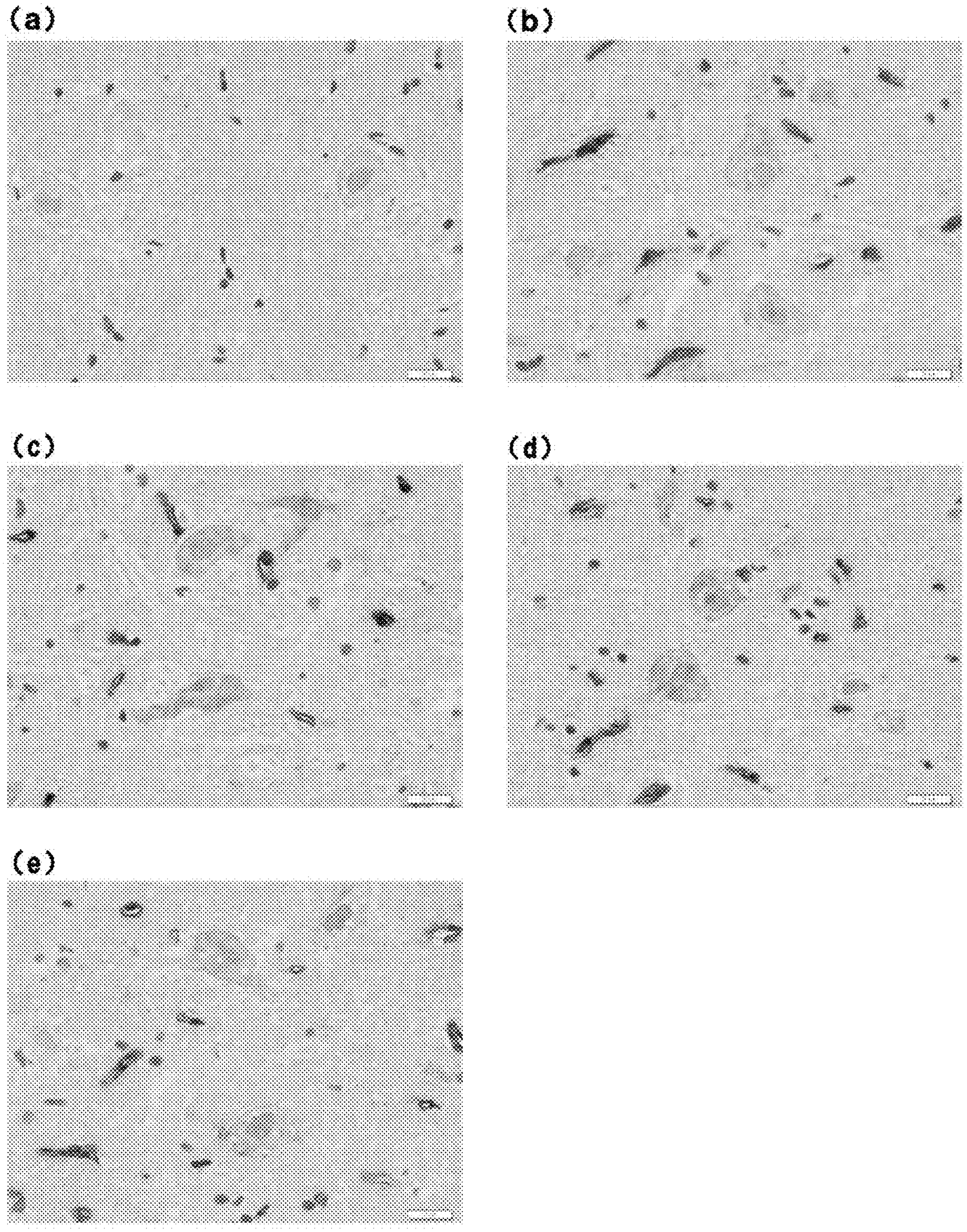
FIG. 8 A figure showing the result of immunohistochemical staining with a humanized anti-hTfR antibody of medulla oblongata of a cynomolgus monkey after single intravenous administration. (a) Administration of HERCEPTIN, (b) administration of a humanized anti-hTfR antibody No. 3, (c) administration of a humanized anti-hTfR antibody No. 3-2, (d) administration of a humanized anti-hTfR antibody No. 3 (IgG4), and (e) administration of a humanized anti-hTfR antibody No. 3-2 (IgG4). The bar on the right bottom of each photograph is a gauge indicating 20 μm.

FIG. 8 shows a result of immunohistochemical staining of a humanized anti-hTfR antibody of a medulla oblongata. In the medulla oblongata of a monkey administered with the humanized anti-hTfR antibody No. 3, the humanized anti-hTfR antibody 3-2, the humanized anti-hTfR antibody No. 3 (IgG4), and the humanized anti-hTfR antibody No. 3-2 (IgG4), specific staining of the blood vessel and the nerve-like cells was checked (respectively, FIGS. 8*b* to 8*e*). In the medulla oblongata of a monkey administered with HERCEPTIN as a control, staining was not recognized, and it was shown that the tissue staining observed in FIGS. 8*b* to 8*e* was specific to the humanized anti-hTfR antibody (FIG. 8*a*).

From the result of immunohistochemical staining of the cerebrum and the cerebellum of Example 8, it was shown that the anti-hTfR antibody No. 3 which is a mouse antibody after humanization can bind to hTfR present on the cerebrovascular endothelial surface, after binding to hTfR, the anti-hTfR antibody No. 3 passes through the blood-brain barrier and migrates into the brain parenchyma, and is inserted, from the brain parenchyma to the nerve-like cells in the hippocampus, and to the Purkinje cells in the cerebellum.

From a result of immunohistochemical staining of the cerebrum, the hippocampus, the cerebellum, and the medulla oblongata of Example 15, it was known that the four kinds of humanized anti-hTfR antibodies obtained by humanizing the anti-hTfR antibody No. 3 provided to an experiment bind to hTfR present on the cerebrovascular endothelial surface, after binding to hTfR, the anti-hTfR antibodies pass through the blood-brain barrier and migrate into the brain parenchyma, and are inserted, to the nerve-like cells in the cerebral cortex, from the brain parenchyma to the nerve-like cells in the hippocampus, to the Purkinje cells in the cerebellum, and to the nerve-like cells in medulla oblongata.

[Example 15-2] Production of Cell for hBDNF-Humanized Anti-hTfR Antibody Fusion Protein (hBDNF-Anti-hTfR Antibody Fusion Protein) Expression A DNA fragment having the nucleic acid sequence represented by SEQ ID NO: 78 including a gene encoding a fusion protein obtained by fusing a humanized anti-hTfR antibody Fab heavy chain having an amino acid sequence represented by SEQ ID NO: 77 with a C-terminal side of a pro-protein of hBDNF having an amino acid sequence represented by SEQ ID NO: 56 via a linker sequence formed of a total of 27 amino acids obtained by repeating the amino acid sequence Gly-Gly-Gly-Gly-Ser represented by SEQ ID NO: 3 subsequent to Gly-Ser five times was artificially synthesized. Here, the amino acid sequence represented by SEQ ID NO: 77 corresponds to an amino acid sequence at the positions first to the 226$^{th}$ from an N-terminal side of the amino acid sequence represented by SEQ ID NO: 37. Here, an amino acid sequence at the positions first to the 118$^{th}$ from the N-terminal side corresponds to SEQ ID NO: 32 (amino acid sequence 2 of variable region of heavy chain of humanized anti-hTfR antibody No. 3), an amino acid sequence at the positions 119$^{th}$ to 216$^{th}$ corresponds to a $C_H1$ region, and an amino acid sequence at the positions 217$^{th}$ to 226$^{th}$ corresponds to a hinge region.

The DNA fragment encodes a fusion protein of a pro-protein of hBDNF and a humanized anti-hTfR antibody Fab heavy chain having an amino acid sequence represented by SEQ ID NO: 79. The fusion protein having an amino acid sequence represented by SEQ ID NO: 79 is subjected to a processing after expression and becomes a fusion protein of hBDNF and a humanized anti-hTfR antibody Fab heavy chain having an amino acid sequence represented by SEQ ID NO: 80. In the amino acid sequence represented by SEQ ID NO: 79, an amino acid sequence at the positions first to 110$^{th}$ from the N-terminal side is a portion removed at a time at which hBDNF is processed from a pro-protein to a mature type. The DNA fragment was digested with MluI and NotI, and inserted between MluI and NotI of a pE-neo vector to construct pE-neo (BDNF-Fab HC-1).

CHO cell (CHO-K1: acquired from American Type Culture Collection) was transformed by the pE-neo (BDNF-Fab HC-1) and pE-hygr (LC3) constructed in Example 11 by the method described in Example 12 to obtain a fusion protein of hBDNF and a humanized anti-hTfR antibody. The cell line was set as a hBDNF-anti-hTfR antibody (3) 1 expression line. A fusion protein of hBDNF and a humanized anti-hTfR antibody expressed by the cell line was set as a hBDNF-anti-hTfR antibody (3) 1.

[Example 15-3] Production of hBDNF-Anti-hTfR Antibody (3) 1

Using the hBDNF-anti-hTfR antibody (3) 1 expression line obtained in Example 15-2, a purified product of the hBDNF-anti-hTfR antibody (3) 1 was obtained by the method described in Example 13.

[Example 16] Introduction of Mutation into Heavy Chain of Humanized Anti-hTfR Antibody No. 3

In a variable region of a heavy chain of the humanized anti-hTfR antibody No. 3 represented by SEQ ID NO: 37, a heavy chain of a humanized antibody which substitutes one amino acid sequence of the CDR1 and also substitutes one amino acid sequence of a framework region 3 when CDR1 is represented by SEQ ID NO: 12 was prepared. The new antibody heavy chain includes an amino acid sequence of SEQ ID NO: 66 (or SEQ ID NO: 67 including thereof) in the CDR1, and includes an amino acid sequence of SEQ ID NO: 68 in the framework region 3, and therefore is the one obtained by substituting two amino acids constituting an amino acid sequence of the heavy chain of the humanized anti-hTfR antibody No. 3 represented by SEQ ID NO: 37. The new antibody (humanized anti-hTfR antibody No. 3N) heavy chain includes an amino acid sequence of SEQ ID NO: 70 and the variable region includes an amino acid sequence represented by SEQ ID NO: 69.

Table 10 showed alignment of CDR1 of SEQ ID NO: 12 in the heavy chain of the humanized anti-hTfR antibody No. 3 and CDR1 of SEQ ID NO: 66 in the heavy chain of the humanized anti-hTfR antibody No. 3N. In the alignment, an amino acid at the fifth position from the N-terminal side is substituted from threonine to methionine.

Table 11 shows alignment of an amino acid sequence of the framework region 3 (SEQ ID NO: 83) in the heavy chain of the humanized anti-hTfR antibody No. 3 and an amino acid sequence of the framework region 3 (SEQ ID NO: 68) in the heavy chain of the humanized anti-hTfR antibody No. 3N. In the alignment, an amino acid at the 17$^{th}$ position from the N-terminal side is substituted from tryptophan to leucine.

TABLE 10

Alignment of amino acid sequence of CDR1

| | CDR1 |
|---|---|
| Humanized anti-hTfR antibody No. 3 | GYSFTNYW |
| | **** *** |
| Humanized aHumanized anti-hTfR antibody No. 3N | GYSFMNYW |

* indicates the identical amino acid. Sequence of CDR1 of humanized anti-hTfR antibody No. 3 and sequence of CDR1 of humanized anti-hTfR antibody No. 3N are represented by SEQ ID NO: 12 and SEQ ID NO: 66, respectively.

TABLE 11

Alignment of amino acid sequence of framework region 3 (FR3)

| | FR3 |
|---|---|
| Humanized anti-hTfR antibody No. 3 | QVTISADKSISTAYLQWSSLKASDTAMYYC |
| | **************** ************* |
| Humanized anti-hTfR antibody No. 3N | QVTISADKSISTAYLQLSSLKASDTAMYYC |

* indicates the identical amino acid. Sequence of FR3 of humanized anti-hTfR antibody No. 3 and sequence of FR3 of humanized anti-hTfR antibody No. 3N are identical represented by SEQ ID NO: 83 and by SEQ ID NO: 68, respectively.

[Example 17] Construction of Cell for Humanized Anti-hTfR Antibody No. 3N Expression A DNA fragment (SEQ ID NO: 71) including a gene encoding a heavy chain of an antibody formed of an amino acid sequence represented by SEQ ID NO: 70 was artificially synthesized. An MluI sequence in an order from a 5' end and a sequence encoding leader peptide were introduced into a 5' side of the DNA fragment, and a NotI sequence was introduced into a 3' side thereof. The DNA synthesized in this manner was inserted into the pE-neo vector by the method described in Example 11, and the obtained vector was set as pE-neo (HC3) N of a heavy chain expression vector of the humanized anti-hTfR antibody No. 3N. Using the pE-neo (HC3) N and the light chain expression vector pE-hygr (LC3) constructed in Example 11, CHO cell was transformed by the method described in Example 12 to obtain a humanized anti-hTfR antibody No. 3N expression line.

[Example 18] Purification of Humanized Anti-hTfR Antibody No. 3N

Using the humanized anti-hTfR antibody No 3N expressing cell line obtained in Example 17, a purified product of the humanized anti-hTfR antibody No. 3N was obtained by the method described in Example 13. The humanized anti-hTfR antibody No. 3N is obtained by substituting amino acids at two sites shown in Tables 10 and 11 in the amino acid sequence of the heavy chain of the humanized anti-hTfR antibody No. 3. On the other hand, the amino acid sequences of the respective light chain of the humanized anti-hTfR antibody No. 3N and the humanized anti-hTfR antibody No. 3 are the same.

[Example 19] Comparison Between Affinity of Humanized Anti-hTfR Antibody No. 3 to Human TfR and Monkey TfR and Affinity of Humanized Anti-hTfR Antibody No. 3N to Human TfR and Monkey TfR Affinity of the humanized anti-hTfR antibody No. 3 obtained in Example 13 to human TfR and to monkey TfR and affinity of the humanized anti-hTfR antibody No. 3N obtained in Example 17 to human TfR and monkey TfR were measured by the method described in Example 7. Table 12 shows a result of measurement of the association rate constant (kon) and the dissociation rate constant (koff) of each antibodies to human TfR, and the dissociation constant ($K_D$). Although the measurement value exhibiting affinity of the humanized anti-hTfR antibody No. 3 to human TfR was different from that shown in Table 6, that is an experimental error.

TABLE 12

Affinity of humanized anti-hTfR antibody to human TfR

| | kon ($M^{-1}s^{-1}$) | koff ($s^{-1}$) | $K_D$ (M) |
|---|---|---|---|
| Humanized anti-hTfR antibody 3 | $8.47 \times 10^5$ | $<1.0 \times 10^{-7}$ | $<1.0 \times 10^{-12}$ |
| Humanized anti-hTfR antibody 3N | $7.84 \times 10^5$ | $<1.0 \times 10^{-7}$ | $<1.0 \times 10^{-12}$ |

Affinity of the humanized anti-hTfR antibody No. 3 obtained in Example 13 to human TfR and to monkey TfR, and affinity of the humanized anti-hTfR antibody No. 3N obtained in Example 18 to human TfR and to monkey TfR were measured by the method described in Example 7. Table 13 shows the result of measurement of the association rate constant (kon) and the dissociation rate constant (koff) of each of the antibodies to monkey TfR, and a dissociation constant ($K_D$). Although the measurement value exhibiting affinity of the humanized anti-hTfR antibody No. 3 to monkey TfR was different from that shown in Table 7, that was an experimental error.

TABLE 13

Affinity of humanized anti-hTfR antibody to monkey TfR

| | kon ($M^{-1}s^{-1}$) | koff ($s^{-1}$) | $K_D$ (M) |
|---|---|---|---|
| Humanized anti-hTfR antibody 3 | $6.09 \times 10^5$ | $8.06 \times 10^{-4}$ | $1.32 \times 10^{-9}$ |
| Humanized anti-hTfR antibody 3N | $3.86 \times 10^5$ | $1.96 \times 10^{-5}$ | $5.07 \times 10^{-11}$ |

In comparison between a $K_D$ value of the humanized anti-hTfR antibody No. 3N and a $K_D$ value of the humanized anti-hTfR antibody No. 3, with monkey TfR, the former was $5.07\times10^{-11}$ M and the latter was $1.32\times10^{-9}$ M, and a $K_D$ value of the humanized anti-hTfR antibody No. 3N with monkey TfR was approximately 1/30 compared to that of the humanized anti-hTfR antibody No. 3. On the other hand, in comparison with a $K_D$ value of the humanized anti-hTfR antibody No. 3N and a $K_D$ value of the humanized anti-hTfR antibody No. 3, with human TfR, the both values were less than $1\times10^{-12}$ M, and the both antibodies also had high affinity to human TfR. And, the both antibodies also had higher affinity to human TfR than affinity to monkey TfR.

As a non-clinical test performed at a time of developing a humanized anti-hTfR antibody as a drug, there are many cases where a pharmacological test using a monkey is performed. Here, since the result of the pharmacological test in cynomolgus monkey is used for determination of validity in performing a clinical test in human, behaviors in the monkey body are preferably more similar to behaviors in a case of being administered to a human. As the above result, since the humanized anti-hTfR antibody No. 3N exhibits a high value of affinity to a monkey TfR approximately 30 times that of the humanized anti-hTfR antibody No. 3, behaviors in the monkey body of the humanized anti-hTfR antibody No. 3N are more similar to behaviors in a case of being administered to a human. Therefore, by using the humanized anti-hTfR antibody No. 3N, a result more reflecting behaviors in a case of being administered to a human is obtained in a test using a monkey. Therefore, a more useful result is obtained as a determination material at the time of performing a clinical study.

[Example 20] Comparison of Brain Uptake Between Humanized Anti-hTfR Antibody No. 3 and Humanized Anti-hTfR Antibody No. 3N Each of the humanized anti-hTfR antibody No. 3 obtained in Example 13 and the humanized anti-hTfR antibody No. 3N obtained in Example 17 was respectively administered to each male cynomolgus monkey at a dose of 5.0 mg/kg by single intravenous injection, and systemic perfusion was performed after 8 hours from administration. After perfusion, the brain tissue and the spinal cord tissue including medulla oblongata were extracted. The brain tissue was divided into a cerebral cortex, a cerebellum, a hippocampus, and medulla oblongata after extraction.

Concentration measurement of the humanized anti-hTfR antibody included in each tissue was performed according to the measurement method described in Example 15.

The result of the concentration measurement of the humanized anti-hTfR antibody in the brain tissue is shown in Table 14. In comparison between concentrations in the cerebrum, the cerebellum, and the hippocampus of the humanized anti-hTfR antibody No. 3N and concentrations in the cerebrum, the cerebellum, and the hippocampus of the humanized anti-hTfR antibody No. 3, the concentration of the humanized anti-hTfR antibody No. 3N was higher than that of the humanized anti-hTfR antibody No. 3, for example, approximately 1.42 times in the cerebrum, approximately 1.56 times in the cerebellum, and approximately 1.29 times in the hippocampus. In the medulla oblongata, concentrations of the both antibodies were almost equivalent to each other. Also in the cervical spinal cord, the concentration of the humanized anti-hTfR antibody No. 3N was higher than that of the humanized anti-hTfR antibody No. 3, for example, approximately 1.47 times. The result shows that the humanized anti-hTfR antibody No. 3N has a property of more efficiently passing through the blood-brain barrier and being accumulated in the brain tissue such as the cerebrum, the cerebellum, and the hippocampus compared to the humanized anti-hTfR antibody No. 3. That is, the result shows that by binding a drug to function in the brain tissue to the antibody, the humanized anti-hTfR antibody No. 3N has a property of being able to more efficiently accumulate the drug in the brain tissue.

TABLE 14

| Concentration of anti-hTfR antibody in brain tissue (μg/g wet weight) | | | | | |
|---|---|---|---|---|---|
| Antibody number | Cerebrum | Cerebellum | Hippocampus | Medulla oblongata | Cervical spinal cord |
| 3 | 0.670 | 0.610 | 0.490 | 0.589 | 0.589 |
| 3N | 0.953 | 0.950 | 0.631 | 0.586 | 0.672 |

[Example 20-2] Production of Cell for hFc-Humanized Anti-hTfR Antibody Expression A DNA fragment (SEQ ID NO: 82) including a gene encoding an amino acid sequence of a Fab heavy chain of the humanized anti-hTfR antibody No. 3N into which a human IgG Fc region formed of an amino acid sequence represented by SEQ ID NO: 81 was artificially synthesized. A MluI sequence and a sequence encoding leader peptide in an order from a 5' end was introduced into a 5' side of the DNA fragment, and a NotI sequence was introduced into a 3' side thereof. The DNA synthesized in this manner was inserted into a pE-neo vector by the method described in Example 11, and the obtained vector was set as pE-neo (Fc-Fab HC (3N). Using the pE-neo (Fc-Fab HC (3N)) and the light chain expression vector pE-hygr (LC3) constructed in Example 11, CHO cell was transformed by the method described in Example 12 to obtain an Fc-Fab (3N) expression line.

[Example 20-3] Production of hFc-Humanized Anti-hTfR Antibody

Using the Fc-Fab (3N) expression line, a purified product of Fc-Fab (3N) was obtained by the method described in Example 13.

[Example 20-4] Comparison Between Affinity of hFc-Humanized Anti-hTfR Antibody to Human TfR and Affinity of hFc-Humanized Anti-hTfR Antibody to Monkey TfR Affinities of the purified product of the Fc-Fab (3N) obtained in Example 20-3 to human TfR and to monkey TfR were measured by the method described in Example 7. The result is shown in Table 14-2. The result shows that the Fc-Fab (3N) has property to be able to accumulate the drug into the brain tissue efficiently by conjugating the drug which function in the brain tissue, with the antibody.

TABLE 14-2

| Affinity of hFc-humanized anti-hTfR antibody to human TfR and monkey TfR | | | |
|---|---|---|---|
| | kon ($M^{-1}s^{-1}$) | koff ($s^{-1}$) | $K_D$ (M) |
| Human TfR | $6.67 \times 10^5$ | $<1.0 \times 10^{-7}$ | $<1.0 \times 10^{-12}$ |
| Monkey TfR | $2.43 \times 10^5$ | $2.09 \times 10^{-4}$ | $8.61 \times 10^{-10}$ |

[Example 20-5] Evaluation of Brain Uptake of hFc-Humanized Anti-hTfR Antibody in Monkey The Fc-Fab (3N) obtained in Example 20-3 was administered to a male cynomolgus monkey at a dose of 5.0 mg/kg by single intravenous injection, and systemic perfusion was performed after 8 hours from administration. After perfusion, the brain tissue and the spinal cord tissue including the medulla oblongata were extracted. The brain tissue was divided into a cerebral cortex, a cerebellum, a hippocampus, and medulla oblongata.

Concentration measurement of the humanized anti-hTfR antibody in each tissue was performed according to the measurement method described in Example 15.

The result of the concentration measurement of the anti-hTfR antibody in the brain tissue is shown in Table 14-3. Concentrations in the cerebrum, the cerebellum, and the hippocampus of the Fc-Fab (3N) were respectively 0.80 μg/g wet weight, 0.08 μg/g wet weight, and 1.05 μg/g wet weight. In addition, concentrations in the medulla oblongata and the cervical spinal cord were respectively 0.67 μg/g wet weight and 0.68 μg/g wet weight. The result shows that even in a case where the Fc region binds to the N-terminal side of a humanized anti-hTfR antibody which is Fab, the anti-hTfR antibody passes through the BBB. Therefore, in a case where a binding body in which BDNF binds to Fab is not stable at a time of being administered in a living body, by binding the Fc region to the N-terminal side of Fab, it is possible to stabilize the binding body while maintaining a property of passing through the BBB, for example, it is possible to increase half-life in blood of the binding body.

TABLE 14-3

| Concentration of hFc-humanized anti-hTfR antibody in brain tissue (μg/g wet weight) | | | | | |
|---|---|---|---|---|---|
| | Cerebrum | Cerebellum | Hippocampus | Medulla oblongata | Cervical spinal cord |
| hFc-humanized anti-hTfR antibody | 0.80 | 0.80 | 1.05 | 0.67 | 0.68 |

[Example 21] Production of Cell for hBDNF-Humanized Anti-hTfR Antibody Fusion Protein (hBDNF-Anti-hTfR Antibody Fusion Protein) Expression (1) A DNA fragment having the nucleic acid sequence represented by SEQ ID NO: 62 including a gene encoding a fusion protein obtained by fusing a humanized anti-hTfR antibody 3NFab heavy chain having an amino acid sequence represented by SEQ ID NO: 61 with a C-terminal side of a pro-protein of hBDNF having an amino acid sequence represented by SEQ ID NO: 56 via a linker sequence formed of a total of 25 amino acids obtained by repeating amino acid sequence Gly-Gly-Gly-Gly-Ser represented by SEQ ID NO: 3 five times was artificially synthesized. Here, the amino acid sequence represented by SEQ ID NO: 61 corresponds to an amino acid sequence at the positions first to the $226^{th}$ from an N-terminal side of the amino acid sequence of a heavy chain of a humanized anti-hTfR antibody No. 3N represented by SEQ ID NO: 70. Here, an amino acid sequence at the positions first to $118^{th}$ from the N-terminal side corresponds to SEQ ID NO: 69 (amino acid sequence of variable region of heavy chain of humanized anti-hTfR antibody No. 3N), an amino acid sequence at the positions $119^{th}$ to $216^{th}$ corresponds to a $C_H1$ region, and an amino acid sequence at the positions $217^{th}$ to $226^{th}$ corresponds to a hinge region.

The DNA fragment encodes a fusion protein of a pro-protein of hBDNF and a humanized anti-hTfR antibody 3NFab heavy chain having an amino acid sequence represented by SEQ ID NO: 63. The fusion protein having an amino acid sequence represented by SEQ ID NO: 63 is subjected to processing after expression and becomes a fusion protein of hBDNF and a humanized anti-hTfR antibody Fab heavy chain having an amino acid sequence represented by SEQ ID NO: 65. In the amino acid sequence represented by SEQ ID NO: 63, an amino acid sequence at the positions first to $110^{th}$ from the N-terminal side is a portion removed at a time at which hBDNF is processed from a pro-protein to a mature type. The DNA fragment was digested with MluI and NotI, and inserted between MluI and NotI of a pE-neo vector to construct pE-neo (BDNF-Fab HC (3N)).

(2) In addition, a DNA fragment having the nucleic acid sequence represented by SEQ ID NO: 73, including a gene encoding a fusion protein obtained by fusing humanized anti-hTfR antibody 3NFab heavy chain having a sequence of a Fc region of SEQ ID NO: 75, a linker sequence formed of a total of 25 amino acids obtained by repeating amino acid sequence Gly-Gly-Gly-Gly-Ser represented by SEQ ID NO: 3 five times, and an amino acid sequence represented by SEQ ID NO: 61 in an order from the N-terminal side to the C-terminal side with a C-terminal side of a pro-protein of hBDNF having an amino acid sequence represented by SEQ ID NO: 56 via a linker sequence formed of a total of 25 amino acids obtained by repeating an amino acid sequence Gly-Gly-Gly-Gly-Ser represented by SEQ ID NO: 3 five times was artificially synthesized.

The DNA fragment encodes a fusion protein represented by SEQ ID NO: 74. The fusion protein having an amino acid sequence represented by SEQ ID NO: 74 is subjected to a processing after expression and the pro-protein portion of hBDNF becomes hBDNF. In the amino acid sequence represented by SEQ ID NO: 74, an amino acid sequence at the positions first to $110^{th}$ from the N-terminal side is a portion removed at a time at which hBDNF is processed from a pro-protein to a mature type. The DNA fragment was digested with MluI and NotI, and inserted between MluI and NotI of a pE-neo vector to construct pE-neo (BDNF-Fc-Fab HC (3N)).

CHO cell (CHO-K1: acquired from American Type Culture Collection) was transformed by pE-neo (BDNF-Fab HC (3N)) and pE-hygr (LC3) constructed in Example 11 to obtain a cell line expressing a fusion protein of hBDNF and a humanized anti-hTfR antibody 3N. The cell line was set as hBDNF-anti-hTfR antibody (3N) 1 expression line. A fusion protein of hBDNF and a humanized anti-hTfR antibody expressed by the cell line was set as hBDNF-anti-hTfR antibody (3N) 1. In addition, the CHO cell was transformed by pE-neo (BDNF-Fc-Fab HC (3N)) and pE-hygr (LC3) constructed in Example 11 to obtain a cell line expressing another fusion protein of hBDNF and a humanized anti-hTfR antibody 3N. The cell line was set as a hBDNF-anti-hTfR antibody (3N) 2 expression line. A fusion protein of hBDNF and a humanized anti-hTfR antibody expressed by the cell line was set as a hBDNF-anti-hTfR antibody (3N) 2.

[Example 21-2] Production of Cell for Albumin-Binding Domain (ABD)-Added hBDNF-Humanized Anti-hTfR Antibody Fusion Protein Expression A DNA fragment having the nucleic acid sequence represented by SEQ ID NO: 86, including a gene encoding a fusion protein obtained by fusing a humanized anti-hTfR antibody 3NFab heavy chain having an amino acid sequence (SEQ ID NO: 84) corresponding from an amino acid sequence at the positions first to $216^{th}$ of the amino acid sequence represented by SEQ ID NO: 61 with a C-terminal side of a pro-protein of hBDNF having an amino acid sequence represented by SEQ ID NO: 56 via a linker sequence formed of a total of 25 amino acids obtained by repeating an amino acid sequence Gly-Gly-Gly-Gly-Ser represented by SEQ ID NO: 3 five times, and then further fusing ABD represented by SEQ ID NO: 85 with the C-terminal side via a linker sequence formed of a total of 15 amino acids obtained by repeating an amino acid sequence Gly-Gly-Gly-Gly-Ser represented by SEQ ID NO: 3 three times was artificially synthesized. Here, the amino acid sequence represented by SEQ ID NO: 84 corresponds to an amino acid sequence at the positions first to $216^{th}$ from the N-terminal side of the amino acid sequence of a heavy chain of a humanized anti-hTfR antibody No 3N represented by SEQ ID NO: 70. Here, an amino acid sequence at the positions first to $118^{th}$ from the N-terminal side corresponds to SEQ ID NO: 69 (amino acid sequence of variable region of heavy chain of humanized anti-hTfR antibody No. 3N), and an amino acid sequence at the positions $119^{th}$ to $216^{th}$ corresponds to a $C_H1$ region.

The DNA fragment encodes a fusion protein in which ABD is added to a C-terminal side of a fusion protein of a pro-protein of hBDNF and a humanized anti-hTfR antibody 3NFab heavy chain, having an amino acid sequence represented by SEQ ID NO: 87. The fusion protein having an amino acid sequence represented by SEQ ID NO: 87 is subjected to a processing after expression and becomes a fusion protein in which ABD is added to a C-terminal side of a fusion protein of hBDNF and a humanized anti-hTfR antibody Fab heavy chain having an amino acid sequence represented by SEQ ID NO: 88. In the amino acid sequence represented by SEQ ID NO: 87, an amino acid sequence at the positions first to $110^{th}$ from the N-terminal side is a portion removed at a time at which hBDNF is processed from a pro-protein to a mature type. The DNA fragment was digested with MluI and NotI, and inserted between MluI and NotI of a pE-neo vector to construct pE-neo (BDNF-Fab HC (3N)) ABD.

CHO cell (CHO-K1: acquired from American Type Culture Collection) was transformed by pE-neo (BDNF-Fab HC (3N)) ABD and pE-hygr (LC3) constructed in Example 11 to obtain a cell line expressing a fusion protein in which ABD is added to a C terminal side of a fusion protein of hBDNF and a humanized anti-hTfR antibody 3N. The cell line was set as hBDNF-anti-hTfR antibody (3N) ABD expression line. A fusion protein in which ABD is added to a C-terminal side of a fusion protein of hBDNF and a humanized anti-hTfR antibody expressed by the cell line was set as hBDNF-anti-hTfR antibody (3N) ABD.

[Example 22] Production of hBDNF-Humanized Anti-hTfR Antibody Fusion Protein

An hBDNF-humanized anti-hTfR antibody fusion protein was produced by the following method. The hBDNF-anti-hTfR antibody (3N) 1 expressing cell line obtained in Example 21 was diluted with CD OPTICHO medium to have a cell concentration of approximately $2\times10^5$ cells/mL, and 200 ml of cell suspension was then added to 1 L-conical flask, and cultured at 37° C. in humid environment consisting of 5% $CO_2$ and 95% air, at a stirring rate of approximately 70 rpm for 6 to 7 days. The culture supernatant was harvested by centrifugation, and then filtered through a 0.22 μm filter (Millipore Corporation) to obtain culture supernatant. 5 column volumes of 20 mM Tris buffer solution (pH 8.0) containing 150 mL NaCl was added to the harvested culture supernatant, and then loaded onto a Protein L column (column volume: 1 mL, GE Healthcare Corporation) which had been equilibrated in advance with three column volumes of 20 mM Tris buffer solution (pH 8.0) containing 150 mM NaCl. Then, the column was washed with five column volumes of same buffer, adsorbed hBDNF-anti-hTfR antibody (3N) 1 was eluted with four column volumes of 50 mM glycine buffer solution (pH 2.8) containing 150 mM NaCl. Immediately after elution, the pH of the elution was adjusted to pH 7.0 with 1 M Tris buffer solution (pH 8.0). The resultant was used as purified product of a hBDNF-anti-hTfR antibody (3N) 1 in the subsequent test.

Also regarding a hBDNF-anti-hTfR antibody (3N) 2, the purified product was obtained by the same method as that of the hBDNF-anti-hTfR antibody (3N) 1.

[Example 22-2] Production of hBDNF-Anti-hTfR Antibody (3N) ABD

A hBDNF-anti-hTfR antibody fusion protein was produced by the following method. The hBDNF-anti-hTfR antibody (3N) ABD expressing cell line obtained in Example 21-2 was diluted with CD OPTICHO medium to have a cell concentration of approximately $2\times10^5$ cells/mL, and 200 ml of cell suspension was then added to 1 L-conical flask, and cultured at 37° C. in humid environment consisting of 5% $CO_2$ and 95% air, at a stirring rate of approximately 70 rpm for 6 to 7 days. The culture supernatant was harvested by centrifugation, and then filtered through a 0.22 μm filter (Millipore Corporation), to obtained culture supernatant.

The harvested culture supernatant was loaded onto a HR-S column (column volume: 5 mL, Bio Rad Laboratories Inc.) which had been equilibrated in advance with five column volume of 10 mM HEPES buffer solution (pH 7.0) containing 50 mM of NaCl. Then, the column was washed with five times of the same buffer, and adsorbed hBDNF-anti-hTfR antibody (3N) ABD was eluted with fifteen column volumes of 10 mM HEPES buffer solution (pH 8.2) containing 1 M of NaCl, and a fraction containing the hBDNF-anti-hTfR antibody (3N) ABD was collected. This step was performed four times.

The elution fraction described above was diluted by adding four fold volumes of 10 mM HEPES buffer solution (pH 7.0). The diluted elution fraction was loaded onto a Nuvia cPrime column (column volume: 5 mL, Bio Rad Laboratories Inc.) which had been equilibrated with five column volumes of 10 mM HEPES buffer solution (pH 7.0) containing 50 mM of NaCl. Then the column was washed with twenty-five column volumes of 10 mM HEPES buffer solution (pH 8.2) containing 1 M NaCl, and adsorbed hBDNF-anti-hTfR antibody (3N) ABD was eluted with fifteen fold volumes of 10 mM HEPES buffer solution (pH 8.5) containing 2 M of NaCl and 0.4 M arginine, and a fraction containing the hBDNF-anti-hTfR antibody (3N) ABD was collected. The resultant product recovered in this manner was used as purified product of the hBDNF-anti-hTfR antibody (3N) ABD in the following test.

[Example 23] Evaluation of BDNF Activity of hBDNF-Anti-hTfR Antibody Fusion Protein Using BDNF Receptor (TrkB) Expressing Cells BDNF bioactivity of the hBDNF-anti-hTfR antibody fusion protein produced in Examples 16, 22, and 22-2 was evaluated by measurement of intracellular signaling-enhancing activity, using a change in the Ca concentration as an indicator, in CHO-TrkB cells prepared by transfection of a TrkB gene into Chinese hamster ovary cells (CHO cell).

CHO cells were cultured in a subculture medium (Nutrient Mixture F-12 Ham, 10% fetal calf serum). After that, the medium was exchanged with a medium for evaluation (Nutrient Mixture F-12 Ham, 3% fetal calf serum, 10 mM Hepes (pH 7.4)) to produce a cell suspension solution. A virus expressing apoaequorin and human TrkB (GenBank Acc. No. NP_001018074.1) was transfected into the cells, and the resulting cells seeded on a black colored bottom clear plate for 384 cell culture to be $2\times10^3$ cells/well. Thereafter, the cells were subjected to a static culture overnight in a $CO_2$ incubator (37° C., 95% Air, 5% $CO_2$).

HHBS solution (1×Hanks' Balanced Salt Solution, 20 mM HEPES (pH 7.4)) including 1 μM of Viviren (Promega Corporation) was added thereto by 20 μL/well, and left still at room temperature for 4 hours. BDNF and hBDNF-anti-hTfR antibody fusion protein (hBDNF-anti-hTfR antibody (3N) 1 and 2, and hBDNF-anti-hTfR antibody (3N) ABD) were diluted to a targeted concentration with an HHBS solution including 0.1% of bovine serum albumin, respectively, and after addition, light emission intensity was chronologically measured by FDSS7000 (Hamamatsu Photonics). The light emission intensity shown by 111 ng/mL BDNF (#450-02, Peprotech Corporation) was set at 100%, and a relative TrkB agonistic activity was calculated from the obtained light emission intensity. EC50 was calculated from a dose response curve, and the obtained value was defined as BDNF activity. Table 15 shows the evaluation result of BDNF activity of hBDNF-anti-hTfR antibody fusion protein.

TABLE 15

BDNF Activity of hBDNF-anti-hTfR antibody fusion protein

| (No.) Name | BDNF activity (TrkB agonistic: EC50, nmol/L) |
|---|---|
| hBDNF-anti-hTfR antibody (3) 1 | 0.16 |
| hBDNF-anti-hTfR antibody (3N) 1 | 0.43 |
| hBDNF-anti-hTfR. antibody (3N) 2 | 0.2 |
| hBDNF-anti-hTfR antibody (3N) ABD | 0.3 |

[Example 24] Evaluation of TrkB Receptor Signal Potentiation Action of hBDNF-Anti-hTfR Antibody Fusion Protein Using Rat Primary Cultured Neurons BDNF bioactivity of the hBDNF-anti-hTfR antibody fusion protein produced in Examples 22 and 22-2 was evaluated by measurement of intracellular signaling-enhancing activity, using as an indicator, the Erk phosphorylation in a rat primary cultured neurons. The primary cultured neurons are commonly prepared from each part, for example, corpus striatum, cortex, hippocampus and the like, of the fetal brain of a mouse or rat embryo, or purchased commercially available first-generation cultured nerve cell. However, this time, the primary cultured neurons were prepared from corpus striatum of a rat embryo.

A corpus striatum was collected from a foetal rat brain at embryonic age $15^{th}$-$19^{th}$ day, and immersed in an ice cold cHBSS solution (Hanks' Balanced Salt Solution including 1 mM pyrubic acid, 0.5% D (+) glucose, and 10 mM HEPES). After the cHBSS solution was removed, it was incubated in a cHBSS solution (enzymatic reaction solution) including 0.1 mg/mL DNase I, 5 mM $MgCl_2$, and 0.3 mg/mL papain at 37° C. for 1 to 5 minutes. The enzymatic reaction was stopped by removing the enzymatic reaction solution and adding an ice cold 10% FBS-containing NGPS solution (Neurobasal Medium including 0.5 mM L-glutamic acid and penicillin/streptomycin solution (DS Pharma Biomedical Co., Ltd.). After removing the 10% FBS-containing NGPS solution, the corpus striatum was rinsed with the ice cold cHBSS solution three times. Subsequently, nerve cells were dispersed in the ice cold cHBSS solution and filtered by using a 70 μm cell strainer (Falcon 2350). The filtrate was centrifuged (1,000 rpm, 4 min, room temperature) to collect sediment. The sediment was resuspended in the cHBSS solution and then the number of cells in the suspension was counted. The resultant product was diluted with an NGPS solution including B-27™ (Serum-Free Supplement (50×), Invitrogen Corporation) to be $1\times10^6$ cell/mL, seeded in a Poly-D-Lysine plate, and then subjected to a static culture in a $CO_2$ incubator (37° C., 95% Air, 5% $CO_2$) for 1 week.

A culture solution was removed from each well, and the cells were washed with an NGPS solution. After adding the NGPS solution, the cells were subjected to a static culture in the $CO_2$ incubator (37° C., 95% Air, 5% $CO_2$) for 2 hours. BDNF and the hBDNF-anti-hTfR antibody fusion protein were respectively diluted to a targeted concentration with the NGPS solution, and added to the cells, and the cells were subjected to a static culture in the $CO_2$ incubator (37° C., 95% Air, 5% $CO_2$) for 30 minutes. After reaction, the plate was placed on an ice, and washed with an ice cold Phosphate Buffered Saline After washing, a RIPA buffer (Pierce) including Halt Protease and Phosphatase Inhibitor Cocktail (Thermo Fischer Scientific) was added, and stood on ice for 10 minutes. The cells were scraped off by using a cell scraper, transferred to a tube, stirred by a vortex, and then stood on ice for 10 minutes. After centrifugation (13,500 rpm, 10 minutes, 4° C.), a supernatant was collected and cryopreserved at −80° C. until Erk phosphorylation assay (protein quantification was performed by using a part thereof).

The protein quantification was performed by using Pierce BCA Protein Assay Kit (Thermo Fischer Scientific). The collected sample was diluted with distilled water so that the protein concentration was within the detection range, and dispensed into a 96-well plate by 10 μL/well. In addition, the protein assay solution (Reagent A: Reagent B=50:1 mixture solution) was added thereto by 200 μL/well. After incubation at 37° C. for 30 minutes, light absorbance (562 nm) was measured by using a plate reader, and a protein concentration was calculated from a standard curve prepared from light absorbance of a bovine serum albumin standard solution.

Erk phosphorylation assay was performed by using Erk 1/2 ELISA Kit Simple Step (pT202/Y204+Total) (Abcam). The collected sample was diluted with a RIPA buffer (Pierce) including Halt Protease and Phosphatase Inhibitor Cocktail (Thermo) to 0.5 mg/mL, and dispensed into a Simple Step Pre-Coated 96-well plate bundled in the assay kit by 50 μL/well. Antibody Cocktail was added by 50 μL/well, and incubation was performed at room temperature for 1 hour while stirring. After washing in the well with a Wash Buffer (350 μL/well), a TMB substrate was added thereto by 100 μL/well, and incubation was performed at room temperature under shading for 15 minutes while stirring. A Stop Solution (100 μL/well) was added thereto by 100 μL/well to stop reaction, and light absorbance was measured by using a plate reader (450 nm). By evaluating a relative increase amount of a phosphorylation Erk level due to BDNF or hBDNF-anti-hTfR antibody fusion protein with respect to the phosphorylation Erk level checked by solvent treatment, BDNF bioactivity that the hBDNF-anti-hTfR antibody fusion protein has was evaluated. Table 15-2 shows the evaluation result of Erk phosphorylation activity.

TABLE 15-2

Erk phosphorylation activity of hBDNF-anti-hTfR antibody fusion protein

| (No.) Name | Erk phosphorylation activity (EC50, nmol/L) |
|---|---|
| hBDNF-anti-hTfR antibody (3N) 1 | 0.02 |
| hBDNF-anti-hTfR antibody (3N) ABD | 0.02 |

[Example 25] Measurement of Affinities of hBDNF-Anti-hTfR Antibody (3N) 1 to Human TfR and Monkey TfR Affinities of the hBDNF-anti-hTfR antibody (3N) 1 prepared in Example 22, to human TfR and to monkey TfR were measured. The measurement was generally performed by the following method. The biotin-labeled rabbit anti-human BDNF polyclonal antibodies (anti-human BDNF antibodies: PeproTech Corporation) was diluted with HBS-P+(1% BSA) (10 mM HEPES containing 150 mM NaCl, 50 μM EDTA, 0.05% Surfactant P20, and 1% BSA) to prepare the 15 μg/mL of solution, and the solution was designated as ligand solution 1. The purified product of an anti-hTfR antibody fusion BDNF (hBDNF-anti-hTfR antibody (3N) 1) was diluted with HBS-P+(1% BSA), and the solution was designated as ligand solution 2. And, as the reference control sample, the purified product of the hBDNF-anti-hTfR antibody (3) 1 obtained in Example 15-3 was also diluted with HBS-P+(1% BSA) to prepare ligand solution 3. r human TfR and r monkey TfR were respectively two fold serial diluted with HBS-P+(1% BSA) to prepare seven different concentrations of 0.78125 to 50 nM (0.585 to 3.74 μg/mL). These TfR solution were used as TfR sample solutions.

The sample solution prepared by the two fold serial dilution was filled, 200 μL/well, to 96 well plate, black (greiner bioone Inc.). Each of the prepared ligand solution 1, ligand solution 2, and ligand solution 3 was filled, 200

μL/well, to predetermined well. To each of well for baseline, dissociation, and washing, HBS-P+(1% BSA) was filled by 200 μL/well. The plate and biosensor (Biosensor/SA: ForteBio Inc., a division of Pall Corporation) were set to prescribed position of the OctetRED96.

The OctetRED96 was run under the condition shown in the following Table 15-3 to immobilize the anti-human BDNF antibody onto the sensor. Subsequently, after the OctetRED96 was run under the condition shown in the following Table 15-4 to obtain data, binding interaction curve was fitted to a 1:1 binding model or to a 2:1 binding model using the analysis software attached to the OctetRED96, the association rate constant (kon) and the dissociation rate constant (koff) of the anti-hTfR antibody fusion BDNF to r human TfR, and to r monkey TfR were measured, and the dissociation constant ($K_D$) were calculated. The measurement was performed at 25° C. to 30° C.

TABLE 15-3

Operating condition of OctetRED96 at time of solid phasing of anti-hTfR BDNF antibody

| | Step | Contact time (sec) | Speed (rpm) | Threshold |
|---|---|---|---|---|
| 1 | Baseline 1 | 60 | 1000 | — |
| 2 | Load | 600 | 1000 | 4.0 |
| 3 | Baseline 2 | 60 | 1000 | — |

TABLE 15-4

Operating condition of OctetRED96 for kinetics analysis

| | Step | Contact time (sec) | Speed (rpm) | Threshold |
|---|---|---|---|---|
| 1 | Baseline 1 | 60 | 1000 | — |
| 2 | Load | 600 | 1000 | 1.3 |
| 3 | Baseline 2 | 60 | 1000 | — |
| 4 | Association | 120 | 1000 | — |
| 5 | Dissociation | 300 | 1000 | — |

Steps 1-5 were repeated until all the samples were measured.

Table 16 shows the measurement result of the association rate constant (kon) and the dissociation rate constant (koff) of the hBDNF-anti-hTfR antibody (3N) 1, to human TfR and monkey TfR, and the dissociation constant ($K_D$). The dissociation constant of the hBDNF-anti-hTfR antibody (3N) 1 to human TfR was $7.42\times10^{-12}$ M, and the dissociation constant to monkey TfR was $7.94\times10^{-10}$ M. The result shows that the hBDNF-anti-hTfR antibody (3N) 1 has high affinity to human TfR and monkey TfR. And, the dissociation constant of the hBDNF-anti-hTfR antibody (3) 1 to human TfR and to monkey TfR were $2.51\times10^{-10}$ M and $3.94\times10^{-8}$ M, respectively. That is, it can be understood that the hBDNF-anti-hTfR antibody (3N) 1 has extremely high affinity to human TfR and monkey TfR, compared to the hBDNF-anti-hTfR antibody (3) 1.

TABLE 16

Affinity of hBDNF-anti-hTfR antibody (3N) 1 to human TfR and monkey TfR

| | kon ($M^{-1}s^{-1}$) | koff ($s^{-1}$) | $K_D$ (M) |
|---|---|---|---|
| Human TfR | $4.77\times10^{5}$ | $3.54\times10^{-6}$ | $7.42\times10^{-12}$ |
| Monkey TfR | $2.45\times10^{5}$ | $1.96\times10^{-4}$ | $7.94\times10^{-10}$ |

[Example 25-2] Measurement of Affinity of hBDNF-Anti-hTfR Antibody (3N) ABD to Human TfR, Monkey TfR, and HSA Affinities of a hBDNF-anti-hTfR antibody (3N) ABD to human TfR, monkey TfR, and human serum albumin (HSA) were measured on OctetRED96 (ForteBio Corporation, a division of Pall Corporation) which is a system for biomolecular interaction analysis utilizing biolayer interferometry (BLI), as same as Example 25. The measurement was generally performed by operation manual attached to the OctetRED96.

The biotin-labeled rabbit anti-human BDNF polyclonal antibodies (anti-human BDNF antibody: PeproTech Corporation) was diluted with HBS-P+(1% BSA) (10 mM HEPES containing 150 mM NaCl, 50 μM EDTA, 0.05% Surfactant P20, and 1% BSA) to prepare 25 μg/mL of solution, and the solution was designated as ligand solution 1. A purified product of an hBDNF-anti-hTfR antibody (3N) ABD was diluted with HBS-P+, and the solution was designated as ligand solution 2. r human TfR and r monkey TfR were respectively two-fold serial diluted with HBS-P+ to prepare seven-different concentration of 0.78125 to 50 nM (0.0585 to 3.74 μg/mL). These TfR solution were designated as a TfR sample solution. The r human TfR and the r monkey TfR, those described in Example 7 were used. And, human serum albumin preparation (HSA) (blood donation albumin 25-Nichiyaku, Nihon Pharmaceutical Co., Ltd.) was two-fold serial diluted with HBS-P+ to prepare solution of seven-different concentration of 3.13 to 200 nM (0.208 to 13.3 μg/mL). The HSA solution were designated as an HSA sample solution.

The TfR sample solution and HSA sample solution prepared by the two-fold serial dilution were filled, 200 μL/well to a 96 well plate, black (greiner bioone Inc.). Each of the prepared ligand solution 1 and ligand solution 2 was filled, 200 μL/well to a predetermined well. To each of well for baseline, dissociation, and washing, HBS-P+ was filled by 200 μL/well. The plate and biosensor (Biosensor/SA: ForteBio Inc., a division of Pall Corporation) were set to predetermined position of the OctetRED96.

The OctetRED96 was run under the condition shown in the following Table 15-3 described in Example 25 to immobilize the anti-human BDNF antibody onto the sensor. Subsequently, after the OctetRED96 was run under the condition shown in Table 16-2 to obtain data, binding interaction curve was fitted to a 1:1 binding model using the analysis software attached to the OctetRED96, the association rate constant (kon) and the dissociation rate constant (koff) of the hBDNF-anti-hTfR antibody (3N) ABD, to r human TfR, r monkey TfR, and HSA were measured, and a dissociation constant ($K_D$) were calculated. The measurement was performed at 25° C. to 30° C.

TABLE 16-2

Operating condition of OctetRED96 forkinetics analysis

| | Step | Contact time (sec) | Speed (rpm) | Threshold |
|---|---|---|---|---|
| 1 | Baseline 1 | 120 | 1000 | — |
| 2 | Load | 600 | 1000 | 1.3 |
| 3 | Baseline 2 | 300 | 1000 | — |
| 4 | Association | 120 | 1000 | — |
| 5 | Dissociation | 300 | 1000 | — |

Steps 1-5 were repeated until all the samples were measured.

Table 16-3 shows the result of measurement of the association rate constant (kon) and the dissociation rate constant (koff) of the hBDNF-anti-hTfR antibody (3N) ABD, to human TfR, monkey TfR, and HSA, and the dissociation constant ($K_D$).

TABLE 16-3

Affinity of hBDNF-anti-hTfR antibody (3N) ABD to human TfR, monkey TfR, and HSA

| | kon ($M^{-1}s^{-1}$) | koff ($s^{-1}$) | $K_D$ (M) |
|---|---|---|---|
| Human TfR | $7.07 \times 10^5$ | $4.00 \times 10^{-5}$ | $5.66 \times 10^{-11}$ |
| Monkey TfR | $2.31 \times 10^5$ | $1.45 \times 10^{-4}$ | $6.26 \times 10^{-10}$ |
| HSA | $6.13 \times 10^4$ | $8.29 \times 10^{-4}$ | $1.35 \times 10^{-8}$ |

The dissociation constant of the hBDNF-anti-hTfR antibody (3N) ABD to human TfR and to monkey TfR were $5.66\times10^{-11}$ M and $6.26\times10^{-10}$ M, respectively. These results show that even in a case where ABD was fused to C-terminus of the fusion protein consisting of hBDNF and anti-hTfR antibody, high affinity of the fusion protein to human TfR and monkey TfR were maintained. And, the dissociation constant of the hBDNF-anti-hTfR antibody (3N) ABD with HSA was $1.35\times10^{-8}$ M. The result shows that the hBDNF-anti-hTfR antibody (3N) ABD has also high affinity to both of TfR (human and monkey) and HSA. That is, the result shows that both can be achieved that the half-life in blood can be increased by binding to albumin via ABD and pass through BBB via TfR when the hBDNF-anti-hTfR antibody (3N) ABD was administrated into human blood Furthermore, the result also shows that the immunogenicity of hBDNF-anti-hTfR antibody (3N) ABD can be decreased by binding the hBDNF-anti-hTfR antibody (3N) ABD to albumin.

[Example 26] Evaluation of Brain Uptake of hBDNF-Anti-hTfR Antibody (3N) 1 in Mice The hBDNF-anti-hTfR antibody (3N) 1 passing through BBB and migrating in the brain was evaluated using a hTfR knock-in mouse (hTfR-KI mouse) obtained by substituting a gene encoding an extracellular region of a mouse transferrin receptor with a gene encoding an extracellular region of a human transferrin receptor gene. The hTfR-KI mouse was generally produced by the following method. In addition, as the hBDNF-anti-hTfR antibody (3N) 1, a purified product described in Example 22 was used.

A DNA fragment having the nucleic acid sequence represented by SEQ ID NO: 45, in which a neomycin-resistant gene sandwiched between loxP sequences was disposed on a 3' side of cDNA encoding a chimeric hTfR in which the intracellular region is an amino acid sequence of mouse hTfR and the extracellular region is an amino acid sequence of human hTfR, was chemically synthesized. The DNA fragment was inserted into a targeting vector having the nucleic acid sequence represented by SEQ ID NO: 46 as a 5' arm sequence and the nucleic acid sequence represented by SEQ ID NO: 47 as a 3' arm sequence by a common method, and this was introduced into a mouse ES cell by an electroporation method. The mouse ES cell after gene introduction was subjected to selective culturing in the presence of neomycin to select the mouse ES cell in which the targeting vector was inserted into chromosome by homologous recombination. The obtained gene recombinant mouse ES cell was injected into an eight-cell embryo (host embryo) of ICR mouse, and transplanted into a pseudo-pregnant mouse (recipient mouse) obtained by hybridization with a mouse subjected to vasoligation. Hair color determination was performed on the obtained offspring (chimera mouse), and an entity of which ES cell contributed to the formation of a living body with high efficiency, that is, an entity with a high ratio of white color hair to total hair was selected. The chimera mouse entity was in conjunction with the ICR mouse to obtain an F1 mouse. An F1 mouse of white color was selected, DNA extracted from a tail tissue was analyzed, and a mouse in which a mouse transferrin receptor gene was substituted with a chimeric hTfR on a chromosome was set as a hTfR-KI mouse.

A hBDNF-anti-hTfR antibody (3N) 1 solution was intravenously administered to three hTfR-KI mice (male, 21 to 28 weeks) at each time point such that the administered dose was 5 mg/kg. After 0.17, 1, 3, 8, 24, and 48 hours from the intravenous administration, peripheral blood was collected, systemic perfusion was performed with a physiological saline after collection, and the brain (portion including cerebrum and cerebellum) was collected. After a weight (wet weight) of the extracted brain was measured, a RIPA buffer (Nacalai Tesque Inc.) including Protease Inhibitor Cocktail (Sigma Corporation) was added to homogenate the brain tissue. The homogenate was centrifuged to recover a supernatant, and an amount of the hBDNF-anti-hTfR antibody (3N) 1 included in the supernatant was measured by the following method.

First, a Rabbit Anti-Human IgG H&L pre-adsorbed (Abcam) was added to each well of Standard Plate (Meso Scale Diagnostics Corporation) by 25 μL, left still for 1 hour, and fixed onto the plate. Subsequently, SuperBlock (PBS) Blocking buffer was added to each well by 150 μL, and shaken for 1 hour to block the plate. Subsequently, each well was washed with Tris Buffered Saline with Tween 20, a supernatant of the homogenate of the brain tissue was added thereto by 50 μL, and shaken for 1 hour. Subsequently, a Sulfo-tag-labeled Anti-BDNF antibody (35928.11) (AB10505) (Abcam) was added to each well by 50 μL, and shaken for 1 hour. Subsequently, Read buffer T (Meso Scale Diagnostics Corporation) was added to each well by 150 μL, and a light emission amount from each well was measured using a SECTOR Imager 6000 reader. A calibration curve was prepared from a measurement value of a standard sample with known concentrations, and by interpolating a measurement value of each specimen thereto, an amount of the fusion protein included per gram weight (wet weight) of the brain was calculated.

Figure 9:
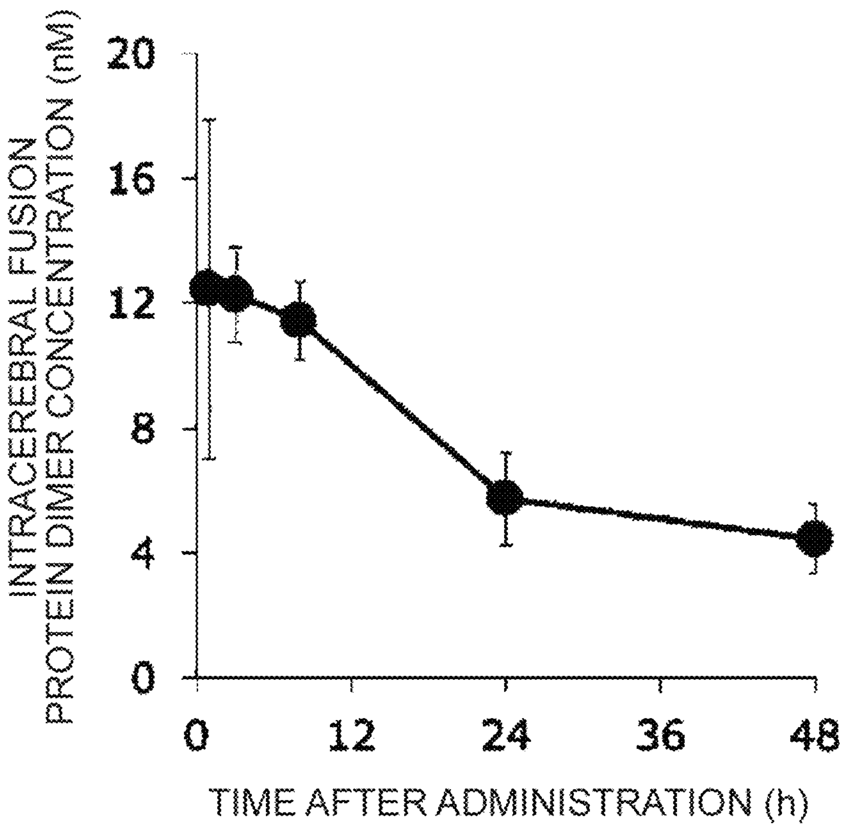
FIG. 9 A figure showing the concentration in the brain of hTfR-KI mouse after single intravenous administration of BDNF-anti-hTfR antibody fusion protein. The axis of abscissa indicates time after administration (hour), and the axis of ordinate indicates concentration (nM, in terms of dimer) of BDNF-anti-hTfR antibody fusion protein per gram weight (wet weight) of the brain.

FIG. 9 shows a result of concentration measurement of the hBDNF-anti-hTfR antibody (3N) 1 in the brain. Since the hBDNF-anti-hTfR antibody (3N) 1 forms a dimer and exhibits the functions in a living body, in FIG. 9, a value in terms of dimer was set as a concentration (molar concentration) of the hBDNF-anti-hTfR antibody (3N) 1. Hereinafter, concentrations of hBDNF-anti-hTfR antibody (3N) 1 shown in FIG. 10, Table 17, and Table 18 are the same as above. The hBDNF-anti-hTfR antibody (3N) 1 exhibited a high cerebral concentration of 5.7 nM even 24 hours after administration. In addition, the half-life of the cerebral concentration was 29 hours. This result shows that the hBDNF-anti-hTfR antibody (3N) 1 has a property of passing through the blood-brain barrier and being accumulated in the brain tissue, and by binding BDNF which is a drug to function in the brain tissue to an anti-hTfR antibody (3N) 1 or the antigen-binding fragment (antibody fragment), it is possible to efficiently accumulate the drug in the brain tissue.

Subsequently, Table 17 shows a result of measurement of kinetics in blood of the hBDNF-anti-hTfR antibody (3N) 1. It was shown that the hBDNF-anti-hTfR antibody (3N) 1 exhibited a high concentration in blood of 15 nM even 1 hour after administration and was stabilized in the blood (Table 17). In addition, the half-life of the concentration in blood was 0.4 hours. This result shows that the half-life of the cerebral concentration is remarkably longer than the half-life of the concentration in blood. In addition, kinetics in blood of Fc-Fab (3N) in a hTfR-KI mouse were also measured in the same test, and the half-life of the concentration in blood was 5.3 hours. This result shows that by introducing a human IgG Fc region, the half-life of the concentration in blood is remarkably extended.

TABLE 17

| Kinetics in blood of hBDNF-anti-hTfR antibody (3N) 1 in mouse (nM) | | | | |
|---|---|---|---|---|
| | Elapse time after administration | | | |
| | 5 Minutes | 1 Hour | 3 Hours | 48 Hours |
| hBDNF-anti-hTfR antibody (3N) 1 | 170 | 15 | 1.4 | 0.1 |

[Example 27] Evaluation of Brain Uptake of hBDNF-Anti-hTfR Antibody (3N) 1 in Cynomolgus Monkey The hBDNF-anti-hTfR antibody (3N) 1 was administered to an each of male cynomolgus monkey at a dose of 5.0 mg/kg by single intravenous administration, peripheral blood was collected 0.083, 0.5, 1, 3, 24, and 72 hours after administration, and brain perfusion was performed with a physiological saline after collection. After perfusion, the brain tissue was extracted.

Using the brain tissue, the following concentration measurement and immunohistochemical staining of the hBDNF-anti-hTfR antibody (3N) 1 were performed. In addition, as the hBDNF-anti-hTfR antibody (3N) 1, a purified product described in Example 22 was used.

The concentration measurement of the hBDNF-anti-hTfR antibody (3N) 1 in the brain tissue was generally performed in the following procedure. The collected brain tissue was divided into the cerebral cortex, the cerebellum, the hippocampus, and the medulla oblongata, and then each of the tissue was homogenated with an RIPA Buffer (Nacalai Tesque Inc.) including Protease Inhibitor Cocktail (Sigma-Aldrich Corporation), and centrifuged to recover a supernatant. Anti-Human Kappa Light Chain Goat IgG Biotin (Immuno-Biological Laboratories Co, Ltd.), Sulfotag anti-BDNF antibody (Abcam), and the brain tissue homogenate were added to a streptavidin plate (Meso Scale Diagnostics Corporation) blocked with SuperBlock blocking buffer in PBS (Thermo Fisher Scientific Corporation), left still for 1 hour, and fixed onto the plate. Subsequently, Read buffer T (Meso Scale Diagnostics Corporation) was added to each well by 150 μL, and a light emission amount was measured from each well using a SECTOR Imager 6000 reader. A calibration curve was prepared from a measurement value of a standard sample with known concentrations, and by interpolating a measurement value of each specimen thereto, an amount (concentration in brain tissue) of a fusion protein included per gram weight (wet weight) of each brain tissue was calculated.

Figure 10:
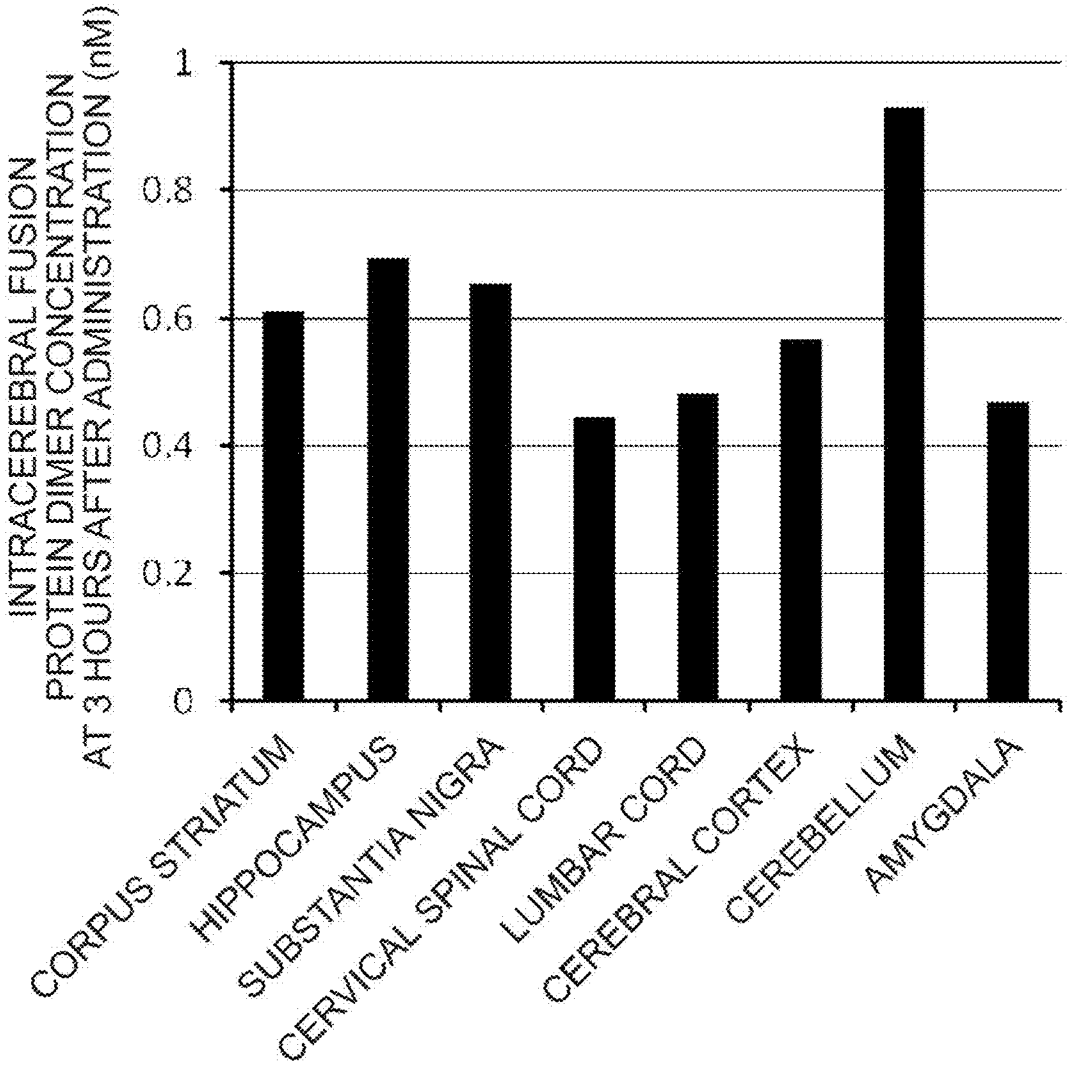
FIG. 10 A figure showing the concentration (nM, in terms of dimer) of BDNF-anti-hTfR antibody fusion protein in various regions of the brain of a cynomolgus monkey at three hours after single intravenous administration of BDNF-anti-hTfR antibody fusion protein.

A result of the concentration measurement of the hBDNF-anti-hTfR antibody (3N) 1 in the brain tissue is shown in FIG. 10. The result shows that the hBDNF-anti-hTfR antibody (3N) 1 has a property of passing through the blood-brain barrier and being accumulated in the brain tissue, and by binding BDNF which is a drug to function in the brain tissue to an anti-hTfR antibody (3N) 1 or the antigen-binding fragment (antibody fragment), it is possible to efficiently accumulate the drug in the brain tissue.

Subsequently, Table 18 shows a result of measurement of kinetics in blood of the hBDNF-anti-hTfR antibody (3N) 1. It was shown that the hBDNF-anti-hTfR antibody (3N) 1 exhibited a high concentration in blood of 30 nM even 1 hour after administration and was stabilized in the blood (Table 18).

TABLE 18

| Kinetics in blood of hBDNF-anti-hTfR antibody (3N) 1 in cynomolgus monkey (nM) | | | | | |
|---|---|---|---|---|---|
| | Elapse time after administration | | | | |
| | 5 Minutes | 30 Minutes | 1 Hour | 3 Hours | 8 Hours |
| hBDNF-anti-hTfR antibody (3N) 1 | 246 | 89 | 30 | 8.3 | 0.73 |

Immunohistochemical staining of the hBDNF-humanized anti-hTfR antibody fusion protein in the brain tissue can be performed by the method described in Example 15.

[Example 28] Evaluation of Brain Uptake of hBDNF-Anti-hTfR Antibody (3N) ABD in Mice The hBDNF-anti-hTfR antibody (3N) ABD passing through BBB and migrating in the brain was evaluated using a hTfR knock-in mouse (hTfR-KI mouse) obtained by substituting a gene encoding an extracellular region of a mouse transferrin receptor with a gene encoding an extracellular region of a human transferrin receptor gene. The hTfR-KI mouse was generally produced by the method described in Example 7-2. In addition, as the hBDNF-anti-hTfR antibody (3N) ABD, a purified product described in Example 22-2 was used.

A hBDNF-anti-hTfR antibody (3N) ABD solution was intravenously administered to three hTfR-KI mice (male, 19 to 21 weeks) at each time point such that the administered dose was 2.15 mg/kg. After 0.167, 1, 3, 8, 24, 48, and 72 hours from the intravenous administration, systemic perfusion was performed with a physiological saline, and the brain (portion including cerebrum and cerebellum) was collected. After a weight (wet weight) of the extracted brain was measured, a RIPA buffer (Nacalai Tesque Inc.) including Protease Inhibitor Cocktail was added to homogenate the brain tissue. The homogenate was centrifuged to recover a supernatant, and an amount of the hBDNF-anti-hTfR antibody (3N) ABD included in the supernatant was measured by the following method.

First, a Rabbit Anti-Human IgG H&L pre-adsorbed (Abcam) was added to each well of Standard Plate (Meso Scale Diagnostics Corporation) by 25 μL, left still at 4° C. overnight, and fixed onto the plate. Subsequently, SuperBlock (PBS) Blocking buffer was added to each well by 150 μL, and shaken for 1 hour to block the plate. Subsequently, each well was washed with Tris Buffered Saline with Tween 20, a supernatant of the homogenate of the brain tissue was added thereto by 50 μL, and shaken for 1 hour. Subsequently, a Sulfo-tag-labeled Anti-BDNF antibody (35928.11) (ab10505) (Abcam) was added to each well by 50 μL, and shaken for 1 hour. Subsequently, Read buffer T (Meso Scale Diagnostics Corporation) was added to each well by 150 μL, and a light emission amount from each well was measured using a SECTOR Imager 6000 reader. A calibration curve was prepared from a measurement value of a standard sample with known concentrations, and by interpolating a measurement value of each specimen thereto, an amount of the antibody included per gram weight (wet weight) of the brain was calculated.

Figure 11:
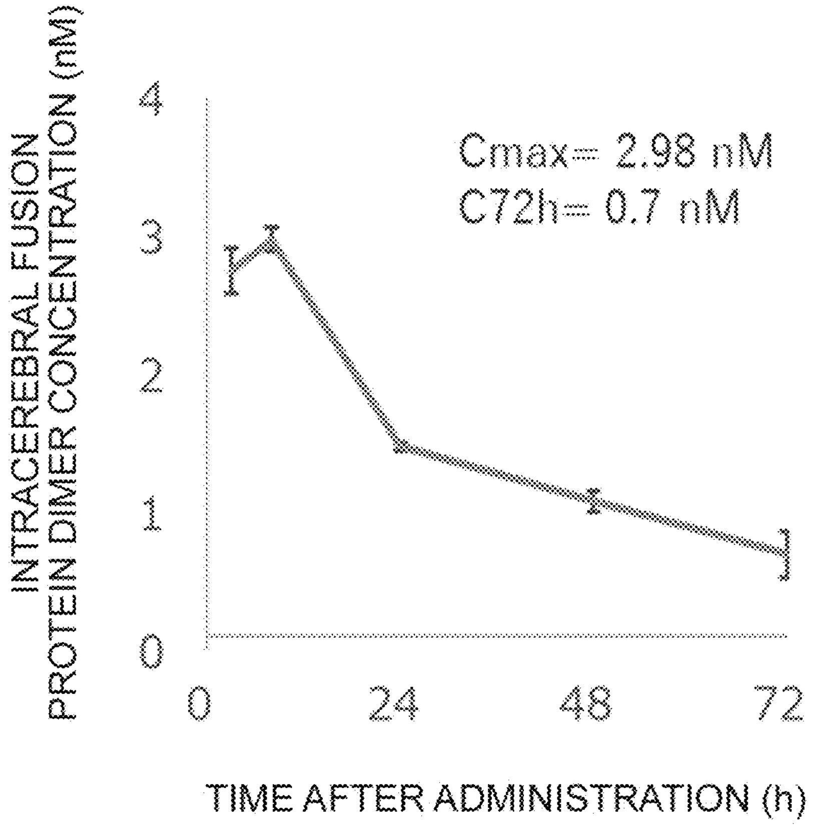
FIG. 11 A figure showing the change of the concentration in the brain of hTfR-KI mouse after single intravenous administration of BDNF-anti-hTfR antibody fusion protein (hBDNF-anti-hTfR antibody (3N) ABD). The axis of abscissa indicates time after administration (hour), and the axis of ordinate indicates concentration (nM, in terms of dimer) of BDNF-anti-hTfR antibody fusion protein per gram weight (wet weight) of the brain.

A result of the concentration measurement of the hBDNF-anti-hTfR antibody (3N) ABD in the brain tissue is shown in FIG. 11. The result shows that the cerebral concentration of the hBDNF-anti-hTfR antibody (3N) ABD was exhibited as $C_{max}$ of 2.98 nM 8 hours after administration, and 0.7 nM 72 hours after administration.

The result shows that the hBDNF-anti-hTfR antibody (3N) ABD has a property of passing through the blood-brain barrier and being accumulated in the brain tissue, and shows that by binding BDNF which is a drug to function in the brain tissue to the antibody, it is possible to efficiently accumulate the drug in the brain tissue.

Subsequently, Table 19 shows a result of measurement of kinetics in blood of the hBDNF-anti-hTfR antibody (3N) ABD. It was shown that the hBDNF-anti-hTfR antibody (3N) ABD exhibited a high concentration in blood of 179.8 nM even 1 hour after administration and 53.4 nM even 3 hours after administration, and was stabilized in the blood (Table 19). The result shows that by introducing albumin-affinity peptide, stability in blood was improved and the half-life in blood was remarkably extended.

TABLE 19

Kinetics in blood of hBDNF-anti-hTfR antibody (3N) ABD in mice (nM)

| | Elapse time after administration | | | |
|---|---|---|---|---|
| | 10 Minutes | 1 Hour | 3 Hours | 8 Hours |
| hBDNF-anti-hTfR antibody (3N) ABD | 117.1 | 179.8 | 53.4 | 3.6 |

[Example 29] Studies Regarding the Ameliorating Effect of Fusion Protein of Present Invention on Movement Function in Parkinson's Disease Model Mice Treated with 1-methyl-4-phenyl-1,2,3,6-tetrahydropyridine (MPTP)

The in vivo BDNF bioactivity of the hBDNF-anti-hTfR antibody fusion protein produced in Example 22 can be evaluated by the effect of improvement in Parkinson's disease symptoms in MPTP-treated hTfR-KI mice using a method described below, for example.

(1) Preparation of Parkinson's Disease Model Mice

A hTfR-KI mice (8 to 15 weeks) described in Example 26 is used. A physiological saline or MPTP dissolved in a physiological saline (25 or 30 mg/kg) is intraperitoneally administered to quarantined/normalized mice once a day for five days, or is intraperitoneally administered to the mice at a dose of 20 mg/kg every two hours 4 times in a day.

Three days after the final administration, bradykinesia symptoms is evaluated by a Pole test, or motor incoordination is evaluated by a Rota-rod test.

(2) Pole Test

MPTP-treated mice are allowed to hold a position around 5 cm from the top of a vertical wooden pole with the heads of the mice upward. The time required for the mice from holding the bar to changing the direction downward ($T_{turn}$), and the time required for the mice from holding the bar to going down to the floor ($T_{LA}$) are measured. In addition, the movement of the mice is observed, and the symptoms thereof are scored as below.

0: Going down to the floor using four limbs well/normal movement
1: Awkwardness is observed when changed the direction at the upper portion of the pole.
2: The mouse cannot straddle the bar and moves like side-slipping.
3: The mouse falls down from the pole.

After training is firstly performed once, the test is repeated three times every five minutes. An average time from the three trial is used as grouping data. Based on the body weight and the data from the Pole test, MPTP-treated mice are assigned to three or four groups to the multivariable completely randomized allocation.

Repeated intravenous administration is carried out on a total of 4 to 5 groups consisting of normal saline-treated mice (a solvent-treated group), MPTP-treated mice (a solvent-treated group, and groups treated with fusion protein of present invention), once or twice a week, for 4 to 8 weeks. One week after, the final administration, a Pole test (the same protocol as that of collection of the above grouping data) is performed again, and action for improvement in bradykinesia symptoms is evaluated. The intravenously administered fusion protein of the present invention migrates into the brain, and then it exerts BDNF activity in the brain, so that it can improve movement dysfunctions, such as bradykinesia, in Parkinson's disease model animals.

In this manner, it can be checked that the intravenously administered fusion protein of the present invention migrates into the brains of disease model animals and exhibits BDNF activity.

(3) Rota-Rod Test

Mice are placed on a rotary shaft of a Rota-rod device (MK-610A, Muromachi Kikai Co., Ltd.) by one for each lane, and then leave to stand for 30 seconds. Thereafter, the mice are acclimatized to the rotation of the shaft at 8 rpm for 1 minute, and are then trained under conditions where the rotation speed was increased to 25 rpm for 3 minutes. One hour after training, the following evaluation test is performed.

In this test, the mice are acclimatized to the movement of the shaft rotating at 8 rpm for 30 seconds, and the time required until the mice fell from the shaft under conditions where the rotation speed is increased to 40 rpm for 5 minutes is measured. This test is repeated three times at intervals of 1 hour, and an average time from the three trials is used for grouping data. Based on the body weight and the data and the Rota-rod test, the MPTP-treated mice are assigned to three or four groups by multivariable completely randomized allocation.

Repeated intravenous administration is carried out on a total of 4 or 5 groups consisting of physiological saline-treated mice (a solvent-treated group), MPTP-treated mice (a solvent-treated group, and groups treated fusion protein of the present invention), once or twice a week, for 4 to 8 weeks. One week after the final administration, a Rota-rod test (the same protocol as that of collection of the above grouping data) is performed again, and action to improve motor incoordination is evaluated. The intravenously administered fusion protein of the present invention migrates into the brain, and then it exerts BDNF activity in the brain, so that it can improve movement dysfunction, such as motor incoordination, in Parkinson's disease model animals.

In this manner, it can be checked that the intravenously administered fusion protein of the present invention migrates into the brains of disease model animals and exhibits BDNF activity.

[Example 30] Studies Regarding the Ameliorating Effect of Fusion Protein of Present Invention on Movement Function in Parkinson's Disease Model Monkeys Treated with 1-methyl-4-phenyl-1,2,3,6-tetrahydropyridine (MPTP)

The in vivo BDNF bioactivity of the hBDNF-anti-hTfR antibody fusion protein produced in Example 22 can be evaluated by the ameliorating effect in Parkinson's disease symptoms in an MPTP-treated hTfR-KI monkey using a method described below, for example.

MPTP (0.2 mg/kg or more, 2 mg/kg as the upper limit) is administered to a male rhesus monkey (5 to 8 years old) or a cynomolgus monkey (4 to 8 years old), of which normal behaviors have been evaluated for five days before MPTP treatment in advance, for up to 5 consecutive days a week, by intravenous administration, intramuscular administration, or subcutaneous administration for 4 weeks or more. A decrease in UPDRS scores or a decrease in momentum is checked. Otherwise, MPTP (0.2 mg/kg or more, 2 mg/kg as the upper limit) is administered only to one side of internal carotid artery, once or twice, at an administration interval of 5 to 10 days, and Parkinson's disease-like symptoms are checked using UPDRS scores (J Neurosci Methods. 2000; 96: 71-76), momentum, and turning momentum as indicators, and the MPTP treatment is finished.

After it is checked that Parkinson's disease-like symptoms are stabilized 1 week or thereafter from the final administration of MPTP, the hBDNF-anti-hTfR antibody fusion protein (0.03 to 10 mg/kg) is intravenously or subcutaneously administered once or twice a week, and a degree of improvement of movement function is evaluated by the evaluation of UPDRS, momentum, or turning momentum. The intravenously or subcutaneously administered hBDNF-anti-hTfR antibody fusion protein migrates into the brain and it then exerts BDNF activity in the brain, so that it can improve movement dysfunction in Parkinson's disease model animals.

In this manner, it can be checked that the intravenously administered fusion protein of the present invention migrates into the brains of disease model animals (monkeys) and exerts BDNF activity.

INDUSTRIAL APPLICABILITY

The fusion protein of hBDNF and an anti-hTfR antibody of the present invention can efficiently pass through the blood-brain barrier, and thus is highly useful to provide improved means to allow hBDNF to act on the central nervous system.

SEQUENCE LISTING FREE TEXT

SEQ ID NO: 3: Amino acid sequence of linker example 1

SEQ ID NO: 4: Amino acid sequence of linker example 2

SEQ ID NO: 5: Amino acid sequence of linker example 3

SEQ ID NO: 6: Amino acid sequence 1 of light chain CDR1 of mouse anti-hTfR antibody No. 3

SEQ ID NO: 7: Amino acid sequence 2 of light chain CDR1 of mouse anti-hTfR antibody No. 3

SEQ ID NO: 8: Amino acid sequence 1 of light chain CDR2 of mouse anti-hTfR antibody No. 3

SEQ ID NO: 9: Amino acid sequence 2 of light chain CDR2 of mouse anti-hTfR antibody No. 3

SEQ ID NO: 10: Amino acid sequence of light chain CDR3 of mouse anti-hTfR antibody No. 3

SEQ ID NO: 11: Amino acid sequence 1 of heavy chain CDR1 of mouse anti-hTfR antibody No. 3

SEQ ID NO: 12: Amino acid sequence 2 of heavy chain CDR1 of mouse anti-hTfR antibody No. 3

SEQ ID NO: 13: Amino acid sequence 1 of heavy chain CDR2 of mouse anti-hTfR antibody No. 3

SEQ ID NO: 14: Amino acid sequence 2 of heavy chain CDR2 of mouse anti-hTfR antibody No. 3

SEQ ID NO: 15: Amino acid sequence 1 of heavy chain CDR3 of mouse anti-hTfR antibody No. 3

SEQ ID NO: 16: Amino acid sequence 2 of heavy chain CDR3 of mouse anti-hTfR antibody No. 3

SEQ ID NO: 17: Amino acid sequence 1 of variable region of light chain of humanized anti-hTfR antibody No. 3

SEQ ID NO: 18: Amino acid sequence 2 of variable region of light chain of humanized anti-hTfR antibody No. 3

SEQ ID NO: 19: Amino acid sequence 3 of variable region of light chain of humanized anti-hTfR antibody No. 3

SEQ ID NO: 20: Amino acid sequence 4 of variable region of light chain of humanized anti-hTfR antibody No. 3

SEQ ID NO: 21: Amino acid sequence 5 of variable region of light chain of humanized anti-hTfR antibody No. 3

SEQ ID NO: 22: Amino acid sequence 6 of variable region of light chain of humanized anti-hTfR antibody No. 3

SEQ ID NO: 23: Amino acid sequence of light chain including amino acid sequence 2 as variable region, of humanized anti-hTfR antibody No. 3

SEQ ID NO: 24: Nucleic acid sequence encoding amino acid sequence of light chain including amino acid sequence 2 as variable region, of humanized anti-hTfR antibody No. 3, synthetic sequence SEQ ID NO: 25: Amino acid sequence of light chain including amino acid sequence 4 as variable region, of humanized anti-hTfR antibody No. 3

SEQ ID NO: 26: Nucleic acid sequence encoding amino acid sequence of light chain including amino acid sequence 4 as variable region, of humanized anti-hTfR antibody No. 3, synthetic sequence SEQ ID NO: 27: Amino acid sequence of light chain including amino acid sequence 5 as variable region, of humanized anti-hTfR antibody No. 3

SEQ ID NO: 28: Nucleic acid sequence encoding amino acid sequence of light chain including amino acid sequence 5 as variable region, of humanized anti-hTfR antibody No. 3, synthetic sequence SEQ ID NO: 29: Amino acid sequence of light chain including amino acid sequence 6 as variable region, of humanized anti-hTfR antibody No. 3

SEQ ID NO: 30: Nucleic acid sequence encoding amino acid sequence of light chain including amino acid sequence 6 as variable region, of humanized anti-hTfR antibody No. 3, synthetic sequence SEQ ID NO: 31: Amino acid sequence 1 of variable region of heavy chain of humanized anti-hTfR antibody No. 3

SEQ ID NO: 32: Amino acid sequence 2 of variable region of heavy chain of humanized anti-hTfR antibody No. 3

SEQ ID NO: 33: Amino acid sequence 3 of variable region of heavy chain of humanized anti-hTfR antibody No. 3

SEQ ID NO: 34: Amino acid sequence 4 of variable region of heavy chain of humanized anti-hTfR antibody No. 3

SEQ ID NO: 35: Amino acid sequence 5 of variable region of heavy chain of humanized anti-hTfR antibody No. 3

SEQ ID NO: 36: Amino acid sequence 6 of variable region of heavy chain of humanized anti-hTfR antibody No. 3

SEQ ID NO: 37: Amino acid sequence of heavy chain including amino acid sequence 2 as variable region, of humanized anti-hTfR antibody No. 3

SEQ ID NO: 38: Nucleic acid sequence encoding amino acid sequence of heavy chain including amino acid sequence 2 as variable region, of humanized anti-hTfR antibody No. 3, synthetic sequence SEQ ID NO: 39: Amino acid sequence of heavy chain (IgG4) including amino acid sequence 2 as variable region, of humanized anti-hTfR antibody No. 3

SEQ ID NO: 40: Nucleic acid sequence encoding amino acid sequence of heavy chain (IgG4) including amino acid sequence 2 as variable region, of humanized anti-hTfR antibody No. 3, synthetic sequence SEQ ID NO: 41: Primer hTfR5', synthetic sequence SEQ ID NO: 42: Primer hTfR3', synthetic sequence SEQ ID NO: 43: Primer Hyg-Sfi5', synthetic sequence SEQ ID NO: 44: Primer Hyg-BstX3', synthetic sequence SEQ ID NO: 45: Nucleic acid sequence of DNA, in which neomycin-resistant gene sandwiched between loxP sequences is disposed on 3' side of cDNA encoding chimeric hTfR, synthetic sequence SEQ ID NO: 46: 5' Arm sequence of targeting vector, synthetic sequence SEQ ID NO: 47: 3' Arm sequence of targeting vector, synthetic sequence SEQ ID NO: 48: Amino acid sequence of variable region of light chain of mouse anti-hTfR antibody No. 3

SEQ ID NO: 49: Amino acid sequence of variable region of heavy chain of mouse anti-hTfR antibody No. 3

SEQ ID NO: 52: Amino acid sequence of fusion protein (1) between heavy chain and hBDNF of humanized anti-hTfR antibody No. 3N SEQ ID NO: 53: Nucleic acid sequence encoding amino acid sequence of fusion protein (1) between heavy chain and hBDNF of humanized anti-hTfR antibody No. 3N, synthetic sequence SEQ ID NO: 54: Amino acid sequence of fusion protein (2) between heavy chain and hBDNF of humanized anti-hTfR antibody No. 3N SEQ ID NO: 55: Nucleic acid sequence encoding amino acid sequence of fusion protein (2) between heavy chain and hBDNF of humanized anti-hTfR antibody No. 3N, synthetic sequence SEQ ID NO: 57: Amino acid sequence of single-chain humanized anti-hTfR antibody No. 3N SEQ ID NO: 58: Nucleic acid sequence encoding amino acid sequence of fusion protein of pro-protein of hBDNF and single-chain humanized anti-hTfR antibody No. 3N, synthetic sequence SEQ ID NO: 59: Amino acid sequence of fusion protein of pro-protein of hBDNF and single-chain humanized anti-hTfR antibody No. 3N SEQ ID NO: 60: Amino acid sequence of fusion protein of hBDNF and single-chain humanized anti-hTfR antibody No. 3N SEQ ID NO: 61: Amino acid sequence of Fab heavy chain of humanized anti-hTfR antibody No. 3N SEQ ID NO: 62: Nucleic acid sequence encoding amino acid sequence of fusion protein of pro-protein of hBDNF and Fab heavy chain of humanized anti-hTfR antibody No. 3N, synthetic sequence SEQ ID NO: 63: Amino acid sequence of fusion protein of pro-protein of hBDNF and Fab heavy chain of humanized anti-hTfR antibody No. 3N SEQ ID NO: 64: Nucleic acid sequence encoding amino acid sequence of fusion protein of hBDNF and Fab heavy chain of humanized anti-hTfR antibody No. 3N, synthetic sequence SEQ ID NO: 65: Amino acid sequence of fusion protein of hBDNF and Fab heavy chain of humanized anti-hTfR antibody No. 3N SEQ ID NO: 66: Amino acid sequence 1 of heavy chain CDR1 of humanized anti-hTfR antibody No. 3N SEQ ID NO: 67: Amino acid sequence 2 of heavy chain CDR1 of humanized anti-hTfR antibody No. 3N SEQ ID NO: 68: Amino acid sequence of heavy chain framework region 3 of humanized anti-hTfR antibody No. 3N SEQ ID NO: 69: Amino acid sequence of variable region of heavy chain of humanized anti-hTfR antibody No. 3N SEQ ID NO: 70: Amino acid sequence of heavy chain of humanized anti-hTfR antibody No. 3N SEQ ID NO: 71: Nucleic acid sequence encoding amino acid sequence of heavy chain of humanized anti-hTfR antibody No. 3N, synthetic sequence SEQ ID NO: 72: Amino acid sequence of heavy chain (IgG4) of humanized anti-hTfR antibody No. 3N SEQ ID NO: 73: Nucleic acid sequence encoding amino acid sequence of fusion protein of pro-protein of hBDNF and Fab heavy chain of humanized anti-hTfR antibody No. 3N introduced with human IgG Fc region, synthetic sequence SEQ ID NO: 74: Amino acid sequence of fusion protein of pro-protein of hBDNF and Fab heavy chain of humanized anti-hTfR antibody No. 3N introduced with human IgG Fc region SEQ ID NO: 75: An example of amino acid sequence of Fc region of human IgG SEQ ID NO: 76: Nucleic acid sequence encoding amino acid sequence of heavy chain (IgG4) of humanized anti-hTfR antibody No. 3N, synthetic sequence SEQ ID NO: 77: Amino acid sequence of Fab heavy chain of humanized anti-hTfR antibody 3

SEQ ID NO: 78: Nucleic acid sequence encoding amino acid sequence of fusion protein of pro-protein of hBDNF and Fab heavy chain of humanized anti-hTfR antibody No. 3, synthetic sequence SEQ ID NO: 79: Amino acid sequence of fusion protein of pro-protein of hBDNF and Fab heavy chain of humanized anti-hTfR antibody No. 3

SEQ ID NO: 80: Amino acid sequence of fusion protein of hBDNF and Fab heavy chain of humanized anti-hTfR antibody No. 3

SEQ ID NO: 81: Amino acid sequence of Fab heavy chain of humanized anti-hTfR antibody No. 3N introduced with human IgG Fc region SEQ ID NO: 82: Nucleic acid sequence encoding amino acid sequence of Fab heavy chain of humanized anti-hTfR antibody No. 3N introduced with human IgG Fc region, synthetic sequence SEQ ID NO: 83: Amino acid sequence of heavy chain framework region 3 of humanized anti-hTfR antibody No. 3

SEQ ID NO: 84: Amino acid sequence (2) of Fab heavy chain of humanized anti-hTfR antibody No. 3N SEQ ID NO: 85: Amino acid sequence of albumin-binding domain SEQ ID NO: 86: Nucleic acid sequence encoding amino acid sequence of pro-protein of hBDNF, Fab heavy chain of humanized anti-hTfR antibody No. 3N, and fusion protein of ABD, synthetic sequence SEQ ID NO: 87: Amino acid sequence of pro-protein of hBDNF, Fab heavy chain of humanized anti-hTfR antibody No. 3N, and fusion protein of ABD SEQ ID NO: 88: Amino acid sequence of hBDNF, Fab heavy chain of humanized anti-hTfR antibody No. 3N, and fusion protein of ABD SEQ ID NO: 89: Amino acid sequence of Fab heavy chain introduced with albumin-affinity peptide SEQ ID NO: 90: Amino acid sequence of single-chain humanized anti-hTfR antibody No. 3N (2)

SEQUENCE LISTING

```
<160> NUMBER OF SEQ ID NOS: 90

<210> SEQ ID NO 1
<211> LENGTH: 760
<212> TYPE: PRT
<213> ORGANISM: Homo sapiens

<400> SEQUENCE: 1

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255
```

-continued

```
Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670
```

```
Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760


<210> SEQ ID NO 2
<211> LENGTH: 760
<212> TYPE: PRT
<213> ORGANISM: Macaca fascicularis

<400> SEQUENCE: 2

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Asp Glu Glu Asn Ala
        35                  40                  45

Asp Asn Asn Thr Lys Ala Asn Gly Thr Lys Pro Lys Arg Cys Gly Gly
    50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
        115                 120                 125

Arg Lys Leu Ser Glu Lys Leu Asp Thr Thr Asp Phe Thr Ser Thr Ile
    130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285
```

-continued

Pro Ile Val Lys Ala Asp Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
        355                 360                 365

Glu Asn Lys Ser Val Lys Leu Thr Val Ser Asn Val Leu Lys Glu Thr
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Ser Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asp
            500                 505                 510

Val Lys His Pro Val Thr Gly Arg Ser Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Val Glu Arg Ile Pro Glu Leu Asn Lys Val Ala Arg Ala Ala Ala Glu
            580                 585                 590

Val Ala Gly Gln Phe Val Ile Lys Leu Thr His Asp Thr Glu Leu Asn
        595                 600                 605

Leu Asp Tyr Glu Arg Tyr Asn Ser Gln Leu Leu Leu Phe Leu Arg Asp
    610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Ser Ala Leu Leu Glu Ser Leu Lys Leu Arg Arg
705 710 715 720

Gln Asn Asn Ser Ala Phe Asn Glu Thr Leu Phe Arg Asn Gln Leu Ala
725 730 735

Leu Ala Thr Trp Thr Ile Gln Gly Ala Ala Asn Ala Leu Ser Gly Asp
740 745 750

Val Trp Asp Ile Asp Asn Glu Phe
755 760

<210> SEQ ID NO 3
<211> LENGTH: 5
<212> TYPE: PRT
<213> ORGANISM: Artificial Sequence
<220> FEATURE:
<223> OTHER INFORMATION: Amino acid sequence of exemplified linker 1

<400> SEQUENCE: 3

Gly Gly Gly Gly Ser
1 5

<210> SEQ ID NO 4
<211> LENGTH: 6
<212> TYPE: PRT
<213> ORGANISM: Artificial Sequence
<220> FEATURE:
<223> OTHER INFORMATION: Amino acid sequence of exemplified linker 2

<400> SEQUENCE: 4

Gly Gly Gly Gly Gly Ser
1 5

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence of exemplified linker 3

<400> SEQUENCE: 5

Ser Gly Gly Gly Gly
1 5

<210> SEQ ID NO 6
<211> LENGTH: 11
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.3

<400> SEQUENCE: 6

Gln Ser Leu Val His Ser Asn Gly Asn Thr Tyr
1 5 10

<210> SEQ ID NO 7
<211> LENGTH: 16
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.3

<400> SEQUENCE: 7

Arg Ser Ser Gln Ser Leu Val His Ser Asn Gly Asn Thr Tyr Leu His
1 5 10 15

<210> SEQ ID NO 8
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.3

<400> SEQUENCE: 8

Lys Val Ser Asn Arg Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.3

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No. 3

<400> SEQUENCE: 10

Ser Gln Ser Thr His Val Pro Trp Thr
1               5

<210> SEQ ID NO 11
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.3

<400> SEQUENCE: 11

Asn Tyr Trp Leu Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.3

<400> SEQUENCE: 12

Gly Tyr Ser Phe Thr Asn Tyr Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.3

<400> SEQUENCE: 13

Ile Tyr Pro Gly Gly Asp Tyr Pro
1 5

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.3

<400> SEQUENCE: 14

Asp Ile Tyr Pro Gly Gly Asp Tyr Pro Thr Tyr Ser Glu Lys Phe Lys
1 5 10 15

Val

<210> SEQ ID NO 15
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.3

<400> SEQUENCE: 15

Ser Gly Asn Tyr Asp Glu Val Ala Tyr
1 5

<210> SEQ ID NO 16
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.3

<400> SEQUENCE: 16

Ala Arg Ser Gly Asn Tyr Asp Glu Val Ala Tyr
1 5 10

<210> SEQ ID NO 17
<211> LENGTH: 112
<212> TYPE: PRT
<213> ORGANISM: Artificial Sequence
<220> FEATURE:
<223> OTHER INFORMATION: Amino acid sequence 1 of the variable region of the light chain of humanized anti-hTfR antibody No.3

<400> SEQUENCE: 17

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asn Gly Asn Thr Tyr Leu His Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gly Gly Thr Lys Val Glu Ile Lys

```
            100                 105                 110


<210> SEQ ID NO 18
<211> LENGTH: 112
<212> TYPE: PRT
<213> ORGANISM: Artificial Sequence
<220> FEATURE:
<223> OTHER INFORMATION: Amino acid sequence 2 of the variable region of
      the light chain of humanized anti-hTfR antibody No.3

<400> SEQUENCE: 18

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110


<210> SEQ ID NO 19
<211> LENGTH: 112
<212> TYPE: PRT
<213> ORGANISM: Artificial Sequence
<220> FEATURE:
<223> OTHER INFORMATION: Amino acid sequence 3 of the variable region of
      the light chain of humanized anti-hTfR antibody No.3

<400> SEQUENCE: 19

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110


<210> SEQ ID NO 20
<211> LENGTH: 112
<212> TYPE: PRT
<213> ORGANISM: Artificial Sequence
<220> FEATURE:
<223> OTHER INFORMATION: Amino acid sequence 4 of the variable region of
      the light chain of humanized anti-hTfR antibody No.3

<400> SEQUENCE: 20

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110


<210> SEQ ID NO 21
<211> LENGTH: 112
<212> TYPE: PRT
<213> ORGANISM: Artificial Sequence
<220> FEATURE:
<223> OTHER INFORMATION: Amino acid sequence 5 of the variable region of
      the light chain of humanized anti-hTfR antibody No.3

<400> SEQUENCE: 21

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Arg Leu Glu Ile Lys
            100                 105                 110


<210> SEQ ID NO 22
<211> LENGTH: 112
<212> TYPE: PRT
<213> ORGANISM: Artificial Sequence
<220> FEATURE:
<223> OTHER INFORMATION: Amino acid sequence 6 of the variable region of
      the light chain of humanized anti-hTfR antibody No.3

<400> SEQUENCE: 22

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Phe Cys Ser Gln Ser
                85                  90                  95
```

```
Thr His Val Pro Trp Thr Phe Gly Gln Gly Thr Lys Val Glu Ile Lys
            100                 105                 110


<210> SEQ ID NO 23
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 2
      as the variable region

<400> SEQUENCE: 23

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 24
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 2 as the variable region, synthetic
      sequence

<400> SEQUENCE: 24

acgcgtgccg ccaccatggg ctggagctgg attctgctgt tcctcctgag cgtgacagca      60

ggagtgcaca gcgacatcgt gatgacccag actcccctga gcctgagcgt gacacctggc     120

cagcctgcca gcatcagctg cagaagctct cagagcctgg tgcacagcaa cggcaacacc     180

tacctgcact ggtatctgca gaagcccggc cagagccctc agctgctgat ctacaaggtg     240
```

-continued

```
tccaacagat tcagcggcgt gcccgacaga ttctccggca gcggctctgg caccgacttc    300

accctgaaga tttccagagt ggaagccgag gacgtgggcg tgtactactg cagccagagc    360

acccacgtgc cctggacatt cggccagggc accaaggtgg aaatcaagag aaccgtggcc    420

gctcccagcg tgttcatctt cccacctagc gacgagcagc tgaagtccgg cacagcctct    480

gtcgtgtgcc tgctgaacaa cttctacccc cgcgaggcca aggtgcagtg gaaggtggac    540

aacgccctgc agagcggcaa cagccaggaa agcgtgaccg agcaggactc caaggacagc    600

acctacagcc tgagcagcac cctgaccctg agcaaggccg actacgagaa gcacaaggtg    660

tacgcctgcg aagtgaccca ccagggcctg tctagccccg tgaccaagag cttcaacaga    720

ggcgagtgct aagcggccgc                                                740
```

<210> SEQ ID NO 25
<211> LENGTH: 219
<212> TYPE: PRT
<213> ORGANISM: Artificial Sequence
<220> FEATURE:
<223> OTHER INFORMATION: Amino acid sequence of the light chain of humanized anti-hTfR antibody No.3 containing amino acid sequence 4 as the variable region

<400> SEQUENCE: 25

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 26
<211> LENGTH: 740
<212> TYPE: DNA
<213> ORGANISM: Artificial Sequence
<220> FEATURE:
<223> OTHER INFORMATION: Nucleotide sequence encoding the amino acid sequence of the light chain of humanized anti-hTfR antibody No.3 containing amino acid sequence 4 as the variable region, synthetic sequence

<400> SEQUENCE: 26
acgcgtgccg ccaccatggg ctggagctgg attctgctgt tcctcctgag cgtgacagca 60
ggagtgcaca gcgacatcgt gatgacccag agccccctga gcctgcctgt gacacctggc 120
gagcctgcca gcatcagctg cagatctagc cagagcctgg tgcacagcaa cggcaacacc 180
tacctgcact ggtatctgca gaagcccggc cagagccctc agctgctgat ctacaaggtg 240
tccaacagat tcagcggcgt gcccgacaga ttctccggca gcggctctgg caccgacttc 300
accctgaaga tctccagagt ggaagccgag gacgtgggcg tgtactactg cagccagagc 360
acccacgtgc cctggacatt cggccagggc accaaggtgg aaatcaagag aaccgtggcc 420
gctcccagcg tgttcatctt cccacctagc gacgagcagc tgaagtccgg cacagcctct 480
gtcgtgtgcc tgctgaacaa cttctacccc cgcgaggcca aggtgcagtg gaaggtggac 540
aacgccctgc agagcggcaa cagccaggaa agcgtgaccg agcaggactc caaggacagc 600
acctacagcc tgagcagcac cctgaccctg agcaaggccg actacgagaa gcacaaggtg 660
tacgcctgcg aagtgaccca ccagggcctg tctagccccg tgaccaagag cttcaacaga 720
ggcgagtgct aagcggccgc 740

<210> SEQ ID NO 27
<211> LENGTH: 219
<212> TYPE: PRT
<213> ORGANISM: Artificial Sequence
<220> FEATURE:
<223> OTHER INFORMATION: Amino acid sequence of the light chain of humanized anti-hTfR antibody No.3 containing amino acid sequence 5 as the variable region

<400> SEQUENCE: 27

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gln Gly Thr Arg Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28
<211> LENGTH: 740
<212> TYPE: DNA
<213> ORGANISM: Artificial Sequence
<220> FEATURE:
<223> OTHER INFORMATION: Nucleotide sequence encoding the amino acid sequence of the light chain of humanized anti-hTfR antibody No.3 containing amino acid sequence 5 as the variable region, synthetic sequence

<400> SEQUENCE: 28
acgcgtgccg ccaccatggg ctggagctgg attctgctgt tcctcctgag cgtgacagca 60
ggagtgcaca gcgacatcgt gatgacccag acacccctga gcctgcctgt gacacctggc 120
gagcctgcca gcatcagctg cagatctagc cagagcctgg tgcacagcaa cggcaacacc 180
tacctgcact ggtatctgca gaagcccggc cagagccctc agctgctgat ctacaaggtg 240
tccaacagat tcagcggcgt gcccgacaga ttctccggca gcggctctgg caccgacttc 300
accctgaaga tctccagagt ggaagccgag gacgtgggcg tgtactactg cagccagagc 360
acccacgtgc cctggacatt cggccagggc accaggctgg aaatcaagag aaccgtggcc 420
gctcccagcg tgttcatctt cccacctagc gacgagcagc tgaagtccgg cacagcctct 480
gtcgtgtgcc tgctgaacaa cttctacccc cgcgaggcca aggtgcagtg gaaggtggac 540
aacgccctgc agagcggcaa cagccaggaa agcgtgaccg agcaggactc caaggacagc 600
acctacagcc tgagcagcac cctgaccctg agcaaggccg actacgagaa gcacaaggtg 660
tacgcctgcg aagtgaccca ccagggcctg tctagccccg tgaccaagag cttcaacaga 720
ggcgagtgct aagcggccgc 740

<210> SEQ ID NO 29
<211> LENGTH: 219
<212> TYPE: PRT
<213> ORGANISM: Artificial Sequence
<220> FEATURE:
<223> OTHER INFORMATION: Amino acid sequence of the light chain of humanized anti-hTfR antibody No.3 containing amino acid sequence 6 as the variable region

<400> SEQUENCE: 29

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Phe Cys Ser Gln Ser
                85                  90                  95

Thr His Val Pro Trp Thr Phe Gly Gln Gly Thr Lys Val Glu Ile Lys
            100                 105                 110

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 30
<211> LENGTH: 740
<212> TYPE: DNA
<213> ORGANISM: Artificial Sequence
<220> FEATURE:
<223> OTHER INFORMATION: Nucleotide sequence encoding the amino acid sequence of the light chain of humanized anti-hTfR antibody No.3 containing amino acid sequence 6 as the variable region, synthetic sequence

<400> SEQUENCE: 30

```
acgcgtgccg ccaccatggg ctggagctgg attctgctgt tcctcctgag cgtgacagca     60

ggagtgcaca gcgacatcgt gatgacccag actcccctga gcctgagcgt gacacctggc    120

cagcctgcca gcatcagctg cagatccagc cagagcctgg tgcacagcaa cggcaacacc    180

tacctgcact ggtatctgca gaagcccggc cagagccctc agctgctgat ctacaaggtg    240

tccaacagat tcagcggcgt gcccgacaga ttctccggca gcggctctgg caccgacttc    300

accctgaaga tttccagagt ggaagccgag gacgtgggcg tgttcttctg cagccagagc    360

acccacgtgc cctggacatt cggccagggc accaaggtgg aaatcaagag aaccgtggcc    420

gctcccagcg tgttcatctt cccacctagc gacgagcagc tgaagtccgg cacagcctct    480

gtcgtgtgcc tgctgaacaa cttctacccc cgcgaggcca aggtgcagtg gaaggtggac    540

aacgccctgc agagcggcaa cagccaggaa agcgtgaccg agcaggactc caaggacagc    600

acctacagcc tgagcagcac cctgaccctg agcaaggccg actacgagaa gcacaaggtg    660

tacgcctgcg aagtgaccca ccagggcctg tctagccccg tgaccaagag cttcaacaga    720

ggcgagtgct aagcggccgc                                                740
```

<210> SEQ ID NO 31
<211> LENGTH: 118
<212> TYPE: PRT
<213> ORGANISM: Artificial Sequence
<220> FEATURE:
<223> OTHER INFORMATION: Amino acid sequence 1 of the variable region of the heavy chain of humanized anti-hTfR antibody No.3

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45
```

```
Gly Asp Ile Tyr Pro Gly Gly Asp Tyr Pro Thr Tyr Ser Glu Lys Phe
    50                  55                  60

Lys Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115


<210> SEQ ID NO 32
<211> LENGTH: 118
<212> TYPE: PRT
<213> ORGANISM: Artificial Sequence
<220> FEATURE:
<223> OTHER INFORMATION: Amino acid sequence 2 of the variable region of
      the heavy chain of humanized anti-hTfR antibody No.3

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115


<210> SEQ ID NO 33
<211> LENGTH: 118
<212> TYPE: PRT
<213> ORGANISM: Artificial Sequence
<220> FEATURE:
<223> OTHER INFORMATION: Amino acid sequence 3 of the variable region of
      the heavy chain of humanized anti-hTfR antibody No.3

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Ser Gly Asn Tyr Asp Glu Val Ala Tyr Trp Gly Gln Gly Thr
            100                 105                 110

Thr Val Thr Val Ser Ser
        115


<210> SEQ ID NO 34
<211> LENGTH: 118
<212> TYPE: PRT
<213> ORGANISM: Artificial Sequence
<220> FEATURE:
<223> OTHER INFORMATION: Amino acid sequence 4 of the variable region of
      the heavy chain of humanized anti-hTfR antibody No.3

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Arg Leu Glu Trp Met
        35                  40                  45

Gly Asp Ile Tyr Pro Gly Gly Asp Tyr Pro Thr Tyr Ser Glu Lys Phe
    50                  55                  60

Lys Val Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115


<210> SEQ ID NO 35
<211> LENGTH: 118
<212> TYPE: PRT
<213> ORGANISM: Artificial Sequence
<220> FEATURE:
<223> OTHER INFORMATION: Amino acid sequence 5 of the variable region of
      the heavy chain of humanized anti-hTfR antibody No.3

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
            100                 105                 110

Val Val Thr Val Ser Ser
        115


<210> SEQ ID NO 36
```

<211> LENGTH: 118
<212> TYPE: PRT
<213> ORGANISM: Artificial Sequence
<220> FEATURE:
<223> OTHER INFORMATION: Amino acid sequence 6 of the variable region of the heavy chain of humanized anti-hTfR antibody No.3

<400> SEQUENCE: 36

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Ile
        35                  40                  45

Gly Asp Ile Tyr Pro Gly Gly Asp Tyr Pro Thr Tyr Ser Glu Lys Phe
    50                  55                  60

Lys Val Lys Ala Ile Ile Ser Ala Asp Thr Ser Ile Ser Thr Val Tyr
65                  70                  75                  80

Leu Gln Leu Ser Ser Leu Lys Ala Ser Asp Thr Ala Met Tyr Phe Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115
```

<210> SEQ ID NO 37
<211> LENGTH: 448
<212> TYPE: PRT
<213> ORGANISM: Artificial Sequence
<220> FEATURE:
<223> OTHER INFORMATION: Amino acid sequence of the heavy chain of humanized anti-hTfR antibody No.3 containing amino acid sequence 2 as the variable region

<400> SEQUENCE: 37

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

-continued

```
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 38
<211> LENGTH: 1427
<212> TYPE: DNA
<213> ORGANISM: Artificial Sequence
<220> FEATURE:
<223> OTHER INFORMATION: Nucleotide sequence encoding the amino acid
      sequence of the heavy chain of humanized anti-hTfR antibody No.3
      containing amino acid sequence 2 as the variable region, synthetic
      sequence

<400> SEQUENCE: 38

acgcgtgccg ccaccatggg ctggagctgg attctgctgt tcctcctgag cgtgacagca      60

ggagtgcaca gcgaggtgca actagtgcag tctggagcag aggtgaaaaa gcccggggag     120

tctctgaaga tttcctgtaa gggttctgga tacagcttta ccaactactg gctgggatgg     180

gtgcgccaga tgcccgggaa aggcctggag tggatggggg acatctaccc cggcggagac     240

taccctacat acagcgagaa gttcaaggtc caggtcacca tctcagccga caagtccatc     300

agcaccgcct acctgcagtg gagcagcctg aaggcctcgg acaccgccat gtattactgt     360

gcgagatcag gcaattacga cgaagtggcc tactggggcc aaggaaccct ggtcaccgtc     420

tcctcagcta gcaccaaggg cccatcggtc ttccccctgg caccctcctc caagagcacc     480
```

-continued

```
tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgaccgtgc cctccagcag cttgggcacc    660

cagacctaca tctgcaacgt gaatcacaag cccagcaaca ccaaggtgga caagaaagtt    720

gagcccaaat cttgtgacaa aactcacacg tgcccaccgt gcccagcacc tgaactcctg    780

ggaggtccgt cagtcttcct cttcccccca aaacccaagg acaccctcat gatctcccgg    840

acccctgagg tcacatgcgt ggtggtggac gtgagccacg aagaccctga ggtcaagttc    900

aactggtacg tggacggcgt ggaggtgcat aatgccaaga caaagccgcg ggaggagcag    960

tacaacagca cgtaccgggt ggtcagcgtc ctcaccgtcc tgcaccagga ctggctgaat   1020

ggcaaggagt acaagtgcaa ggtctccaac aaagccctcc cagcccccat cgagaaaacc   1080

atctccaaag ccaaagggca gccccgagaa ccacaggtgt acaccctgcc cccatcccgg   1140

gatgagctga ccaagaacca ggtcagcctg acctgcctgg tcaaaggctt ctatcccagc   1200

gacatcgccg tggagtggga gagcaatggg cagccggaga acaactacaa gaccacgcct   1260

cccgtgctgg actccgacgg ctccttcttc ctctacagca agctcaccgt ggacaagagc   1320

aggtggcagc aggggaacgt cttctcatgc tccgtgatgc atgaggctct gcacaaccac   1380

tacacgcaga agagcctctc cctgtctccg ggtaaataag cggccgc                 1427
```

```
<210> SEQ ID NO 39
<211> LENGTH: 445
<212> TYPE: PRT
<213> ORGANISM: Artificial Sequence
<220> FEATURE:
<223> OTHER INFORMATION: Amino acid sequence of the heavy chain (IgG4)
      of humanized anti-hTfR antibody No.3 containing amino acid
      sequence 2 as the variable region

<400> SEQUENCE: 39

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 40
<211> LENGTH: 1418
<212> TYPE: DNA
<213> ORGANISM: Artificial Sequence
<220> FEATURE:
<223> OTHER INFORMATION: Nucleotide sequence encoding the amino acid sequence of the heavy chain (IgG4) of humanized anti-hTfR antibody No.3 containing amino acid sequence 2 as the variable region, synthetic sequence

<400> SEQUENCE: 40

```
acgcgtgccg ccaccatggg ctggagctgg attctgctgt tcctcctgag cgtgacagca     60

ggagtgcaca gcgaggtgca actagtgcag tctggagcag aggtgaaaaa gcccggggag    120

tctctgaaga tttcctgtaa gggttctgga tacagcttta ccaactactg gctgggatgg    180

gtgcgccaga tgcccgggaa aggcctggag tggatggggg acatctaccc cggcggagac    240

taccctacat acagcgagaa gttcaaggtc caggtcacca tctcagccga caagtccatc    300

agcaccgcct acctgcagtg gagcagcctg aaggcctcgg acaccgccat gtattactgt    360

gcgagatcag gcaattacga cgaagtggcc tactggggcc aaggaaccct ggtcaccgtc    420

tcctcagcta gcaccaaggg cccatcggtc ttccccctgg cgccctgctc caggagcacc    480

tccgagagca cagccgccct gggctgcctg gtcaaggact acttccccga accggtgacg    540
```

gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacg 660
aagacctaca cctgcaacgt agatcacaag cccagcaaca ccaaggtgga caagagagtt 720
gagtccaaat atggtccccc atgcccacca tgcccagcac ctgagttcct ggggggtcca 780
tcagtcttcc tgttcccccc aaaacccaag gacactctca tgatctcccg gacccctgag 840
gtcacgtgcg tggtggtgga cgtgagccag gaagaccccg aggtccagtt caactggtac 900
gtggatggcg tggaggtgca taatgccaag acaaagccgc gggaggagca gttcaacagc 960
acgtaccgtg tggtcagcgt cctcaccgtc ctgcaccagg actggctgaa cggcaaggag 1020
tacaagtgca aggtctccaa caaaggcctc ccgtcctcca tcgagaaaac catctccaaa 1080
gccaaagggc agccccgaga gccacaggtg tacaccctgc ccccatccca ggaggagatg 1140
accaagaacc aggtcagcct gacctgcctg gtcaaaggct tctaccccag cgacatcgcc 1200
gtggagtggg agagcaatgg gcagccggag aacaactaca agaccacgcc tcccgtgctg 1260
gactccgacg gctccttctt cctctacagc aggctcaccg tggacaagag caggtggcag 1320
gaggggaatg tcttctcatg ctccgtgatg catgaggctc tgcacaacca ctacacacag 1380
aagagcctct ccctgtctcc gggtaaataa gcggccgc 1418

<210> SEQ ID NO 41
<211> LENGTH: 43
<212> TYPE: DNA
<213> ORGANISM: Artificial Sequence
<220> FEATURE:
<223> OTHER INFORMATION: Primer hTfR5', synthetic sequence

<400> SEQUENCE: 41
ccgacgcgtc gccaccatga tggatcaagc tagatcagca ttc 43

<210> SEQ ID NO 42
<211> LENGTH: 59
<212> TYPE: DNA
<213> ORGANISM: Artificial Sequence
<220> FEATURE:
<223> OTHER INFORMATION: Primer hTfR3', synthetic sequence

<400> SEQUENCE: 42
ataatgcggc cgcttaatga tgatgatgat gatgaaactc attgtcaatg tcccaaacg 59

<210> SEQ ID NO 43
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 43
gaggccgcct cggcctctga 20

<210> SEQ ID NO 44
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 44
aaccatcgtg atgggtgcta ttcctttgc 29

<210> SEQ ID NO 45
<211> LENGTH: 4460
<212> TYPE: DNA
<213> ORGANISM: Artificial Sequence
<220> FEATURE:
<223> OTHER INFORMATION: "Nucleotide sequence of the DNA formed of a cDNA encoding chimeric hTfR and a loxP-flanked neomycin resistance gene placed on the cDNA's 3' side, synthetic sequence "

<400> SEQUENCE: 45
gtttatcctc ccttgtagca gctgagaatg atggatcaag ccagatcagc attctctaac 60
ttgtttggtg ggaaccatt gtcatacacc cggtttagcc ttgctcggca agtagatgga 120
gataacagtc atgtggagat gaaactggct gcagatgaag aagaaaatgc cgacaataac 180
atgaaggcta gtgtcagaaa acccaagagg tttaatggaa gactctgctt tgcagctatt 240
gcactagtca ttttcttctt gattggattc atgagtggct acctgggcta ttgtaaaggg 300
gtagaaccaa aaactgagtg tgagagactg gcaggaaccg agtctccagt gagggaggag 360
ccaggagagg acttccctgc agcacgtcgc ttatattggg atgacctgaa gagaaagttg 420
tcggagaaac tggacagcac agacttcacc ggcaccatca agctgctgaa tgaaaattca 480
tatgtccctc gtgaggctgg atctcaaaaa gatgaaaatc ttgcgttgta tgttgaaaat 540
caatttcgtg aatttaaact cagcaaagtc tggcgtgatc aacattttgt taagattcag 600
gtcaaagaca gcgctcaaaa ctcggtgatc atagttgata agaacggtag acttgtttac 660
ctggtggaga atcctggggg ttatgtggcg tatagtaagg ctgcaacagt tactggtaaa 720
ctggtccatg ctaattttgg tactaaaaaa gatttgagg atttatacac tcctgtgaat 780
ggatctatag tgattgtcag agcagggaaa atcacctttg cagaaaaggt tgcaaatgct 840
gaaagcttaa atgcaattgg tgtgttgata tacatggacc agactaaatt tcccattgtt 900
aacgcagaac tttcattctt tggacatgct catctgggga caggtgaccc ttacacacct 960
ggattccctt ccttcaatca cactcagttt ccaccatctc ggtcatcagg attgcctaat 1020
atacctgtcc agacaatctc cagagctgct gcagaaaagc tgtttgggaa tatggaagga 1080
gactgtccct ctgactggaa aacagactct acatgtagga tggtaacctc agaaagcaag 1140
aatgtgaagc tcactgtgag caatgtgctg aaagagataa aaattcttaa catctttgga 1200
gttattaaag gctttgtaga accagatcac tatgttgtag ttggggccca gagagatgca 1260
tggggccctg gagctgcaaa atccggtgta ggcacagctc tcctattgaa acttgcccag 1320
atgttctcag atatggtctt aaaagatggg tttcagccca gcagaagcat tatctttgcc 1380
agttggagtg ctggagactt tggatcggtt ggtgccactg aatggctaga gggatacctt 1440
tcgtccctgc atttaaaggc tttcacttat attaatctgg ataaagcggt tcttggtacc 1500
agcaacttca aggtttctgc cagcccactg ttgtatacgc ttattgagaa aacaatgcaa 1560
aatgtgaagc atccggttac tgggcaattt ctatatcagg acagcaactg ggccagcaaa 1620
gttgagaaac tcactttaga caatgctgct ttccctttcc ttgcatattc tggaatccca 1680
gcagtttctt tctgtttttg cgaggacaca gattatcctt atttgggtac caccatggac 1740
acctataagg aactgattga gaggattcct gagttgaaca aagtggcacg agcagctgca 1800
gaggtcgctg gtcagttcgt gattaaacta acccatgatg ttgaattgaa cctggactat 1860
gagaggtaca acagccaact gctttcattt gtgagggatc tgaaccaata cagagcagac 1920
ataaaggaaa tgggcctgag tttacagtgg ctgtattctg ctcgtggaga cttcttccgt 1980
gctacttcca gactaacaac agatttcggg aatgctgaga aaacagacag atttgtcatg 2040

```
aagaaactca atgatcgtgt catgagagtg gagtatcact tcctctctcc ctacgtatct   2100
ccaaaagagt ctcctttccg acatgtcttc tggggctccg gctctcacac gctgccagct   2160
ttactggaga acttgaaact gcgtaaacaa aataacggtg cttttaatga aacgctgttc   2220
agaaaccagt tggctctagc tacttggact attcagggag ctgcaaatgc cctctctggt   2280
gacgtttggg acattgacaa tgagttttaa cgtggctcgc tgatcagcct cgactgtgcc   2340
ttctagttgc cagccatctg ttgtttgccc ctcccccgtg ccttccttga ccctggaagg   2400
tgccactccc actgtccttt cctaataaaa tgaggaaatt gcatcgcatt gtctgagtag   2460
gtgtcattct attctggggg gtggggtggg gcaggacagc aagggggagg attgggaaga   2520
caatagcagg catgctgggg atgcggtggg ctctatggct tctgaggcgg aaagaaccag   2580
ctggggctcg atcctctagt taagcttccc agcggccgct atcgaattcc gatcatattc   2640
aataaccctt aatataactt cgtataatgt atgctatacg aagttattag gtctgaagag   2700
gagtttacgt ccagccaagc taattctacc gggtagggga ggcgcttttc ccaaggcagt   2760
ctggagcatg cgctttagca gccccgctgg gcacttggcg ctacacaagt ggcctctggc   2820
ctcgcacaca ttccacatcc accggtaggc gccaaccggc tccgttcttt ggtggcccct   2880
tcgcgccacc ttctactcct cccctagtca ggaagttccc ccccgccccg cagctcgcgt   2940
cgtgcaggac gtgacaaatg gaagtagcac gtctcactag tctcgtgcag atggacagca   3000
ccgctgagca atggaagcgg gtaggccttt ggggcagcgg ccaatagcag ctttgctcct   3060
tcgctttctg ggctcagagg ctgggaaggg gtgggtccgg gggcgggctc aggggcgggc   3120
tcaggggcgg ggcgggcgcc cgaaggtcct ccggaggccc ggcattctgc acgcttcaaa   3180
agcgcacgtc tgccgcgctg ttctcctctt cctcatctcc gggcctttcg acctgcagcc   3240
aatatgggat cggccattga acaagatgga ttgcacgcag gttctccggc cgcttgggtg   3300
gagaggctat tcggctatga ctgggcacaa cagacaatcg gctgctctga tgccgccgtg   3360
ttccggctgt cagcgcaggg gcgcccggtt ctttttgtca agaccgacct gtccggtgcc   3420
ctgaatgaac tgcaggacga ggcagcgcgg ctatcgtggc tggccacgac gggcgttcct   3480
tgcgcagctg tgctcgacgt tgtcactgaa gcgggaaggg actggctgct attgggcgaa   3540
gtgccggggc aggatctcct gtcatctcac cttgctcctg ccgagaaagt atccatcatg   3600
gctgatgcaa tgcggcggct gcatacgctt gatccggcta cctgcccatt cgaccaccaa   3660
gcgaaacatc gcatcgagcg agcacgtact cggatggaag ccggtcttgt cgatcaggat   3720
gatctggacg aagagcatca ggggctcgcg ccagccgaac tgttcgccag gctcaaggcg   3780
cgcatgcccg acggcgagga tctcgtcgtg acccatggcg atgcctgctt gccgaatatc   3840
atggtggaaa atggccgctt ttctggattc atcgactgtg gccggctggg tgtggcggac   3900
cgctatcagg acatagcgtt ggctacccgt gatattgctg aagagcttgg cggcgaatgg   3960
gctgaccgct tcctcgtgct ttacggtatc gccgctcccg attcgcagcg catcgccttc   4020
tatcgccttc ttgacgagtt cttctgaggg gatccgctgt aagtctgcag aaattgatga   4080
tctattaaac aataaagatg tccactaaaa tggaagtttt tcctgtcata ctttgttaag   4140
aagggtgaga acagagtacc tacattttga atggaaggat tggagctacg gggtggggg    4200
tggggtggga ttagataaat gcctgctctt tactgaaggc tctttactat tgctttatga   4260
taatgtttca tagttggata tcataattta aacaagcaaa accaaattaa gggccagctc   4320
attcctccca ctcatgatct atagatccct cgatcgagat ccggaaccct taatataact   4380
```

tcgtataatg tatgctatac gaagttatta ggtccctcga agaggttcac tagttctaga 4440
gcatttaaat acgtgctagc 4460

<210> SEQ ID NO 46
<211> LENGTH: 5003
<212> TYPE: DNA
<213> ORGANISM: Artificial Sequence
<220> FEATURE:
<223> OTHER INFORMATION: Nucleotide sequence of the 5'-arm of targeting vector, synthetic sequence

<400> SEQUENCE: 46
aaagacattc ccagggtccc taagggctcc atctgggagc gcgctatctg tagtcctgtt 60
gtggtttaag ataccactct ctttgttatt tgtaaattta ccacaggctg ggcagtaaag 120
tacagatagg aagaaaagag tgtgaacgtt tgcagtttta acagaactcc ttttatttgc 180
tatgcattgc aacaaccctc taaaagcaat aatggcgata aacatgcaag ttaatctaca 240
actttatcac cctagtaaat cattggttcc tatttccctt ccataggctg aacatagtga 300
gcactggtag ctctttgctt ggcttaagcg ctgcttgtta aaatctaaaa aaaaaaaaaa 360
aaaagatttg cagttttgct ttaaagtttt tcctttaaag catctctgag ctgcaaaaac 420
tcgtctttag gatatggttt tggcggagac ctaagcctgc aagtaggaat attttaaaga 480
gtaaaggctg atactttcga acttgcaccg cagggttggg tgtcggtcaa ggttaggcgg 540
agggcgacag gccaactcca aagacacggc gggggagggg tgcggtggag aaagcgagcc 600
gcagccaatc gcacgcgctc tcccgacacc tgccgccttg gcgccttttc taggctactc 660
cgcgcacgca ctggctgcgc gcgcagttcg cctccagcgg tcttggggga gcacctcggt 720
aggtgtacgt gcggaaggaa gtgacgtaga tccagagggc cggccggggg gtggggccga 780
gctataagct ttgggtggga ggcagcgctg ccttcagaag gcgtgcggag cgcgggctgc 840
tgcattgcgg actgtagagg cgcttcctag tgagtgactc ccttgtcagc ggcacggccc 900
atcgtggtcc tcgcgtggcg ggcggaccag agcgagacgc cagggcctgg gtggtgcggg 960
cggggaggcg gaggggtgtc gcggagtccg gggctgagga gcgcgggttg caggtgcagc 1020
gcggtgggtg tggggagccg ctgtaccctg cgcccctcgg gtcctccggg ccttcgcagg 1080
ccagtgctag gccgcgggtt cgagagtcac cacgctgagg cgcaggcttg ttccgccggg 1140
agcacgtggt ggcggctgga ggaagtcgcc ccagggaacg gctgtcgggg tacgtgggtg 1200
accttggggc ccctcgcagg agggcgtcac agctgaaaag gacaaagctg ttttctattc 1260
ggttactagt gtcacggaca tttagagggg cggggggagc ttccaataac tgcacgttgg 1320
aacttcggca ccacctggtc ggtttttttg ccagtctctc cctcttggcc cagcgtgtgg 1380
aatctcattt ttctagggca gaataggtct gaacgctgca ggtaatacta agaacgtctc 1440
tagcatctcc taagatggga gaacgtagaa atacgacctc tttgtacgag ctcttttaga 1500
actagctgta gagaaccagc gtgcaccctg gtgttggaca gctctctaaa atggtgtttg 1560
agggtaagaa aactgcattt gcaaattttt cagttagcac actttgtccc gagcgtaaaa 1620
tgaaatgatc tccttatact taggcagaag actggactgg attgctgttc agtttctgtg 1680
ctattttttt aaaataggat ttaagtggga aatagttgtg ttacagaaat tctcggctat 1740
tctgtgctat tttttttaa ataggattta agtgggaaat agttgtgtta cagaaattct 1800
cggctacctg atacttttat tctaagatta gatgagttgg ctctgagctg tgaaatatga 1860
cctctttgac aaagacattt aagctgattc aggatgttat ctacaaagaa aacgggattt 1920

-continued

```
agcttgtgtg ggtccacttg catttatttt ctgttaagga ttataataaa ctgctttata   1980
caggaatcca atatcagctg tttttatat agagagcata atacttttta ctttgagaga   2040
ggatgttgtc aaggaatggt ggctgtgaac ctggcctgtg ttgactggtt agatctgtct   2100
gcctaacccc accctaaggc taagtagtta tatgcttgtg gcaatgtgct tatttataat   2160
agggcaagat tatgggctaa atttgggtta gacaacaatg aaagttaatt aaacgaccct   2220
caggccttgg gtctactatg tgtaagtgat ttccttctct cccagatgag tgctatacaa   2280
aataaacttc agtgacctca agtggttttg accttttggt tgctattcag aaaactatgg   2340
aaatgaaaac ctgctaccta tttcctattg ccttttcaat ttcccaaaga aggtctcccc   2400
tatgaatcca tgggtagcct tgaactcaga tccacctgct tctgtttgga gagtgataag   2460
attaaaggca agtgccacca cacccagcaa agtaggctct taaaactaaa acctttgcag   2520
tcgggcatgg tgccacacac ctttggtccc agcactgggg ggtaaggcag aggcaggtgg   2580
atcactgagt ttgaggtcag ctagtgctga agagtaagag cctgtcttta aaacatctca   2640
acagctgggc agtcgtggtc cattccttta atcccagcac ttgggaggca gaggcaagtg   2700
gatttttgag ttcgaggcca gcctggtcta cagagtgagt tccaggacag ccagggatac   2760
acagagaaac cctgtctcaa aaaaccaaaa tataaataaa taaataaaga ttgggagaga   2820
agtcaaggat ctcataggtg gtcagggagc tacaactgca gtagtaaaga agtaggactt   2880
aaaagaacag ggccggcact aattttgagg atctagatcg ggccctcaat taaggaactt   2940
ccttttgtgt gaactcagaa tttgaaatga aatgtgcttg tcagaaccat tgcatggctt   3000
atttttaat gaaaagtctg gctagtatct gcttatcttc cagcttccag ctcaaagtta   3060
aggtcataga tcaaaagaac tatgtcttta tcttagttgt atcttaattt ttattagaat   3120
tgaatggttt tcctaatgtt tggtaacatc aaaggtgtgt aagtaaaagt gagaaatcaa   3180
gattaacttt ctcttggcaa agattgttga cattggtgac atcttggacc aaatgagaat   3240
tgttttactt ttaaatgtcc catcaacagc tctcagttag gctgttctat ctggtttgtc   3300
ttgccatgct tgcagagtat agatttgaca atttgaaaat tcaaaaagct atataaatag   3360
gtatgttgct atatgtaaga ttttaaatga gtcagttaag acttaaagaa taactgggtt   3420
tattttatct tgtcaggtta tcactgtgta gaccaggttg accttgaaaa caaattctct   3480
gcttcccaag tgctgggatt aaaggcgtgt gtcactagct ctgacactgg ctactttgga   3540
actactatgg tgttcacaaa tgcagagttg agtgttggga ttaaatggaa atttcatgtc   3600
ttttttttta actttccctt ctacacaggg cttctctgtg tagtcctggc tgtccttgta   3660
gctctagact aggctgaatt caaactcaga tccacccacc taagtgctga gattaaaggc   3720
atgtgccacc actgcccagt tctgaattgt tggggttttt tttttgttgt tattcttaat   3780
tttagttcga tgaattaaaa tcgaaataac ttgtttctta gaaaaataag gtgtaattgg   3840
gttataaagc caaatttaga cattaatacc aacagcctgt ttaggctcaa aattgttcaa   3900
tcattttatt agtattatta ttaatcatat caacttgaga cctgtttggg aaagcagaat   3960
attttaggga tagctatttc agacaagcat taatgtgtta gctgtttttt tccccctaga   4020
atatgattaa aattggctca gggtggggcc ttctagttct ggctctagcg attgggtctg   4080
tttctggtga ggtggtagtg ataaactgta acagaaggga caagagattg ggcttctgag   4140
aacatgtatg atctggtatg tgactttaat cattaaagca tggggattca aaaatactaa   4200
tgaataggcc ttagaactag tcctgagtgt tttgtaaaat aacagtctta attctcctag   4260
tttctggatt tttttctttg tctttggata ctaagtttaa gcatttattt ggacagagtg   4320
```

```
gtgcccacta gctgttctat tctagtactt gggaggcaag aggcagaacg aacatggcca   4380

gcttggacaa cttaagaaaa ctgaaaggct tgccatccta gtttttcttt tgattaaaca   4440

cacttatatt ctaactagtt ttctctatcc tttgggtttt gttttgtttt ttatttgttt   4500

tgtagctcta gctggctggc ttcggaattg cctgcctccc aagtgctagg attaaaggca   4560

tcacagtcac tacccaattg atatcatgat tcttaattca acttctaaga acaaattatc   4620

acactctgaa tctaacatgg aatagcatta tccatgttca gatatctttg tctcaaggct   4680

caggtttatc ctttgtagct ttctttttgc tatcccacct ctattcagca tccagtcaag   4740

gatcactgag ttggttatca gtaaattaaa cattttaatt aatgtctagg agacaggtta   4800

tggtatagtt ctcagtgctg ggaagttgac atggtaggat ctcagttcat ggccagccag   4860

aactttctgg tgagatcctg gttcaagcac tacagagctt ttctagaaaa gtaactatat   4920

ttaggagtaa gtttgatata atgacaatcc catcgtaagc cttcagtaac ctgatgcatt   4980

ggtctctgtt ttaatatcag gta                                           5003
```

<210> SEQ ID NO 47
<211> LENGTH: 2604
<212> TYPE: DNA
<213> ORGANISM: Artificial Sequence
<220> FEATURE:
<223> OTHER INFORMATION: Nucleotide sequence of the 3'-arm of targeting vector, synthetic sequence

<400> SEQUENCE: 47

```
gcattctcta acttggtaag gtactttcat ctatctgaaa aaatgttcag taaaaaacaa     60

aacaaaaaca tgacttcacc cagtgagtac aagatgatac ccccaatttt ttttttttt    120

attatatgta tgtacactgt agctgtcttc agacacacca gaagagggcg tcagatctca    180

tcagatggtt gtgagccacc atgtggttgc tgggacttga acactggacc tttggaaaag    240

cagttgggta ctcttaccca ctgagctatc acaccagccc caataccccca aattttgacc    300

agccttttttt tttttttttt tttttttttt aaatctgaac taatggtatt aaggtgaaac    360

agattgcaca aaagaggtac taggtttttc tttgaggcaa ggtctttcta tattgcctca    420

ggttgacctt aaactccaac ttcctttttt tccccaagtg ctggagattg tagacagata    480

tatacaacac cccaaaacaa atatgtttag tttcgattaa gattcattat gtggggctag    540

agggatgact tagaggttaa gaacactgcc tgctcttcca gaggtcctga gttcaattcc    600

cagcaaccac gtggtggctc acaaccatct gtaatgggat ccgatgccct ctttctggtg    660

tgtttgaaga cagctacagt gtcctcatac ataaaaaaaa taaacaaaca gatcttttaa    720

aaaaaaaggt acagtgtact tatacattat ataaatgaat gattctttaa aaaattaatt    780

atgggaaata cttatgaaga atagggtagc tttggctgtt ttggaaacgt tatataacaa    840

ggtagaacta aaatgtatgc cagtaatccc agaggaatca ttagccagtc agggctagtc    900

tgagcaatgt ggcaagataa acccatctct ttaaaaaaaa aaaaaagtat tataaataga    960

aatgttatag gaaacaggaa atagaaaccc tcgaaaggct gaatgaaaga gtattagtgg   1020

gctggagaga tggttcagcg gttaagagca ctatctcctg agttcagttc ccagtgacca   1080

catggtggct cacagccatc tgtaatgaga tctgacgccc tcttctgggg tgtctgaaga   1140

cagcgacagt gtactcacat aaaataaata cataaagact gttagttagc cttcatctac   1200

catttacaga actgggcaca gaaaggagtt catcagttat aaagggtaac tttccatatg   1260

aatgtttgtc atattattat gcatatagta taatgaccaa actactgtaa tgtcttaata   1320
```

-continued

```
tttgtatctc ttttctcttt tttaaaaata tcagtttggt ggggaaccat tgtcatacac   1380

ccggtttagc cttgctcggc aagtagatgg agataacagt catgtggaga tgaaactggc   1440

tgcagatgaa gaagaaaatg ccgacaataa catgaaggct agtgtcagaa aacccaagag   1500

gtttaatgga agactctgct ttgcagctat tgcactagtc attttcttct tgattggtaa   1560

gaatgagtgg ccattcagaa ggatttctta tgactaacta gttcttagac tagctagttc   1620

ttagactagc tagttcttgt ttcttttgga tgaggagatg ctttgtactt taaatggcac   1680

tggggctccc tacctgccgg cagattaggt cctgcaagat gggaaacgtt tacattatgg   1740

atgttttatt agagatatgc aggacatttg gaatagtact aagaaaggct tccagtaaga   1800

caaggtgtgc acccatgtct taaacaggtc actgtaaaat atgacttagt tgtggtaatt   1860

taaattccat taaactcagg ttcataattt tctattagat tctcatagtt taattaaaag   1920

ttttcaggga taagttaaaa atgagttctg tgagtttagc tctaaaactt cctgtttttta   1980

ggattcatga gtggctacct gggctattgt aagcgtgtag aacaaaaaga ggagtgtgtg   2040

aaactggctg aaacggagga gacagacaag tcagaaacca tggaaacaga ggatgttcct   2100

acatcatctc gcttatattg ggcagacctc aaaacactgt tgtcagagaa gttgaactcc   2160

atagagtttg ctgacaccat caagtaagct caacttccca agttcagtcc tgatggaaac   2220

gtttttgttg ggggggtagg gagacttgaa aggctttcag agggtcctcc tgacaatgtg   2280

gaactatgct gacaggaaat taggacttac ctggagagcc tcatagcctc ctttttcttc   2340

agaatcgttt tatcagttgt agtttagtgt gggatgtcag attttcttct gttctaatat   2400

tcctttttaaa aattttttaa aattaaaatt actttttatg tattatgagt atagcctgca   2460

tatatgaatg aatgtgcatt actaattaca cttatctcct agtgcctaca taagccttat   2520

agatggttgt gagccagcat gtgggtgctg gaatccaaaa tggttcttgc aagaccaaat   2580

atgttacatc ccagagccat taca                                         2604
```

<210> SEQ ID NO 48
<211> LENGTH: 113
<212> TYPE: PRT
<213> ORGANISM: Artificial Sequence
<220> FEATURE:
<223> OTHER INFORMATION: Amino acid sequence of the variable region of the light chain of mouse anti-hTfR antibody No.3

<400> SEQUENCE: 48

```
Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Ser
                85                  90                  95

Thr His Val Pro Trp Thr Phe Gly Gly Gly Thr Lys Leu Glu Ile Lys
            100                 105                 110

Arg
```

<210> SEQ ID NO 49
<211> LENGTH: 118
<212> TYPE: PRT
<213> ORGANISM: Artificial Sequence
<220> FEATURE:
<223> OTHER INFORMATION: Amino acid sequence of the variable region of the heavy chain of mouse anti-hTfR antibody No.3

<400> SEQUENCE: 49

```
Glu Val Gln Leu Gln Glu Ser Gly Ala Glu Leu Val Arg Pro Gly Thr
1               5                   10                  15

Ser Val Lys Ile Ser Cys Lys Ala Ser Gly Tyr Ser Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Asp Tyr Pro Thr Tyr Ser Glu Lys Phe
    50                  55                  60

Lys Val Lys Ala Ile Leu Thr Ala Asp Thr Ser Ser Ser Ser Val Tyr
65                  70                  75                  80

Leu His Leu Ser Ser Leu Thr Ser Glu Asp Ser Ala Val Tyr Phe Cys
                85                  90                  95

Ala Arg Ser Gly Asn Tyr Asp Glu Val Ala Tyr Trp Gly Gln Gly Thr
            100                 105                 110

Leu Val Thr Val Ser Thr
        115
```

<210> SEQ ID NO 50
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 50

```
cac tct gac cct gcc cgc cga ggg gag ctg agc gtg tgt gac agt att      48
His Ser Asp Pro Ala Arg Arg Gly Glu Leu Ser Val Cys Asp Ser Ile
1               5                   10                  15

agt gag tgg gta acg gcg gca gac aaa aag act gca gtg gac atg tcg      96
Ser Glu Trp Val Thr Ala Ala Asp Lys Lys Thr Ala Val Asp Met Ser
            20                  25                  30

ggc ggg acg gtc aca gtc ctt gaa aag gtc cct gta tca aaa ggc caa     144
Gly Gly Thr Val Thr Val Leu Glu Lys Val Pro Val Ser Lys Gly Gln
        35                  40                  45

ctg aag caa tac ttc tac gag acc aag tgc aat ccc atg ggt tac aca     192
Leu Lys Gln Tyr Phe Tyr Glu Thr Lys Cys Asn Pro Met Gly Tyr Thr
    50                  55                  60

aaa gaa ggc tgc agg ggc ata gac aaa agg cat tgg aac tcc cag tgc     240
Lys Glu Gly Cys Arg Gly Ile Asp Lys Arg His Trp Asn Ser Gln Cys
65                  70                  75                  80

cga act acc cag tcg tac gtg cgg gcc ctt acc atg gat agc aaa aag     288
Arg Thr Thr Gln Ser Tyr Val Arg Ala Leu Thr Met Asp Ser Lys Lys
                85                  90                  95

aga att ggc tgg cga ttc ata agg ata gac act tct tgt gta tgt aca     336
Arg Ile Gly Trp Arg Phe Ile Arg Ile Asp Thr Ser Cys Val Cys Thr
            100                 105                 110

ttg acc att aaa agg gga aga                                         357
Leu Thr Ile Lys Arg Gly Arg
        115
```

```
<210> SEQ ID NO 51
<211> LENGTH: 119
<212> TYPE: PRT
<213> ORGANISM: Homo sapiens

<400> SEQUENCE: 51

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115


<210> SEQ ID NO 52
<211> LENGTH: 569
<212> TYPE: PRT
<213> ORGANISM: Artificial Sequence
<220> FEATURE:
<223> OTHER INFORMATION: Amino acid sequence of fusion protein of the
      heavy chain of humanized anti-hTfR antibody 3N and hBDNF (1)

<400> SEQUENCE: 52

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

-continued

```
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser His Ser Asp Pro Ala Arg Arg Gly Glu Leu Ser Val Cys Asp
    450                 455                 460

Ser Ile Ser Glu Trp Val Thr Ala Ala Asp Lys Lys Thr Ala Val Asp
465                 470                 475                 480

Met Ser Gly Gly Thr Val Thr Val Leu Glu Lys Val Pro Val Ser Lys
                485                 490                 495

Gly Gln Leu Lys Gln Tyr Phe Tyr Glu Thr Lys Cys Asn Pro Met Gly
            500                 505                 510

Tyr Thr Lys Glu Gly Cys Arg Gly Ile Asp Lys Arg His Trp Asn Ser
        515                 520                 525

Gln Cys Arg Thr Thr Gln Ser Tyr Val Arg Ala Leu Thr Met Asp Ser
    530                 535                 540

Lys Lys Arg Ile Gly Trp Arg Phe Ile Arg Ile Asp Thr Ser Cys Val
545                 550                 555                 560

Cys Thr Leu Thr Ile Lys Arg Gly Arg
                565


<210> SEQ ID NO 53
<211> LENGTH: 1790
<212> TYPE: DNA
<213> ORGANISM: Artificial Sequence
<220> FEATURE:
<223> OTHER INFORMATION: Nucleotide seuquence encoding the amino acid
      sequence of fusion protein of the heavy chain of humanized
```

anti-hTfR antibody 3N and hBDNF (1), synthetic sequence

<400> SEQUENCE: 53

```
acgcgtgccg ccaccatggg ctggagctgg attctgctgt tcctcctgag cgtgacagca     60
ggagtgcaca gcgaggtgca actagtgcag tctggagcag aggtgaaaaa gcccggggag    120
tctctgaaga tttcctgtaa gggttctgga tacagcttta tgaactactg gctgggatgg    180
gtgcgccaga tgcccgggaa aggcctggag tggatggggg acatctaccc cggcggagac    240
taccctacat acagcgagaa gttcaaggtc caggtcacca tctcagccga caagtccatc    300
agcaccgcct acctgcagtt gagcagcctg aaggcctcgg acaccgccat gtattactgt    360
gcgagatcag gcaattacga cgaagtggcc tactggggcc aaggaaccct ggtcaccgtc    420
tcctcagcta gcaccaaggg cccatcggtc ttccccctgg caccctcctc caagagcacc    480
tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacacg tgcccaccgt gcccagcacc tgaactcctg    780
ggaggtccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaaggat ctcactctga ccctgcccgc   1440
cgaggggagc tgagcgtgtg tgacagtatt agtgagtggg taacggcggc agacaaaaag   1500
actgcagtgg acatgtcggg cgggacggtc acagtccttg aaaaggtccc tgtatcaaaa   1560
ggccaactga agcaatactt ctacgagacc aagtgcaatc ccatgggtta cacaaaagaa   1620
ggctgcaggg gcatagacaa aaggcattgg aactcccagt gccgaactac ccagtcgtac   1680
gtgcgggccc ttaccatgga tagcaaaaag agaattggct ggcgattcat aaggatagac   1740
acttcttgtg tatgtacatt gaccattaaa aggggaagat aagcggccgc              1790
```

<210> SEQ ID NO 54
<211> LENGTH: 594
<212> TYPE: PRT
<213> ORGANISM: Artificial Sequence
<220> FEATURE:
<223> OTHER INFORMATION: Amino acid sequence of fusion protein of the heavy chain of humanized anti-hTfR antibody 3N and hBDNF (2)

<400> SEQUENCE: 54

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
```

```
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser His Ser Asp Pro Ala
465                 470                 475                 480

Arg Arg Gly Glu Leu Ser Val Cys Asp Ser Ile Ser Glu Trp Val Thr
                485                 490                 495

Ala Ala Asp Lys Lys Thr Ala Val Asp Met Ser Gly Gly Thr Val Thr
            500                 505                 510

Val Leu Glu Lys Val Pro Val Ser Lys Gly Gln Leu Lys Gln Tyr Phe
        515                 520                 525

Tyr Glu Thr Lys Cys Asn Pro Met Gly Tyr Thr Lys Glu Gly Cys Arg
    530                 535                 540

Gly Ile Asp Lys Arg His Trp Asn Ser Gln Cys Arg Thr Thr Gln Ser
545                 550                 555                 560

Tyr Val Arg Ala Leu Thr Met Asp Ser Lys Lys Arg Ile Gly Trp Arg
                565                 570                 575

Phe Ile Arg Ile Asp Thr Ser Cys Val Cys Thr Leu Thr Ile Lys Arg
            580                 585                 590

Gly Arg


<210> SEQ ID NO 55
<211> LENGTH: 1865
<212> TYPE: DNA
<213> ORGANISM: Artificial Sequence
<220> FEATURE:
<223> OTHER INFORMATION: Nucleotide seuquence encoding the amino acid
      sequence of fusion protein of the heavy chain of humanized
      anti-hTfR antibody 3N and hBDNF (2), synthetic sequence

<400> SEQUENCE: 55

acgcgtgccg ccaccatggg ctggagctgg attctgctgt tcctcctgag cgtgacagca     60

ggagtgcaca gcgaggtgca actagtgcag tctggagcag aggtgaaaaa gcccggggag    120

tctctgaaga tttcctgtaa gggttctgga tacagcttta tgaactactg gctgggatgg    180

gtgcgccaga tgcccgggaa aggcctggag tggatggggg acatctaccc cggcggagac    240

taccctacat acagcgagaa gttcaaggtc caggtcacca tctcagccga caagtccatc    300

agcaccgcct acctgcagtt gagcagcctg aaggcctcgg acaccgccat gtattactgt    360

gcgagatcag gcaattacga cgaagtggcc tactggggcc aaggaaccct ggtcaccgtc    420

tcctcagcta gcaccaaggg cccatcggtc ttccccctgg caccctcctc caagagcacc    480

tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgaccgtgc cctccagcag cttgggcacc    660

cagacctaca tctgcaacgt gaatcacaag cccagcaaca ccaaggtgga caagaaagtt    720

gagcccaaat cttgtgacaa aactcacacg tgcccaccgt gcccagcacc tgaactcctg    780

ggaggtccgt cagtcttcct cttcccccca aaacccaagg acaccctcat gatctcccgg    840

acccctgagg tcacatgcgt ggtggtggac gtgagccacg aagaccctga ggtcaagttc    900

aactggtacg tggacggcgt ggaggtgcat aatgccaaga caaagccgcg ggaggagcag    960

tacaacagca cgtaccgggt ggtcagcgtc ctcaccgtcc tgcaccagga ctggctgaat   1020

ggcaaggagt acaagtgcaa ggtctccaac aaagccctcc cagcccccat cgagaaaacc   1080

atctccaaag ccaaagggca gccccgagaa ccacaggtgt acaccctgcc cccatcccgg   1140
```

```
gatgagctga ccaagaacca ggtcagcctg acctgcctgg tcaaaggctt ctatcccagc   1200

gacatcgccg tggagtggga gagcaatggg cagccggaga acaactacaa gaccacgcct   1260

cccgtgctgg actccgacgg ctccttcttc ctctacagca agctcaccgt ggacaagagc   1320

aggtggcagc aggggaacgt cttctcatgc tccgtgatgc atgaggctct gcacaaccac   1380

tacacgcaga agagcctctc cctgtctccg ggtaaaggat ctggtggcgg agggtctgga   1440

ggtggcggat caggcggagg aggttccggg ggcggtggaa gcggaggcgg tggaagccac   1500

tctgaccctg cccgccgagg ggagctgagc gtgtgtgaca gtattagtga gtgggtaacg   1560

gcggcagaca aaaagactgc agtggacatg tcgggcggga cggtcacagt ccttgaaaag   1620

gtccctgtat caaaaggcca actgaagcaa tacttctacg agaccaagtg caatcccatg   1680

ggttacacaa aagaaggctg caggggcata gacaaaaggc attggaactc ccagtgccga   1740

actacccagt cgtacgtgcg ggcccttacc atggatagca aaaagagaat tggctggcga   1800

ttcataagga tagacacttc ttgtgtatgt acattgacca ttaaaagggg aagataagcg   1860

gccgc                                                               1865
```

<210> SEQ ID NO 56
<211> LENGTH: 229
<212> TYPE: PRT
<213> ORGANISM: Homo sapiens

<400> SEQUENCE: 56

```
Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg
225
```

<210> SEQ ID NO 57
<211> LENGTH: 245
<212> TYPE: PRT
<213> ORGANISM: Artificial Sequence
<220> FEATURE:
<223> OTHER INFORMATION: Amino acid sequence of single-chain humanized anti-hTfR antibody No. 3N

<400> SEQUENCE: 57

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Thr Pro Leu Ser Leu
    130                 135                 140

Ser Val Thr Pro Gly Gln Pro Ala Ser Ile Ser Cys Arg Ser Ser Gln
145                 150                 155                 160

Ser Leu Val His Ser Asn Gly Asn Thr Tyr Leu His Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Ser Gln Ser Thr His Val Pro Trp Thr Phe Gly Gln Gly Thr
225                 230                 235                 240

Lys Val Glu Ile Lys
                245
```

<210> SEQ ID NO 58
<211> LENGTH: 1583
<212> TYPE: DNA
<213> ORGANISM: Artificial Sequence
<220> FEATURE:
<223> OTHER INFORMATION: Nucleotide seuquence encoding the amino acid sequence of the fusion protein of the single-chain humanized anti-hTfR antibody 3N and pro-hBDNF, synthetic sequence

<400> SEQUENCE: 58

```
acgcgtgccg ccaccatgac catccttttc cttactatgg ttatttcata ctttggttgc      60

atgaaggctg cccccatgaa agaagcaaac atccgaggac aaggtggctt ggcctaccca     120

ggtgtgcgga cccatgggac tctggagagc gtgaatgggc ccaaggcagg ttcaagaggc     180

ttgacatcat tggctgacac tttcgaacac gtgatagaag agctgttgga tgaggaccag     240
```

```
aaagttcggc ccaatgaaga aaacaataag gacgcagact tgtacacgtc cagggtgatg    300

ctcagtagtc aagtgccttt ggagcctcct cttctctttc tgctggagga atacaaaaat    360

tacctagatg ctgcaaacat gtccatgagg gtccggcgcc actctgaccc tgcccgccga    420

ggggagctga gcgtgtgtga cagtattagt gagtgggtaa cggcggcaga caaaaagact    480

gcagtggaca tgtcgggcgg gacggtcaca gtccttgaaa aggtccctgt atcaaaaggc    540

caactgaagc aatacttcta cgagaccaag tgcaatccca tgggttacac aaaagaaggc    600

tgcaggggca tagacaaaag gcattggaac tcccagtgcc gaactaccca gtcgtacgtg    660

cgggccctta ccatggatag caagaagaga attggctggc gattcataag gatagacact    720

tcttgtgtat gtacattgac cattaaaagg ggaagaggat ctggtggcgg agggtctgga    780

ggtggcggat caggcggagg aggttccggg ggcggtggaa gcggaggcgg tggaagtgag    840

gtgcaactag tgcagtctgg agcagaggtg aaaaagcccg ggagtctct gaagatttcc     900

tgtaagggtt ctggatacag ctttatgaac tactggctgg gatgggtgcg ccagatgccc    960

gggaaaggcc tggagtggat gggggacatc taccccggcg gagactaccc tacatacagc   1020

gagaagttca aggtccaggt caccatctca gccgacaagt ccatcagcac cgcctacctg   1080

cagttgagca gcctgaaggc ctcggacacc gccatgtatt actgtgcgag atcaggcaat   1140

tacgacgaag tggcctactg gggccaagga accctggtca ccgtctcctc aggcggtggt   1200

ggaagtggag gcggtgggtc gggaggaggt ggcagcgaca tcgtgatgac ccagactccc   1260

ctgagcctga gcgtgacacc tggccagcct gccagcatca gctgcagaag ctctcagagc   1320

ctggtgcaca gcaacggcaa cacctacctg cactggtatc tgcagaagcc cggccagagc   1380

cctcagctgc tgatctacaa ggtgtccaac agattcagcg gcgtgcccga cagattctcc   1440

ggcagcggct ctggcaccga cttcaccctg aagatttcca gagtggaagc cgaggacgtg   1500

ggcgtgtact actgcagcca gagcacccac gtgccctgga cattcggcca gggcaccaag   1560

gtggaaatca agtaagcggc cgc                                           1583
```

<210> SEQ ID NO 59
<211> LENGTH: 501
<212> TYPE: PRT
<213> ORGANISM: Artificial Sequence
<220> FEATURE:
<223> OTHER INFORMATION: Amino acid sequence of the fusion protein of the single-chain humanized anti-hTfR antibody 3N and pro-hBDNF

<400> SEQUENCE: 59

```
Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110
```

```
Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg Gly Ser Gly Gly Gly Gly Ser Gly Gly Gly Gly
225                 230                 235                 240

Ser Gly Gly Gly Gly Ser Gly Gly Gly Gly Ser Gly Gly Gly Gly Ser
                245                 250                 255

Glu Val Gln Leu Val Gln Ser Gly Ala Glu Val Lys Lys Pro Gly Glu
            260                 265                 270

Ser Leu Lys Ile Ser Cys Lys Gly Ser Gly Tyr Ser Phe Met Asn Tyr
        275                 280                 285

Trp Leu Gly Trp Val Arg Gln Met Pro Gly Lys Gly Leu Glu Trp Met
    290                 295                 300

Gly Asp Ile Tyr Pro Gly Gly Asp Tyr Pro Thr Tyr Ser Glu Lys Phe
305                 310                 315                 320

Lys Val Gln Val Thr Ile Ser Ala Asp Lys Ser Ile Ser Thr Ala Tyr
                325                 330                 335

Leu Gln Leu Ser Ser Leu Lys Ala Ser Asp Thr Ala Met Tyr Tyr Cys
            340                 345                 350

Ala Arg Ser Gly Asn Tyr Asp Glu Val Ala Tyr Trp Gly Gln Gly Thr
        355                 360                 365

Leu Val Thr Val Ser Ser Gly Gly Gly Gly Ser Gly Gly Gly Gly Ser
    370                 375                 380

Gly Gly Gly Gly Ser Asp Ile Val Met Thr Gln Thr Pro Leu Ser Leu
385                 390                 395                 400

Ser Val Thr Pro Gly Gln Pro Ala Ser Ile Ser Cys Arg Ser Ser Gln
                405                 410                 415

Ser Leu Val His Ser Asn Gly Asn Thr Tyr Leu His Trp Tyr Leu Gln
            420                 425                 430

Lys Pro Gly Gln Ser Pro Gln Leu Leu Ile Tyr Lys Val Ser Asn Arg
        435                 440                 445

Phe Ser Gly Val Pro Asp Arg Phe Ser Gly Ser Gly Ser Gly Thr Asp
    450                 455                 460

Phe Thr Leu Lys Ile Ser Arg Val Glu Ala Glu Asp Val Gly Val Tyr
465                 470                 475                 480

Tyr Cys Ser Gln Ser Thr His Val Pro Trp Thr Phe Gly Gln Gly Thr
                485                 490                 495

Lys Val Glu Ile Lys
            500
```

<210> SEQ ID NO 60
<211> LENGTH: 391
<212> TYPE: PRT

```
<213> ORGANISM: Artificial Sequence
<220> FEATURE:
<223> OTHER INFORMATION: Amino acid sequence of the fusion protein of
      the single-chain humanized anti-hTfR antibody 3N and hBDNF

<400> SEQUENCE: 60

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Glu Val Gln Leu Val Gln Ser Gly Ala Glu Val Lys Lys Pro
145                 150                 155                 160

Gly Glu Ser Leu Lys Ile Ser Cys Lys Gly Ser Gly Tyr Ser Phe Met
                165                 170                 175

Asn Tyr Trp Leu Gly Trp Val Arg Gln Met Pro Gly Lys Gly Leu Glu
            180                 185                 190

Trp Met Gly Asp Ile Tyr Pro Gly Gly Asp Tyr Pro Thr Tyr Ser Glu
        195                 200                 205

Lys Phe Lys Val Gln Val Thr Ile Ser Ala Asp Lys Ser Ile Ser Thr
    210                 215                 220

Ala Tyr Leu Gln Leu Ser Ser Leu Lys Ala Ser Asp Thr Ala Met Tyr
225                 230                 235                 240

Tyr Cys Ala Arg Ser Gly Asn Tyr Asp Glu Val Ala Tyr Trp Gly Gln
                245                 250                 255

Gly Thr Leu Val Thr Val Ser Ser Gly Gly Gly Gly Ser Gly Gly Gly
            260                 265                 270

Gly Ser Gly Gly Gly Gly Ser Asp Ile Val Met Thr Gln Thr Pro Leu
        275                 280                 285

Ser Leu Ser Val Thr Pro Gly Gln Pro Ala Ser Ile Ser Cys Arg Ser
    290                 295                 300

Ser Gln Ser Leu Val His Ser Asn Gly Asn Thr Tyr Leu His Trp Tyr
305                 310                 315                 320

Leu Gln Lys Pro Gly Gln Ser Pro Gln Leu Leu Ile Tyr Lys Val Ser
                325                 330                 335

Asn Arg Phe Ser Gly Val Pro Asp Arg Phe Ser Gly Ser Gly Ser Gly
            340                 345                 350

Thr Asp Phe Thr Leu Lys Ile Ser Arg Val Glu Ala Glu Asp Val Gly
        355                 360                 365

Val Tyr Tyr Cys Ser Gln Ser Thr His Val Pro Trp Thr Phe Gly Gln
    370                 375                 380
```

Gly Thr Lys Val Glu Ile Lys
385 390

<210> SEQ ID NO 61
<211> LENGTH: 226
<212> TYPE: PRT
<213> ORGANISM: Artificial Sequence
<220> FEATURE:
<223> OTHER INFORMATION: Amino acid sequence of the Fab heavy chain of humanized anti-hTfR antibody No. 3N

<400> SEQUENCE: 61

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Met Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Leu Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr
225

<210> SEQ ID NO 62
<211> LENGTH: 1524
<212> TYPE: DNA
<213> ORGANISM: Artificial Sequence
<220> FEATURE:
<223> OTHER INFORMATION: Nucleotide seuquence encoding the amino acid sequence of the fusion protein of the Fab heavy chain of humanized anti-hTfR antibody 3N and pro-hBDNF, synthetic sequence

<400> SEQUENCE: 62
acgcgtcgcc accatgggtt ggagcctcat cttgctcttc cttgtcgctg ttgctacgcg 60
agtcggcagc gcccccatga aagaagcaaa catccgagga caaggtggct tggcctaccc 120
aggtgtgcgg acccatggga ctctggagag cgtgaatggg cccaaggcag gttcaagagg 180
cttgacatca ttggctgaca ctttcgaaca cgtgatagaa gagctgttgg atgaggacca 240

-continued

```
gaaagttcgg cccaatgaag aaaacaataa ggacgcagac ttgtacacgt ccagggtgat    300

gctcagtagt caagtgcctt tggagcctcc tcttctcttt ctgctggagg aatacaaaaa    360

ttacctagat gctgcaaaca tgtccatgag ggtccggcgc cactctgacc ctgcccgccg    420

aggggagctg agcgtgtgtg acagtattag tgagtgggta acggcggcag acaaaaagac    480

tgcagtggac atgtcgggcg ggacggtcac agtccttgaa aaggtccctg tatcaaaagg    540

ccaactgaag caatacttct acgagaccaa gtgcaatccc atgggttaca caaaagaagg    600

ctgcaggggc atagacaaaa ggcattggaa ctcccagtgc cgaactaccc agtcgtacgt    660

gcgggccctt accatggata gcaagaagag aattggctgg cgattcataa ggatagacac    720

ttcttgtgta tgtacattga ccattaaaag gggaagaggt ggcggagggt ctggaggtgg    780

cggatcaggc ggaggaggtt ccgggggcgg tggaagcgga ggcggtggat ccgaggtgca    840

actagtgcag tctggagcag aggtgaaaaa gcccggggag tctctgaaga tttcctgtaa    900

gggttctgga tacagcttta tgaactactg gctgggatgg gtgcgccaga tgcccgggaa    960

aggcctggag tggatggggg acatctaccc cggcggagac taccctacat acagcgagaa   1020

gttcaaggtc caggtcacca tctcagccga caagtccatc agcaccgcct acctgcagtt   1080

gagcagcctg aaggcctcgg acaccgccat gtattactgt gcgagatcag gcaattacga   1140

cgaagtggcc tactggggcc aaggaaccct ggtcaccgtc tcctcagcta gcaccaaggg   1200

cccatcggtc ttccccctgg caccctcctc caagagcacc tctgggggca cagcggccct   1260

gggctgcctg gtcaaggact acttccccga accggtgacg gtgtcgtgga actcaggcgc   1320

cctgaccagc ggcgtgcaca ccttcccggc tgtcctacag tcctcaggac tctactccct   1380

cagcagcgtg gtgaccgtgc cctccagcag cttgggcacc cagacctaca tctgcaacgt   1440

gaatcacaag cccagcaaca ccaaggtgga caagaaagtt gagccgaaga gctgtgataa   1500

gacgcatacg taataagcgg ccgc                                          1524
```

<210> SEQ ID NO 63
<211> LENGTH: 480
<212> TYPE: PRT
<213> ORGANISM: Artificial Sequence
<220> FEATURE:
<223> OTHER INFORMATION: Amino acid sequence of the fusion protein of the Fab heavy chain of humanized anti-hTfR antibody 3N and pro-hBDNF

<400> SEQUENCE: 63

```
Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125
```

```
Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg Gly Gly Gly Gly Ser Gly Gly Gly Gly Ser Gly
225                 230                 235                 240

Gly Gly Gly Ser Gly Gly Gly Gly Ser Gly Gly Gly Gly Ser Glu Val
                245                 250                 255

Gln Leu Val Gln Ser Gly Ala Glu Val Lys Lys Pro Gly Glu Ser Leu
            260                 265                 270

Lys Ile Ser Cys Lys Gly Ser Gly Tyr Ser Phe Met Asn Tyr Trp Leu
        275                 280                 285

Gly Trp Val Arg Gln Met Pro Gly Lys Gly Leu Glu Trp Met Gly Asp
    290                 295                 300

Ile Tyr Pro Gly Gly Asp Tyr Pro Thr Tyr Ser Glu Lys Phe Lys Val
305                 310                 315                 320

Gln Val Thr Ile Ser Ala Asp Lys Ser Ile Ser Thr Ala Tyr Leu Gln
                325                 330                 335

Leu Ser Ser Leu Lys Ala Ser Asp Thr Ala Met Tyr Tyr Cys Ala Arg
            340                 345                 350

Ser Gly Asn Tyr Asp Glu Val Ala Tyr Trp Gly Gln Gly Thr Leu Val
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Lys Val Glu Pro Lys Ser Cys Asp Lys Thr His Thr
465                 470                 475                 480
```

<210> SEQ ID NO 64
<211> LENGTH: 1196
<212> TYPE: DNA
<213> ORGANISM: Artificial Sequence
<220> FEATURE:
<223> OTHER INFORMATION: Nucleotide seuquence encoding the amino acid sequence of the fusion protein of the Fab heavy chain of humanized anti-hTfR antibody 3N and hBDNF, synthetic sequence

<400> SEQUENCE: 64

```
acgcgtgccg ccaccatgac catccttttc cttactatgg ttatttcata ctttggttgc     60

atgaaggctc actctgaccc tgcccgccga ggggagctga gcgtgtgtga cagtattagt    120

gagtgggtaa cggcggcaga caaaaagact gcagtggaca tgtcgggcgg gacggtcaca    180

gtccttgaaa aggtccctgt atcaaaaggc caactgaagc aatacttcta cgagaccaag    240

tgcaatccca tgggttacac aaaagaaggc tgcaggggca tagacaaaag gcattggaac    300

tcccagtgcc gaactaccca gtcgtacgtg cgggccctta ccatggatag caaaaagaga    360

attggctggc gattcataag gatagacact tcttgtgtat gtacattgac cattaaaagg    420

ggaagaggat ctggtggcgg agggtctgga ggtggcggat caggcggagg aggttccggg    480

ggcggtggaa gcggaggcgg tggaagtgag gtgcaactag tgcagtctgg agcagaggtg    540

aaaaagcccg ggagtctct gaagatttcc tgtaagggtt ctggatacag ctttatgaac    600

tactggctgg gatgggtgcg ccagatgccc gggaaaggcc tggagtggat gggggacatc    660

taccccggcg gagactaccc tacatacagc gagaagttca aggtccaggt caccatctca    720

gccgacaagt ccatcagcac cgcctacctg cagttgagca gcctgaaggc ctcggacacc    780

gccatgtatt actgtgcgag atcaggcaat tacgacgaag tggcctactg gggccaagga    840

accctggtca ccgtctcctc agctagcacc aagggcccat cggtcttccc cctggcaccc    900

tcctccaaga gcacctctgg gggcacagcg gccctgggct gcctggtcaa ggactacttc    960

cccgaaccgg tgacggtgtc gtggaactca ggcgccctga ccagcggcgt gcacaccttc   1020

ccggctgtcc tacagtcctc aggactctac tccctcagca gcgtggtgac cgtgccctcc   1080

agcagcttgg gcacccagac ctacatctgc aacgtgaatc acaagcccag caacaccaag   1140

gtggacaaga aagttgagcc caaatcttgt gacaaaactc acacgtaagc ggccgc       1196
```

```
<210> SEQ ID NO 65
<211> LENGTH: 370
<212> TYPE: PRT
<213> ORGANISM: Artificial Sequence
<220> FEATURE:
<223> OTHER INFORMATION: Amino acid sequence of the fusion protein of
      the Fab heavy chain of humanized anti-hTfR antibody 3N and hBDNF

<400> SEQUENCE: 65

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Glu Val Gln Leu Val Gln Ser Gly Ala Glu Val Lys Lys Pro Gly Glu
```

-continued

```
145                 150                 155                 160

Ser Leu Lys Ile Ser Cys Lys Gly Ser Gly Tyr Ser Phe Met Asn Tyr
                165                 170                 175

Trp Leu Gly Trp Val Arg Gln Met Pro Gly Lys Gly Leu Glu Trp Met
            180                 185                 190

Gly Asp Ile Tyr Pro Gly Gly Asp Tyr Pro Thr Tyr Ser Glu Lys Phe
        195                 200                 205

Lys Val Gln Val Thr Ile Ser Ala Asp Lys Ser Ile Ser Thr Ala Tyr
    210                 215                 220

Leu Gln Leu Ser Ser Leu Lys Ala Ser Asp Thr Ala Met Tyr Tyr Cys
225                 230                 235                 240

Ala Arg Ser Gly Asn Tyr Asp Glu Val Ala Tyr Trp Gly Gln Gly Thr
                245                 250                 255

Leu Val Thr Val Ser Ser Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350

Asn Thr Lys Val Asp Lys Lys Val Glu Pro Lys Ser Cys Asp Lys Thr
        355                 360                 365

His Thr
    370


<210> SEQ ID NO 66
<211> LENGTH: 8
<212> TYPE: PRT
<213> ORGANISM: Artificial Sequence
<220> FEATURE:
<223> OTHER INFORMATION: Amino acid sequence 1 of CDR1 in the heavy
      chain of humanized anti-hTfR antibody No. 3N

<400> SEQUENCE: 66

Gly Tyr Ser Phe Met Asn Tyr Trp
1               5


<210> SEQ ID NO 67
<211> LENGTH: 10
<212> TYPE: PRT
<213> ORGANISM: Artificial Sequence
<220> FEATURE:
<223> OTHER INFORMATION: Amino acid sequence 2 of CDR1 in the heavy
      chain of humanized anti-hTfR antibody No. 3N

<400> SEQUENCE: 67

Gly Tyr Ser Phe Met Asn Tyr Trp Leu Gly
1               5                   10


<210> SEQ ID NO 68
<211> LENGTH: 30
<212> TYPE: PRT
<213> ORGANISM: Artificial Sequence
<220> FEATURE:
<223> OTHER INFORMATION: Amino acid sequence of framework region 3 in
```

the heavy chain of humanized anti-hTfR antibody No. 3N

<400> SEQUENCE: 68

Gln Val Thr Ile Ser Ala Asp Lys Ser Ile Ser Thr Ala Tyr Leu Gln
1 5 10 15

Leu Ser Ser Leu Lys Ala Ser Asp Thr Ala Met Tyr Tyr Cys
20 25 30

<210> SEQ ID NO 69
<211> LENGTH: 118
<212> TYPE: PRT
<213> ORGANISM: Artificial Sequence
<220> FEATURE:
<223> OTHER INFORMATION: Amino acid sequence of the variable region of the heavy chain of humanized anti-hTfR antibody No. 3N

<400> SEQUENCE: 69

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Met Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Leu Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser
115

<210> SEQ ID NO 70
<211> LENGTH: 448
<212> TYPE: PRT
<213> ORGANISM: Artificial Sequence
<220> FEATURE:
<223> OTHER INFORMATION: Amino acid sequence of the heavy chain of humanized anti-hTfR antibody No. 3N

<400> SEQUENCE: 70

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Met Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Leu Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 71
<211> LENGTH: 1427
<212> TYPE: DNA
<213> ORGANISM: Artificial Sequence
<220> FEATURE:
<223> OTHER INFORMATION: Nucleotide seuquence encoding the amino acid sequence of the heavy chain of humanized anti-hTfR antibody No. 3N, synthetic sequence

<400> SEQUENCE: 71

```
acgcgtgccg ccaccatggg ctggagctgg attctgctgt tcctcctgag cgtgacagca      60

ggagtgcaca gcgaggtgca actagtgcag tctggagcag aggtgaaaaa gcccggggag     120

tctctgaaga tttcctgtaa gggttctgga tacagcttta tgaactactg gctgggatgg     180
```

-continued

```
gtgcgccaga tgcccgggaa aggcctggag tggatggggg acatctaccc cggcggagac     240

taccctacat acagcgagaa gttcaaggtc caggtcacca tctcagccga caagtccatc     300

agcaccgcct acctgcagtt gagcagcctg aaggcctcgg acaccgccat gtattactgt     360

gcgagatcag gcaattacga cgaagtggcc tactggggcc aaggaaccct ggtcaccgtc     420

tcctcagcta gcaccaaggg cccatcggtc ttccccctgg caccctcctc caagagcacc     480

tctgggggca cagcggccct gggctgcctg gtcaaggact acttccccga accggtgacg     540

gtgtcgtgga actcaggcgc cctgaccagc ggcgtgcaca ccttcccggc tgtcctacag     600

tcctcaggac tctactccct cagcagcgtg gtgaccgtgc cctccagcag cttgggcacc     660

cagacctaca tctgcaacgt gaatcacaag cccagcaaca ccaaggtgga caagaaagtt     720

gagcccaaat cttgtgacaa aactcacacg tgcccaccgt gcccagcacc tgaactcctg     780

ggaggtccgt cagtcttcct cttcccccca aaacccaagg acaccctcat gatctcccgg     840

acccctgagg tcacatgcgt ggtggtggac gtgagccacg aagaccctga ggtcaagttc     900

aactggtacg tggacggcgt ggaggtgcat aatgccaaga caaagccgcg ggaggagcag     960

tacaacagca cgtaccgggt ggtcagcgtc ctcaccgtcc tgcaccagga ctggctgaat    1020

ggcaaggagt acaagtgcaa ggtctccaac aaagccctcc cagcccccat cgagaaaacc    1080

atctccaaag ccaaagggca gccccgagaa ccacaggtgt acaccctgcc cccatcccgg    1140

gatgagctga ccaagaacca ggtcagcctg acctgcctgg tcaaaggctt ctatcccagc    1200

gacatcgccg tggagtggga gagcaatggg cagccggaga acaactacaa gaccacgcct    1260

cccgtgctgg actccgacgg ctccttcttc ctctacagca agctcaccgt ggacaagagc    1320

aggtggcagc aggggaacgt cttctcatgc tccgtgatgc atgaggctct gcacaaccac    1380

tacacgcaga agagcctctc cctgtctccg ggtaaataag cggccgc                  1427
```

```
<210> SEQ ID NO 72
<211> LENGTH: 445
<212> TYPE: PRT
<213> ORGANISM: Artificial Sequence
<220> FEATURE:
<223> OTHER INFORMATION: Amino acid sequence of the heavy chain of
      humanized anti-hTfR antibody No. 3N (IgG4)

<400> SEQUENCE: 72

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140
```

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Lys Thr Tyr Thr Cys Asn Val Asp His Lys Pro Ser
195 200 205

Asn Thr Lys Val Asp Lys Arg Val Glu Ser Lys Tyr Gly Pro Pro Cys
210 215 220

Pro Pro Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Gln Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 73
<211> LENGTH: 2253
<212> TYPE: DNA
<213> ORGANISM: Artificial Sequence
<220> FEATURE:
<223> OTHER INFORMATION: Nucleotide seuquence encoding the amino acid sequence of the fusion protein of the Fab heavy chain of humanized anti-hTfR antibody 3N and pro-hBDNF, further introduced with Fc region of human IgG, synthetic sequence

<400> SEQUENCE: 73
acgcgtcgcc accatgggtt ggagcctcat cttgctcttc cttgtcgctg ttgctacgcg 60
agtcggcagc gcccccatga aagaagcaaa catccgagga caaggtggct tggcctaccc 120
aggtgtgcgg acccatggga ctctggagag cgtgaatggg cccaaggcag gttcaagagg 180
cttgacatca ttggctgaca ctttcgaaca cgtgatagaa gagctgttgg atgaggacca 240

-continued

```
gaaagttcgg cccaatgaag aaaacaataa ggacgcagac ttgtacacgt ccagggtgat    300
gctcagtagt caagtgcctt tggagcctcc tcttctcttt ctgctggagg aatacaaaaa    360
ttacctagat gctgcaaaca tgtccatgag ggtccggcgc cactctgacc ctgcccgccg    420
aggggagctg agcgtgtgtg acagtattag tgagtgggta acggcggcag acaaaaagac    480
tgcagtggac atgtcgggcg ggacggtcac agtccttgaa aaggtccctg tatcaaaagg    540
ccaactgaag caatacttct acgagaccaa gtgcaatccc atgggttaca caaaagaagg    600
ctgcaggggc atagacaaaa ggcattggaa ctcccagtgc cgaactaccc agtcgtacgt    660
gcgggccctt accatggata gcaagaagag aattggctgg cgattcataa ggatagacac    720
ttcttgtgta tgtacattga ccattaaaag gggaagaggc ggtggtggaa gtggaggcgg    780
tgggtcggga ggaggtggca gcggtggagg cggatcaggc ggtggtggca gtccagcacc    840
tgaactcctg ggaggtccgt cagtcttcct cttcccccca aaacccaagg acaccctcat    900
gatctcccgg acccctgagg tcacatgcgt ggtggtggac gtgagccacg aagaccctga    960
ggtcaagttc aactggtacg tggacggcgt ggaggtgcat aatgccaaga caaagccgcg   1020
ggaggagcag tacaacagca cgtaccgtgt ggtcagcgtc ctcaccgtcc tgcaccagga   1080
ctggctgaat ggcaaggagt acaagtgcaa ggtctccaac aaagccctcc cagcccccat   1140
cgagaaaacc atctccaaag ccaaagggca gccccgagaa ccacaggtgt acaccctgcc   1200
cccatcccgg gaggagatga ccaagaacca ggtcagcctg acctgcctgg tcaaaggctt   1260
ctatcccagc gacatcgccg tggagtggga gagcaatggg cagccggaga acaactacaa   1320
gaccacgcct cccgtgctgg actccgacgg ctccttcttc ctctacagca agctcaccgt   1380
ggacaagagc aggtggcagc aggggaacgt cttctcatgc tccgtgatgc acgaggctct   1440
gcacaaccac tacacgcaga agagcctctc cctgtctccg ggtaaaggtg gcggagggtc   1500
tggaggaggc ggtagcggcg gaggaggttc cgggggcggt ggaagcggag gcggtggatc   1560
cgaggtgcaa ctagtgcagt ctggagcaga ggtgaaaaag cccggggagt ctctgaagat   1620
ttcctgtaag ggttctggat acagctttat gaactactgg ctgggatggg tgcgccagat   1680
gcccgggaaa ggcctggagt ggatggggga catctacccc ggcggagact accctacata   1740
cagcgagaag ttcaaggtcc aggtcaccat ctcagccgac aagtccatca gcaccgccta   1800
cctgcagttg agcagcctga aggcctcgga caccgccatg tattactgtg cgagatcagg   1860
caattacgac gaagtggcct actggggcca aggaaccctg gtcaccgtct cctcagctag   1920
caccaagggc ccatcggtct tccccctggc accctcctcc aagagcacct ctgggggcac   1980
agcggccctg ggctgcctgg tcaaggacta cttccccgaa ccggtgacgg tgtcgtggaa   2040
ctcaggcgcc ctgaccagcg gcgtgcacac cttcccggct gtcctacagt cctcaggact   2100
ctactccctc agcagcgtgg tgaccgtgcc ctccagcagc ttgggcaccc agacctacat   2160
ctgcaacgtg aatcacaagc ccagcaacac caaggtggac aagaaagttg agccgaagag   2220
ctgtgataag acgcatacgt aataagcggc cgc                                2253
```

<210> SEQ ID NO 74
<211> LENGTH: 723
<212> TYPE: PRT
<213> ORGANISM: Artificial Sequence
<220> FEATURE:
<223> OTHER INFORMATION: Amino acid sequence of the fusion protein of the Fab heavy chain of humanized anti-hTfR antibody 3N and pro-hBDNF, further introduced with Fc region of human IgG

<400> SEQUENCE: 74

```
Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg Gly Gly Gly Gly Ser Gly Gly Gly Gly Ser Gly
225                 230                 235                 240

Gly Gly Gly Ser Gly Gly Gly Gly Ser Gly Gly Gly Gly Ser Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415
```

```
Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys Gly Gly Gly Gly Ser Gly Gly Gly
465                 470                 475                 480

Gly Ser Gly Gly Gly Gly Ser Gly Gly Gly Gly Ser Gly Gly Gly Gly
                485                 490                 495

Ser Glu Val Gln Leu Val Gln Ser Gly Ala Glu Val Lys Lys Pro Gly
            500                 505                 510

Glu Ser Leu Lys Ile Ser Cys Lys Gly Ser Gly Tyr Ser Phe Met Asn
        515                 520                 525

Tyr Trp Leu Gly Trp Val Arg Gln Met Pro Gly Lys Gly Leu Glu Trp
    530                 535                 540

Met Gly Asp Ile Tyr Pro Gly Gly Asp Tyr Pro Thr Tyr Ser Glu Lys
545                 550                 555                 560

Phe Lys Val Gln Val Thr Ile Ser Ala Asp Lys Ser Ile Ser Thr Ala
                565                 570                 575

Tyr Leu Gln Leu Ser Ser Leu Lys Ala Ser Asp Thr Ala Met Tyr Tyr
            580                 585                 590

Cys Ala Arg Ser Gly Asn Tyr Asp Glu Val Ala Tyr Trp Gly Gln Gly
        595                 600                 605

Thr Leu Val Thr Val Ser Ser Ala Ser Thr Lys Gly Pro Ser Val Phe
    610                 615                 620

Pro Leu Ala Pro Ser Ser Lys Ser Thr Ser Gly Gly Thr Ala Ala Leu
625                 630                 635                 640

Gly Cys Leu Val Lys Asp Tyr Phe Pro Glu Pro Val Thr Val Ser Trp
                645                 650                 655

Asn Ser Gly Ala Leu Thr Ser Gly Val His Thr Phe Pro Ala Val Leu
            660                 665                 670

Gln Ser Ser Gly Leu Tyr Ser Leu Ser Ser Val Val Thr Val Pro Ser
        675                 680                 685

Ser Ser Leu Gly Thr Gln Thr Tyr Ile Cys Asn Val Asn His Lys Pro
    690                 695                 700

Ser Asn Thr Lys Val Asp Lys Lys Val Glu Pro Lys Ser Cys Asp Lys
705                 710                 715                 720

Thr His Thr


<210> SEQ ID NO 75
<211> LENGTH: 218
<212> TYPE: PRT
<213> ORGANISM: Artificial Sequence
<220> FEATURE:
<223> OTHER INFORMATION: Amino acid sequence of an exemplified Fc region
      of human IgG

<400> SEQUENCE: 75

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45
```

-continued

```
Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

```
<210> SEQ ID NO 76
<211> LENGTH: 1418
<212> TYPE: DNA
<213> ORGANISM: Artificial Sequence
<220> FEATURE:
<223> OTHER INFORMATION: Nucleotide seuquence encoding the amino acid
      sequence of the heavy chain of humanized anti-hTfR antibody No. 3N
      (IgG4), synthetic sequence

<400> SEQUENCE: 76

acgcgtgccg ccaccatggg ctggagctgg attctgctgt tcctcctgag cgtgacagca     60

ggagtgcaca gcgaggtgca actagtgcag tctggagcag aggtgaaaaa gcccggggag    120

tctctgaaga tttcctgtaa gggttctgga tacagcttta tgaactactg gctgggatgg    180

gtgcgccaga tgcccgggaa aggcctggag tggatggggg acatctaccc cggcggagac    240

taccctacat acagcgagaa gttcaaggtc caggtcacca tctcagccga caagtccatc    300

agcaccgcct acctgcagtt gagcagcctg aaggcctcgg acaccgccat gtattactgt    360

gcgagatcag gcaattacga cgaagtggcc tactggggcc aaggaaccct ggtcaccgtc    420

tcctcagcta gcaccaaggg cccatcggtc ttccccctgg cgccctgctc caggagcacc    480

tccgagagca cagccgccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgaccgtgc cctccagcag cttgggcacg    660

aagacctaca cctgcaacgt agatcacaag cccagcaaca ccaaggtgga caagagagtt    720

gagtccaaat atggtccccc atgcccacca tgcccagcac ctgagttcct ggggggtcca    780

tcagtcttcc tgttcccccc aaaacccaag gacactctca tgatctcccg gacccctgag    840

gtcacgtgcg tggtggtgga cgtgagccag gaagaccccg aggtccagtt caactggtac    900

gtggatggcg tggaggtgca taatgccaag acaaagccgc gggaggagca gttcaacagc    960

acgtaccgtg tggtcagcgt cctcaccgtc ctgcaccagg actggctgaa cggcaaggag   1020
```

```
tacaagtgca aggtctccaa caaaggcctc ccgtcctcca tcgagaaaac catctccaaa   1080

gccaaagggc agccccgaga gccacaggtg tacaccctgc ccccatccca ggaggagatg   1140

accaagaacc aggtcagcct gacctgcctg gtcaaaggct tctaccccag cgacatcgcc   1200

gtggagtggg agagcaatgg gcagccggag aacaactaca agaccacgcc tcccgtgctg   1260

gactccgacg gctccttctt cctctacagc aggctcaccg tggacaagag caggtggcag   1320

gaggggaatg tcttctcatg ctccgtgatg catgaggctc tgcacaacca ctacacacag   1380

aagagcctct ccctgtctcc gggtaaataa gcggccgc                           1418
```

```
<210> SEQ ID NO 77
<211> LENGTH: 226
<212> TYPE: PRT
<213> ORGANISM: Artificial Sequence
<220> FEATURE:
<223> OTHER INFORMATION: Amino acid sequence of the Fab heavy chain of
      humanized anti-hTfR antibody No. 3

<400> SEQUENCE: 77

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225


<210> SEQ ID NO 78
<211> LENGTH: 1526
<212> TYPE: DNA
<213> ORGANISM: Artificial Sequence
<220> FEATURE:
<223> OTHER INFORMATION: Nucleotide seuquence encoding the amino acid
      sequence of the fusion protein of the Fab heavy chain of humanized
      anti-hTfR antibody 3 and pro-hBDNF, synthetic sequence
```

<400> SEQUENCE: 78
acgcgtgccg ccaccatgac catccttttc cttactatgg ttatttcata ctttggttgc 60
atgaaggctg cccccatgaa agaagcaaac atccgaggac aaggtggctt ggcctaccca 120
ggtgtgcgga cccatgggac tctggagagc gtgaatgggc ccaaggcagg ttcaagaggc 180
ttgacatcat tggctgacac tttcgaacac gtgatagaag agctgttgga tgaggaccag 240
aaagttcggc ccaatgaaga aaacaataag gacgcagact tgtacacgtc cagggtgatg 300
ctcagtagtc aagtgccttt ggagcctcct cttctctttc tgctggagga atacaaaaat 360
tacctagatg ctgcaaacat gtccatgagg gtccggcgcc actctgaccc tgcccgccga 420
ggggagctga gcgtgtgtga cagtattagt gagtgggtaa cggcggcaga caaaaagact 480
gcagtggaca tgtcgggcgg gacggtcaca gtccttgaaa aggtccctgt atcaaaaggc 540
caactgaagc aatacttcta cgagaccaag tgcaatccca tgggttacac aaaagaaggc 600
tgcaggggca tagacaaaag gcattggaac tcccagtgcc gaactaccca gtcgtacgtg 660
cgggccctta ccatggatag caagaagaga attggctggc gattcataag gatagacact 720
tcttgtgtat gtacattgac cattaaaagg ggaagaggat ctggtggcgg agggtctgga 780
ggtggcggat caggcggagg aggttccggg ggcggtggaa gcggaggcgg tggaagtgag 840
gtgcaactag tgcagtctgg agcagaggtg aaaaagcccg gggagtctct gaagatttcc 900
tgtaagggtt ctggatacag ctttaccaac tactggctgg gatgggtgcg ccagatgccc 960
gggaaaggcc tggagtggat gggggacatc taccccggcg gagactaccc tacatacagc 1020
gagaagttca aggtccaggt caccatctca gccgacaagt ccatcagcac cgcctacctg 1080
cagtggagca gcctgaaggc ctcggacacc gccatgtatt actgtgcgag atcaggcaat 1140
tacgacgaag tggcctactg gggccaagga accctggtca ccgtctcctc agctagcacc 1200
aagggcccat cggtcttccc cctggcaccc tcctccaaga gcacctctgg gggcacagcg 1260
gccctgggct gcctggtcaa ggactacttc cccgaaccgg tgacggtgtc gtggaactca 1320
ggcgccctga ccagcggcgt gcacaccttc ccggctgtcc tacagtcctc aggactctac 1380
tccctcagca gcgtggtgac cgtgccctcc agcagcttgg gcacccagac ctacatctgc 1440
aacgtgaatc acaagcccag caacaccaag gtggacaaga aagttgagcc caaatcttgt 1500
gacaaaactc acacgtaagc ggccgc 1526

<210> SEQ ID NO 79
<211> LENGTH: 482
<212> TYPE: PRT
<213> ORGANISM: Artificial Sequence
<220> FEATURE:
<223> OTHER INFORMATION: Amino acid sequence of the fusion protein of the Fab heavy chain of humanized anti-hTfR antibody 3 and pro-hBDNF

<400> SEQUENCE: 79

Ala Pro Met Lys Glu Ala Asn Ile Arg Gly Gln Gly Gly Leu Ala Tyr
1 5 10 15

Pro Gly Val Arg Thr His Gly Thr Leu Glu Ser Val Asn Gly Pro Lys
20 25 30

Ala Gly Ser Arg Gly Leu Thr Ser Leu Ala Asp Thr Phe Glu His Val
35 40 45

Ile Glu Glu Leu Leu Asp Glu Asp Gln Lys Val Arg Pro Asn Glu Glu
50 55 60

-continued

```
Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg Gly Ser Gly Gly Gly Gly Ser Gly Gly Gly Gly
225                 230                 235                 240

Ser Gly Gly Gly Gly Ser Gly Gly Gly Gly Ser Gly Gly Gly Gly Ser
                245                 250                 255

Glu Val Gln Leu Val Gln Ser Gly Ala Glu Val Lys Lys Pro Gly Glu
            260                 265                 270

Ser Leu Lys Ile Ser Cys Lys Gly Ser Gly Tyr Ser Phe Thr Asn Tyr
        275                 280                 285

Trp Leu Gly Trp Val Arg Gln Met Pro Gly Lys Gly Leu Glu Trp Met
    290                 295                 300

Gly Asp Ile Tyr Pro Gly Gly Asp Tyr Pro Thr Tyr Ser Glu Lys Phe
305                 310                 315                 320

Lys Val Gln Val Thr Ile Ser Ala Asp Lys Ser Ile Ser Thr Ala Tyr
                325                 330                 335

Leu Gln Trp Ser Ser Leu Lys Ala Ser Asp Thr Ala Met Tyr Tyr Cys
            340                 345                 350

Ala Arg Ser Gly Asn Tyr Asp Glu Val Ala Tyr Trp Gly Gln Gly Thr
        355                 360                 365

Leu Val Thr Val Ser Ser Ala Ser Thr Lys Gly Pro Ser Val Phe Pro
    370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
        435                 440                 445

Ser Leu Gly Thr Gln Thr Tyr Ile Cys Asn Val Asn His Lys Pro Ser
    450                 455                 460

Asn Thr Lys Val Asp Lys Lys Val Glu Pro Lys Ser Cys Asp Lys Thr
465                 470                 475                 480

His Thr
```

<210> SEQ ID NO 80
<211> LENGTH: 372
<212> TYPE: PRT
<213> ORGANISM: Artificial Sequence
<220> FEATURE:
<223> OTHER INFORMATION: Amino acid sequence of the fusion protein of the Fab heavy chain of humanized anti-hTfR antibody 3 and hBDNF

<400> SEQUENCE: 80

```
His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Glu Val Gln Leu Val Gln Ser Gly Ala Glu Val Lys Lys Pro
145                 150                 155                 160

Gly Glu Ser Leu Lys Ile Ser Cys Lys Gly Ser Gly Tyr Ser Phe Thr
                165                 170                 175

Asn Tyr Trp Leu Gly Trp Val Arg Gln Met Pro Gly Lys Gly Leu Glu
            180                 185                 190

Trp Met Gly Asp Ile Tyr Pro Gly Gly Asp Tyr Pro Thr Tyr Ser Glu
        195                 200                 205

Lys Phe Lys Val Gln Val Thr Ile Ser Ala Asp Lys Ser Ile Ser Thr
    210                 215                 220

Ala Tyr Leu Gln Trp Ser Ser Leu Lys Ala Ser Asp Thr Ala Met Tyr
225                 230                 235                 240

Tyr Cys Ala Arg Ser Gly Asn Tyr Asp Glu Val Ala Tyr Trp Gly Gln
                245                 250                 255

Gly Thr Leu Val Thr Val Ser Ser Ala Ser Thr Lys Gly Pro Ser Val
            260                 265                 270

Phe Pro Leu Ala Pro Ser Ser Lys Ser Thr Ser Gly Gly Thr Ala Ala
        275                 280                 285

Leu Gly Cys Leu Val Lys Asp Tyr Phe Pro Glu Pro Val Thr Val Ser
    290                 295                 300

Trp Asn Ser Gly Ala Leu Thr Ser Gly Val His Thr Phe Pro Ala Val
305                 310                 315                 320

Leu Gln Ser Ser Gly Leu Tyr Ser Leu Ser Ser Val Val Thr Val Pro
                325                 330                 335

Ser Ser Ser Leu Gly Thr Gln Thr Tyr Ile Cys Asn Val Asn His Lys
            340                 345                 350

Pro Ser Asn Thr Lys Val Asp Lys Lys Val Glu Pro Lys Ser Cys Asp
```

-continued 355 360 365

Lys Thr His Thr
370

<210> SEQ ID NO 81
<211> LENGTH: 469
<212> TYPE: PRT
<213> ORGANISM: Artificial Sequence
<220> FEATURE:
<223> OTHER INFORMATION: Amino acid sequence of the Fab heavy chain of humanized anti-hTfR antibody 3N, further introduced with Fc region of human IgG

<400> SEQUENCE: 81

Pro Ala Pro Glu Leu Leu Gly Gly Pro Ser Val Phe Leu Phe Pro Pro
1 5 10 15

Lys Pro Lys Asp Thr Leu Met Ile Ser Arg Thr Pro Glu Val Thr Cys
20 25 30

Val Val Val Asp Val Ser His Glu Asp Pro Glu Val Lys Phe Asn Trp
35 40 45

Tyr Val Asp Gly Val Glu Val His Asn Ala Lys Thr Lys Pro Arg Glu
50 55 60

Glu Gln Tyr Asn Ser Thr Tyr Arg Val Val Ser Val Leu Thr Val Leu
65 70 75 80

His Gln Asp Trp Leu Asn Gly Lys Glu Tyr Lys Cys Lys Val Ser Asn
85 90 95

Lys Ala Leu Pro Ala Pro Ile Glu Lys Thr Ile Ser Lys Ala Lys Gly
100 105 110

Gln Pro Arg Glu Pro Gln Val Tyr Thr Leu Pro Pro Ser Arg Glu Glu
115 120 125

Met Thr Lys Asn Gln Val Ser Leu Thr Cys Leu Val Lys Gly Phe Tyr
130 135 140

Pro Ser Asp Ile Ala Val Glu Trp Glu Ser Asn Gly Gln Pro Glu Asn
145 150 155 160

Asn Tyr Lys Thr Thr Pro Pro Val Leu Asp Ser Asp Gly Ser Phe Phe
165 170 175

Leu Tyr Ser Lys Leu Thr Val Asp Lys Ser Arg Trp Gln Gln Gly Asn
180 185 190

Val Phe Ser Cys Ser Val Met His Glu Ala Leu His Asn His Tyr Thr
195 200 205

Gln Lys Ser Leu Ser Leu Ser Pro Gly Lys Gly Gly Gly Gly Ser Gly
210 215 220

Gly Gly Gly Ser Gly Gly Gly Gly Ser Gly Gly Gly Gly Ser Gly Gly
225 230 235 240

Gly Gly Ser Glu Val Gln Leu Val Gln Ser Gly Ala Glu Val Lys Lys
245 250 255

Pro Gly Glu Ser Leu Lys Ile Ser Cys Lys Gly Ser Gly Tyr Ser Phe
260 265 270

Met Asn Tyr Trp Leu Gly Trp Val Arg Gln Met Pro Gly Lys Gly Leu
275 280 285

Glu Trp Met Gly Asp Ile Tyr Pro Gly Gly Asp Tyr Pro Thr Tyr Ser
290 295 300

Glu Lys Phe Lys Val Gln Val Thr Ile Ser Ala Asp Lys Ser Ile Ser
305 310 315 320

Thr Ala Tyr Leu Gln Leu Ser Ser Leu Lys Ala Ser Asp Thr Ala Met
325 330 335

```
Tyr Tyr Cys Ala Arg Ser Gly Asn Tyr Asp Glu Val Ala Tyr Trp Gly
            340                 345                 350

Gln Gly Thr Leu Val Thr Val Ser Ser Ala Ser Thr Lys Gly Pro Ser
        355                 360                 365

Val Phe Pro Leu Ala Pro Ser Ser Lys Ser Thr Ser Gly Gly Thr Ala
    370                 375                 380

Ala Leu Gly Cys Leu Val Lys Asp Tyr Phe Pro Glu Pro Val Thr Val
385                 390                 395                 400

Ser Trp Asn Ser Gly Ala Leu Thr Ser Gly Val His Thr Phe Pro Ala
                405                 410                 415

Val Leu Gln Ser Ser Gly Leu Tyr Ser Leu Ser Ser Val Val Thr Val
            420                 425                 430

Pro Ser Ser Ser Leu Gly Thr Gln Thr Tyr Ile Cys Asn Val Asn His
        435                 440                 445

Lys Pro Ser Asn Thr Lys Val Asp Lys Lys Val Glu Pro Lys Ser Cys
    450                 455                 460

Asp Lys Thr His Thr
465


<210> SEQ ID NO 82
<211> LENGTH: 1491
<212> TYPE: DNA
<213> ORGANISM: Artificial Sequence
<220> FEATURE:
<223> OTHER INFORMATION: Nucleotide seuquence encoding the amino acid
      sequence of the Fab heavy chain of humanized anti-hTfR antibody
      3N, further introduced with Fc region of human IgG

<400> SEQUENCE: 82

acgcgtcgcc accatgggtt ggagcctcat cttgctcttc cttgtcgctg ttgctacgcg     60

agtcggcagc ccagcacctg aactcctggg aggtccgtca gtcttcctct tcccccccaaa    120

acccaaggac accctcatga tctcccggac ccctgaggtc acatgcgtgg tggtggacgt    180

gagccacgaa gaccctgagg tcaagttcaa ctggtacgtg gacggcgtgg aggtgcataa    240

tgccaagaca aagccgcggg aggagcagta caacagcacg taccgtgtgg tcagcgtcct    300

caccgtcctg caccaggact ggctgaatgg caaggagtac aagtgcaagg tctccaacaa    360

agccctccca gcccccatcg agaaaaccat ctccaaagcc aaagggcagc cccgagaacc    420

acaggtgtac accctgcccc catcccggga ggagatgacc aagaaccagg tcagcctgac    480

ctgcctggtc aaaggcttct atcccagcga catcgccgtg gagtgggaga gcaatgggca    540

gccggagaac aactacaaga ccacgcctcc cgtgctggac tccgacggct ccttcttcct    600

ctacagcaag ctcaccgtgg acaagagcag gtggcagcag gggaacgtct tctcatgctc    660

cgtgatgcac gaggctctgc acaaccacta cacgcagaag agcctctccc tgtctccggg    720

taaaggtggc ggagggtctg gaggaggcgg tagcggcgga ggaggttccg gggcggtgg    780

aagcggaggc ggtggatccg aggtgcaact agtgcagtct ggagcagagg tgaaaaagcc    840

cggggagtct ctgaagattt cctgtaaggg ttctggatac agctttatga actactggct    900

gggatgggtg cgccagatgc ccgggaaagg cctggagtgg atgggggaca tctaccccgg    960

cggagactac cctacataca gcgagaagtt caaggtccag gtcaccatct cagccgacaa   1020

gtccatcagc accgcctacc tgcagttgag cagcctgaag gcctcggaca ccgccatgta   1080

ttactgtgcg agatcaggca attacgacga agtggcctac tggggccaag gaaccctggt   1140

caccgtctcc tcagctagca ccaagggccc atcggtcttc cccctggcac cctcctccaa   1200
```

gagcacctct gggggcacag cggccctggg ctgcctggtc aaggactact tccccgaacc 1260
ggtgacggtg tcgtggaact caggcgccct gaccagcggc gtgcacacct tcccggctgt 1320
cctacagtcc tcaggactct actccctcag cagcgtggtg accgtgccct ccagcagctt 1380
gggcacccag acctacatct gcaacgtgaa tcacaagccc agcaacacca aggtggacaa 1440
gaaagttgag ccgaagagct gtgataagac gcatacgtaa taagcggccg c 1491

<210> SEQ ID NO 83
<211> LENGTH: 30
<212> TYPE: PRT
<213> ORGANISM: Artificial Sequence
<220> FEATURE:
<223> OTHER INFORMATION: Amino acid sequence of framework region 3 in the heavy chain of humanized anti-hTfR antibody No. 3

<400> SEQUENCE: 83

Gln Val Thr Ile Ser Ala Asp Lys Ser Ile Ser Thr Ala Tyr Leu Gln
1 5 10 15

Trp Ser Ser Leu Lys Ala Ser Asp Thr Ala Met Tyr Tyr Cys
20 25 30

<210> SEQ ID NO 84
<211> LENGTH: 216
<212> TYPE: PRT
<213> ORGANISM: Artificial Sequence
<220> FEATURE:
<223> OTHER INFORMATION: Amino acid sequence of the Fab heavy chain of humanized anti-hTfR antibody No. 3N (2)

<400> SEQUENCE: 84

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Met Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Leu Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val

```
    210                 215


<210> SEQ ID NO 85
<211> LENGTH: 46
<212> TYPE: PRT
<213> ORGANISM: Artificial Sequence
<220> FEATURE:
<223> OTHER INFORMATION: Amino acid sequence of albumin binding domain

<400> SEQUENCE: 85

Leu Ala Glu Ala Lys Val Leu Ala Leu Arg Glu Leu Asp Lys Tyr Gly
1               5                   10                  15

Val Ser Asp Tyr Tyr Lys Asp Leu Ile Asp Lys Ala Lys Thr Val Glu
            20                  25                  30

Gly Val Lys Ala Leu Ile Asp Glu Ile Leu Ala Ala Leu Pro
        35                  40                  45


<210> SEQ ID NO 86
<211> LENGTH: 1674
<212> TYPE: DNA
<213> ORGANISM: Artificial Sequence
<220> FEATURE:
<223> OTHER INFORMATION: Nucleotide seuquence encoding the amino acid
      sequence of the fusion protein of the Fab heavy chain of humanized
      anti-hTfR antibody 3N, pro-hBDNF, and ABD, synthetic sequence

<400> SEQUENCE: 86

acgcgtcgcc accatgggtt ggagcctcat cttgctcttc cttgtcgctg ttgctacgcg      60

agtcggcagc gcccccatga aagaagcaaa catccgagga caaggtggct tggcctaccc     120

aggtgtgcgg acccatggga ctctggagag cgtgaatggg cccaaggcag gttcaagagg     180

cttgacatca ttggctgaca ctttcgaaca cgtgatagaa gagctgttgg atgaggacca     240

gaaagttcgg cccaatgaag aaaacaataa ggacgcagac ttgtacacgt ccagggtgat     300

gctcagtagt caagtgcctt tggagcctcc tcttctcttt ctgctggagg aatacaaaaa     360

ttacctagat gctgcaaaca tgtccatgag ggtccggcgc cactctgacc ctgcccgccg     420

aggggagctg agcgtgtgtg acagtattag tgagtgggta acggcggcag acaaaaagac     480

tgcagtggac atgtcgggcg ggacggtcac agtccttgaa aaggtccctg tatcaaaagg     540

ccaactgaag caatacttct acgagaccaa gtgcaatccc atgggttaca caaaagaagg     600

ctgcaggggc atagacaaaa ggcattggaa ctcccagtgc cgaactaccc agtcgtacgt     660

gcgggccctt accatggata gcaagaagag aattggctgg cgattcataa ggatagacac     720

ttcttgtgta tgtacattga ccattaaaag gggaagaggt ggcggagggt ctggaggtgg     780

cggatcaggc ggaggaggtt ccgggggcgg tggaagcgga ggcggtggat ccgaggtgca     840

actagtgcag tctggagcag aggtgaaaaa gcccggggag tctctgaaga tttcctgtaa     900

gggttctgga tacagcttta tgaactactg gctgggatgg gtgcgccaga tgcccgggaa     960

aggcctggag tggatggggg acatctaccc cggcggagac taccctacat acagcgagaa    1020

gttcaaggtc caggtcacca tctcagccga caagtccatc agcaccgcct acctgcagtt    1080

gagcagcctg aaggcctcgg acaccgccat gtattactgt gcgagatcag gcaattacga    1140

cgaagtggcc tactggggcc aaggaaccct ggtcaccgtc tcctcagcta gcaccaaggg    1200

cccatcggtc ttccccctgg caccctcctc caagagcacc tctgggggca cagcggccct    1260

gggctgcctg gtcaaggact acttccccga accggtgacg gtgtcgtgga actcaggcgc    1320

cctgaccagc ggcgtgcaca ccttcccggc tgtcctacag tcctcaggac tctactccct    1380
```

```
cagcagcgtg gtgaccgtgc cctccagcag cttgggcacc cagacctaca tctgcaacgt   1440

gaatcacaag cccagcaaca ccaaggtgga caagaaagtt ggaggtggcg gatcaggcgg   1500

aggaggttcc gggggcggtg gaagcctggc tgaggccaag gtgctggccc tgagggagct   1560

ggacaagtac ggcgtgtccg actactacaa ggacctgatc gacaaggcca agaccgtgga   1620

gggcgtgaag gccctgatcg acgagatcct ggccgccctg ccctaagcgg ccgc         1674


<210> SEQ ID NO 87
<211> LENGTH: 531
<212> TYPE: PRT
<213> ORGANISM: Artificial Sequence
<220> FEATURE:
<223> OTHER INFORMATION: Amino acid sequence of the fusion protein of
      the Fab heavy chain of humanized anti-hTfR antibody 3N, pro-hBDNF,
      and ABD

<400> SEQUENCE: 87

Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg Gly Gly Gly Gly Ser Gly Gly Gly Gly Ser Gly
225                 230                 235                 240

Gly Gly Gly Ser Gly Gly Gly Gly Ser Gly Gly Gly Gly Ser Glu Val
                245                 250                 255

Gln Leu Val Gln Ser Gly Ala Glu Val Lys Lys Pro Gly Glu Ser Leu
            260                 265                 270

Lys Ile Ser Cys Lys Gly Ser Gly Tyr Ser Phe Met Asn Tyr Trp Leu
        275                 280                 285

Gly Trp Val Arg Gln Met Pro Gly Lys Gly Leu Glu Trp Met Gly Asp
    290                 295                 300
```

Ile Tyr Pro Gly Gly Asp Tyr Pro Thr Tyr Ser Glu Lys Phe Lys Val
305 310 315 320

Gln Val Thr Ile Ser Ala Asp Lys Ser Ile Ser Thr Ala Tyr Leu Gln
325 330 335

Leu Ser Ser Leu Lys Ala Ser Asp Thr Ala Met Tyr Tyr Cys Ala Arg
340 345 350

Ser Gly Asn Tyr Asp Glu Val Ala Tyr Trp Gly Gln Gly Thr Leu Val
355 360 365

Thr Val Ser Ser Ala Ser Thr Lys Gly Pro Ser Val Phe Pro Leu Ala
370 375 380

Pro Ser Ser Lys Ser Thr Ser Gly Gly Thr Ala Ala Leu Gly Cys Leu
385 390 395 400

Val Lys Asp Tyr Phe Pro Glu Pro Val Thr Val Ser Trp Asn Ser Gly
405 410 415

Ala Leu Thr Ser Gly Val His Thr Phe Pro Ala Val Leu Gln Ser Ser
420 425 430

Gly Leu Tyr Ser Leu Ser Ser Val Val Thr Val Pro Ser Ser Ser Leu
435 440 445

Gly Thr Gln Thr Tyr Ile Cys Asn Val Asn His Lys Pro Ser Asn Thr
450 455 460

Lys Val Asp Lys Lys Val Gly Gly Gly Gly Ser Gly Gly Gly Gly Ser
465 470 475 480

Gly Gly Gly Gly Ser Leu Ala Glu Ala Lys Val Leu Ala Leu Arg Glu
485 490 495

Leu Asp Lys Tyr Gly Val Ser Asp Tyr Tyr Lys Asp Leu Ile Asp Lys
500 505 510

Ala Lys Thr Val Glu Gly Val Lys Ala Leu Ile Asp Glu Ile Leu Ala
515 520 525

Ala Leu Pro
530

<210> SEQ ID NO 88
<211> LENGTH: 421
<212> TYPE: PRT
<213> ORGANISM: Artificial Sequence
<220> FEATURE:
<223> OTHER INFORMATION: Amino acid sequence of the fusion protein of the Fab heavy chain of humanized anti-hTfR antibody 3N, hBDNF, and ABD

<400> SEQUENCE: 88

His Ser Asp Pro Ala Arg Arg Gly Glu Leu Ser Val Cys Asp Ser Ile
1 5 10 15

Ser Glu Trp Val Thr Ala Ala Asp Lys Lys Thr Ala Val Asp Met Ser
20 25 30

Gly Gly Thr Val Thr Val Leu Glu Lys Val Pro Val Ser Lys Gly Gln
35 40 45

Leu Lys Gln Tyr Phe Tyr Glu Thr Lys Cys Asn Pro Met Gly Tyr Thr
50 55 60

Lys Glu Gly Cys Arg Gly Ile Asp Lys Arg His Trp Asn Ser Gln Cys
65 70 75 80

Arg Thr Thr Gln Ser Tyr Val Arg Ala Leu Thr Met Asp Ser Lys Lys
85 90 95

Arg Ile Gly Trp Arg Phe Ile Arg Ile Asp Thr Ser Cys Val Cys Thr
100 105 110

Leu Thr Ile Lys Arg Gly Arg Gly Gly Gly Gly Ser Gly Gly Gly Gly

-continued

```
        115                 120                 125

Ser Gly Gly Gly Gly Ser Gly Gly Gly Gly Ser Gly Gly Gly Gly Ser
    130                 135                 140

Glu Val Gln Leu Val Gln Ser Gly Ala Glu Val Lys Lys Pro Gly Glu
145                 150                 155                 160

Ser Leu Lys Ile Ser Cys Lys Gly Ser Gly Tyr Ser Phe Met Asn Tyr
                165                 170                 175

Trp Leu Gly Trp Val Arg Gln Met Pro Gly Lys Gly Leu Glu Trp Met
            180                 185                 190

Gly Asp Ile Tyr Pro Gly Gly Asp Tyr Pro Thr Tyr Ser Glu Lys Phe
        195                 200                 205

Lys Val Gln Val Thr Ile Ser Ala Asp Lys Ser Ile Ser Thr Ala Tyr
    210                 215                 220

Leu Gln Leu Ser Ser Leu Lys Ala Ser Asp Thr Ala Met Tyr Tyr Cys
225                 230                 235                 240

Ala Arg Ser Gly Asn Tyr Asp Glu Val Ala Tyr Trp Gly Gln Gly Thr
                245                 250                 255

Leu Val Thr Val Ser Ser Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350

Asn Thr Lys Val Asp Lys Lys Val Gly Gly Gly Gly Ser Gly Gly Gly
        355                 360                 365

Gly Ser Gly Gly Gly Gly Ser Leu Ala Glu Ala Lys Val Leu Ala Leu
    370                 375                 380

Arg Glu Leu Asp Lys Tyr Gly Val Ser Asp Tyr Tyr Lys Asp Leu Ile
385                 390                 395                 400

Asp Lys Ala Lys Thr Val Glu Gly Val Lys Ala Leu Ile Asp Glu Ile
                405                 410                 415

Leu Ala Ala Leu Pro
            420


<210> SEQ ID NO 89
<211> LENGTH: 277
<212> TYPE: PRT
<213> ORGANISM: Artificial Sequence
<220> FEATURE:
<223> OTHER INFORMATION: Amino acid sequence of the Fab heavy chain of
      humanized anti-hTfR antibody 3N introduced with ABD

<400> SEQUENCE: 89

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Met
        35                  40                  45
```

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Leu Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Gly Gly Gly Gly Ser Gly Gly Gly
210 215 220

Gly Ser Gly Gly Gly Gly Ser Leu Ala Glu Ala Lys Val Leu Ala Leu
225 230 235 240

Arg Glu Leu Asp Lys Tyr Gly Val Ser Asp Tyr Tyr Lys Asp Leu Ile
245 250 255

Asp Lys Ala Lys Thr Val Glu Gly Val Lys Ala Leu Ile Asp Glu Ile
260 265 270

Leu Ala Ala Leu Pro
275

<210> SEQ ID NO 90
<211> LENGTH: 477
<212> TYPE: PRT
<213> ORGANISM: Artificial Sequence
<220> FEATURE:
<223> OTHER INFORMATION: Amino acid sequence of single-chain humanized anti-hTfR antibody No. 3N (2)

<400> SEQUENCE: 90

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Met Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Leu Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

-continued

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Gly Gly Gly Gly Ser Gly Gly Gly Gly Ser Gly Gly Gly Gly
225                 230                 235                 240

Ser Gly Gly Gly Gly Ser Gly Gly Gly Gly Ser Gly Gly Gly Gly Ser
                245                 250                 255

Gly Gly Asp Ile Val Met Thr Gln Thr Pro Leu Ser Leu Ser Val Thr
            260                 265                 270

Pro Gly Gln Pro Ala Ser Ile Ser Cys Arg Ser Ser Gln Ser Leu Val
        275                 280                 285

His Ser Asn Gly Asn Thr Tyr Leu His Trp Tyr Leu Gln Lys Pro Gly
    290                 295                 300

Gln Ser Pro Gln Leu Leu Ile Tyr Lys Val Ser Asn Arg Phe Ser Gly
305                 310                 315                 320

Val Pro Asp Arg Phe Ser Gly Ser Gly Ser Gly Thr Asp Phe Thr Leu
                325                 330                 335

Lys Ile Ser Arg Val Glu Ala Glu Asp Val Gly Val Tyr Tyr Cys Ser
            340                 345                 350

Gln Ser Thr His Val Pro Trp Thr Phe Gly Gln Gly Thr Lys Val Glu
        355                 360                 365

Ile Lys Arg Thr Val Ala Ala Pro Ser Val Phe Ile Phe Pro Pro Ser
    370                 375                 380

Asp Glu Gln Leu Lys Ser Gly Thr Ala Ser Val Val Cys Leu Leu Asn
385                 390                 395                 400

Asn Phe Tyr Pro Arg Glu Ala Lys Val Gln Trp Lys Val Asp Asn Ala
                405                 410                 415

Leu Gln Ser Gly Asn Ser Gln Glu Ser Val Thr Glu Gln Asp Ser Lys
            420                 425                 430

Asp Ser Thr Tyr Ser Leu Ser Ser Thr Leu Thr Leu Ser Lys Ala Asp
        435                 440                 445

Tyr Glu Lys His Lys Val Tyr Ala Cys Glu Val Thr His Gln Gly Leu
    450                 455                 460

Ser Ser Pro Val Thr Lys Ser Phe Asn Arg Gly Glu Cys
465                 470                 475
```

The invention claimed is:

1. A fusion protein of human brain-derived neurotrophic factor (human BDNF) and an anti-human transferrin receptor antibody, selected from (1) or (2) below:

(1) the fusion protein wherein in a heavy chain variable region of the antibody, (a) CDR1 comprises the amino acid sequence of SEQ ID NO: 66, (b) CDR2 comprises the amino acid sequence of SEQ ID NO: 13, (c) CDR3 comprises the amino acid sequence of SEQ ID NO: 15, and (d) framework region 3 comprises the amino acid sequence of SEQ ID NO: 68, wherein in a light chain variable region of the antibody, (a) CDR1 comprises the amino acid sequence of SEQ ID NO: 6, (b) CDR2 comprises the amino acid sequence of SEQ ID NO: 8, and (c) CDR3 comprises the amino acid sequence of SEQ ID NO: 10, and wherein the human BDNF binds to the N-terminus of the heavy chain of the antibody via a linker;

(2) the fusion protein wherein in a heavy chain variable region of the antibody, (a) CDR1 comprises the amino acid sequence of SEQ ID NO: 67, (b) CDR2 comprises the amino acid sequence of SEQ ID NO: 14, (c) CDR3 comprises the amino acid sequence of SEQ ID NO: 16, and (d) framework region 3 comprises the amino acid sequence of SEQ ID NO: 68, and wherein in a light chain variable region of the antibody, (a) CDR1 comprises the amino acid sequence of SEQ ID NO: 7, (b) CDR2 comprises the amino acid sequence of SEQ ID NO: 9, and (c) CDR3 comprises the amino acid sequence of SEQ ID NO: 10, and wherein the human BDNF binds to the N-terminus of the heavy chain of the antibody via a linker.

2. The fusion protein according to claim 1, wherein the heavy chain variable region comprises the amino acid sequence of SEQ ID NO: 69.

3. The fusion protein according to claim 2, wherein the heavy chain amino acid sequence comprises the amino acid sequence of SEQ ID NO: 70 or SEQ ID NO: 72.

4. The fusion protein according to claim 1, wherein the light chain variable region of the antibody comprises the amino acid sequence of SEQ ID NO: 17, SEQ ID NO: 18, SEQ ID NO: 19, SEQ ID NO: 20, SEQ ID NO: 21, or SEQ ID NO: 22.

5. The fusion protein according to claim 1, wherein the light chain of the antibody comprises the amino acid sequence of SEQ ID NO: 23, SEQ ID NO: 25, SEQ ID NO: 27, or SEQ ID NO: 29.

6. The fusion protein according to claim 1, wherein the antibody is a Fab antibody, a $F(ab')_2$ antibody, or a F(ab') antibody.

7. The fusion protein according to claim 1, wherein the antibody is a single-chain antibody selected from the group consisting of scFab, scF(ab'), $scF(ab')_2$, and scFv.

8. The fusion protein according to claim 7, wherein the light chain binds to a C-terminus of the heavy chain of the antibody via a linker sequence.

9. The fusion protein according to claim 8, wherein the linker sequence is formed of 8 to 50 amino acid residues.

10. The fusion protein according to claim 8, wherein the linker sequence is selected from the group consisting of the amino acid sequence Gly-Ser, the amino acid sequence Gly-Gly-Ser, the amino acid sequence Gly-Gly-Gly, the amino acid sequence of SEQ ID NO: 3, the amino acid sequence of SEQ ID NO: 4, and the amino acid sequence of SEQ ID NO: 5, the amino acid sequence corresponding to three consecutive amino acid sequences of SEQ ID NO: 3, and the amino acid sequence consisting of 2 to 10 of the aforementioned amino acid sequences consecutively linked.

11. The fusion protein according to claim 1, wherein the linker is a peptide including 1 to 50 amino acid residues.

12. The fusion protein according to claim 1, wherein the linker is a peptide including the amino acid sequence selected from the group consisting of the amino acid sequence Gly-Ser, the amino acid sequence Gly-Gly-Ser, the amino acid sequence of SEQ ID NO: 3, the amino acid sequence of SEQ ID NO: 4, the amino acid sequence of SEQ ID NO: 5, and the amino acid sequence consisting of 2 to 10 of the aforementioned amino acid sequences consecutively linked.

13. The fusion protein according to claim 1, wherein the human BDNF comprises the amino acid sequence of SEQ ID NO: 51.

14. The fusion protein according to claim 1, wherein the fusion protein having affinity to both of an extracellular region of a human transferrin receptor and an extracellular region of a monkey transferrin receptor.

15. The fusion protein according to claim 14, wherein a dissociation constant of the anti-human transferrin receptor antibody with the extracellular region of the human transferrin receptor is equal to or less than $1\times10^{-10}$ M, and a dissociation constant of the anti-human transferrin receptor antibody with the extracellular region of the monkey transferrin receptor is equal to or less than $1\times10^{-9}$ M.

16. The fusion protein according to claim 1, wherein the antibody is an antigen-binding fragment.

17. The fusion protein according to claim 16, wherein the human BDNF binds to the N-terminus of the antigen-binding fragment via the linker.

18. The fusion protein according to claim 16, wherein the antigen-binding fragment is a single-chain antibody.

19. The fusion protein according to claim 18, wherein the light chain variable region binds to the C-terminus of the heavy chain variable region via a linker sequence.

20. The fusion protein according to claim 19, wherein the linker sequence includes 8 to 50 amino acid residues.

21. The fusion protein according to claim 19, wherein the linker sequence is selected from the group consisting of the amino acid sequence Gly-Ser, the amino acid sequence Gly-Gly-Ser, the amino acid sequence Gly-Gly-Gly, the amino acid sequence of SEQ ID NO: 3, the amino acid sequence of SEQ ID NO: 4, the amino acid sequence of SEQ ID NO: 5, the amino acid sequence corresponding to three consecutive amino acid sequences of SEQ ID NO: 3, and the amino acid sequence consisting of 2 to 10 of the aforementioned amino acid sequences consecutively linked.

22. The fusion protein according to claim 18, wherein the antibody comprises a heavy chain variable region having the amino acid sequence of SEQ ID NO: 69 and a light chain variable region having the amino acid sequence of SEQ ID NO: 18.

23. The fusion protein according to claim 22, wherein the antibody is formed of the amino acid sequence of SEQ ID NO: 57, and the human BDNF binds to the N-terminus of the heavy chain of the antibody via the linker.

24. The fusion protein according to claim 23, wherein the antibody is formed of the amino acid sequence of SEQ ID NO: 57, the human BDNF is human pro-BDNF, and binds to the N-terminus of the heavy chain of the antibody via the linker, and the fusion protein comprises the amino acid sequence of SEQ ID NO: 59.

25. The fusion protein according to claim 23, wherein the antibody is formed of the amino acid sequence of SEQ ID NO: 57, the human BDNF binds to the N-terminus of the heavy chain of the antibody via the linker, and the fusion protein comprises the amino acid sequence of SEQ ID NO: 60.

26. The fusion protein according to claim 16, wherein the antigen-binding fragment is any one of Fab, $F(ab')_2$, or F(ab').

27. The fusion protein according to claim 26, wherein the human BDNF binds to the N-terminus of a heavy chain of any one of Fab, $F(ab')_2$, or F(ab') via the linker.

28. The fusion protein according to claim 27, wherein the light chain of the antibody is formed of the amino acid sequence of SEQ ID NO: 23, the heavy chain of the antibody is a Fab heavy chain formed of the amino acid sequence of SEQ ID NO: 61, and the human BDNF binds to the N-terminus of the heavy chain via the linker.

29. The fusion protein according to claim 28, wherein the linker is a peptide including the amino acid sequence selected from the group consisting of the amino acid sequence Gly-Ser, the amino acid sequence Gly-Gly-Ser, the amino acid sequence of SEQ ID NO: 3, the amino acid sequence of SEQ ID NO: 4, the amino acid sequence of SEQ ID NO: 5, and the amino acid sequence consisting of 2 to 10 of the aforementioned amino acid sequences consecutively linked.

30. The fusion protein according to claim 28, wherein the light chain comprises the amino acid sequence of SEQ ID NO: 23, and wherein the human BDNF is human pro-BDNF, and a portion including the Fab heavy chain and human pro-BDNF binding to the N-terminus of the Fab heavy chain via the linker forms the amino acid sequence of SEQ ID NO: 63.

31. The fusion protein according to claim 28, wherein the light chain comprises the amino acid sequence of SEQ ID NO: 23, and wherein a portion including the Fab heavy chain and human BDNF binding to the N-terminus of the Fab heavy chain via the linker forms the amino acid sequence of SEQ ID NO: 65.

32. The fusion protein according to claim 16, wherein the fusion protein further comprises an albumin-affinity peptide.

33. The fusion protein according to claim 32, wherein the albumin-affinity peptide binds to the C-terminus of the antibody directly or via a linker sequence.

34. The fusion protein according to claim 32, wherein the albumin-affinity peptide comprises the amino acid sequence represented by SEQ ID NO: 85.

35. The fusion protein according to claim 34, wherein the heavy chain binds to the C-terminus of the human BDNF via the linker sequence, and the albumin-affinity peptide binds to the C-terminus of the heavy chain directly or via a linker sequence.

36. The fusion protein according to claim 35, wherein the light chain comprises the amino acid sequence of SEQ ID NO: 23, and wherein the human BDNF is human pro-BDNF, and the heavy chain binds to the C-terminus of human pro-BDNF via the linker sequence, and the albumin-affinity peptide binds to the C-terminus of the heavy chain via a linker sequence and thereby forms the amino acid sequence of SEQ ID NO: 87.

37. The fusion protein according to claim 35, wherein the light chain comprises the amino acid sequence of SEQ ID NO: 23, and wherein the heavy chain binds to the C-terminus of the human BDNF via the linker sequence, and the albumin-affinity peptide binds to the C-terminus of the heavy chain via a linker sequence and thereby forms the amino acid sequence of SEQ ID NO: 88.

38. The fusion protein according to claim 1, wherein the linker is a peptide including the amino acid sequence consisting of at least five amino acids of SEQ ID NO: 3 consecutively linked.

39. A pharmaceutical composition comprising the fusion protein according to claim 1 as an active ingredient.

40. The pharmaceutical composition according to claim 39, for improving a function of human BDNF in a patient, thereby alleviating a symptom of Huntington's disease that obtains benefits by exposing a brain to human BDNF.

41. A method of alleviating a symptom of Huntington's disease in a patient that obtains benefits by exposure to human BDNF, the method comprising:

administering a pharmaceutical composition containing a therapeutically effective amount of the fusion protein according to claim 1 to blood of the patient.

* * * * *